(12) United States Patent
Steinberg

(10) Patent No.: US 8,814,946 B2
(45) Date of Patent: *Aug. 26, 2014

(54) CUSHION BEARING IMPLANTS FOR LOAD BEARING APPLICATIONS

(75) Inventor: Amiram Steinberg, Moshav Avihail (IL)

(73) Assignee: Active Implants Corporation, Stamford, CT (US)

(*) Notice: Subject to any disclaimer, the term of this patent is extended or adjusted under 35 U.S.C. 154(b) by 841 days.

This patent is subject to a terminal disclaimer.

(21) Appl. No.: 12/505,086

(22) Filed: Jul. 17, 2009

(65) Prior Publication Data

US 2010/0185297 A1 Jul. 22, 2010

Related U.S. Application Data

(63) Continuation of application No. 10/497,897, filed as application No. PCT/IL02/00972 on Dec. 3, 2002, now Pat. No. 7,572,295.

(60) Provisional application No. 60/338,349, filed on Dec. 4, 2001, provisional application No. 60/351,755, filed on Jan. 24, 2002, provisional application No. 60/383,483, filed on May 23, 2002.

(51) Int. Cl.
*A61F 2/34* (2006.01)
*A61F 2/30* (2006.01)

(52) U.S. Cl.
CPC .......... *A61F 2/34* (2013.01); *A61F 2002/30016* (2013.01)
USPC .................. 623/22.26; 623/22.23; 623/22.38

(58) Field of Classification Search
USPC .......... 623/22.18, 22.19, 22.21, 22.23, 22.24, 623/22.26–22.28, 22.3–22.32, 22.38
See application file for complete search history.

(56) References Cited

U.S. PATENT DOCUMENTS

| | | |
|---|---|---|
| 2,765,787 A | 10/1956 | Pellet |
| 3,576,133 A | 4/1971 | Krupick et al. |
| 3,600,717 A | 8/1971 | McKeehan |
| 3,875,594 A | 4/1975 | Swanson |
| 3,879,767 A | 4/1975 | Stubstad |
| 3,938,198 A | 2/1976 | Kahn et al. |
| 4,089,071 A | 5/1978 | Kalnberz et al. |
| 4,279,041 A | 7/1981 | Buchholz |
| 4,292,695 A | 10/1981 | Koeneman |

(Continued)

FOREIGN PATENT DOCUMENTS

| | | |
|---|---|---|
| CH | 626 249 A | 11/1981 |
| CH | 626249 A | 11/1981 |

(Continued)

*Primary Examiner* — David H Willse
*Assistant Examiner* — Javier Blanco
(74) *Attorney, Agent, or Firm* — Haynes and Boone, LLP

(57) ABSTRACT

An acetabular implant for use in a hip joint prosthesis is disclosed. The implant includes a body portion comprising a polycarbonate polyurethane. The body portion includes a substantially semispherical inner articulating surface defining a socket sized to receive a head portion of a femoral component of the hip joint prosthesis and an outer engagement surface having an annular protrusion extending outwardly therefrom. The annular protrusion is configured for snap-fit engagement with a corresponding recess in the acetabulum. The implant also includes a deformation control element having an increased durometer hardness relative to the polycarbonate polyurethane and positioned within the body portion between the inner articulating surface and the outer engagement surface.

14 Claims, 112 Drawing Sheets

(56) References Cited

U.S. PATENT DOCUMENTS

| | | |
|---|---|---|
| 4,344,193 A | 8/1982 | Kenny |
| 4,433,440 A | 2/1984 | Cohen |
| 4,570,270 A | 2/1986 | Oechsle, III |
| 4,624,674 A | 11/1986 | Pappas et al. |
| 4,650,491 A | 3/1987 | Parchinski |
| 4,661,112 A | 4/1987 | Muller |
| 4,662,889 A | 5/1987 | Zichner et al. |
| 4,664,668 A | 5/1987 | Beck et al. |
| 4,715,859 A | 12/1987 | Schelhas et al. |
| 4,733,654 A | 3/1988 | Marino |
| 4,735,625 A | 4/1988 | Davidson |
| 4,795,470 A | 1/1989 | Goyman et al. |
| 4,795,474 A | 1/1989 | Horvath |
| 4,808,186 A | 2/1989 | Smith |
| 4,813,962 A | 3/1989 | Deckner et al. |
| 4,822,365 A | 4/1989 | Walker et al. |
| 4,824,674 A | 4/1989 | Becker et al. |
| 4,888,020 A | 12/1989 | Horber |
| 4,892,551 A | 1/1990 | Haber |
| 4,904,269 A | 2/1990 | Elloy et al. |
| 4,908,035 A | 3/1990 | Deckner et al. |
| 4,919,674 A | 4/1990 | Schelhas |
| 4,919,678 A | 4/1990 | Kranz |
| 4,936,856 A | 6/1990 | Keller |
| 4,938,771 A | 7/1990 | Vecsei et al. |
| 4,938,773 A | 7/1990 | Strand |
| 4,950,298 A | 8/1990 | Gustilo et al. |
| 4,955,912 A | 9/1990 | Berchem |
| 4,955,919 A | 9/1990 | Pappas et al. |
| 4,963,153 A | 10/1990 | Noesberger et al. |
| 4,963,154 A | 10/1990 | Anapliotis et al. |
| 4,997,444 A | 3/1991 | Farling |
| 4,997,447 A | 3/1991 | Shelley |
| 5,002,579 A | 3/1991 | Conf et al. |
| 5,002,581 A | 3/1991 | Paxson et al. |
| 5,011,497 A | 4/1991 | Persson et al. |
| 5,019,107 A | 5/1991 | Schelahs |
| 5,032,134 A | 7/1991 | Lindwer |
| 5,041,140 A | 8/1991 | Teinturier |
| 5,049,393 A | 9/1991 | Noon et al. |
| 5,080,675 A | 1/1992 | Lawes et al. |
| 5,080,677 A | 1/1992 | Shelley |
| 5,080,678 A | 1/1992 | Spotorno et al. |
| 5,108,446 A | 4/1992 | Wagner et al. |
| 5,108,449 A | 4/1992 | Gray |
| 5,108,451 A | 4/1992 | Forte |
| 5,116,374 A | 5/1992 | Stone |
| 5,133,762 A | 7/1992 | Branemark |
| 5,133,763 A | 7/1992 | Mullers |
| 5,146,933 A | 9/1992 | Boyd |
| 5,147,406 A | 9/1992 | Houston et al. |
| 5,147,408 A | 9/1992 | Noble et al. |
| 5,151,521 A | 9/1992 | Morita et al. |
| 5,156,631 A | 10/1992 | Merlette |
| 5,171,276 A | 12/1992 | Caspari et al. |
| 5,181,925 A | 1/1993 | Houston et al. |
| 5,181,929 A | 1/1993 | Prats et al. |
| 5,197,987 A | 3/1993 | Koch et al. |
| 5,197,989 A | 3/1993 | Hinckfuss et al. |
| 5,201,881 A | 4/1993 | Evans |
| 5,201,882 A | 4/1993 | Paxson et al. |
| 5,211,666 A | 5/1993 | Fetto |
| 5,214,184 A | 5/1993 | Matuzaki et al. |
| 5,217,498 A | 6/1993 | Henssge et al. |
| 5,217,499 A | 6/1993 | Shelley |
| 5,222,985 A | 6/1993 | Homsy |
| 5,246,461 A | 9/1993 | Tepic |
| 5,281,226 A | 1/1994 | Davydov et al. |
| 5,282,868 A | 2/1994 | Bahler |
| 5,282,968 A | 2/1994 | Lee |
| 5,282,985 A | 2/1994 | Zabioski |
| 5,290,314 A | 3/1994 | Koch et al. |
| 5,314,478 A | 5/1994 | Oka et al. |
| 5,314,492 A | 5/1994 | Hamilton et al. |
| 5,314,493 A | 5/1994 | Mikhail |
| 5,314,494 A | 5/1994 | Huiskes et al. |
| 5,316,550 A | 5/1994 | Forte |
| 5,323,765 A | 6/1994 | Brown |
| 5,326,376 A | 7/1994 | Warner et al. |
| 5,330,534 A | 7/1994 | Herrington et al. |
| 5,334,459 A | 8/1994 | Oskarsson et al. |
| 5,336,268 A | 8/1994 | Rispeter |
| 5,358,525 A | 10/1994 | Fox et al. |
| 5,364,839 A | 11/1994 | Gerhart et al. |
| 5,370,699 A | 12/1994 | Hood et al. |
| 5,373,621 A | 12/1994 | Ducheyne et al. |
| 5,376,064 A | 12/1994 | Cerny |
| 5,376,120 A | 12/1994 | Sarver et al. |
| 5,376,123 A | 12/1994 | Klaue et al. |
| 5,376,125 A | 12/1994 | Winkler |
| 5,376,126 A | 12/1994 | Lin |
| 5,387,244 A | 2/1995 | Breard |
| 5,389,107 A | 2/1995 | Nassar et al. |
| 5,393,739 A | 2/1995 | Bentz et al. |
| 5,397,359 A | 3/1995 | Mittelmeier et al. |
| 5,405,394 A | 4/1995 | Davidson |
| 5,405,403 A | 4/1995 | Mikhail |
| 5,405,411 A | 4/1995 | McCoy |
| 5,413,610 A | 5/1995 | Amino et al. |
| 5,415,662 A | 5/1995 | Ferrante et al. |
| 5,425,779 A | 6/1995 | Schlasser et al. |
| 5,433,750 A | 7/1995 | Gradinger et al. |
| 5,443,383 A | 8/1995 | Kuehn |
| 5,443,512 A | 8/1995 | Parr et al. |
| 5,448,489 A | 9/1995 | Reuben |
| 5,458,643 A | 10/1995 | Oka et al. |
| 5,458,651 A | 10/1995 | Lawes et al. |
| 5,480,437 A | 1/1996 | Draenert |
| 5,480,449 A | 1/1996 | Hamilton et al. |
| 5,489,311 A | 2/1996 | Cipalletti |
| 5,491,882 A | 2/1996 | Walston et al. |
| 5,496,375 A | 3/1996 | Sisk et al. |
| 5,507,814 A | 4/1996 | Gilbert et al. |
| 5,507,817 A | 4/1996 | Craig et al. |
| 5,507,818 A | 4/1996 | McLaughlin |
| 5,507,820 A | 4/1996 | Pappas |
| 5,507,823 A | 4/1996 | Walston et al. |
| 5,507,829 A | 4/1996 | Thongpreda et al. |
| 5,507,830 A | 4/1996 | DeMane et al. |
| 5,507,832 A | 4/1996 | Michielli et al. |
| 5,507,833 A | 4/1996 | Bohn |
| 5,507,834 A | 4/1996 | Laghi |
| 5,507,835 A | 4/1996 | Fore |
| 5,507,836 A | 4/1996 | Pohlig |
| 5,510,418 A | 4/1996 | Rhee et al. |
| 5,514,182 A | 5/1996 | Shea |
| 5,514,184 A | 5/1996 | Dai |
| 5,522,894 A | 6/1996 | Draenert |
| 5,522,904 A | 6/1996 | Moran |
| 5,641,323 A | 6/1997 | Caldarise |
| 5,658,345 A | 8/1997 | Willi |
| 5,660,225 A | 8/1997 | Saffran |
| 5,743,818 A | 4/1998 | Marucka |
| 5,755,799 A | 5/1998 | Oeby et al. |
| 5,755,801 A | 5/1998 | Walker et al. |
| 5,755,804 A | 5/1998 | Schnetzer et al. |
| 5,755,810 A | 5/1998 | Cunningham |
| 5,755,811 A | 5/1998 | Tananal |
| 5,766,257 A | 6/1998 | Goodman et al. |
| 5,766,260 A | 6/1998 | Whiteside |
| 5,776,202 A | 7/1998 | Copf et al. |
| 5,782,925 A | 7/1998 | Collaco |
| 5,782,928 A | 7/1998 | Ries et al. |
| 5,788,704 A | 8/1998 | Timperley |
| 5,800,553 A | 9/1998 | Albrektsson et al. |
| 5,800,554 A | 9/1998 | Scholz |
| 5,800,555 A | 9/1998 | Gray, III |
| 5,800,557 A | 9/1998 | Elhami |
| 5,800,558 A | 9/1998 | La Haise, Sr. |
| 5,800,560 A | 9/1998 | Draenert |
| 5,824,098 A | 10/1998 | Stein |
| 5,824,101 A | 10/1998 | Pappas |
| 5,824,102 A | 10/1998 | Buscaynet |
| 5,824,103 A | 10/1998 | Williams |

(56) References Cited

U.S. PATENT DOCUMENTS

| | | |
|---|---|---|
| 5,824,107 A | 10/1998 | Tschirren |
| 5,824,108 A | 10/1998 | Huebner |
| 5,871,547 A | 2/1999 | Abouaf et al. |
| 5,871,548 A | 2/1999 | Sanders et al. |
| 5,879,387 A | 3/1999 | Jones et al. |
| 5,879,390 A | 3/1999 | Kubein-Meesenburg et al. |
| 5,879,392 A | 3/1999 | McMinn |
| 5,879,393 A | 3/1999 | Whiteside et al. |
| 5,879,395 A | 3/1999 | Tornier et al. |
| 5,879,396 A | 3/1999 | Walston et al. |
| 5,879,397 A | 3/1999 | Kalberer et al. |
| 5,879,398 A | 3/1999 | Swarts et al. |
| 5,879,401 A | 3/1999 | Besemer et al. |
| 5,879,402 A | 3/1999 | Lawes et al. |
| 5,879,404 A | 3/1999 | Bateman et al. |
| 5,879,405 A | 3/1999 | Ries et al. |
| 5,879,407 A | 3/1999 | Waggener |
| 5,882,206 A | 3/1999 | Gillis |
| 5,888,204 A | 3/1999 | Ralph et al. |
| 5,902,340 A | 5/1999 | White et al. |
| 5,904,688 A | 5/1999 | Gilbert et al. |
| 5,904,720 A | 5/1999 | Farrar et al. |
| 5,906,210 A | 5/1999 | Herbert |
| 5,906,643 A | 5/1999 | Walker et al. |
| 5,906,644 A | 5/1999 | Powell |
| 5,910,171 A | 6/1999 | Kummer et al. |
| 5,910,172 A | 6/1999 | Penenberg |
| 5,911,758 A | 6/1999 | Oeby et al. |
| 5,911,759 A | 6/1999 | Bogala |
| 5,913,858 A | 6/1999 | Calandruccio et al. |
| 5,916,268 A | 6/1999 | Schollner et al. |
| 5,916,269 A | 6/1999 | Serbousek et al. |
| 5,916,270 A | 6/1999 | Lipman |
| 5,919,236 A | 7/1999 | Pfaff et al. |
| 5,928,285 A | 7/1999 | Bigliani et al. |
| 5,928,286 A | 7/1999 | Ashby et al. |
| 5,928,287 A | 7/1999 | Keller |
| 5,928,288 A | 7/1999 | Wilson |
| 5,928,289 A | 7/1999 | Deckner |
| 5,931,870 A | 8/1999 | Cuckler et al. |
| 5,931,871 A | 8/1999 | Baur et al. |
| 5,935,171 A | 8/1999 | Schneider et al. |
| 5,935,172 A | 8/1999 | Ochoa et al. |
| 5,935,173 A | 8/1999 | Roger et al. |
| 5,935,174 A | 8/1999 | Dye |
| 5,935,175 A | 8/1999 | Ostiguy et al. |
| 5,938,702 A | 8/1999 | Lopez et al. |
| 5,944,756 A | 8/1999 | Fischetti et al. |
| 5,944,757 A | 8/1999 | Grammont |
| 5,944,758 A | 8/1999 | Mansat et al. |
| 5,944,759 A | 8/1999 | Link |
| 6,136,038 A | 10/2000 | Raab |
| 6,258,126 B1 | 7/2001 | Colleran |
| 6,314,494 B1 | 11/2001 | Keltcher et al. |

FOREIGN PATENT DOCUMENTS

| | | |
|---|---|---|
| DE | 2247721 | 9/1972 |
| DE | 20003360 | 9/1972 |
| DE | 2247721 | 4/1974 |
| DE | 3215583 | 12/1982 |
| DE | 200 03 360 U | 6/2001 |
| EP | 0010527 | 4/1980 |
| EP | A-0 010 527 | 4/1980 |
| EP | 0066092 | 4/1982 |
| EP | 0066092 | 7/1985 |
| EP | 0190446 | 12/1985 |
| EP | 0253941 | 7/1986 |
| EP | 0308081 | 8/1988 |
| EP | 0382395 | 8/1990 |
| EP | A-0 382 395 | 8/1990 |
| EP | 0253941 | 10/1990 |
| EP | 0308081 B1 | 12/1991 |
| EP | 0190446 B2 | 1/1992 |
| FR | 2684544 | 6/1993 |
| FR | 2684544 A1 * | 6/1993 |
| GB | 2069338 | 1/1981 |
| GB | 2069338 A | 8/1981 |
| GB | 2126096 | 9/1982 |
| GB | 2126096 A | 3/1984 |
| WO | WO 9710776 | 3/1997 |
| WO | WO 9710776 A2 * | 3/1997 |

* cited by examiner

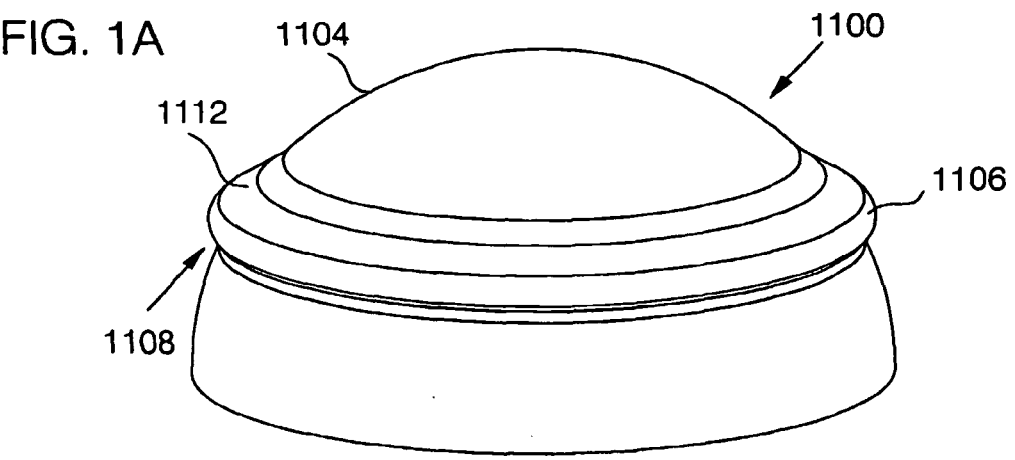
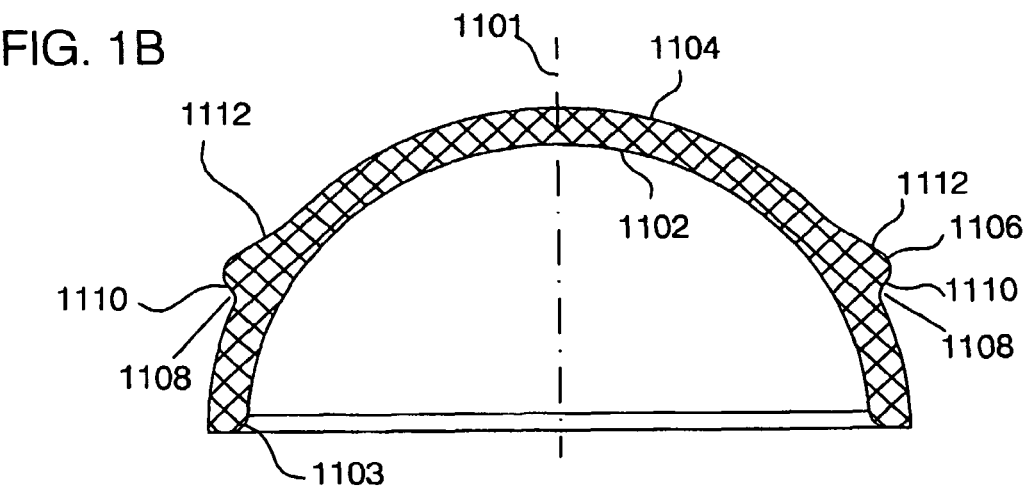
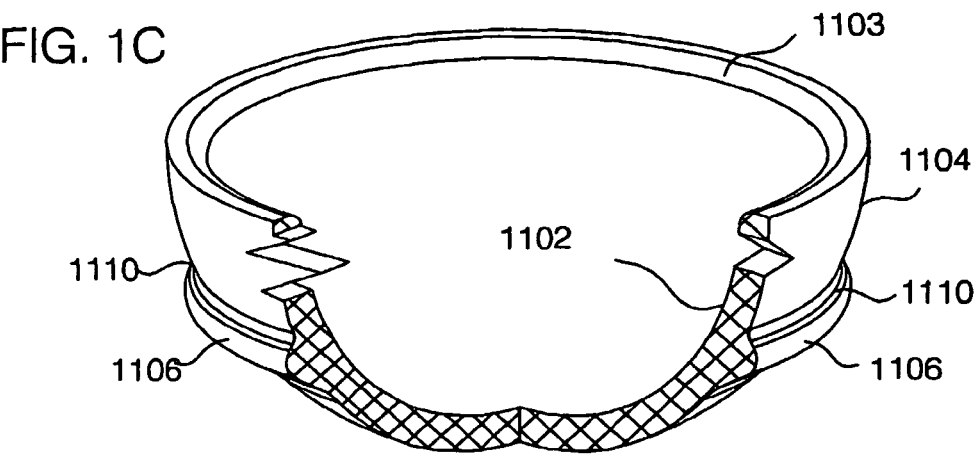

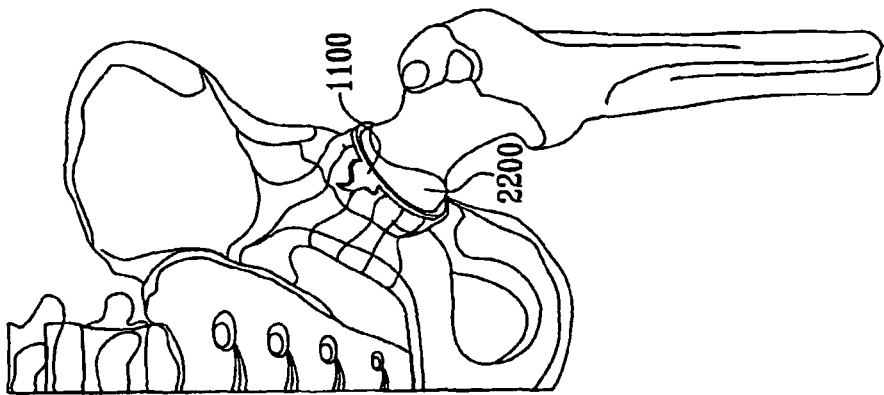
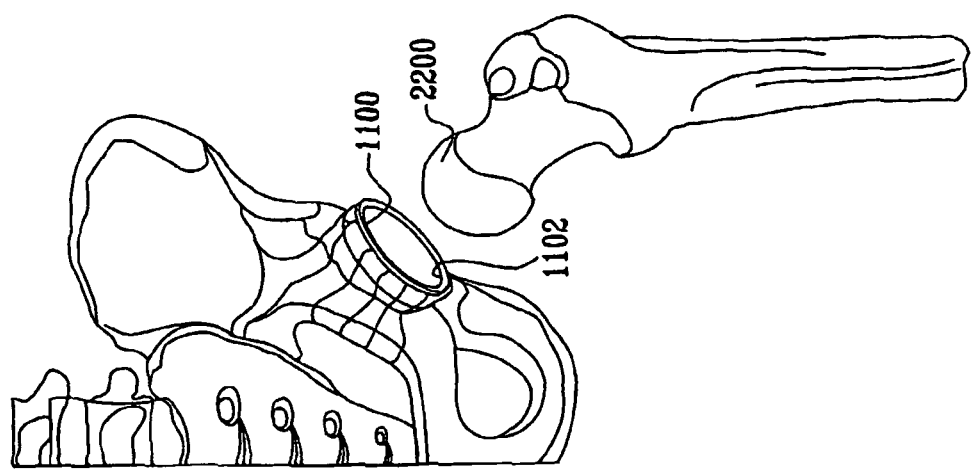

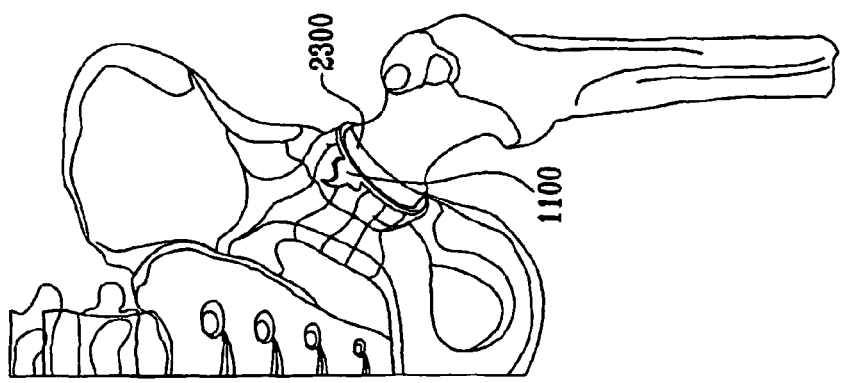
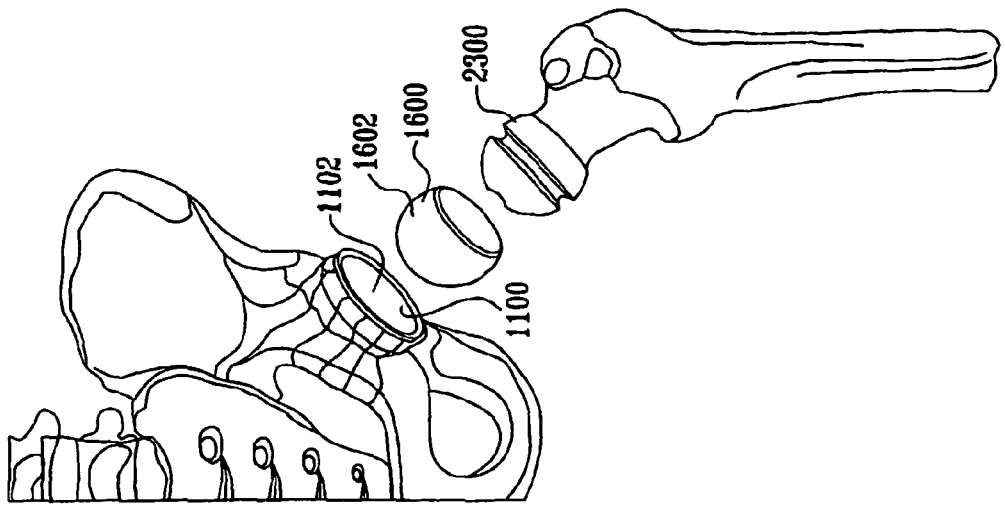

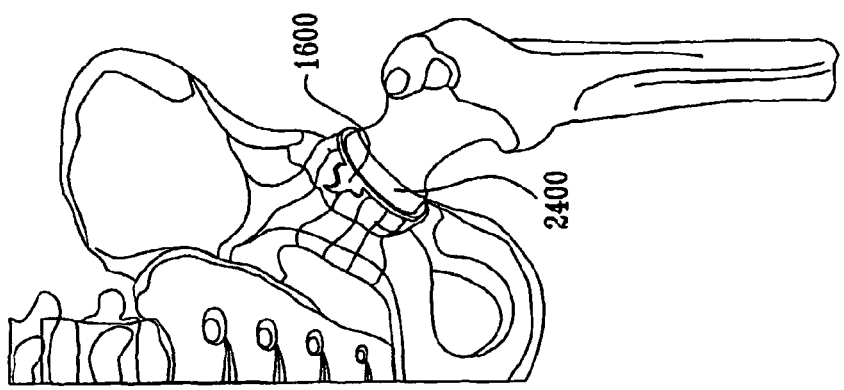
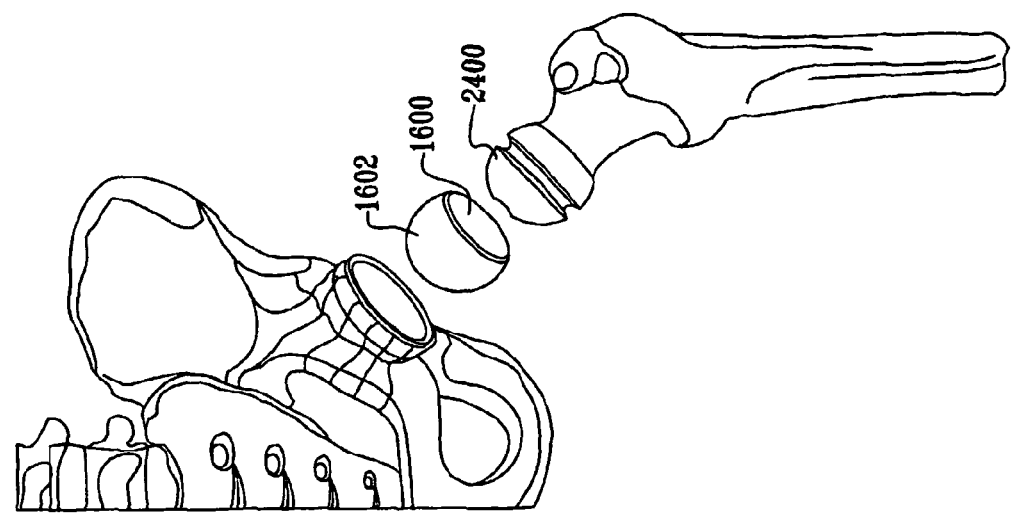

FIG. 17A
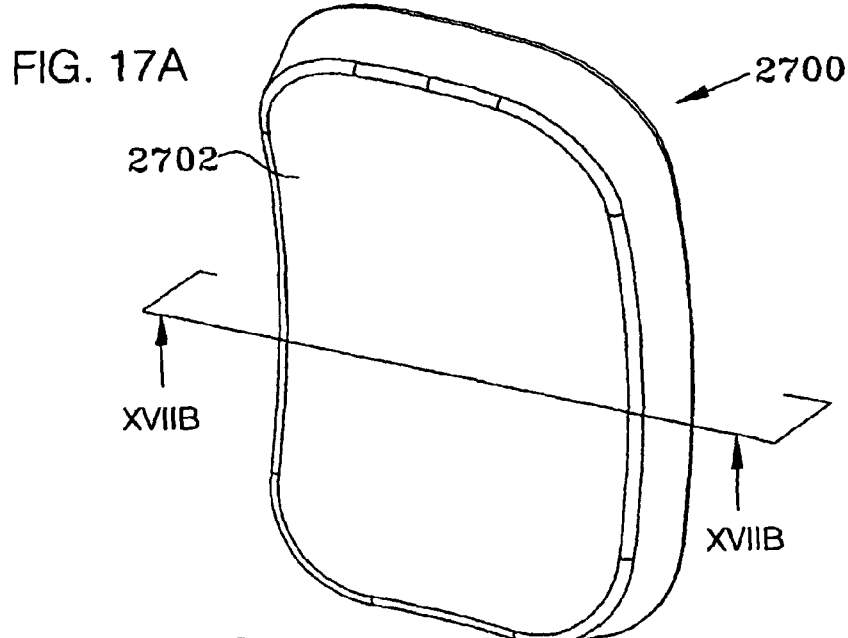
FIG. 17B
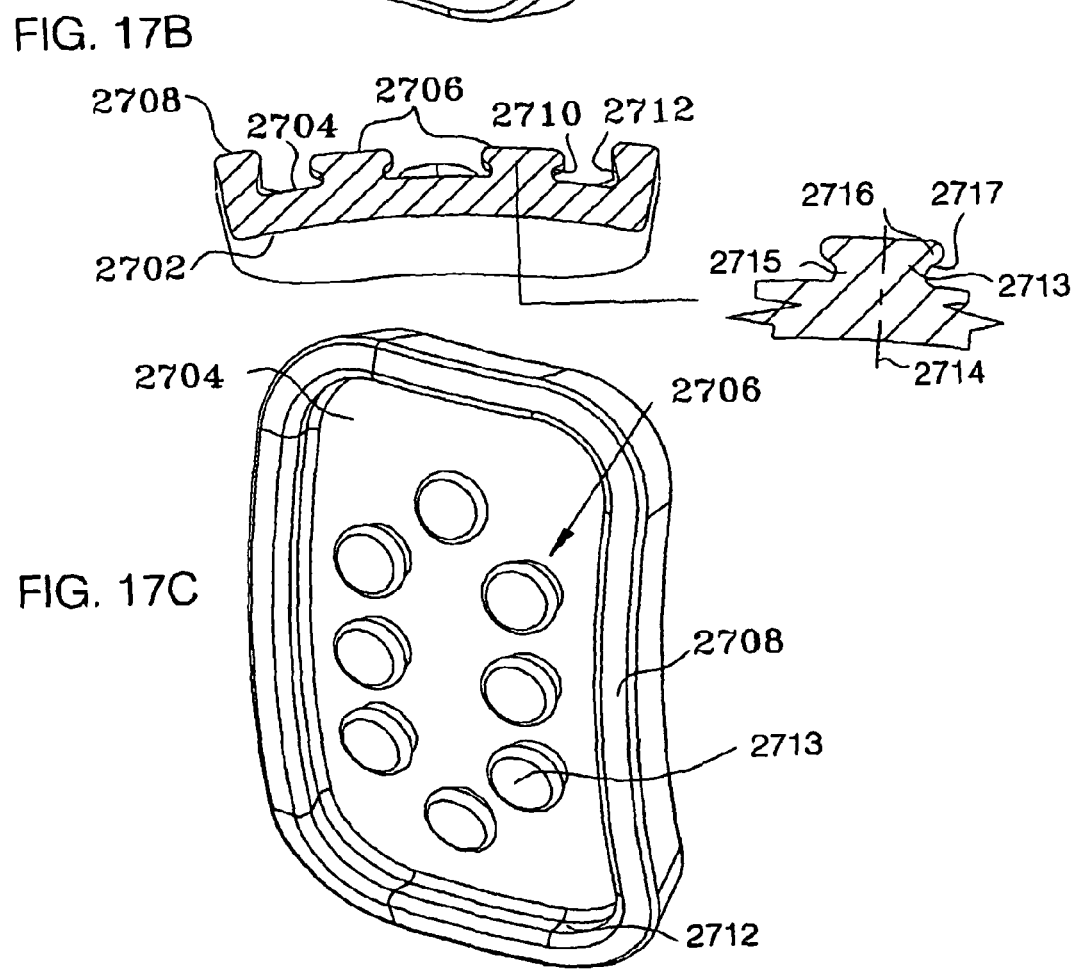
FIG. 17C

FIG. 20A
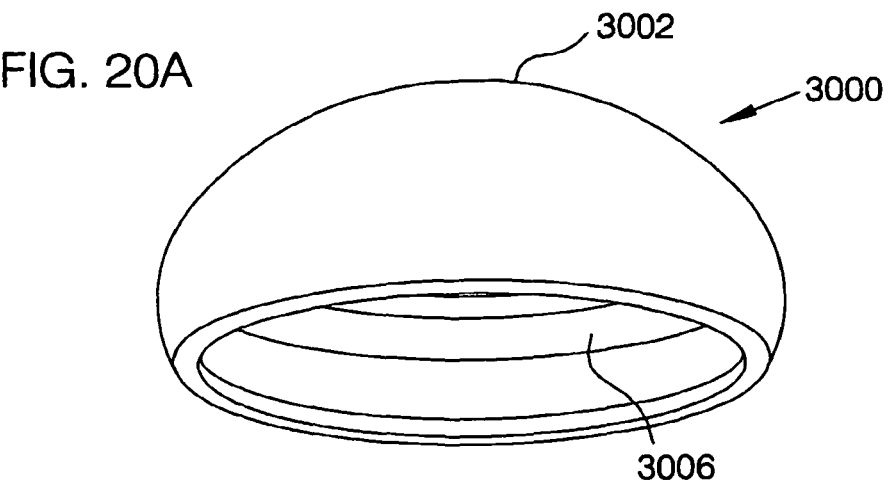
FIG. 20B
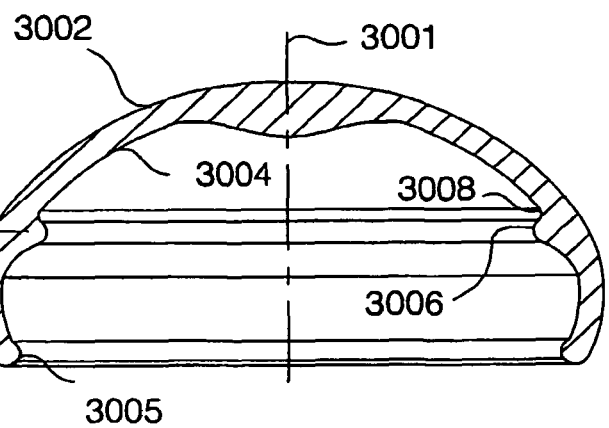
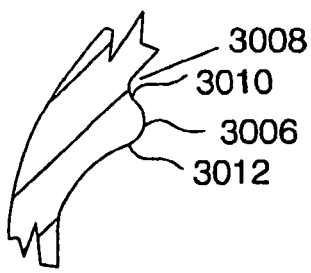
FIG. 20C
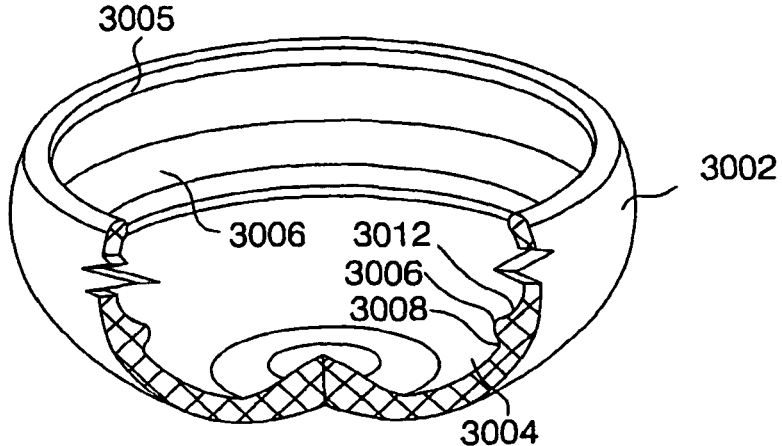

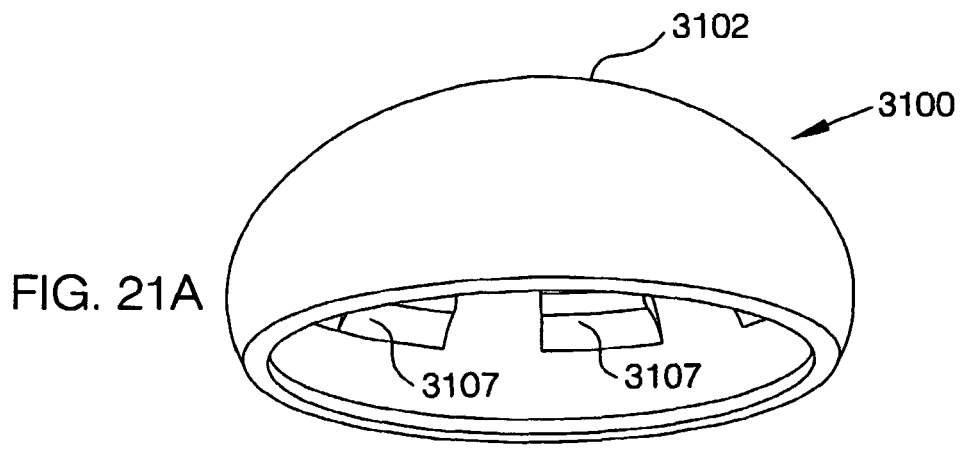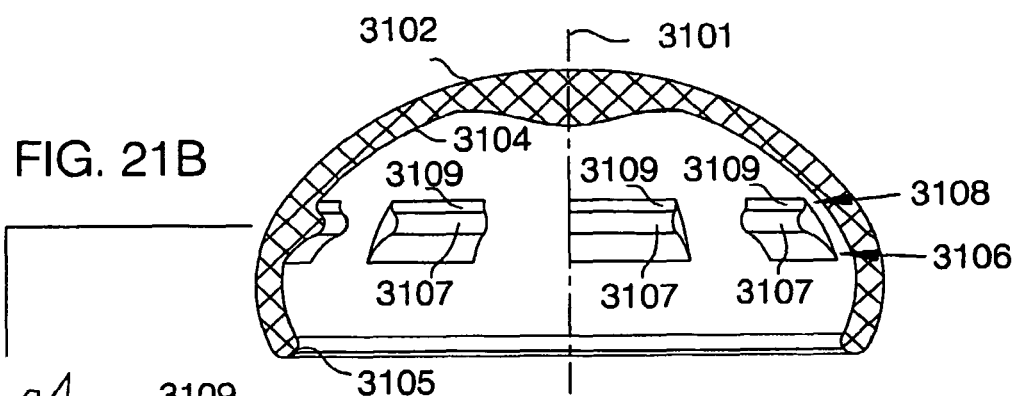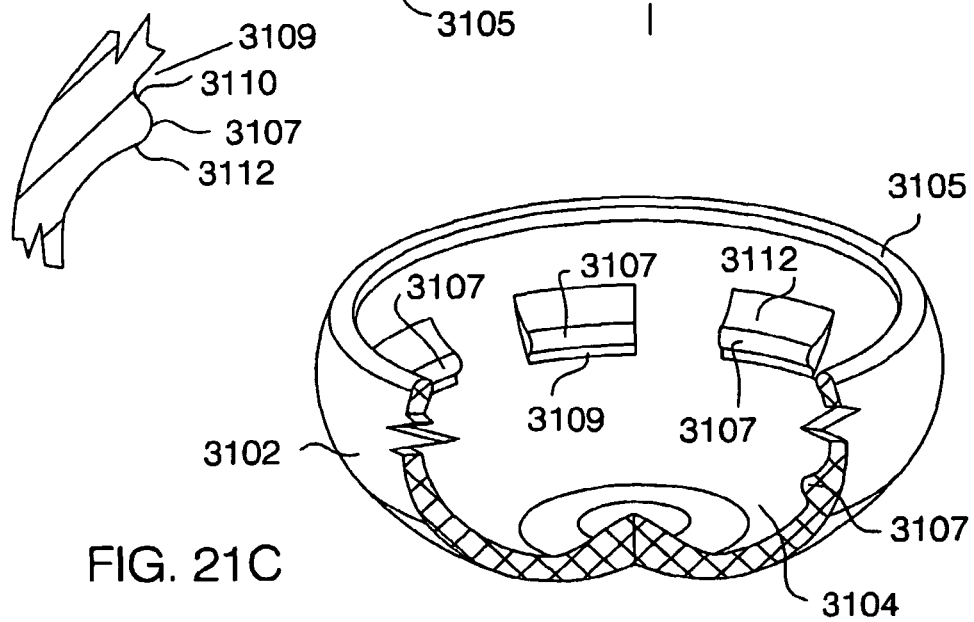

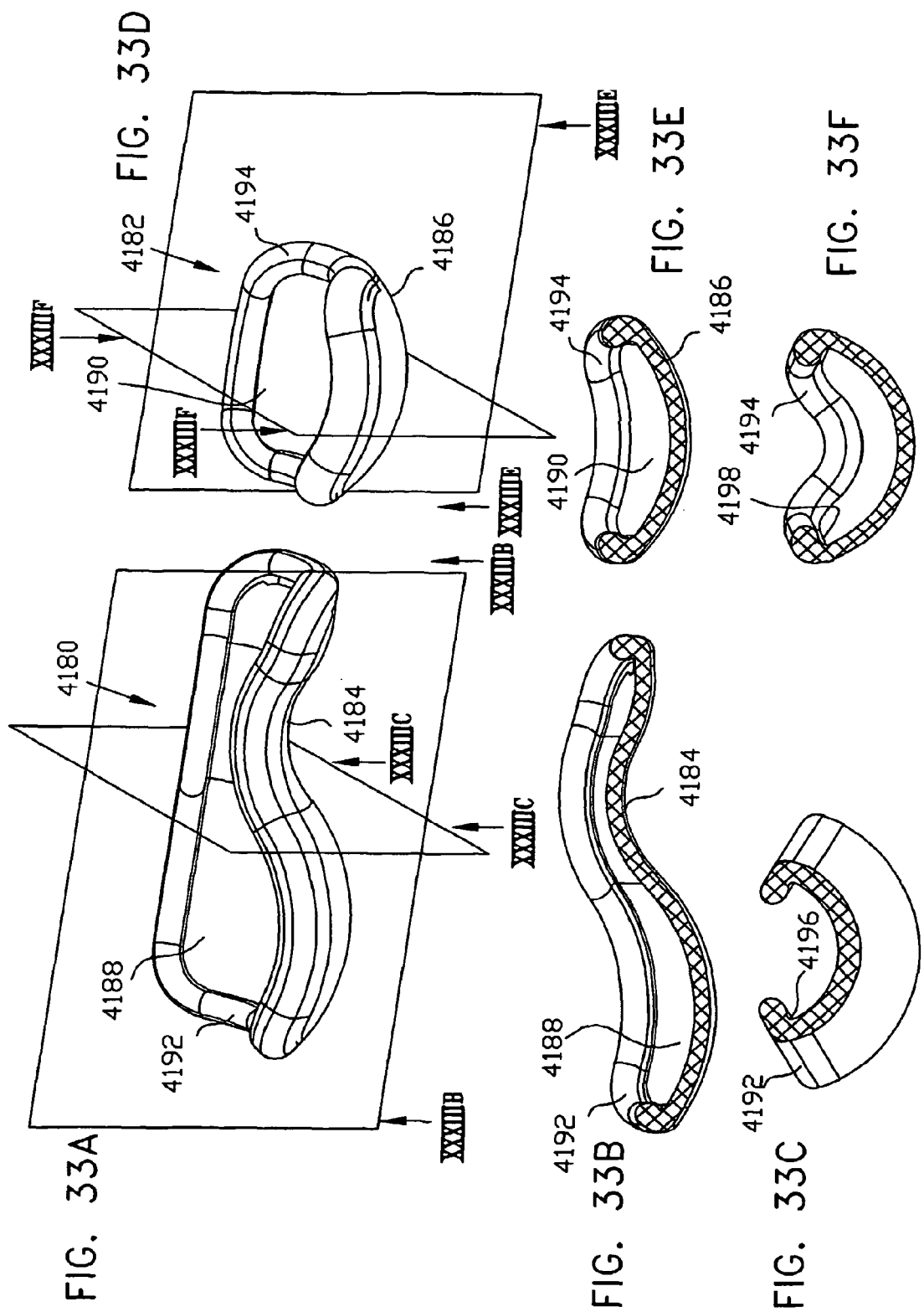

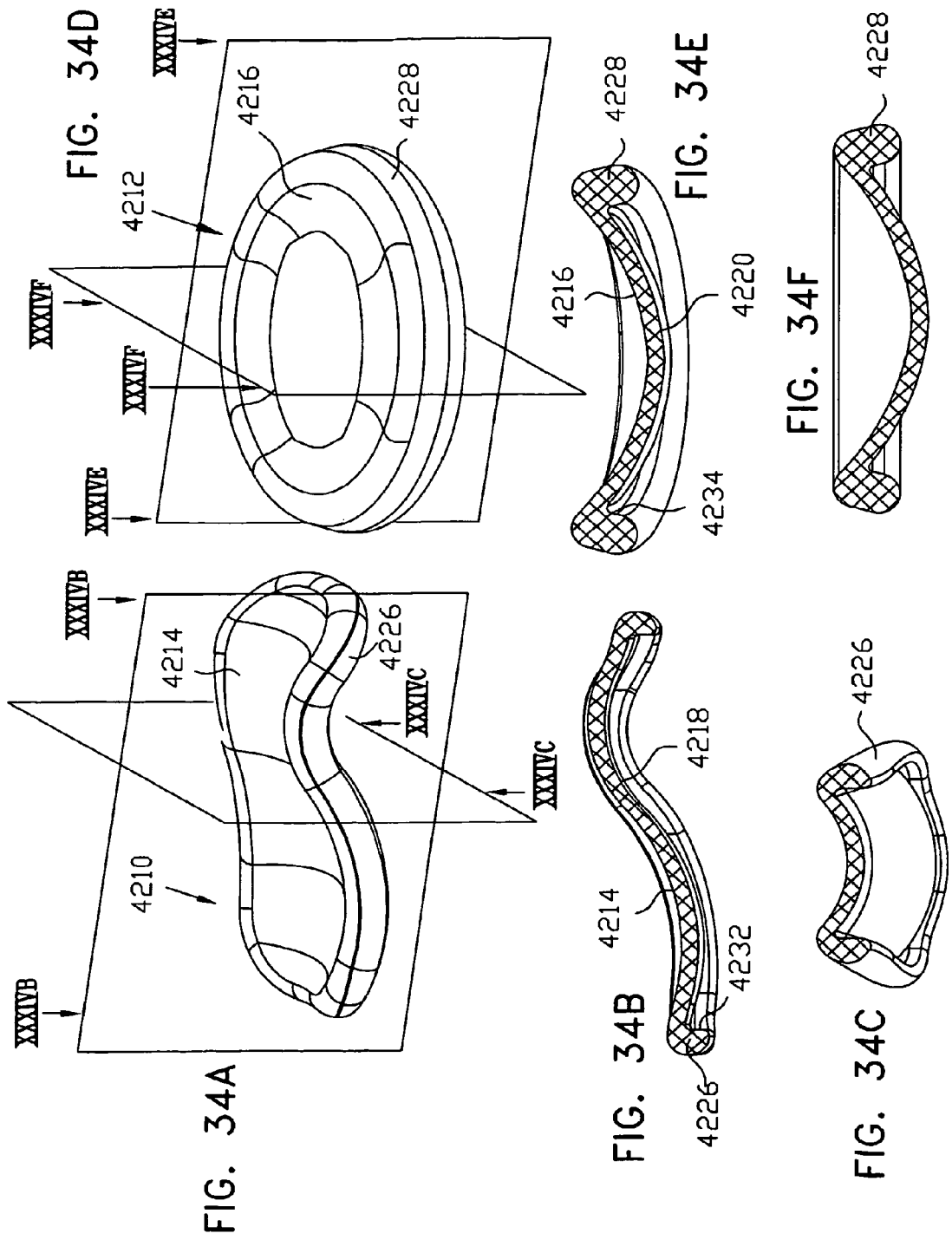

FIG. 35B
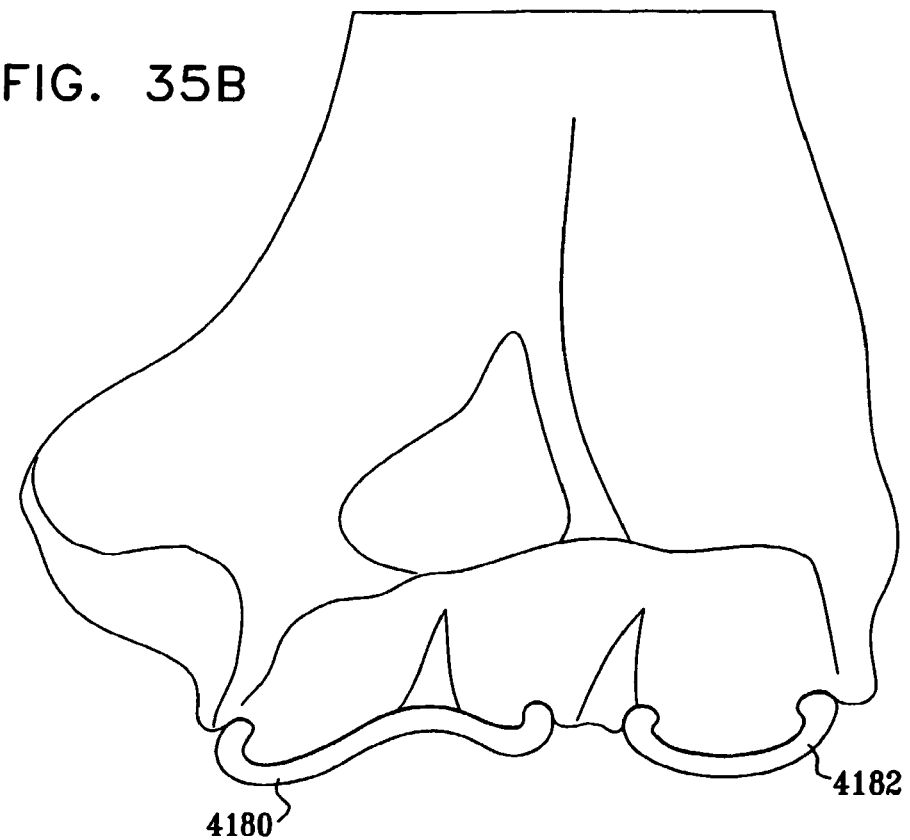
4180  4182
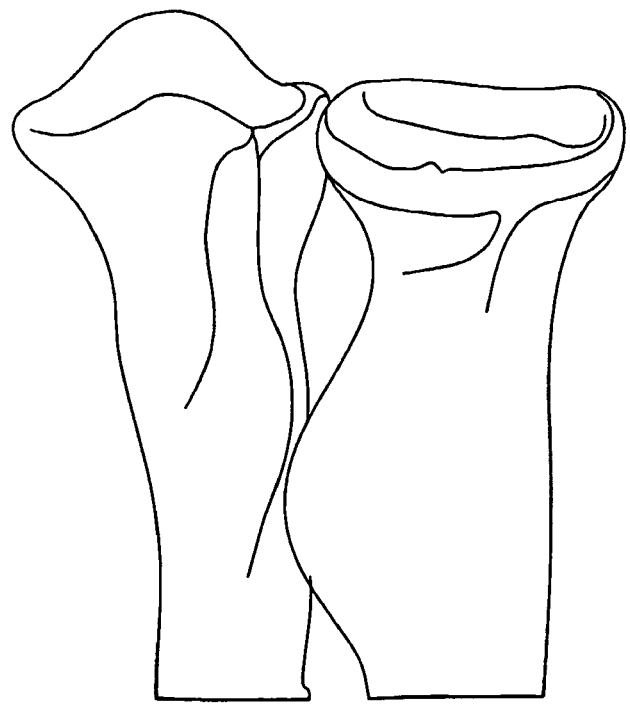

FIG. 36B
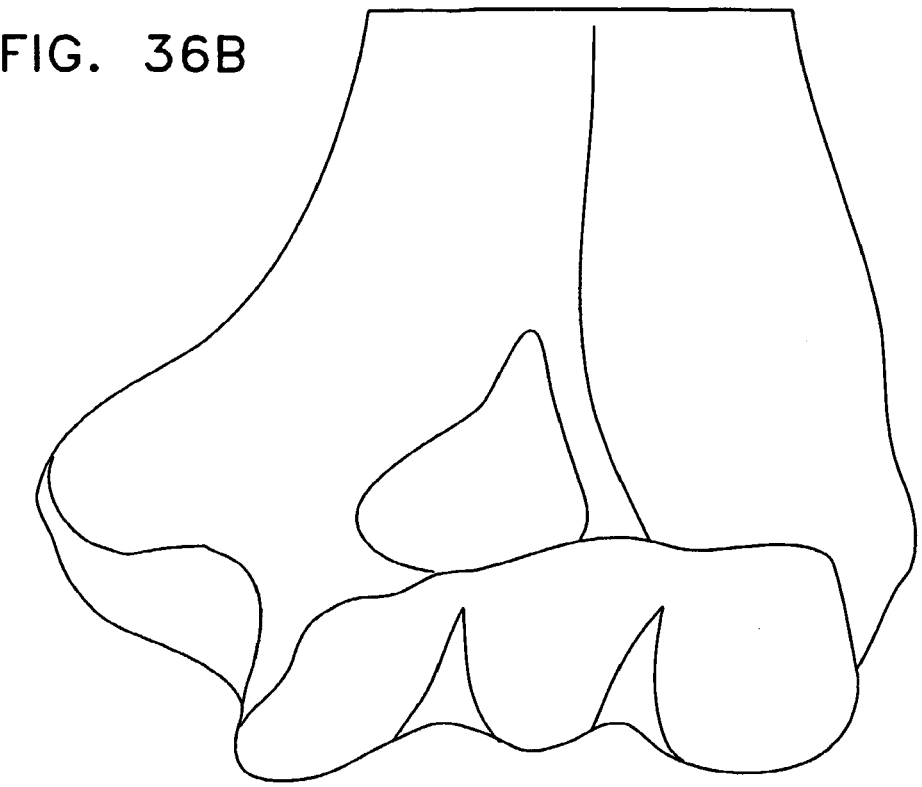
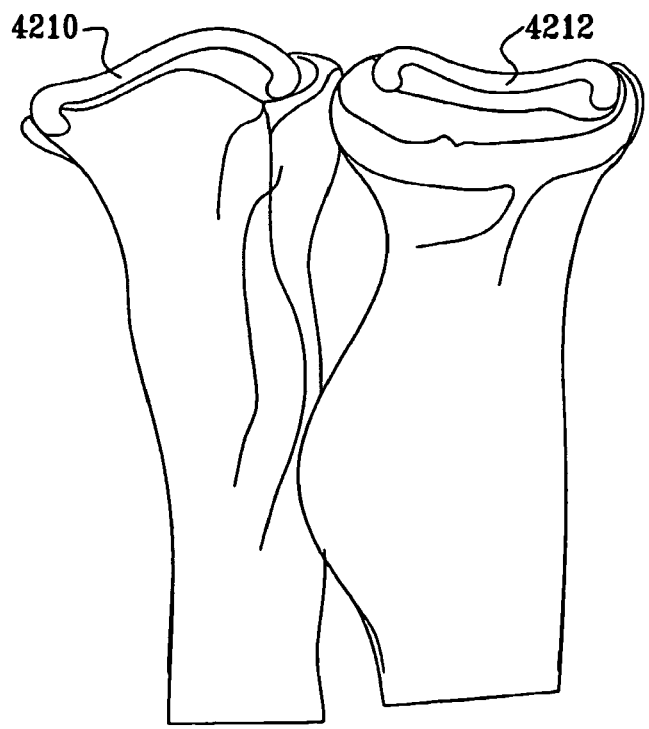

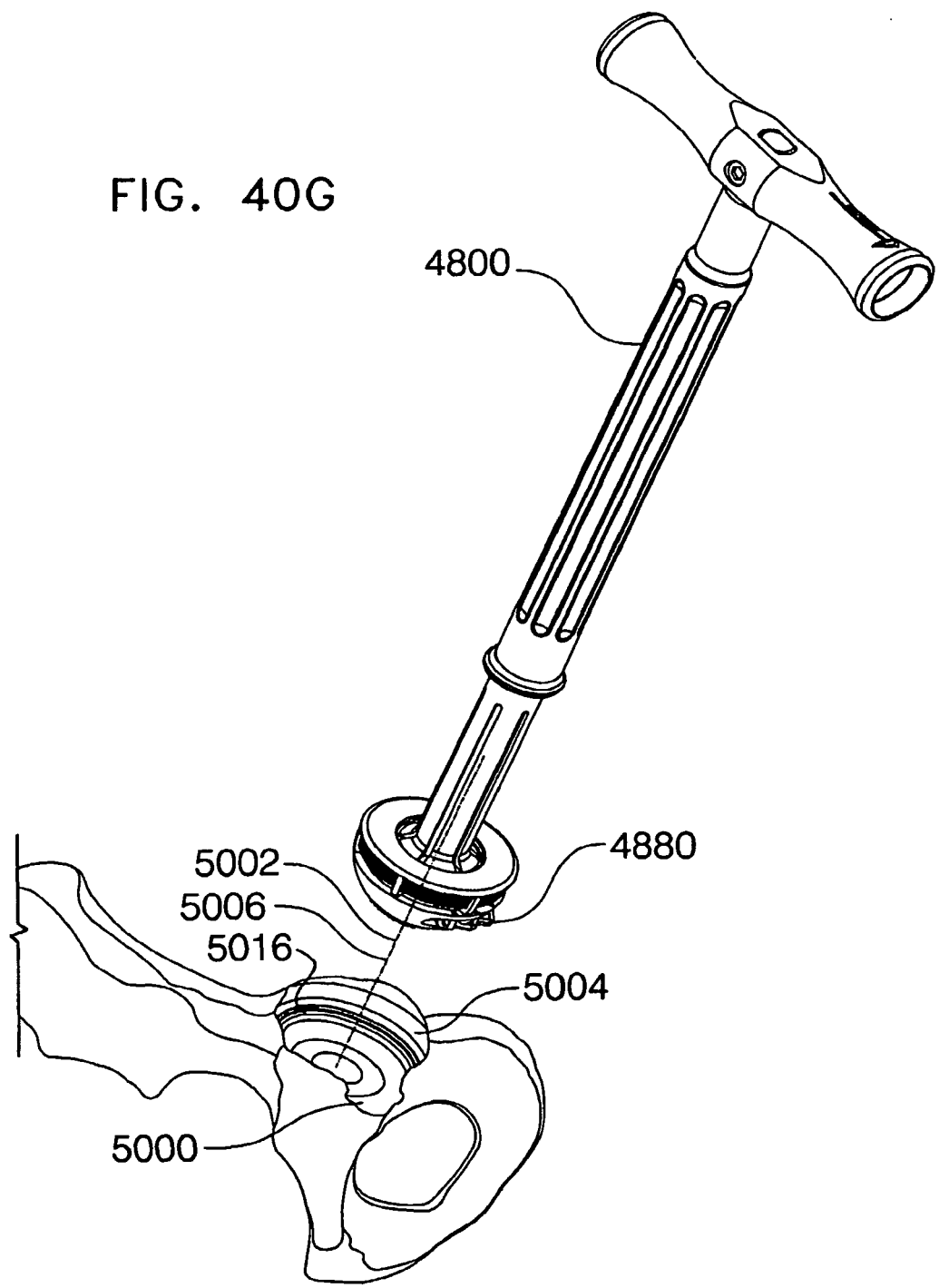

5100

5102

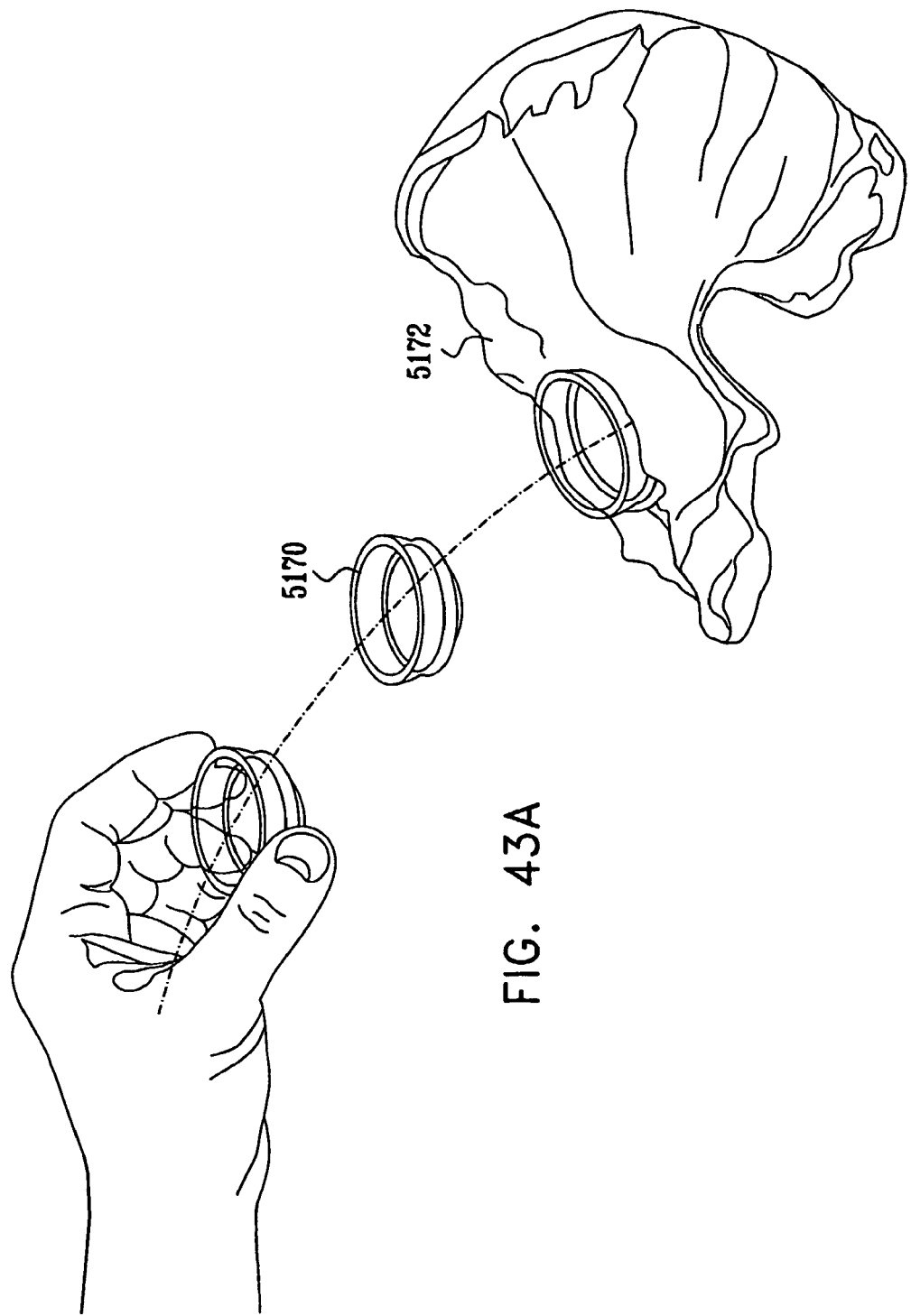

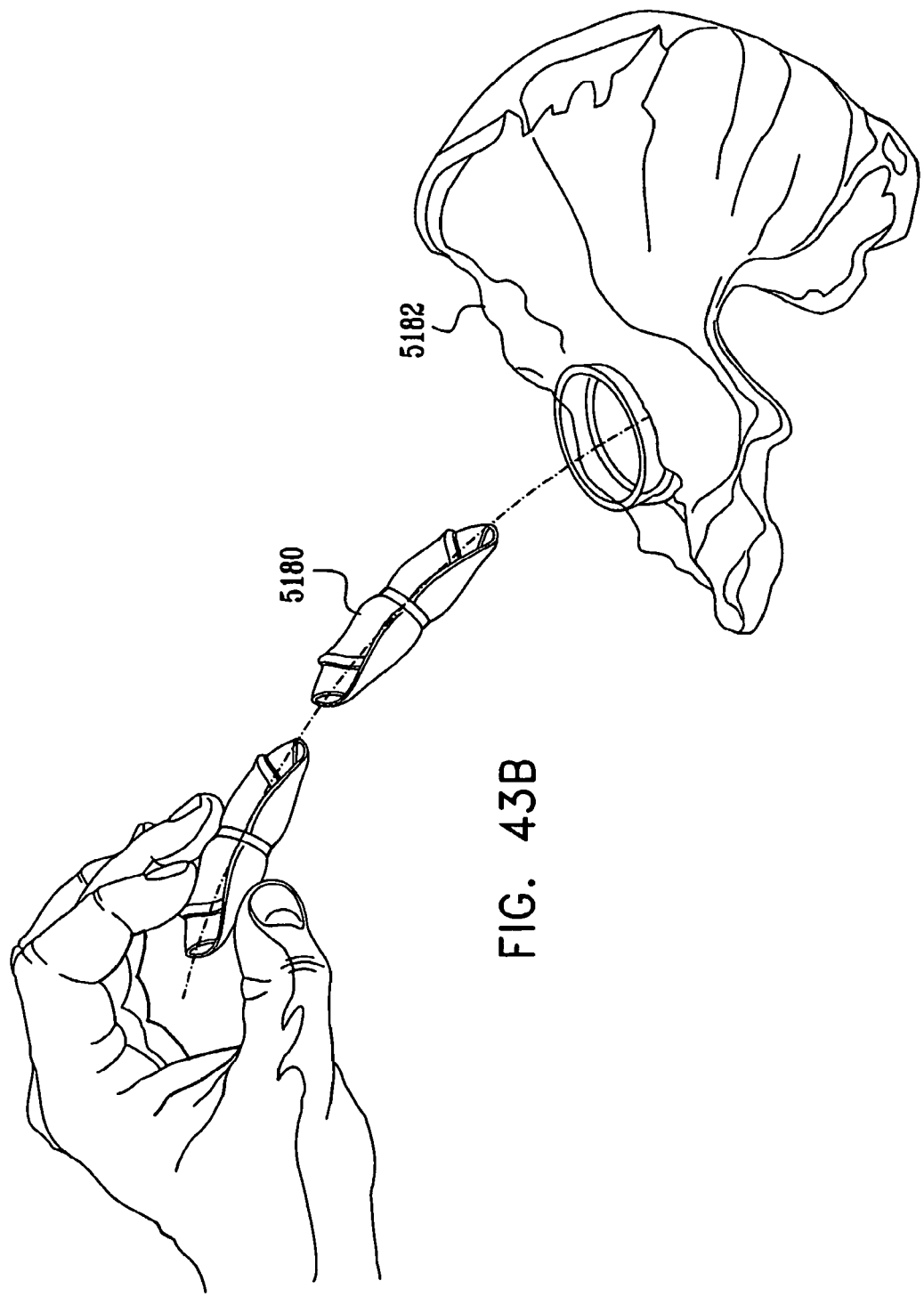

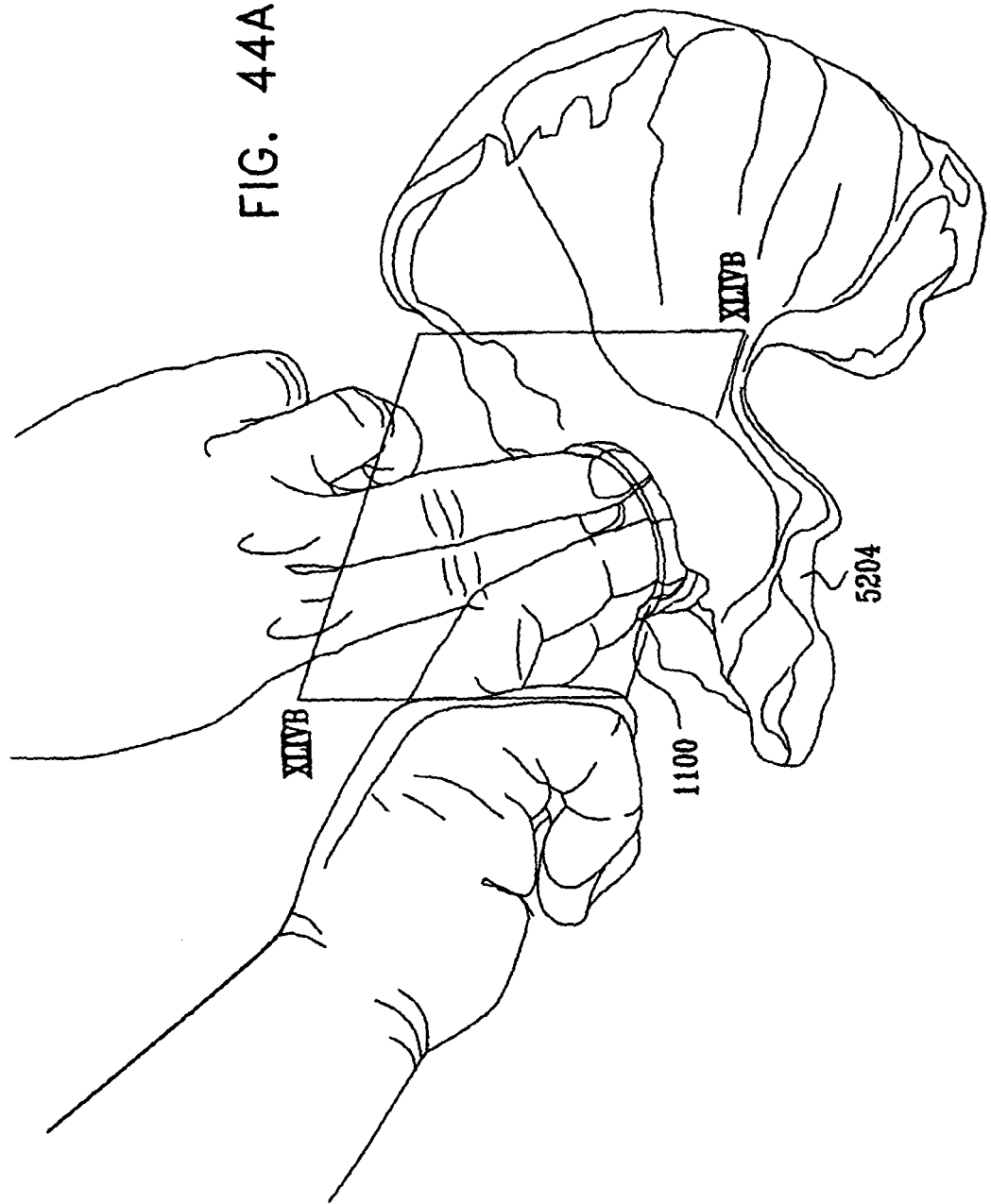

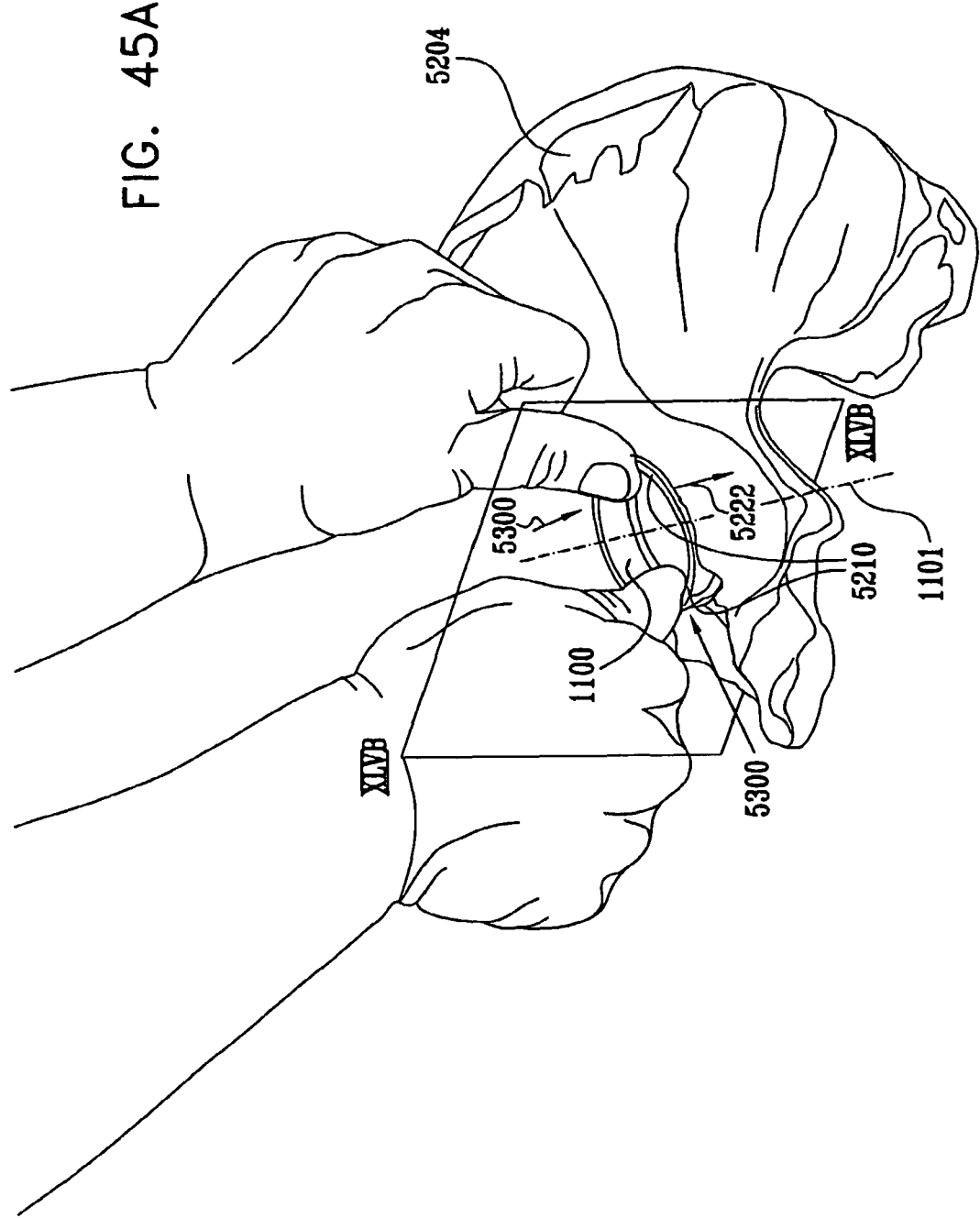

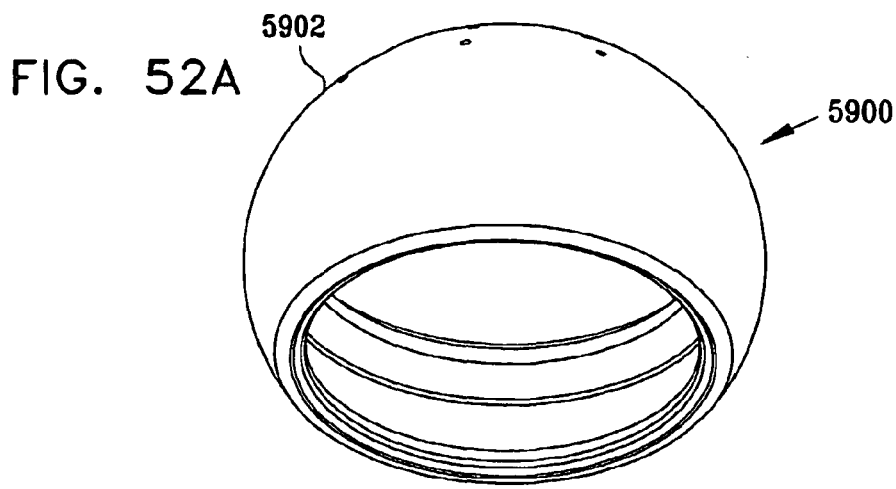
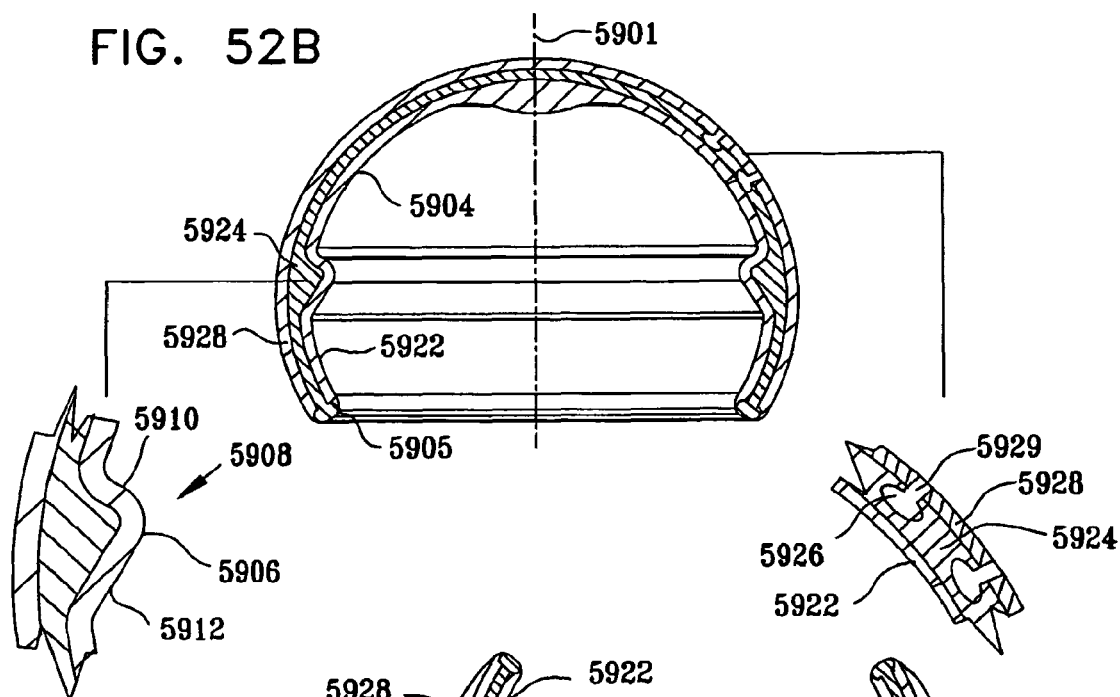
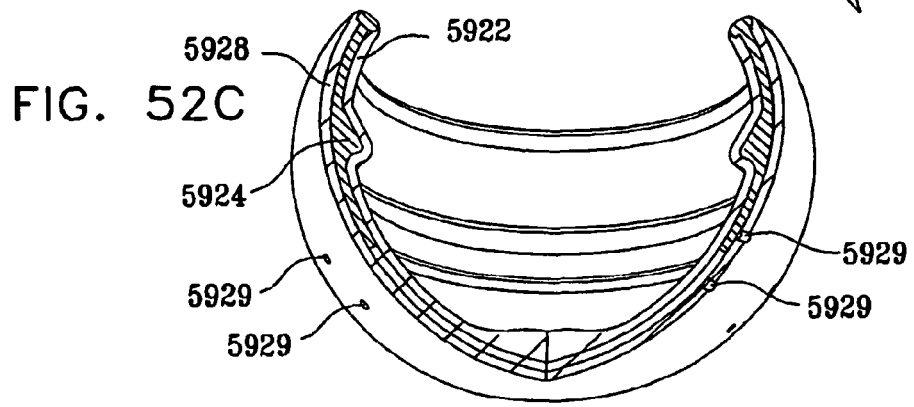

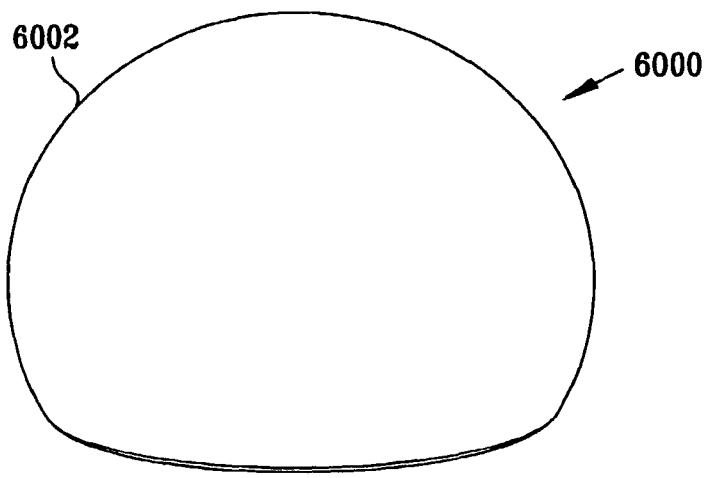
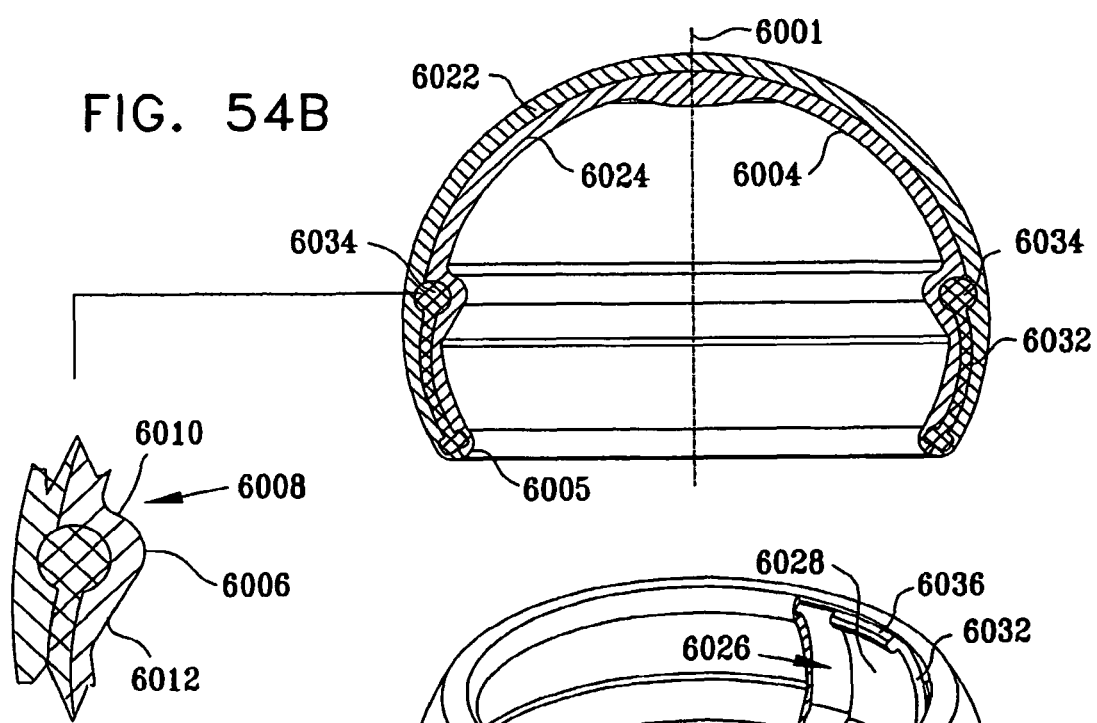
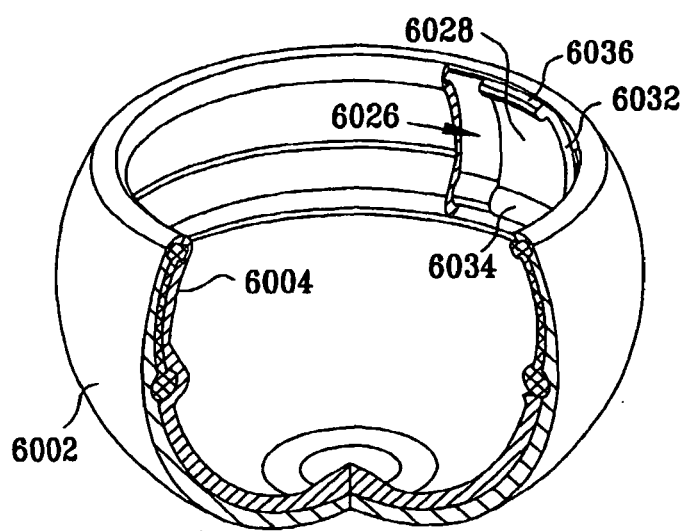
FIG. 54A
FIG. 54B
FIG. 54C

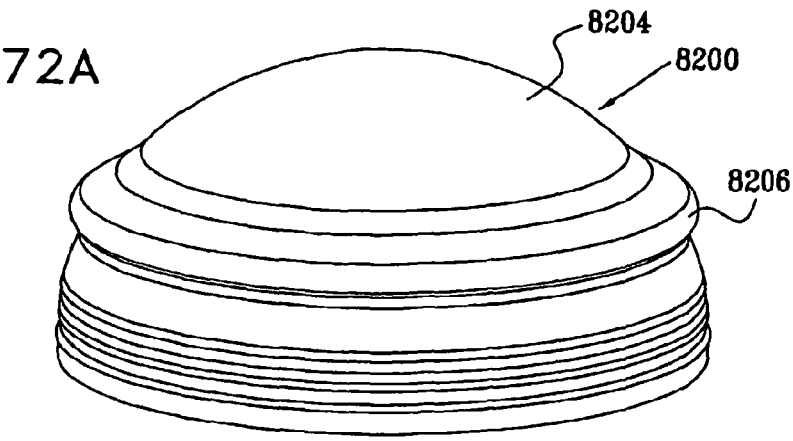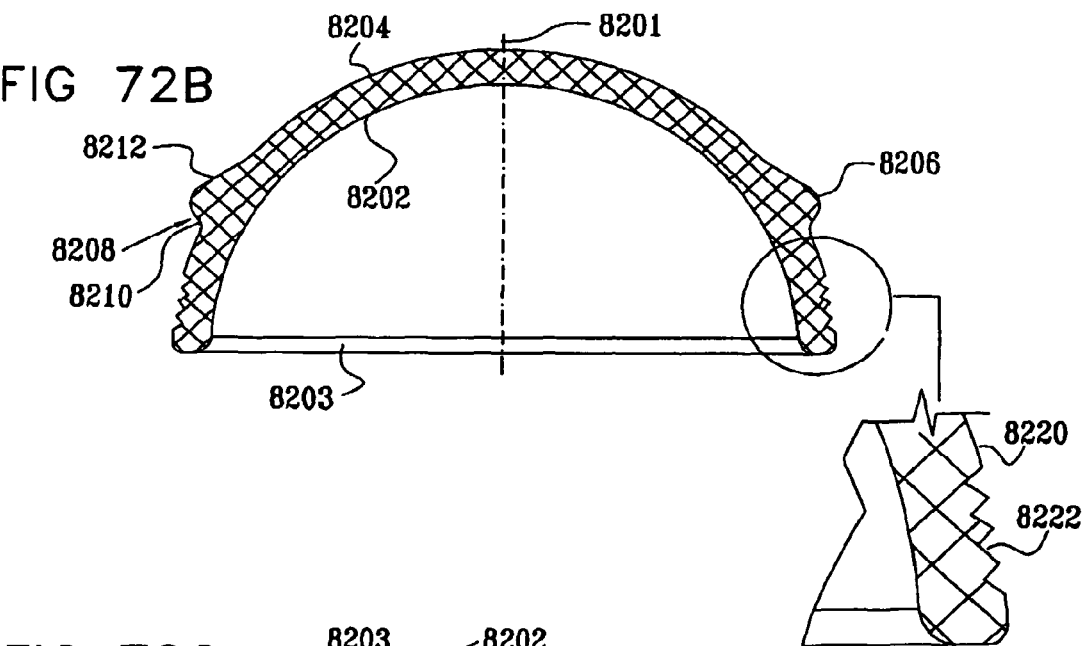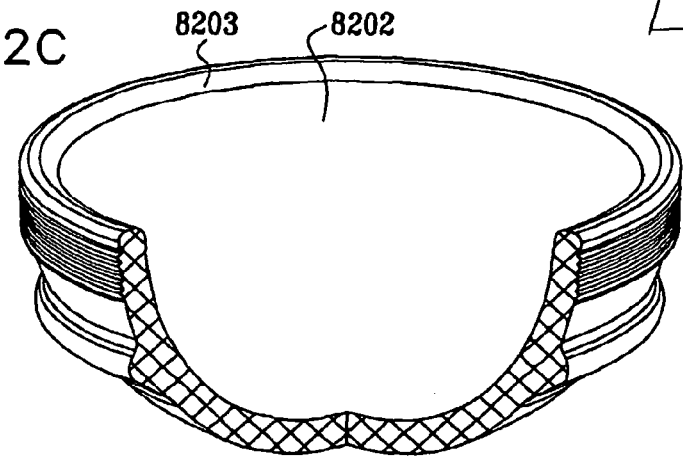

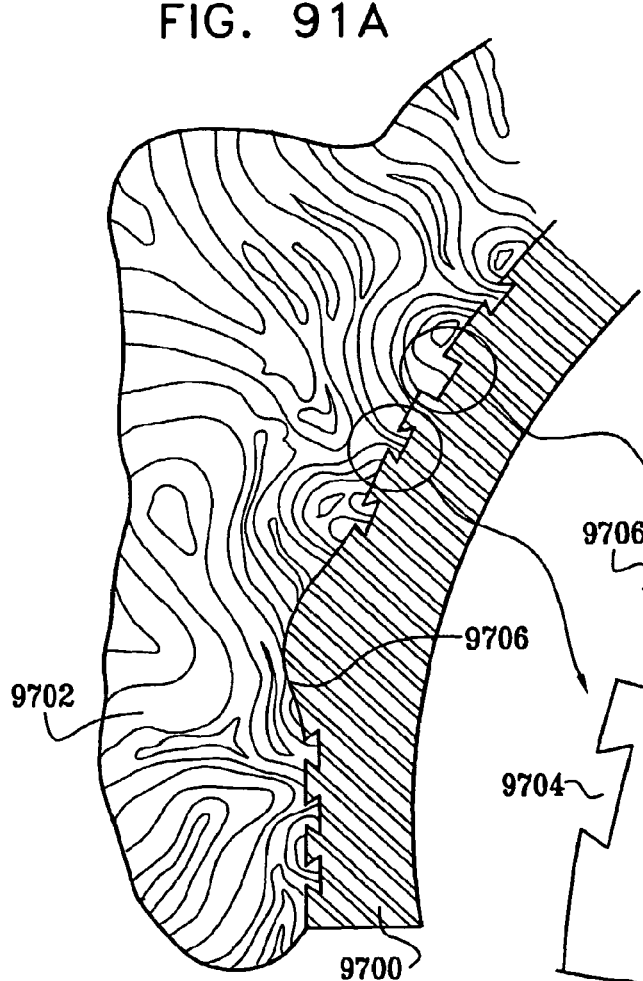
FIG. 91A
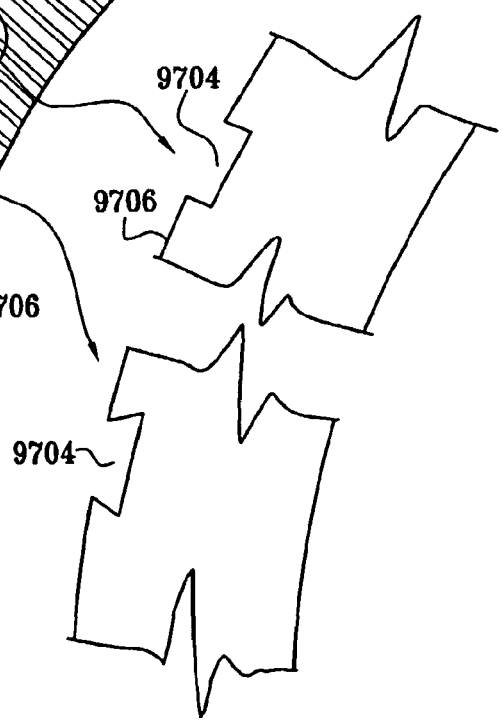
FIG. 91B
FIG. 91C

CUSHION BEARING IMPLANTS FOR LOAD BEARING APPLICATIONS

REFERENCE TO RELATED APPLICATIONS

This application is a continuation of U.S. patent application Ser. No. 10/497,897 filed Nov. 15, 2004, now U.S. Pat. No. 7,572,295, hereby incorporated by reference in its entirety, and titled "CUSHION BEARING IMPLANTS FOR LOAD BEARING APPLICATIONS", which is a 371 international application and claims priority to PCT/IL02/00972 filed Dec. 3, 2002, and is partially based upon and claims priority from U.S. Provisional Patent Application Ser. No. 60/338,349 filed Dec. 4, 2001 and entitled "RESURFACING FEMORAL HEAD"; U.S. Provisional Patent Application Ser. No. 60/351,755 filed Jan. 24, 2002 and entitled "CONFIGURATION-PATTERN, TEXTURE, REINFORCEMENT AND COATING ON PROSTHESIS SURFACE ENGAGING BONE; AND SURFACE TREATMENT OF ARTICULATING SURFACE" and U.S. Provisional Patent Application Ser. No. 60/383,483 filed May 23, 2002 and entitled "JOINT IMPLANTS SYSTEM AND METHODOLOGY AND IMPLANTS AND TOOLS USEFUL THEREWITH".

FIELD OF THE INVENTION

The present invention relates generally to joint implants and methods relating thereto.

BACKGROUND OF THE INVENTION

The following patents are believed to be relevant to the subject matter of this application:

U.S. Pat. Nos. 5,201,881; 5,011,497; 4,279,041; 5,080,675; 4,650,491; 3,938,198; 4,292,695; 4,624,674; 2,765,787; 4,735,625; 5,370,699; 5,641,323; 5,323,765; 5,658,345; 3,875,594; 3,938,198; 4,292,695; 4,344,193; 4,570,270; 4,650,491; 4,279,041; 4,661,112; 4,662,889; 4,664,668; 4,715,859; 4,795,470; 4,795,474; 4,808,186; 4,813,962; 4,822,365; 4,888,020; 4,904,269; 4,908,035; 4,919,674; 4,919,678; 4,936,856; 4,938,771; 4,938,773; 4,950,298; 4,955,912; 4,955,919; 4,963,153; 4,963,154; 4,997,447; 5,002,581; 5,019,107; 5,041,140; 5,049,393; 5,080,677; 5,108,446; 5,108,451; 5,116,374; 5,133,763; 5,146,933; 5,417,406; 5,151,521; 5,156,631; 5,171,276; 5,181,925; 5,197,987; 5,197,989; 5,201,881; 5,201,881; 5,217,498; 5,217,499; 5,222,985; 5,282,868; 5,290,314; 5,314,478; 5,314,494; 5,316,550; 5,326,376; 5,330,534; 5,314,493; 5,336,268; 5,344,459; 5,358,525; 5,370,699; 5,376,064; 5,376,125; 5,387,244; 5,389,107; 5,405,403; 5,405,411; 5,415,662; 5,425,779; 5,448,489; 5,458,643; 5,458,651; 5,480,311; 5,491,882; 5,507,814; 5,507,818; 5,507,820; 5,507,823; 5,507,830; 5,507,833; 5,507,836; 5,514,182; 5,514,184; 5,522,904; 5,507,835; 5,246,461; 5,364,839; 5,376,120; 5,393,739; 5,480,449; 5,510,418; 5,522,894; 4,892,551; 5,660,225; 4,089,071; 5,281,226; 5,443,383; 5,480,437; 5,032,134; 4,997,444; 5,002,579; 5,443,512; 5,133,762; 5,080,678; 5,944,759; 5,944,758; 5,944,757; 5,944,756; 5,938,702; 5,935,174; 5,935,175; 5,935,173; 5,935,172; 5,935,171; 5,931,871; 5,931,870; 5,928,289; 5,928,288; 5,928,287; 5,928,286; 5,928,285; 5,910,236; 5,916,270; 5,916,269; 5,916,268; 5,913,858; 5,911,759; 5,911,758; 5,910,172; 5,910,171; 5,906,644; 5,906,643; 5,906,210; 5,904,720; 5,904,688; 5,902,340; 5,882,206; 5,888,204; 5,879,407; 5,879,405; 5,879,404; 5,879,402; 5,879,401; 5,879,398; 5,879,397; 5,879,396; 5,879,395; 5,879,393; 5,879,392; 5,879,390; 5,879,387; 5,871,548; 5,871,547; 5,824,108; 5,824,107; 5,824,103; 5,824,102; 5,824,101; 5,824,098; 5,800,560; 5,800,558; 5,800,557; 5,800,555; 5,800,554; 5,800,553; 5,788,704; 5,782,928; 5,782,925; 5,776,202; 5,766,260; 5,766,257; 5,755,811; 5,755,810; 5,755,804; 5,755,801; 5,755,799; 5,743,918; 5,910,172; 5,211,666; 5,507,832; 4,433,440; 5,397,359; 5,507,834; 5,314,492; 5,405,394; 5,316,550; 5,314,494; 5,413,610; 5,507,835; 5,373,621; 5,433,750; 3,879,767; 5,376,123; 5,480,437; 3,576,133; 5,376,126; 5,496,375; 3,600,718; 5,108,449; 5,507,817; 5,181,929 and 5,507,829.

Foreign patents DE 2,247,721; EP 0,308,081; GB 2,126,096; GB 2,069,338; EP 0,190,446; EP 0,066,092 and EP 0,253,941.

SUMMARY OF THE INVENTION

The present invention seeks to provide improved joint implants and methods relating to joint implantation.

The present invention seeks to provide improved joint implants and methods relating to joint implantation.

There is thus provided in accordance with a preferred embodiment of the present invention an implantable artificial socket for a joint formed by molding of polyurethane.

There is also provided in accordance with a preferred embodiment of the present invention a unitary implantable artificial socket for a joint formed of a resilient material.

There is further provided in accordance with a preferred embodiment of the present invention an implantable artificial socket for a joint and including a one-piece resilient element which is snap-fit engageable with a bone and which defines a wear resistant articulation surface.

There is also provided in accordance with another preferred embodiment of the present invention a manufacturing method for an implantable artificial socket for a joint including forming the socket by molding of polyurethane.

Further in accordance with a preferred embodiment of the present invention the implantable artificial socket for a joint is generally of uniform thickness.

Typically, the implantable artificial socket is symmetric about an axis of rotation.

Preferably, the implantable artificial socket includes a hemispherical concave inner articulation surface.

Preferably, the hemispherical concave inner articulation surface has a beveled edge.

Still further in accordance with a preferred embodiment of the present invention the implantable artificial socket for a joint includes a generally hemispherical outer bone engagement surface.

Additionally in accordance with a preferred embodiment of the present invention the generally hemispherical outer bone engagement surface has formed thereon, at a location between an apex and a rim thereof, a generally annular outwardly extending protrusion.

Further in accordance with a preferred embodiment of the present invention the generally annular outwardly extending protrusion defines a generally annular undercut.

Typically, the generally annular outwardly extending protrusion is a generally peripheral protrusion.

Further in accordance with a preferred embodiment of the present invention the generally annular outwardly extending protrusion is arranged for snap-fit engagement with a corresponding groove formed by reaming of a bone.

Still further in accordance with a preferred embodiment of the present invention the generally annular outwardly extending protrusion has a cross-sectional configuration, which is characterized in that an underlying surface portion thereof, at an undercut, defines a slope which is sharper than a corresponding slope of an overlying surface portion thereof.

Additionally in accordance with a preferred embodiment of the present invention the generally hemispherical outer bone engagement surface has formed thereon, at a location between an apex and a rim thereof, a generally annular outwardly extending array of discrete protrusions.

Preferably, the generally annular outwardly extending array of discrete protrusions defines a generally annular array of undercuts.

Further in accordance with a preferred embodiment of the present invention the generally annular outwardly extending array of discrete protrusions defines a generally peripheral array of protrusions.

Still further in accordance with a preferred embodiment of the present invention the generally annular outwardly extending array of discrete protrusions is arranged for snap-fit engagement with corresponding grooves formed in a bone.

Preferably, each protrusion within the array of protrusions has a cross-sectional configuration, which is characterized in that an underlying surface portion of the protrusion, at an undercut, defines a slope, which is sharper than a corresponding slope of an overlying surface portion of the protrusion.

Typically, each protrusion within the array of protrusions has a generally button-like configuration, which is symmetric about an axis and includes a body portion and an enlarged head portion.

Additionally or alternatively, protrusion within the array of protrusions is generally characterized in that an underlying surface portion of the protrusion defines a peripheral undercut with respect to the axis.

Further in accordance with a preferred embodiment of the present invention the generally hemispherical outer bone engagement surface has formed thereon, at a location between an apex and a rim thereof, a generally annular inwardly extending recess.

Still further in accordance with a preferred embodiment of the present invention the generally annular inwardly extending recess defines a generally annular undercut.

Typically, the generally annular inwardly extending recess is a generally peripheral recess.

Additionally in accordance with a preferred embodiment of the present invention the generally annular inwardly extending recess is arranged for snap-fit engagement with a corresponding protrusion formed in a bone.

Moreover in accordance with a preferred embodiment of the present invention the generally annular inwardly extending recess has a cross-sectional configuration which is characterized in that an underlying surface portion thereof, at an undercut, defines a slope, which is sharper than a corresponding slope of an overlying surface portion thereof.

Further in accordance with a preferred embodiment of the present invention the generally hemispherical outer bone engagement surface has formed thereon, at a location between an apex and a rim thereof, a generally annular inwardly extending array of discrete recesses.

Still further in accordance with a preferred embodiment of the present invention the generally annular inwardly extending array of discrete recesses defines a generally annular array of undercuts.

Additionally in accordance with a preferred embodiment of the present invention the generally annular inwardly extending array of discrete recesses defines a generally peripheral array of recesses.

Typically, the generally annular inwardly extending array of discrete recesses is arranged for snap-fit engagement with corresponding protrusions formed in a bone.

Further in accordance with a preferred embodiment of the present invention each recess of the array of recesses has a cross-sectional configuration, which is characterized in that an underlying surface portion of the recess, at an undercut, defines a slope which is sharper than a corresponding slope of an overlying surface portion of the recess.

Additionally in accordance with a preferred embodiment of the present invention each recess of the array of recesses has a generally button-like configuration, which is symmetric about an axis and includes a body portion and an enlarged head portion.

Still further in accordance with a preferred embodiment of the present invention each recess of the array of recesses is generally characterized in that an underlying surface portion of the recess defines a peripheral undercut with respect to the axis There is also provided in accordance with a preferred embodiment of the present invention an implantable artificial femoral head resurfacing element for a joint formed by molding of polyurethane.

There is further provided in accordance with yet another preferred embodiment of the present invention a manufacturing method for an implantable artificial humeral head resurfacing element for a joint. The method includes forming the resurfacing element by molding of polyurethane.

Further in accordance with a preferred embodiment of the present invention the implantable artificial femoral head resurfacing element for a joint is generally of uniform thickness other than at its apex, which is thickened.

Typically, the implantable artificial femoral head resurfacing element for a joint is symmetric about an axis of rotation.

Still further in accordance with a preferred embodiment of the present invention the implantable artificial femoral head resurfacing element for a joint includes a hemispherical outer articulation surface.

Typically, the hemispherical outer articulation surface has a beveled edge.

Further in accordance with a preferred embodiment of the present invention the implantable artificial femoral head resurfacing element for a joint includes a generally hemispherical inner bone engagement surface.

Typically, the generally hemispherical inner bone engagement surface has limited thereon, at a location between an apex and a rim thereof, a generally annular inwardly extending protrusion.

Further in accordance with a preferred embodiment of the present invention the generally annular inwardly extending protrusion defines a generally annular undercut.

Still further in accordance with a preferred embodiment of the present invention the generally annular inwardly extending protrusion is a generally peripheral protrusion.

Additionally in accordance with a preferred embodiment of the present invention the generally annular inwardly extending protrusion is arranged for snap-fit engagement with a corresponding groove formed by reaming of a bone.

Typically, the generally annular inwardly extending protrusion has a cross-sectional configuration, which is characterized in that an underlying surface portion thereof at an undercut defines a slope, which is sharper than a corresponding slope of an overlying surface portion thereof.

Further in accordance with a preferred embodiment of the present invention the generally hemispherical inner bone engagement surface has formed thereon, at a location between an apex and a rim thereof, a generally annular inwardly extending array of discrete protrusions.

Additionally in accordance with a preferred embodiment of the present invention the generally annular inwardly extending array of discrete protrusions defines a generally annular array of undercuts.

Additionally or alternatively, the generally annular inwardly extending array of discrete protrusions defines a generally peripheral array of protrusions.

Typically, the generally annular inwardly extending array of discrete protrusions is arranged for snap-fit engagement with corresponding grooves formed in a bone.

Further in accordance with a preferred embodiment of the present invention each protrusion within the array of protrusions has a cross-sectional configuration, which is characterized in that an underlying surface portion of the protrusion, at an undercut, defines a slope which is sharper than a corresponding slope of an overlying surface portion of the protrusion.

Typically, each protrusion within the array of protrusions has a generally button-like configuration, which is symmetric about an axis and includes a body portion and an enlarged head portion.

Typically, each protrusion within the array of protrusions is generally characterized in that an underlying surface portion of the protrusion defines a peripheral undercut with respect to the axis.

Further in accordance with a preferred embodiment of the present invention the generally hemispherical inner bone engagement surface has formed thereon, at a location between an apex and a rim thereof, a generally annular outwardly extending recess.

Still further in accordance with a preferred embodiment of the present invention the generally annular outwardly extending recess defines a generally annular undercut.

Typically, the generally annular outwardly extending recess is a generally peripheral recess.

Additionally in accordance with a preferred embodiment of the present invention the generally annular outwardly extending recess is arranged for snap-fit engagement with a corresponding protrusion formed in a bone.

Further in accordance with a preferred embodiment of the present invention the generally annular outwardly extending recess has a cross-sectional configuration, which is characterized in that an underlying surface portion thereof at an undercut defines a slope, which is sharper than a corresponding slope of an overlying surface portion thereof.

Still further in accordance with a preferred embodiment of the present invention the generally hemispherical inner bone engagement surface has formed thereon, at a location between an apex and a rim thereof, a generally annular outwardly extending array or discrete recesses.

Typically, the generally annular outwardly extending array of discrete recesses defines a generally annular array of undercuts.

Additionally or alternatively, the generally outwardly extending array of discrete recesses defines a generally peripheral array of recesses.

Further in accordance with a preferred embodiment of the present invention the generally annular outwardly extending array of discrete recesses is arranged for snap-fit engagement with corresponding protrusions formed in a bone.

Still further in accordance with a preferred embodiment of the present invention each recess in the array of recesses has a cross-sectional configuration, which is characterized in that an underlying surface portion of the recess, at an undercut, defines a slope which is sharper than a corresponding slope of an overlying surface portion of the recess.

Typically, each recess within the array of recesses has a generally button-like configuration, which is symmetric about an axis and includes a body portion and an enlarged head portion.

Preferably, each recess within the array of recesses is generally characterized in that an underlying surface portion of the recess defines a peripheral undercut with respect to the axis.

Further in accordance with a preferred embodiment of the present invention the implantable artificial socket is typically snap-fitted into a suitably machined natural acetabulum of a patient and having an artificial femoral head mounted into a conventional femoral stem and arranged for articulation with an articulation surface of the socket.

Still further in accordance with a preferred embodiment of the present invention the implantable artificial socket is typically snap-fitted into a suitably machined natural acetabulum of a patient and having a natural femoral head arranged for articulation with an articulation surface of the socket.

Additionally in accordance with a preferred embodiment of the present invention the size and configuration of an articulation surface of the socket is identical to that of the natural acetabulum socket of the patient, in order that a natural femoral head may articulate therewith with desired dimensional clearances and without requiring machining of the femoral head.

Further in accordance with a preferred embodiment of the present invention the implantable artificial socket is typically snap-fitted into a suitably machined natural acetabulum of a patient and having a natural femoral head having an implantable artificial femoral head resurfacing element and is preferably snap-fit mounted thereon arranged for articulation of an articulation surface thereof with an articulation surface of the socket.

Typically, the implantable artificial femoral head resurfacing element is snap-fit mounted onto a natural femoral head and arranged for articulation of an articulation surface thereof with a natural articulation surface of a natural acetabulum.

Further in accordance with a preferred embodiment of the present invention the implantable artificial femoral head resurfacing element is snap-fit mounted onto a natural femoral head and arranged for articulation of an articulation surface thereof with a natural acetabulum socket of a patient, wherein the size and configuration of an articulation surface of the artificial femoral head resurfacing element is identical to that of the natural acetabulum socket of the patient, in order that the natural femoral head onto which artificial femoral head resurfacing element is mounted may articulate therewith with desired dimensional clearances and without requiring machining of the natural acetabulum.

Preferably, the implantable artificial socket for a joint includes a spherical concave inner articulation surface.

Typically, the spherical concave inner articulation surface has a beveled edge.

Further in accordance with a preferred embodiment of the present invention the implantable artificial socket for a joint includes an outer bone engagement surface Preferably, the outer bone engagement surface has multiple protrusions formed thereon.

Further in accordance with a preferred embodiment of the present invention the multiple protrusions include inner and outer protrusions.

Preferably, the multiple protrusions include undercuts.

Still further in accordance with a preferred embodiment of the present invention the multiple protrusions are arranged for snap-fit engagement with a corresponding groove formed in a bone.

Additionally in accordance with a preferred embodiment of the present invention the multiple protrusions include a cross-sectional configuration which is characterized in that an underlying surface portion thereof at an undercut defines a slope, which is sharper than a corresponding slope of an overlying surface portion thereof.

Typically, the multiple protrusions include an array of outwardly extending discrete protrusions.

Further in accordance with a preferred embodiment of the present invention the array of discrete protrusions defines an array of undercuts.

Typically, the array of discrete protrusions includes a generally peripheral array of protrusions.

Still further in accordance with a preferred embodiment of the present invention the array of discrete protrusions is arranged for snap-fit engagement with corresponding grooves formed in a bone.

Additionally in accordance with a preferred embodiment of the present invention each protrusion within the array of protrusions has a cross-sectional configuration, which is characterized in that an underlying surface portion of the protrusion, at an undercut, defines a slope which is sharper than a corresponding slope of an overlying surface portion of the protrusion.

Typically, each protrusion within the array of protrusions has a generally button-like configuration, which is symmetric about an axis and includes a body portion and an enlarged head portion.

Further in accordance with a preferred embodiment of the present invention the protrusion within the array of protrusions is generally characterized in that an underlying surface portion of the protrusion defines a peripheral undercut with respect to the axis.

Still further in accordance with a preferred embodiment of the present invention the outer bone engagement surface has multiple recesses formed thereon.

Typically, the multiple recesses include undercuts.

Further in accordance with a preferred embodiment of the present invention the multiple recesses include an inner recess and outer protrusions.

Typically, the multiple recesses are arranged for snap-fit engagement with corresponding protrusions formed in a bone.

Further in accordance with a preferred embodiment of the present invention the multiple recesses has a cross-sectional configuration which is characterized in that an underlying surface portion thereof at an undercut defines a slope which is sharper than a corresponding slope of an overlying surface portion thereof.

Additionally in accordance with a preferred embodiment of the present invention the outer bone engagement surface has formed thereon an inwardly extending array of discrete recesses.

Typically, the array of discrete recesses includes an array of undercuts.

Further in accordance with a preferred embodiment of the present invention the array of discrete recesses includes a generally peripheral array of recesses.

Still further in accordance with a preferred embodiment of the present invention the array of discrete recesses is arranged for snap-fit engagement with corresponding protrusions formed in a bone.

Additionally in accordance with a preferred embodiment of the present invention each recess within the array of recesses has a cross-sectional configuration which is characterized in that an underlying surface portion of each recess, at an undercut, defines a slope which is sharper than a corresponding slope of an overlying surface portion of the recess.

Typically, each recess within the array of recesses has a generally button-like configuration, which is symmetric about an axis and includes a body portion and an enlarged head portion.

Further in accordance with a preferred embodiment of the present invention each recess within the array of recesses is generally characterized in that an underlying surface portion of the recess defines a peripheral undercut with respect to the axis.

There is further provided in accordance with a preferred embodiment of the present invention an implantable artificial humeral head resurfacing element for a joint formed by molding of polyurethane.

There is further provided in accordance with yet another preferred embodiment of the present invention a manufacturing method for an implantable artificial femoral head resurfacing element for a joint. The method includes forming the resurfacing element by molding of polyurethane.

Further in accordance with a preferred embodiment of the present invention the implantable artificial humeral head resurfacing element for a joint is generally of uniform thickness other than at its apex, which is thickened.

Still further in accordance with a preferred embodiment of the present invention the implantable artificial humeral head resurfacing element for a joint is symmetric about an axis of rotation.

Additionally in accordance with a preferred embodiment of the present invention the implantable artificial humeral head resurfacing element for a joint includes a convex spherical outer articulation surface.

Typically, the convex spherical outer articulation surface has a beveled edge.

Further in accordance with a preferred embodiment of the present invention the implantable artificial humeral head resurfacing element for a joint includes a generally convex spherical inner bone engagement surface.

Typically, the generally convex spherical inner bone engagement surface has formed thereon, at a location between an apex and a rim thereof, a generally annular inwardly extending protrusion.

Additionally in accordance with a preferred embodiment of the present invention the generally annular inwardly extending protrusion defines a generally annular undercut.

Preferably, the generally annular inwardly extending protrusion is a generally peripheral protrusion.

Further in accordance with a preferred embodiment of the present invention the generally annular inwardly extending protrusion is arranged for snap-fit engagement with a corresponding groove formed by reaming of a bone.

Further in accordance with a preferred embodiment of the present invention the generally annular inwardly extending protrusion has a cross-sectional configuration, which is characterized in that an underlying surface portion thereof at an undercut defines a slope, which is sharper than a corresponding slope of an overlying surface portion thereof.

Further in accordance with a preferred embodiment of the present invention the generally convex spherical inner bone engagement surface has formed thereon, at a location between an apex and a rim thereof, a generally annular inwardly extending array of discrete protrusions.

Preferably, the generally annular inwardly extending array of discrete protrusions defines a generally annular array of undercuts.

Additionally or alternatively, the generally annular inwardly extending array of discrete protrusions includes a generally peripheral array of protrusions.

Still further in accordance with a preferred embodiment of the present invention the generally annular inwardly extending array of discrete protrusions is arranged for snap-fit engagement with corresponding grooves formed in a bone.

Further in accordance with a preferred embodiment of the present invention each protrusion within the array of protrusions has a cross-sectional configuration, which is characterized in that an underlying surface portion of the protrusion, at an undercut, defines a slope which is sharper than a corresponding slope or an overlying surface portion of the protrusion.

Typically, each protrusion within the array of protrusions has a generally button-like configuration, which is symmetric about an axis and includes a body portion and an enlarged head portion.

Still further in accordance with a preferred embodiment of the present invention each protrusion within the array of protrusions is generally characterized in that an underlying surface portion of the protrusion defines a peripheral undercut with respect to the axis.

Additionally in accordance with a preferred embodiment of the present invention the generally convex spherical inner bone engagement surface includes thereon, at a location between an apex and a rim thereof, a generally annular outwardly extending recess.

Further in accordance with a preferred embodiment of the present invention the generally annular outwardly extending recess defines a generally annular undercut.

Typically, the generally annular outwardly extending recess is a generally peripheral recess.

Further in accordance with a preferred embodiment of the present invention the generally annular outwardly extending recess is arranged for snap-fit engagement with a corresponding protrusion formed in a bone.

Still further in accordance with a preferred embodiment of the present invention the generally annular outwardly extending recess has a cross-sectional configuration, which is characterized in that an underlying surface portion thereof at an undercut defines a slope, which is sharper than a corresponding slope of an overlying surface portion thereof.

Further in accordance with a preferred embodiment of the present invention the generally convex spherical inner bone engagement surface has formed thereon, at a location between an apex and a rim thereof, a generally annular outwardly extending array or discrete recesses.

Preferably, the generally annular outwardly extending array of discrete recesses defines a generally annular array of undercuts.

Typically, the generally annular outwardly extending array of discrete recesses defines a generally peripheral array of recesses.

Additionally in accordance with a preferred embodiment of the present invention the generally annular outwardly extending array of discrete recesses is arranged for snap-fit engagement with corresponding protrusions formed in a bone.

Typically, each recess within the array of recesses has a cross-sectional configuration, which is characterized in that an underlying surface portion of each recess, at an undercut, defines a slope, which is sharper than a corresponding slope of an overlying surface portion of the recess.

Further in accordance with a preferred embodiment of the present invention each recess within the array of recesses has a generally button-like configuration, which is symmetric about an axis and includes a body portion and an enlarged head portion.

Still further in accordance with a preferred embodiment of the present invention each recess within the array of recesses is generally characterized in that an underlying surface portion of each recess defines a peripheral undercut with respect to the axis.

Additionally in accordance with a preferred embodiment of the present invention the implantable artificial socket according is snap-fitted into a suitably machined natural glenoid of a patient and having an artificial humeral head mounted onto a conventional humeral stem and arranged for articulation with an articulation surface of the socket.

Still further in accordance with a preferred embodiment of the present invention the implantable artificial socket is snap-fitted into a suitably machined natural glenoid of a patient and having a natural humeral head arranged for articulation with an articulation surface of the socket.

Typically, the size and configuration of an articulation surface of the socket is identical to that of the natural glenoid socket of the patient, in order that a natural humeral head may articulate therewith with desired dimensional clearances and without requiring machining of the humeral head.

Additionally in accordance with a preferred embodiment of the present invention the implantable artificial socket is snap-fitted into a suitably machined natural glenoid of a patient and having a natural humeral head having an implantable artificial humeral head resurfacing element and is typically snap-fit mounted thereon arranged for articulation of an articulation surface thereof with an articulation surface of the socket.

Further in accordance with a preferred embodiment of the present invention the implantable artificial humeral head resurfacing element is snap-fit mounted onto a natural humeral head and arranged for articulation of an articulation surface thereof with a natural articulation surface of a natural glenoid.

Still further in accordance with a preferred embodiment of the present invention the implantable artificial humeral head resurfacing element is snap-fit mounted onto a natural humeral head and arranged for articulation of an articulation surface thereof with a natural glenoid socket of a patient, wherein the size and configuration of an articulation surface of the artificial humeral head resurfacing element is identical to that of the natural glenoid socket of the patient, in order that the natural humeral head onto which artificial humeral head resurfacing element is mounted may articulate therewith with desired dimensional clearances and without requiring machining of the natural glenoid.

Preferably, the articulation portion is formed with a highly resilient hollow peripheral rim arranged for snap-fit engagement with a corresponding peripheral socket formed in a surface of the bone engagement portion, opposite to the bone engagement surface.

Additionally in accordance with a preferred embodiment of the present invention the articulation portion is formed with a support protrusion, defining an undercut and arranged for resilient snap-fit locking engagement with a corresponding groove formed in the bone engagement portion.

Further in accordance with a preferred embodiment of the present invention the articulation surface has formed therein a plurality of throughgoing apertures and side openings, which allow synovial fluid to pass therethrough for lubrication of the articulation surface.

Still further in accordance with a preferred embodiment of the present invention the implantable artificial socket for a joint is mounted onto a tibia and arranged such that application of force to the joint causes the articulation portion to be resiliently displaced toward the bone engagement portion, thus causing synovial fluid, located between the articulation portion and the bone engagement portion, to be forced through apertures and openings so as to lie on and over the articulation surface and to provide enhanced lubrication for the articulation of an articulation surface of a femur with the articulation surface.

Typically, the application of force causes the movement of the articulation portion by resilient buckling of at least one protrusion and compression of a resilient rim and release of the force causes movement of articulation portion, accompanied by resilient return of the protrusion to its unstressed orientation and decompression of the resilient rim, wherein the application of force does not cause significant deformation of the geometry of the articulation surface.

There is also provided in accordance with another preferred embodiment of the present invention a method for implanting an implantable artificial socket. The method for implanting an implantable artificial socket includes providing an implantable artificial socket, suitably machining a natural acetabulum of a patient to fit the implantable artificial socket, snap-fitting the implantable artificial socket onto the natural acetabulum, mounting an artificial femoral head onto a conventional femoral stem and arranging the femoral head for articulation with an articulation surface of the implantable artificial socket.

There is further provided in accordance with yet another preferred embodiment of the present invention a method for implanting an implantable artificial socket. The method includes providing an implantable artificial socket, suitably machining a natural acetabulum of a patient to fit the implantable artificial socket, snap-fitting the implantable artificial socket onto the natural acetabulum and arranging a natural femoral head for articulation with an articulation surface of the implantable artificial socket.

Further in accordance with a preferred embodiment of the present invention the method for implanting an implantable artificial socket also includes matching the size and configuration of an articulation surface of the socket to that of the natural acetabulum socket of the patient and arranging a natural femoral head for articulation therewith, the matching providing desired dimensional clearances without requiring machining of the femoral head.

There is provided in accordance with still a further embodiment of the present invention a method for implanting an implantable artificial socket. The method includes providing an implantable artificial socket, suitably machining a natural acetabulum of a patient to fit the implantable artificial socket, snap-fitting the implantable artificial socket onto the natural acetabulum, snap-fit mounting an implantable artificial femoral head resurfacing element onto a natural femoral head and arranging an articulation surface of the femoral head for articulation with an articulation surface of the implantable artificial socket.

There is also provided in accordance with another preferred embodiment of the present invention a method for implanting an implantable artificial femoral head resurfacing element. The method includes providing an implantable artificial femoral head resurfacing element, snap-fit mounting the artificial femoral head resurfacing element onto a natural femoral head and arranging an articulation surface of the artificial femoral head resurfacing element for articulation with a natural articulation surface of a natural acetabulum.

Still further in accordance with a preferred embodiment of the present invention the method also includes matching the size and configuration of an articulation surface of the artificial femoral head resurfacing element to that of the natural acetabulum socket of the patient, the matching providing for the natural femoral head unto which the artificial femoral head resurfacing element is mounted to articulate with the natural acetabulum socket with desired dimensional clearances without requiring machining of the natural acetabulum.

There is also provided in accordance with a preferred embodiment of the present invention a method for implanting an implantable artificial socket, which includes providing an implantable artificial socket, suitably machining a natural glenoid of a patient to fit the implantable artificial socket, snap-fitting the implantable artificial socket into the natural glenoid, mounting an artificial humeral head onto a conventional humeral stem and arranging the humeral head for articulation with an articulation surface of the implantable artificial socket.

There is further provided in accordance with another preferred embodiment of the present invention a method for implanting an implantable artificial socket, which includes providing an implantable artificial socket, suitably machining a natural glenoid of a patient to fit the implantable artificial socket, snap-fitting the implantable artificial socket into the natural glenoid and arranging a natural humeral head for articulation with an articulation surface of the implantable artificial socket Further in accordance with a preferred embodiment of the present invention the method for implanting an implantable artificial socket also includes matching the size and configuration of an articulation surface of the socket to that of the natural glenoid socket of the patient and arranging a natural humeral head for articulation therewith, the matching providing desired dimensional clearances without requiring machining of the humeral head.

There is also provided in accordance with a further preferred embodiment of the present invention a method for implanting an implantable artificial socket The method includes providing an implantable artificial socket, suitably machining a natural glenoid of a patient to fit the implantable artificial socket, snap-fitting the implantable artificial socket onto the natural glenoid, snap-fit mounting an implantable artificial humeral head resurfacing element onto a natural humeral head and arranging an articulation surface of the humeral head for articulation with an articulation surface of the implantable artificial socket.

There is further provided in accordance with yet another preferred embodiment of the present invention a method for implanting an implantable artificial humeral head resurfacing element. The method includes providing an implantable artificial humeral head resurfacing element, snap-fit mounting the artificial humeral head resurfacing element onto a natural humeral head and arranging an articulation surface of the artificial humeral head resurfacing element for articulation with a natural articulation surface of a natural glenoid.

Further in accordance with a preferred embodiment of the present invention the method for implanting an implantable artificial humeral head resurfacing element also includes matching the size and configuration of an articulation surface of the artificial humeral head resurfacing element to that of the natural glenoid socket of the patient, the matching providing for the natural humeral head onto which the artificial humeral head resurfacing element is mounted to articulate with the natural glenoid socket with desired dimensional clearances without requiring machining of the natural glenoid.

Further in accordance with a preferred embodiment of the present invention the implantable artificial femoral resurfacing element for a joint defines an articulation portion having a convex outer articulation surface and a bone engagement portion having a bone engagement surface.

Still further in accordance with a preferred embodiment of the present invention the articulation portion of the artificial socket for a joint is formed with a highly resilient hollow peripheral rim arranged for snap-fit engagement with a corresponding peripheral femoral resurfacing element formed in a surface of the bone engagement portion, opposite to the bone engagement surface.

Additionally in accordance with a preferred embodiment of the present invention the articulation portion is formed with a support protrusion, defining an undercut and arranged for resilient snap-fit locking engagement with a corresponding groove formed in the bone engagement portion.

Typically, the articulation surface has formed therein a plurality of thoroughgoing apertures and side openings, which allow synovial fluid to pass therethrough for lubrication of the articulation surface.

Further in accordance with a preferred embodiment of the present invention the implantable artificial femoral resurfacing element for a joint is mounted onto a femur and arranged such that application of force to the joint causes the articulation portion to be resiliently displaced toward the bone engagement portion, thus causing synovial fluid, located between the articulation portion and the bone engagement portion to be forced through apertures and openings so as to lie on and over the articulation surface and to provide enhanced lubrication for the articulation of an articulation surface of a femur with the articulation surface.

Typically, the application of force causes the movement of the articulation portion by resilient buckling of at least one protrusion and compression of a resilient rim and release of the force causes movement of articulation portion, accompanied by resilient return of the protrusion to its unstressed orientation and decompression of the resilient rim, wherein the application of force does not cause significant deformation of the geometry of the articulation surface.

Further in accordance with a preferred embodiment of the present invention the implantable artificial socket is in articulation engagement with an implantable artificial femoral resurfacing element.

There is further provided in accordance with a preferred embodiment of the present invention a groove reaming tool including a shaft, a handle, fixedly coupled to the shaft, an outwardly extendible recess engagement element, which is also rotatably and slidably mounted with respect to the shaft and an elongate grip, rotatably and slidably mounted over the shaft and axially engaging the outwardly extendible recess engagement element.

Further in accordance with a preferred embodiment of the present invention the outwardly extendible recess engagement element is an integrally formed element and includes a generally hollow cylindrical portion formed with a plurality of axially extending slots, which extend from a location spaced from a top edge of the cylindrical portion towards and through a generally radially outwardly extending disk-like portion.

Still further in accordance with a preferred embodiment of the present invention the disk-like portion includes a plurality of azimuthally separated segments, each of which defines a continuation of a corresponding azimuthally separated segment of the cylindrical portion.

Preferably, the disk-like portion has an outer edge which is formed with a high friction engagement surface.

Further in accordance with a preferred embodiment of the present invention the disk-like portion is formed with a central generally conical recess on an underside surface thereof.

Preferably, the groove reaming tool also includes a generally solid, centrally apertured conical element, rotatably mounted onto the shaft such that a conical surface thereof is adapted to operative engage the conical recess in a manner that such engagement produces radially outward displacement of the segments of the disk-like portion.

Further in accordance with a preferred embodiment of the present invention the groove reaming tool further includes a retainer element which is rotatably mounted with respect to the shaft and overlies the disk-like portion.

Additionally in accordance with a preferred embodiment of the present invention the retainer element includes depending plates which engage interstices between the segments.

Further in accordance with a preferred embodiment of the present invention the groove reaming tool also includes a groove cutter assembly.

Preferably, the groove cutter assembly includes a groove cutter mounting element. Fixedly mounted to the shaft for rotation together therewith in response to rotation of the handle.

Further in accordance with a preferred embodiment of the present invention the groove cutter mounting element underlies conical element and is separated therefrom by a washer, in order to enable the groove cutter mounting element to easily rotate with respect to the conical element.

Still further in accordance with a preferred embodiment of the present invention the groove reaming tool further includes an end element, rotatably mounted onto an end of the shaft, underlying the groove cutter mounting element such that the groove cutter mounting element is rotatable with respect thereto.

Typically, the end element is formed with a high friction engagement surface on the underside thereof.

Further in accordance with a preferred embodiment of the present invention the groove cutter mounting element is a generally hollow hemispherical element having a central hub which defines a non-circular thoroughgoing aperture for receiving an end of the shaft, a radially inward extending recess is formed in an outer facing wall of the hub and a corresponding generally elongate aperture is formed in a wall of the groove cutter mounting element opposite the recess and extends azimuthally beyond the recess.

Additionally in accordance with a preferred embodiment of the present invention the groove reaming tool also includes a plurality of cutter elements, removably retained in the groove cutter mounting element.

Preferably, the cutter elements have similar configurations and have at least one differing dimension.

Further in accordance with a preferred embodiment of the present invention each cutter element is formed of a flat piece of metal and includes a hook portion, defining an undercut, a central portion and a cutting portion, which defines a curved cutting edge.

Preferably, the cutting portion defines, inwardly of the curved cutting edge, an aperture having a beveled peripheral edge.

Further in accordance with a preferred embodiment of the present invention the cutter elements are arranged such that their hook portions engage the recess and the cutting portions extend outwardly through the aperture.

Still further in accordance with a preferred embodiment of the present invention the cutter elements are arranged to provide a stepped increase in the extent that the cutting portions extend outwardly, in the direction of operational rotation of the tool Additionally in accordance with a preferred embodiment of the present invention the tool has first and second operative orientations, the first operative orientation being a non-engagement orientation, when the grip is not pushed along the shall towards the groove cutter mounting element and the outwardly extendible recess engagement element is not subject to axial force and thus no axial force is applied between the recess on the underside surface thereof and the conical element.

Preferably, in the second operative orientation is bone recess engagement orientation wherein the grip is pushed along the shaft towards the groove cutter mounting element and engages the outwardly extendible recess engagement element, forcing the recess on the underside surface thereof axially against the conical element and causing radially outward displacement of the segments of the disk-like portion.

Further in accordance with a preferred embodiment of the present invention a method of groove reaming of an acetabulum including engaging a groove reaming tool with an acetabulum which has been at least partially spherically reamed by aligning the cutting portions of the cutting elements with an acetabulum notch and arranging the shaft along an axis which is approximately coaxial with an axis of symmetry of the at least partially spherically reamed acetabulum.

Still further in accordance with a preferred embodiment of the present invention the method also includes applying an axial force on the handle, thereby causing the high friction engagement surface of the end element to frictionally engage the at least partially spherically reamed acetabulum.

Additionally in accordance with a preferred embodiment of the present invention the method further includes applying an axial force on the grip, causing the grip to engage the outwardly extendible recess engagement element and to force the recess on the underside surface thereof axially against the conical element, thereby causing radially outward displacement of the segments into frictional engagement with the at least partially spherically reamed acetabulum.

Further in accordance with a preferred embodiment of the present invention the method also includes rotating the handle through an approximately 180 degree rotation thereby producing corresponding rotation of the groove cutter mounting element and the cutter elements and thereby producing an approximately 180 degree groove in the at least partially spherically reamed acetabulum.

Additionally in accordance with a preferred embodiment of the present invention the method includes rotating the handle through a further approximately 180 degree rotation thereby producing corresponding rotation of the groove cutter mounting element and the cutter elements and thereby producing an approximately 180 degree groove in the at least partially spherically reamed acetabulum.

There is further provided in accordance with a preferred embodiment of the present invention a method for implanting an artificial acetabulum socket in a hip joint, which includes at least partially reaming of a natural acetabulum to provide a snap-fit configured natural acetabulum and resiliently bending an artificial acetabulum socket, so as to provide a bent acetabulum socket having a reduced minimum cross-sectional area, inserting the bent acetabulum socket having a reduced minimum cross-sectional area into the vicinity of the hip joint by a minimally invasive surgical technique and snap fitting the artificial acetabulum socket in the snap-fit configured natural acetabulum.

There is also provided in accordance with a preferred embodiment of the present invention a method for implanting an artificial acetabulum socket in a hip joint. The method includes at least partially reaming of a natural acetabulum to provide a snap-fit configured natural acetabulum and inserting a unitary resilient acetabulum socket into the vicinity of the hip joint and snap fitting the artificial acetabulum socket in the snap-fit configured natural acetabulum.

Further in accordance with a preferred embodiment of the present invention the snap-fit configured natural acetabulum includes a generally spherical portion and a generally cylindrical portion.

Still further in accordance with a preferred embodiment of the present invention the snap-fit configured natural acetabulum defines a recessed rim.

Additionally in accordance with a preferred embodiment of the present invention the snap-fit configured natural acetabulum is naturally formed with a recess which extends deeper than the remainder of the generally spherical surface.

Preferably, the snap fitting the artificial acetabulum socket in the snap-fit configured natural acetabulum includes gently positioning the artificial acetabulum socket into a position for snap-fit engagement with the reamed acetabulum.

Further in accordance with a preferred embodiment of the present invention that during the gently positioning an outwardly extending protrusion of the artificial acetabulum socket lies in touching, generally non-compressive engagement with an annular portion of a generally spherical inner concave machined surface the acetabulum, the annular portion lying above a groove, formed in the generally spherical inner concave surface, which is designed to receive the protrusion.

Still further in accordance with a preferred embodiment of the present invention that during the gently positioning the engagement of the protrusion with the annular portion causes the implantable artificial acetabulum socket to rest at a position wherein an outer edge thereof lies above a corresponding outer edge of the acetabulum.

Further in accordance with a preferred embodiment of the present invention that during the gently positioning, substantially no stress is applied to the implantable artificial acetabulum socket and to the acetabulum by the engagement thereof.

Additionally in accordance with a preferred embodiment of the present invention the method also includes, following the gently positioning, gently engaging the artificial acetabulum socket at locations on an inner concave surface thereof and pressing thereon in a direction generally along an axis of symmetry of the snap-fit configured natural acetabulum, thereby causing displacement of the artificial acetabulum socket, which produces radially inward compression of the artificial acetabulum socket at the protrusion and thereby resulting in deformation of the artificial acetabulum socket at the protrusion and in the general region thereof.

Further in accordance with a preferred embodiment of the present invent ion the radially inward compression and the resulting deformation of the artificial acetabulum socket produce stresses in the acetabulum socket and causes forces to be applied to the acetabulum, producing compression stresses and strains therein.

Additionally in accordance with a preferred embodiment of the present invention the displacement of the artificial acetabulum socket reduces the separation between the planes of the outer edge of the implantable artificial acetabulum socket and the outer edge of the acetabulum.

Still further in accordance with a preferred embodiment of the present invention the method includes, following the gently engaging, pressing further on the artificial acetabulum socket at locations on an inner concave surface thereof, thereby causing further displacement of the artificial acetabulum socket producing sliding pressure engagement between an underlying surface portion of the protrusion at the undercut and a radially outward extending surface portion of the groove, wherein resiliency of the artificial acetabulum socket causes radially outward displacement of the protrusion and corresponding radially outward decompression of the artificial acetabulum socket, resulting in reduced and changed stress patterns in both the artificial acetabulum socket and in the acetabulum.

Further in accordance with a preferred embodiment of the present invention the displacement of the artificial acetabulum socket further reduces the separation between the planes of the outer edge of the implantable artificial acetabulum socket and the outer edge of the acetabulum.

Further in accordance with a preferred embodiment of the present invention the method further includes, following the pressing further, pressing on the artificial acetabulum socket at locations on edges thereof, thereby causing further displacement of the artificial acetabulum socket and producing sliding snap-fit engagement between the protrusion and the groove, wherein the resiliency of the artificial acetabulum socket causes radially outward displacement of the protrusion, thereby generally eliminating deformation of the artificial acetabulum socket at the protrusion and in the general region thereof.

Preferably, the snap fitting provides a generally non-press fit engagement, wherein touching engagement between the artificial acetabulum socket and the acetabulum produces stresses in both the acetabulum socket and in the acetabulum which are generally small and localized in the region of the snap fit engagement therebetween.

Further in accordance with a preferred embodiment of the present invention the snap fitting produces locking of the artificial acetabulum socket in the groove and the undercut prevents disengagement of the protrusion from the groove.

Additionally in accordance with a preferred embodiment of the present invention the snap fitting provides a generally press fit engagement, wherein touching engagement between the artificial acetabulum socket and the acetabulum produces stresses in both the acetabulum socket and in the acetabulum which are not localized in the region of the snap fit engagement therebetween.

Further in accordance with a preferred embodiment of the present invention the snap fitting in a generally press fit engagement produces pressure engagement between the acetabulum and a convex facing surface of the artificial acetabulum socket generally along the entire extent thereof.

There is also provided in accordance with a preferred embodiment of the present invention an artificial femoral head prosthesis for use with a natural femoral head and including a flexible bone interface element including a unitary element molded of a single material and having an inner concave surface which is configured to directly contact the natural femoral head in generally static engagement therewith and a smooth outer convex surface which is configured to be directly contacted by an acetabulum socket in moveable engagement therewith, the flexible bone interface element being formed of material which is more flexible than bone material of the natural femoral head.

There is also provided in accordance with a preferred embodiment of the present invention an artificial femoral head prosthesis for use with a natural femoral head and including a flexible bone interface element configured to be mounted onto the natural femoral head, the flexible bone interface element including a unitary element molded of a single material and having an inner concave surface which is configured to directly contact the natural femoral head in generally static engagement therewith, and a smooth outer convex surface which is configured to be directly contacted by an acetabulum socket in moveable engagement therewith, the flexible bone interface element being formed of material which is more flexible than bone material of particularly configured for retainable snap-fit engagement with a suitably machine-shaped surface of the natural femoral head.

There is also provided in accordance with a preferred embodiment of the present invention an artificial femoral head prosthesis for use with a natural femoral head and including a bone interface element configured to be mounted onto the natural femoral head, the bone interface element having an inner concave surface which is configured to directly contact the natural femoral head in generally static engagement therewith, the bone interface element being particularly configured for retainable snap-fit engagement with a suitably machine-shaped surface of the natural femoral head and a press-fit acetabulum engagement element being particularly configured for retainable press-fit engagement with the bone interface element and having a smooth outer convex surface which is configured to be directly contacted by an acetabulum socket in moveable engagement therewith.

There is also provided in accordance with yet another preferred embodiment of the present invention an artificial femoral head prosthesis for use with a natural femoral head and including a bone interface element configured to be mounted onto the natural femoral head, the bone interface element having an inner concave surface which is configured to directly contact the natural femoral head in generally static engagement therewith, the bone interface element being particularly configured for retainable snap-fit engagement with a suitably machine-shaped surface of the natural femoral head and a snap-fit acetabulum engagement element being particularly configured for retainable snap-fit engagement with the bone interface element and having a smooth outer convex surface which is configured to be directly contacted by an acetabulum socket in moveable engagement therewith.

There is also provided in accordance with a preferred embodiment of the present invention a prosthesis for use with a natural bone and including a flexible bone interface element configured to be mounted onto the natural bone, the flexible bone interface element including a unitary element molded of a single material and having a contact surface which is configured to directly contact the natural bone in generally static engagement therewith, and wherein the contact surface is configured with a configuration-pattern including of bone contact surface portions defined by channels surrounding the bone contact surface portions, and wherein the channels have a bottom surface and walls surfaces. The flexible bone interface element being formed of material, which is more flexible than bone material of the natural bone.

There is further provided in accordance with a preferred embodiment of the present invention A prosthesis for use with a natural bone and including a flexible hone interface element configured to be mounted onto the natural bone, the flexible hone interface element including a unitary element molded of a single material and having a contact surface which is configured to directly contact the natural bone in generally static engagement therewith, and wherein the contact surface is configured with a configuration-pattern including of surface recess portions defined by bone contact ridges surrounding the surface recess portions, and wherein the surface recess portions have a bottom surface and walls surfaces. The flexible bone interface element being formed of material, which is more flexible than bone material of the natural bone.

Further in accordance with a preferred embodiment of the present invention the configuration-pattern of the contact surface is of a fractal design including of bone contact surface portions defined by channels surrounding bone contact surface portions.

Preferably, the contact surface is convex. Alternatively or additionally, the contact surface is concave.

Still further in accordance with a preferred embodiment of the present invention the wall surfaces of channels are inclined inwardly creating an undercut section with a wider lower dimension and an narrower upper dimension.

Additionally in accordance with a preferred embodiment of the present invention the prosthesis (convex) includes a configuration-pattern of the bone contact surface portions is of an hexagonal geometry.

Further in accordance with a preferred embodiment of the present invention the configuration-pattern of the bone contact surface portions is of a spiral geometry defined by spiral channels.

Preferably, spiral bone contact surface portions are of a multiple entry spiral type.

Additionally or alternatively, the configuration-pattern of the bone contact surface portions is of a wavy geometry (tire like treads).

Further in accordance with a preferred embodiment of the present invention the configuration-pattern of the bone contact surface portions is of meshed pattern defined by the absence of a polka dot pattern.

Still further in accordance with a preferred embodiment of the invention the configuration-pattern of the bone contact surface portions is of an hexagonal geometry.

Additionally the configuration-pattern of the bone contact surface portions is of a spiral geometry defined by spiral channels.

Further in accordance with a preferred embodiment of the present invention the prosthesis (concave) includes a configuration-pattern of the bone contact surface portions, which includes a meshed pattern defined by the absence of a polka dot pattern.

Still further in accordance with a preferred embodiment of the present invention the bone contact surface and peripheral channels surfaces is configured with a rough (not smooth) texture.

Additionally in accordance with a preferred embodiment of the present invention the bone contact surface and peripheral channels surfaces is treated by atomic surface treatment.

Further in accordance with a preferred embodiment of the present invention the bone contact surface and peripheral channels surfaces is at least partially coated with a bioactive substance stimulating bone-growth enhancing implant fixation to bone.

Preferably, the bioactive substance is Hydroxyapatite (HA: $Ca10(PO4)6(OH)2$).

In accordance with another preferred embodiment of the present invention a mesh of metal is configured in channels generally in a floating position mostly clear of bottom and walls of the channels. Alternatively, a mesh of composite material is configured in channels generally in a floating positioning mostly clear of bottom and walls of the channels. Preferably, the composite material includes carbon. Additionally or alternatively, the composite material includes KEVLAR®. Additionally or alternatively, the composite material includes DYNEEMA®.

Preferably, the mesh is embedded within bone contact surfaces. Alternatively, the mesh is embedded within non-bone contact surfaces.

There is further provided in accordance with another preferred embodiment of the present invention an artificial meniscus implant assembly formed by molding of polyurethane. Preferably, the artificial meniscus implant assembly includes a convex articulation surface and a concave articulation surface. Additionally, the artificial meniscus implant assembly also includes a bone snap-fit engagement element. Additionally or alternatively, the artificial meniscus implant assembly also includes at least one thoroughgoing aperture. Preferably, the artificial meniscus implant assembly also includes at least one tissue secure assembly.

In accordance with another preferred embodiment of the present invention the tissue secure assembly includes an inner grip element and a clip, and the clip has insert elements formed on each end thereof.

There is also provided in accordance with yet another preferred embodiment of the present invention an artificial patella surface element formed by molding of polyurethane.

Preferably, the artificial patella surface element includes a concave articulation surface. Additionally or alternatively, the artificial patella surface element includes an outer peripheral protrusion. Preferably, the outer peripheral protrusion is arranged for snap-fit engagement with a corresponding recess provided by machining of a patella. In accordance with another preferred embodiment of the present invention, the artificial patella surface element also includes at least one thoroughgoing aperture.

Preferably, the artificial patella surface element is constructed to allow for deformation in response to an impact force. Additionally, the deformation provides a shock-absorbing effect to provide protection from the impact force. Additionally or alternatively, the patella surface element returns to its original orientation after the deformation.

There is still further provided in accordance with still another preferred embodiment of the present invention an artificial humeral surface element formed by molding of polyurethane.

Preferably, the artificial humeral surface element includes a concave saddle shape surface for articulation with an ulna. Alternatively, the artificial humeral surface element includes a convex generally spherical surface for articulation with a radius.

Preferably, the artificial humeral surface element includes a peripheral protrusion element. Additionally, the peripheral protrusion element is arranged for snap-fit engagement with corresponding grooves formed by machining the humerus.

There is yet further provided in accordance with another preferred embodiment of the present invention, an artificial ulnar surface element formed by molding of polyurethane.

Preferably, the artificial ulnar surface element includes a concave saddle shape surface for articulation with a humerus. Additionally, the artificial ulnar surface element includes a peripheral protrusion element. Preferably, the peripheral protrusion element is arranged for snap-fit engagement with corresponding grooves formed by machining the ulna.

There is also provided in accordance with yet another preferred embodiment of the present invention an artificial radial surface element formed by molding of polyurethane.

Preferably, the artificial radial surface element includes a concave generally spherical surface for articulation with a humerus. Additionally, the artificial radial surface element includes a peripheral protrusion element. Preferably, the peripheral protrusion element is arranged for snap-fit engagement with corresponding grooves formed by machining the radius.

In accordance with another preferred embodiment of the present invention, the implantable artificial socket for a joint is foldable.

Additionally, the implantable artificial socket for a joint also includes a deformation control element. Additionally, the deformation element also includes a fluid absorption layer.

Further in accordance with another preferred embodiment of the present invention the implantable artificial socket for a joint also includes a radio opaque ring element.

In accordance with yet another preferred embodiment of the present invention the implantable artificial socket for a joint also includes a bioactive coating. Preferably, the bioactive coating is formed by grit blasting. Alternatively, the bioactive coating is formed by spraying. En accordance with another preferred embodiment, the bioactive coating also includes an elastomer.

In accordance with still another preferred embodiment, the implantable artificial socket for a joint also includes an elastomer coating on an articulating surface.

In accordance with yet another preferred embodiment of the present invention, the implantable artificial socket for a joint also includes a thickened portion corresponding to the natural acetabular notch.

Still further in accordance with another preferred embodiment of the present invention, the implantable artificial socket for a joint also includes an extended portion to prevent dislocation of the natural femoral head following insertion thereof. Alternatively, the implantable artificial socket for a joint also includes an extended portion to prevent dislocation of an artificial femoral head following insertion thereof.

In accordance with still another preferred embodiment of the present invention, the implantable artificial socket for a joint also includes recessed surface portions. Preferably, the recessed surface portions are interconnected. Additionally or alternatively, the recessed surface portions provide for the accumulation of synovial fluid. Preferably, the synovial fluid is provided to lubricate an articulation surface of the artificial socket.

In accordance with another preferred embodiment of the present invention, the implantable artificial femoral head resurfacing element is foldable.

Additionally, the implantable artificial femoral head resurfacing element also includes a deformation control element. Additionally, the deformation element also includes a fluid absorption layer.

Further in accordance with another preferred embodiment of the present invention the implantable artificial femoral head resurfacing element also includes a radio opaque ring element.

In accordance with yet another preferred embodiment of the present invention the implantable artificial femoral head resurfacing element also includes a bioactive coating. Preferably, the bioactive coating is formed by grit blasting. Alternatively, the bioactive coating is formed by spraying. In accordance with another preferred embodiment, the bioactive coating also includes an elastomer.

In accordance with still another preferred embodiment, the implantable artificial femoral head resurfacing element also includes an elastomer coating on an articulating surface.

Further in accordance with another preferred embodiment of the present invention the implantable artificial femoral head resurfacing element also includes a femoral head interface element. Preferably, the femoral head interface element is arranged for snap-fit engagement with corresponding grooves formed by machining the femur. Alternatively, the femoral head interface element is arranged for press fit engagement with a corresponding seating location formed by machining the femur. Additionally, the implantable artificial femoral head resurfacing element is arranged for snap-lit engagement with the femoral head interface element. Alternatively, the femoral head resurfacing element is arranged for press fit engagement with the femoral head interface element.

In accordance with still another preferred embodiment of the present invention, the implantable artificial femoral head resurfacing element also includes recessed surface portions. Preferably, the recessed surface portions are interconnected. Additionally or alternatively, the recessed surface portions provide for the accumulation of synovial fluid. Preferably, the synovial fluid is provided to lubricate an articulation surface of the artificial socket.

BRIEF DESCRIPTION OF THE DRAWINGS

The present invention will be understood and appreciated more fully from the following detailed description, taken in conjunction with the drawings in which:

FIGS. 1A, 1B and 1C are respective pictorial, sectional and partially cut away illustrations of an implantable artificial socket for the acetabulum constructed and operative in accordance with a preferred embodiment of the present invention;

FIGS. 12A and 12B are respective exploded view and assembled view illustrations of the implantable artificial socket of FIGS. 1A-1C in a partial hip replacement environment;

FIGS. 13A and 13B are respective exploded view and assembled view illustrations of the implantable artificial socket of FIGS. 1A-1C and the implantable artificial femoral head resurfacing element of FIGS. 6A-6C in a total hip resurfacing environment;

FIGS. 14A and 14B are respective exploded view and assembled view illustrations of the implantable artificial femoral head resurfacing element of FIGS. 6A-6C in a hemi hip resurfacing environment;

FIGS. 17A, 17B and 17C are respectively, an illustration of an articulation surface, a sectional illustration and an illustration of a bone engagement surface, of an implantable artificial socket for the glenoid constructed and operative in accordance with still another preferred embodiment of the present invention;

FIGS. 20A, 20B and 20C are respective pictorial, sectional and partially cut away illustrations of an implantable artificial humeral head surface element constructed and operative in accordance with a preferred embodiment of the present invention;

FIGS. 21A, 21B and 21C are respective pictorial, sectional and partially cut away illustrations of an implantable artificial humeral head surface element constructed and operative in accordance with another preferred embodiment of the present invention;

FIGS. 33A, 33B, 33C, 33D, 33E and 33F are respective first and second pictorial, and first, second, third and fourth partially cut away sectional illustrations of a pair of implantable artificial humeral elbow surface elements constructed and operative in accordance with a preferred embodiment of the present invention;

FIGS. 34A, 34B, 34C, 34D, 34E and 34F are respective first and second pictorial, and first, second, third and fourth sectional illustrations of a pair of implantable artificial ulna and radius elbow elements constructed and operative in accordance with a preferred embodiment of the present invention;

FIGS. 35A and 35B are respective exploded view and assembled view illustrations of the implantable artificial humeral elbow elements of FIGS. 33A-33F in a partial elbow replacement environment;

FIGS. 36A and 36B are respective exploded view and assembled view illustrations of the implantable artificial ulna and radius elbow elements of FIGS. 34A-34F in a partial elbow replacement environment;

FIGS. 40A, 40B, 40C, 40D, 40E, 40F and 40G are simplified pictorial illustrations of various stages in groove reaming of an acetabulum in accordance with a preferred embodiment of the present invention;

FIGS. 43A and 43B are simplified pictorial illustrations of introduction and pre-snap fit placement of an implantable artificial acetabular socket adjacent a reamed acetabulum in accordance with two alternative embodiments of the present invention;

FIGS. 44A, 44B, 44C and 44D are, respectively, a simplified pictorial illustration and sectional illustrations of a snap-fit installation of an implantable artificial acetabular socket in a reamed acetabulum in accordance with a preferred embodiment of the present invention;

FIGS. 45A and 45B are a simplified pictorial illustration and a sectional illustration of a final stage in snap-fit installation of an implantable artificial acetabular socket in a reamed acetabulum in accordance with a preferred embodiment of the present invention;

FIGS. 52A, 52B and 52C are respective pictorial, sectional and partially cut away illustrations of an implantable artificial femoral head resurfacing element constructed and operative in accordance with another preferred embodiment of the present invention;

FIGS. 54A, 54B and 54C are respective pictorial, sectional and partially cut away illustrations of an implantable artificial femoral head resurfacing element constructed and operative in accordance with yet another preferred embodiment of the present invention;

FIGS. 72A, 72B, and 72C are respective pictorial, sectional and partially cut away illustrations of an implantable artificial acetabular socket constructed and operative in accordance with still another preferred embodiment of the present invention;

FIGS. 91A, 91B and 91C are sectional illustrations showing bone growth adjacent to an implanted acetabular socket in accordance with another preferred embodiment of the present invention;

DETAILED DESCRIPTION OF PREFERRED EMBODIMENTS

Figure 2A:
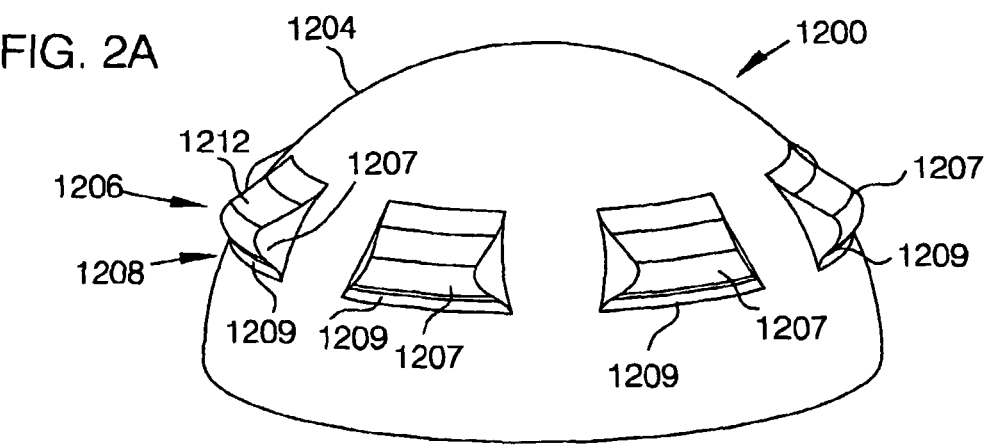
FIGS. 2A, 2B and 2C are respective pictorial, sectional and partially cut away illustrations of an implantable artificial socket for the acetabulum constructed and operative in accordance with another preferred embodiment of the present invention.

Reference is now made to FIGS. 1A, 1B and 1C, which are respective pictorial, sectional and partially cut away illustrations of an implantable artificial socket constructed and operative in accordance with a preferred embodiment of the present invention and which is particularly suitable for use in a hip joint.

As seen in FIGS. 1A, 1B and 1C, an implantable artificial acetabular socket, designated by reference numeral 1100, is formed preferably by injection molding of polyurethane. Preferred polyurethane materials are described hereinbelow.

Preferably, implantable artificial acetabular socket 1100 is of generally uniform thickness, is symmetric about an axis 1101 and defines an hemispherical concave inner articulation surface 1102, having a beveled edge 1103, and a generally hemispherical outer bone engagement surface 1104, which preferably has formed thereon, at any suitable location between its apex and its rim, a generally annular outwardly extending protrusion 1106, preferably defining a generally annular undercut 1108. Alternatively, the protrusion 1106 may be any other suitable non-annular, open or closed, generally peripheral, protrusion. The protrusion 1106 is preferably arranged for snap-fit engagement with a corresponding groove formed by reaming of a bone, examples of which are described hereinbelow.

Preferably, the protrusion 1106 has a cross-sectional configuration, as can be readily seen in FIG. 1B, which is characterized in that an underlying surface portion 1110 of protrusion 1106, at the undercut 1108, defines a slope which is sharper than a corresponding slope of an overlying surface portion 1112 of protrusion 1106.

Figure 2B:
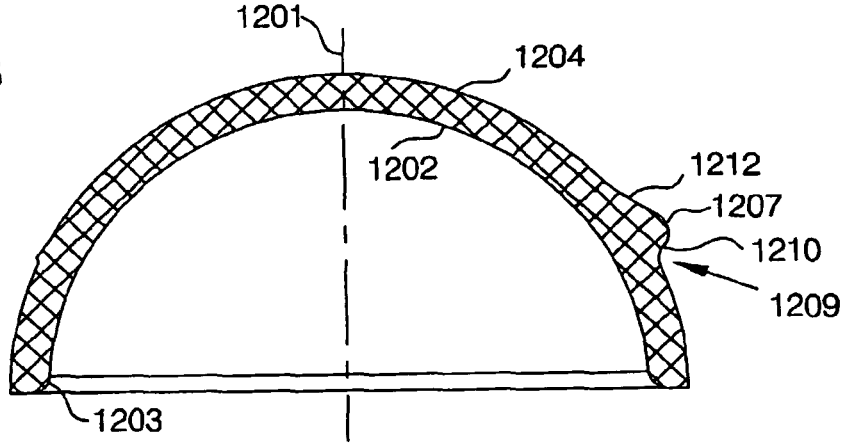
Figure 2C:
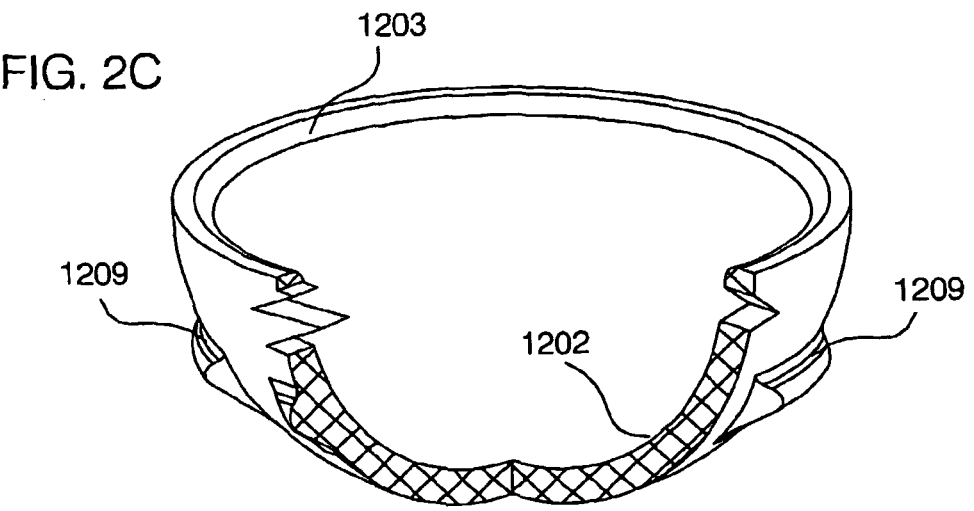

Reference is now made to FIGS. 2A, 2B and 2C, which are respective pictorial, sectional and partially cut away illustrations of an implantable artificial acetabular socket constructed and operative in accordance with another preferred embodiment of the present invention.

As seen in FIGS. 2A, 2B and 2C, an implantable artificial acetabular socket, designated by reference numeral 1200, is formed preferably by injection molding of polyurethane. Preferred polyurethane materials are described hereinbelow.

Preferably, implantable artificial acetabular socket 1200 is of generally uniform thickness, is symmetric about an axis 1201 and defines an hemispherical inner articulation surface 1202, having a beveled edge 1203, and a generally hemispherical outer hone engagement surface 1204 which preferably has formed thereon, at any suitable location between its apex and its rim, a generally annular outwardly extending array 1206 of discrete protrusions 1207, preferably defining a generally annular array 1208 of undercuts 1209. Alternatively, the array 1206 may be any other suitable non-annular, open or closed, generally peripheral, array of protrusions. The array 1206 of protrusions 1207 is preferably arranged for snap-fit engagement with corresponding grooves formed inter alia by reaming of a bone, examples of which are described hereinbelow Preferably, the protrusions 1207 have a cross-sectional configuration, as can be readily seen in FIG. 2B, which is characterized in that an underlying surface portion 1210 of each protrusion 1207, at the undercut 1209, defines a slope which is sharper than a corresponding slope of an overlying surface portion 1212 of the protrusion 1207.

Figure 3A:
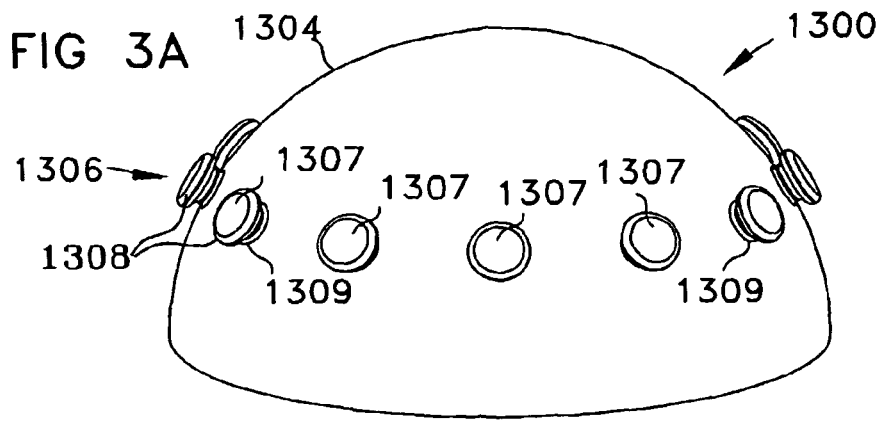
FIGS. 3A, 3B and 3C are respective pictorial, sectional and partially cut away illustrations of an implantable artificial socket for the acetabulum constructed and operative in accordance with still another preferred embodiment of the present invention.
Figure 3B:
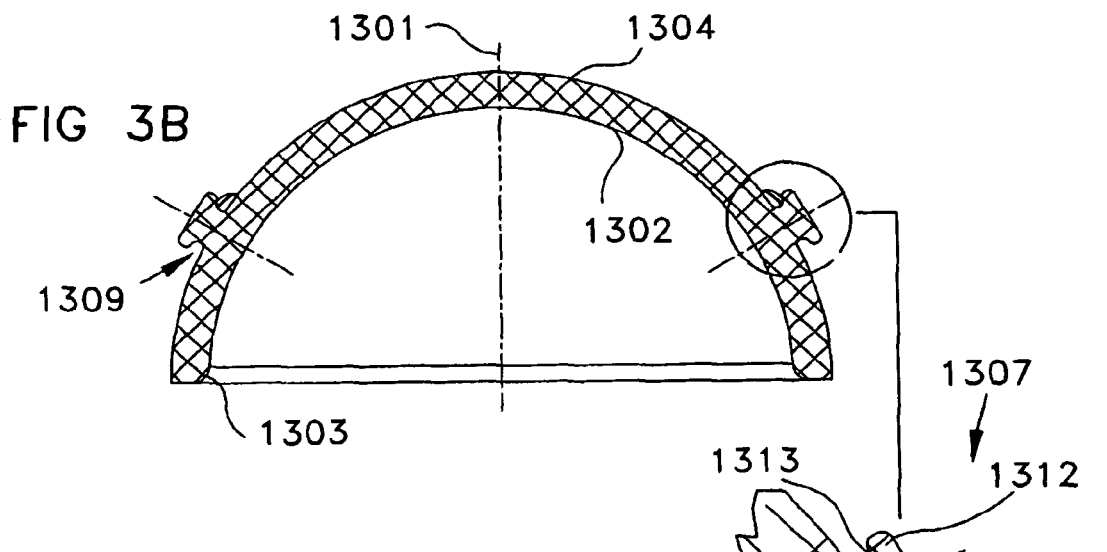
Figure 3C:
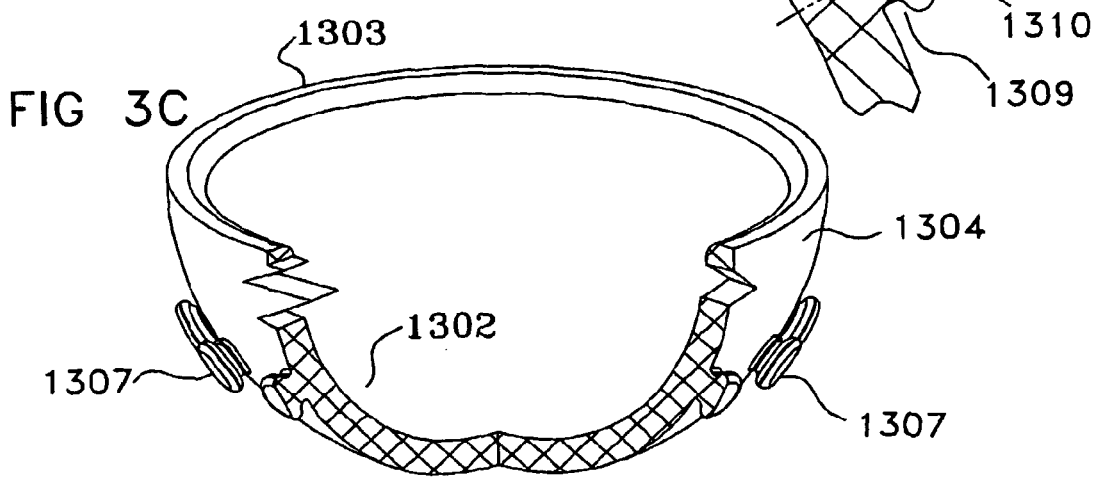

Reference is now made to FIGS. 3A, 3B and 3C, which are respective pictorial, sectional and partially cut away illustrations of an implantable artificial acetabular socket constructed and operative in accordance with still another preferred embodiment of the present invention.

As seen in FIGS. 3A, 3B and 3C, an implantable artificial acetabular socket, designated by reference numeral 1300, is formed preferably by injection molding of polyurethane. Preferred polyurethane materials are described hereinbelow.

Preferably, implantable artificial acetabular socket 1300 is of generally uniform thickness, is symmetric about an axis 1301 and defines an hemispherical inner articulation surface 1302, having a beveled edge 1303, and a generally hemispherical outer hone engagement surface 1304 which preferably has formed thereon, at any suitable location between its apex and its rim, a generally annular outwardly extending array 1306 of discrete protrusions 1307, preferably defining a generally annular array 1308 of undercuts 1309. Alternatively, the array 1306 may be any other suitable non-annular, open or closed, generally peripheral, array of protrusions. The array 1306 of protrusions 1307 is preferably arranged for snap-fit engagement with corresponding recesses formed inter alia by suitable machining of a bone.

Preferably, the protrusions 1307 have a generally button-like configuration which is symmetric about an axis 1310 and include a body portion 1311 and an enlarged head portion 1312, as can be readily seen in FIG. 3B. Protrusions 1307 are generally characterized in that an underlying surface portion 1313 of each protrusion 1307 defines peripheral undercut 1309 with respect to axis 1310.

Figure 4A:
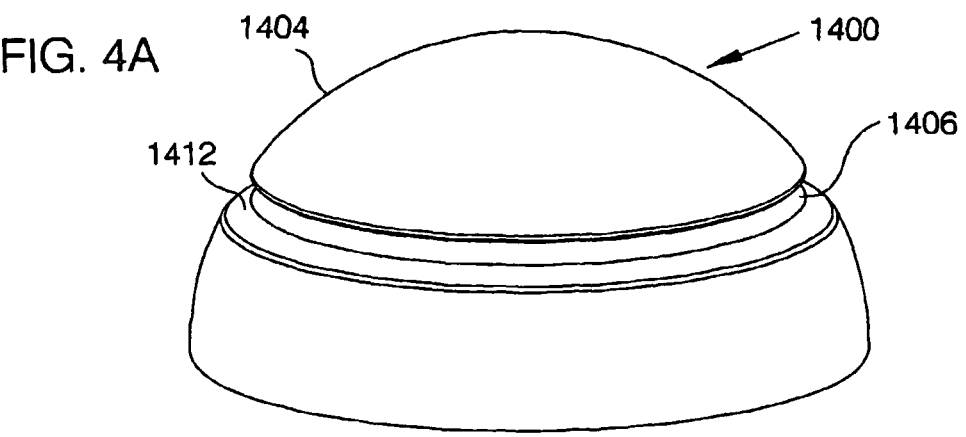
FIGS. 4A, 4B and 4C are respective pictorial, sectional and partially cut away illustrations of an implantable artificial socket for the acetabulum constructed and operative in accordance with yet another preferred embodiment of the present invention.
Figure 4B:
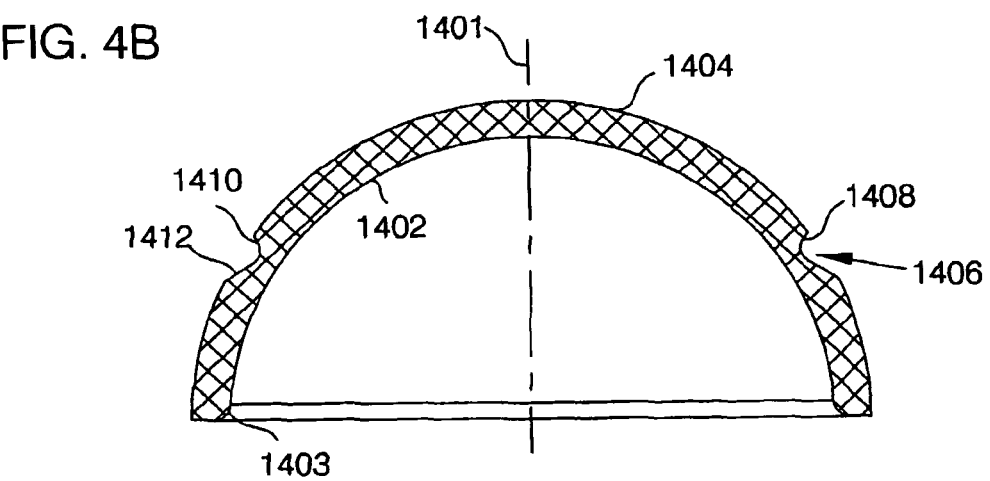
Figure 4C:
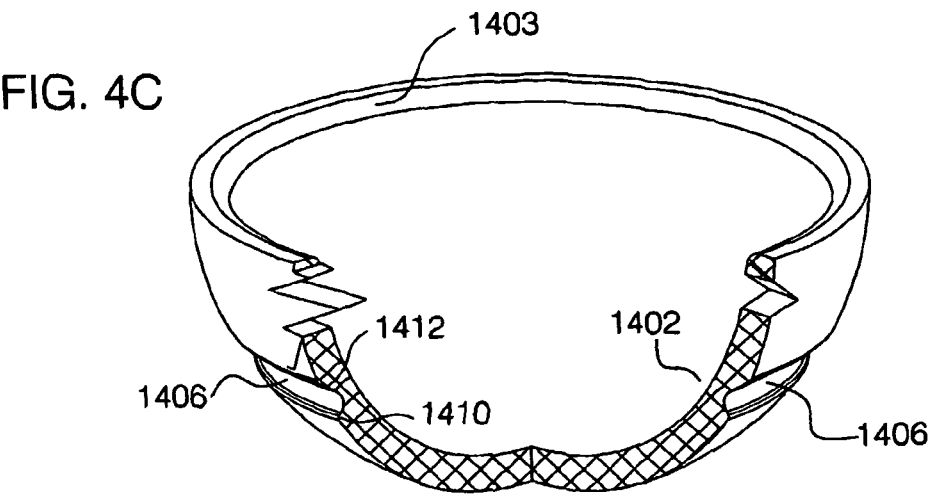

Reference is now made to FIGS. 4A, 4B and 4C, which are respective pictorial, sectional and partially cut away illustrations of an implantable artificial acetabular socket constructed and operative in accordance with yet another preferred embodiment of the present invention.

As seen in FIGS. 4A, 4B and 4C, an implantable artificial acetabular socket, designated by reference numeral 1400, is formed preferably by injection molding of polyurethane. Preferred polyurethane materials are described hereinbelow.

Preferably, implantable artificial acetabular socket 1400 is of generally uniform thickness, is symmetric about an axis 1401 and defines an hemispherical inner articulation surface 1402, having a beveled edge 1403, and a generally hemispherical outer bone engagement surface 1404 which preferably has formed thereon, at any suitable location between its apex and its rim, a generally annular inwardly extending recess 1406, preferably defining a generally annular undercut 1408. Alternatively, the recess 1406 may be any other suitable non-annular, open or closed, generally peripheral, recess. The recess 1406 is preferably arranged for snap-fit engagement with a corresponding protrusion formed by reaming of a bone, examples of which are described hereinbelow.

Preferably, the recess 1406 has a cross-sectional configuration, as can be readily seen in FIG. 4B, which is characterized in that an overlying surface portion 1410 of recess 1406, at the undercut 1408, defines a slope which is sharper than a corresponding slope of an underlying surface portion 1412 of recess 1406.

Figure 5A:
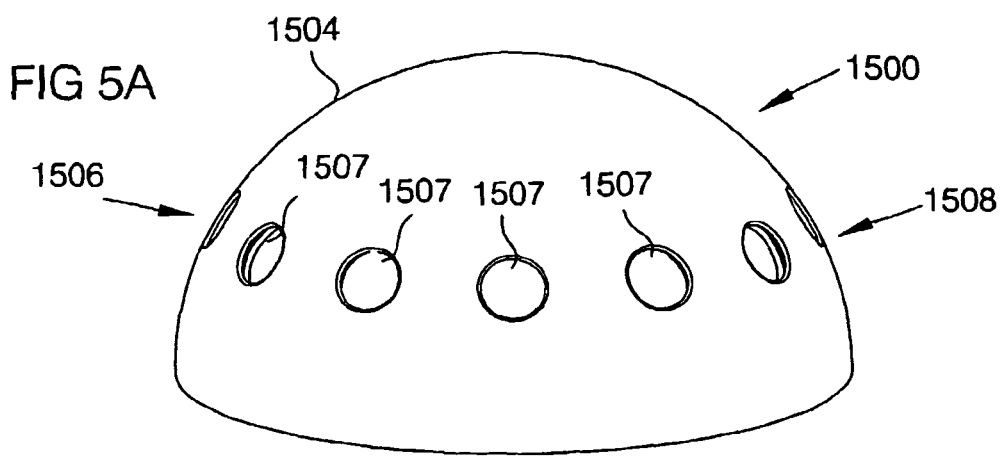
FIGS. 5A, 5B and 5C are respective pictorial, sectional and partially cut away illustrations of an implantable artificial socket for the acetabulum constructed and operative in accordance with a further preferred embodiment of the present invention.
Figure 5B:
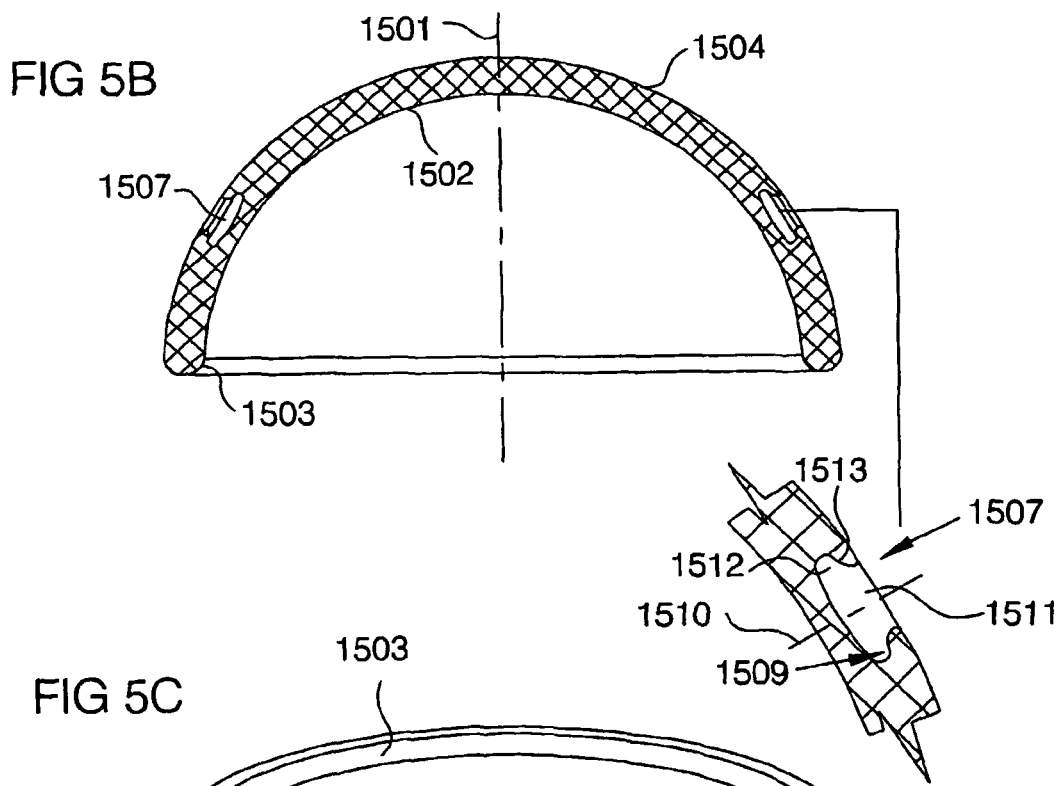
Figure 5C:
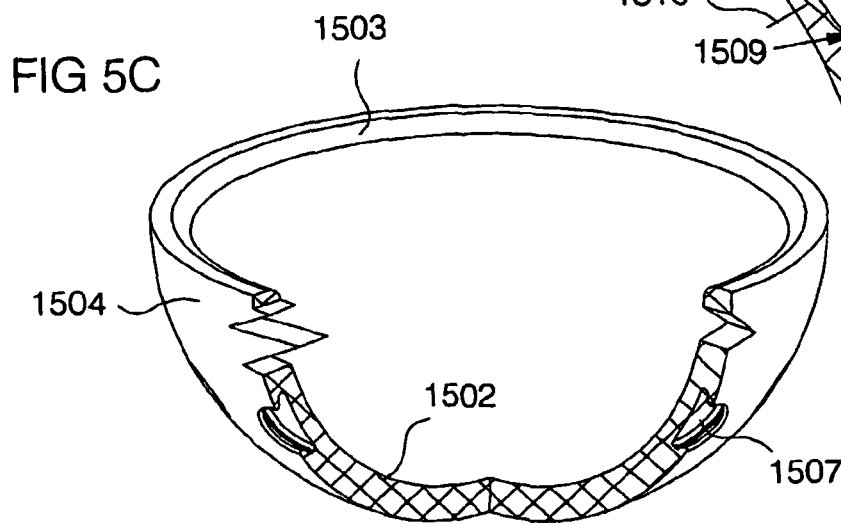

Reference is now made to FIGS. 5A, 5B and 5C, which are respective pictorial, sectional and partially cut away illustrations of an implantable artificial acetabular socket constructed and operative in accordance with still another preferred embodiment of the present invention.

As seen in FIGS. 5A, 5B and 5C, an implantable artificial acetabular socket, designated by reference numeral 1500, is formed preferably by injection molding of polyurethane. Preferred polyurethane materials are described hereinbelow.

Preferably, implantable artificial acetabular socket 1500 is of generally uniform thickness, is symmetric about an axis 1501 and defines an hemispherical inner articulation surface 1502, having a beveled edge 1503, and a generally hemispherical outer bone engagement surface 1504 which preferably has formed thereon, at any suitable location between its apex and its rim, a generally annular inwardly extending array 1506 of discrete recesses 1507, preferably defining a generally annular array 1508 of undercuts 1509. Alternatively, the array 1506 may be any other suitable non-annular, open or closed, generally peripheral, array of recesses. The array 1506 of recesses 1507 is preferably arranged for snap-fit engagement with corresponding protrusions formed inter alia by suitable machining of a bone.

Preferably, the recesses 1507 have a generally button-like configuration which is symmetric about an axis 1510 and include a body portion 1511 and an enlarged head portion 1512, as can be readily seen in FIG. 5B. Recesses 1507 are generally characterized in that an overlying surface portion 1513 of each recess 1507 defines a peripheral undercut with respect to axis 1510.

Figure 6A:
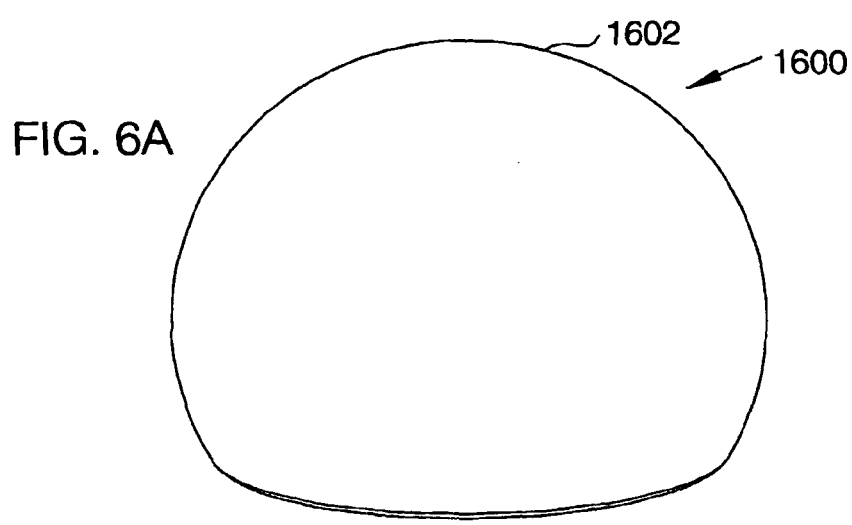
FIGS. 6A, 6B and 6C are respective pictorial, sectional and partially cut away illustrations of an implantable artificial femoral head resurfacing element constructed and operative in accordance with a preferred embodiment of the present invention.
Figure 6B:
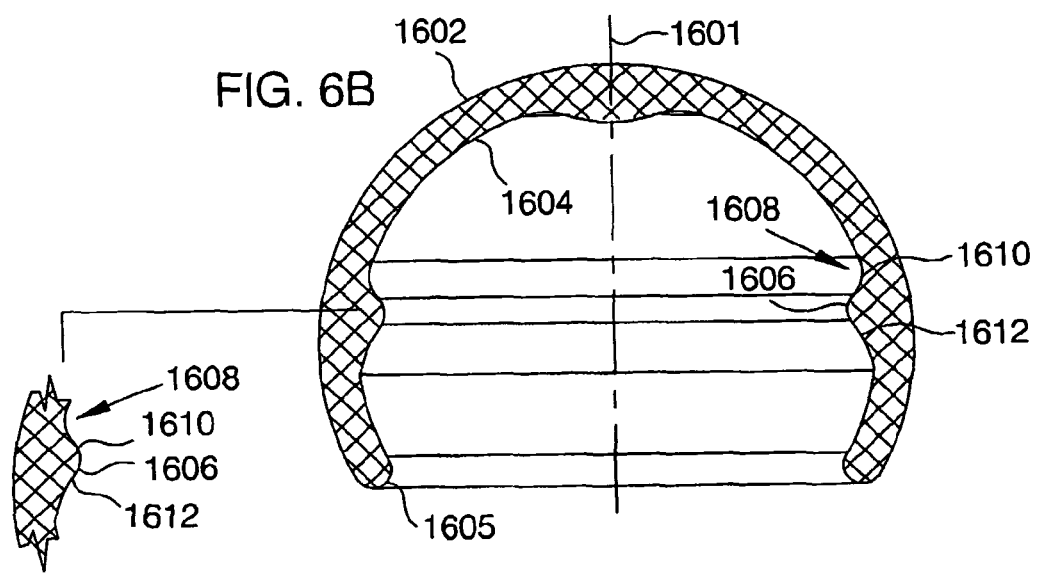
Figure 6C:
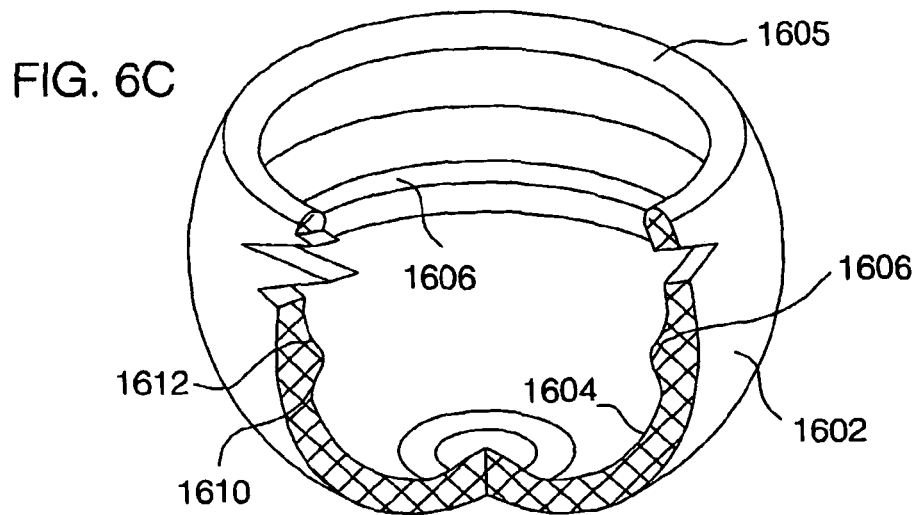

Reference is now made to FIGS. 6A, 6B and 6C, which are respective pictorial, sectional and partially cut away illustrations of an implantable artificial femoral head resurfacing element constructed and operative in accordance with a preferred embodiment of the present invention. The implantable artificial femoral head resurfacing element is intended for mounting onto a natural femoral head in accordance with a preferred embodiment of the present invention.

As seen in FIGS. 6A, 6B and 6C, an implantable artificial femoral head resurfacing element, designated by reference numeral 1600, is formed preferably by injection molding of polyurethane. Preferred polyurethane materials are described hereinbelow.

Preferably, implantable artificial femoral head resurfacing element 1600 is of generally uniform thickness, other than at its apex which is thickened, is symmetric about an axis 1601 and defines an hemispherical outer articulation surface 1602 and a generally hemispherical inner bone engagement surface 1604, having a beveled edge 1605, which preferably has formed thereon, at any suitable location between its apex and its rim, a generally annular inwardly extending protrusion 1606, preferably defining a generally annular undercut 1608. Alternatively, the protrusion 1606 may be any other suitable non-annular, open or closed, generally peripheral, protrusion. The protrusion 1606 is preferably arranged for snap-fit engagement with a corresponding groove formed by reaming of a femoral head.

Preferably, the protrusion 1606 has a cross-sectional configuration, as can be readily seen in FIG. 6B, which is characterized in that an underlying surface portion 1610 of protrusion 1606, at the undercut 1608, defines a slope which is sharper than a corresponding slope of an overlying surface portion 1612 of protrusion 1606.

It is appreciated that, even though the illustrated embodiment shows the non-uniform thickness portion of artificial femoral head resurfacing element 1600 at the apex thereof, any suitable portion thereof may be of non-uniform thickness.

Figure 7A:
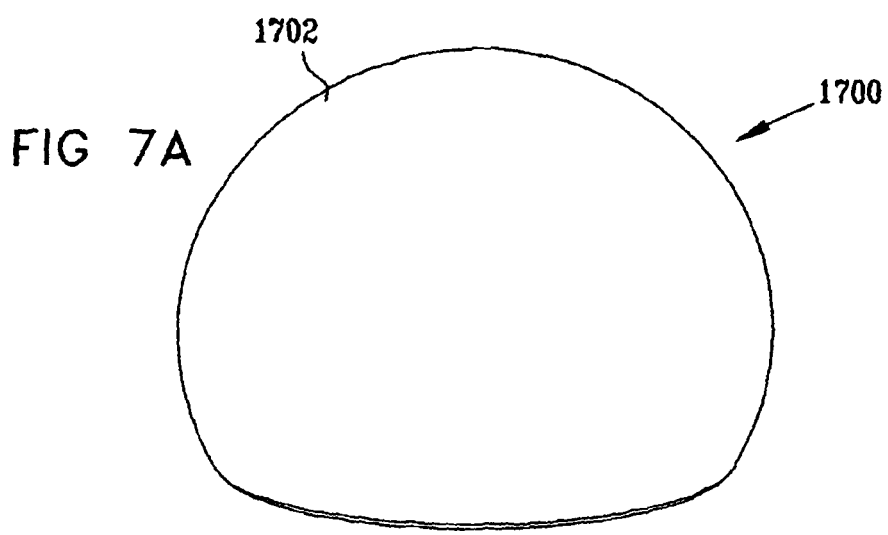
FIGS. 7A, 7B and 7C are respective pictorial, sectional and partially cut away illustrations of an implantable artificial femoral head resurfacing element constructed and operative in accordance with another preferred embodiment of the present invention.
Figure 7B:
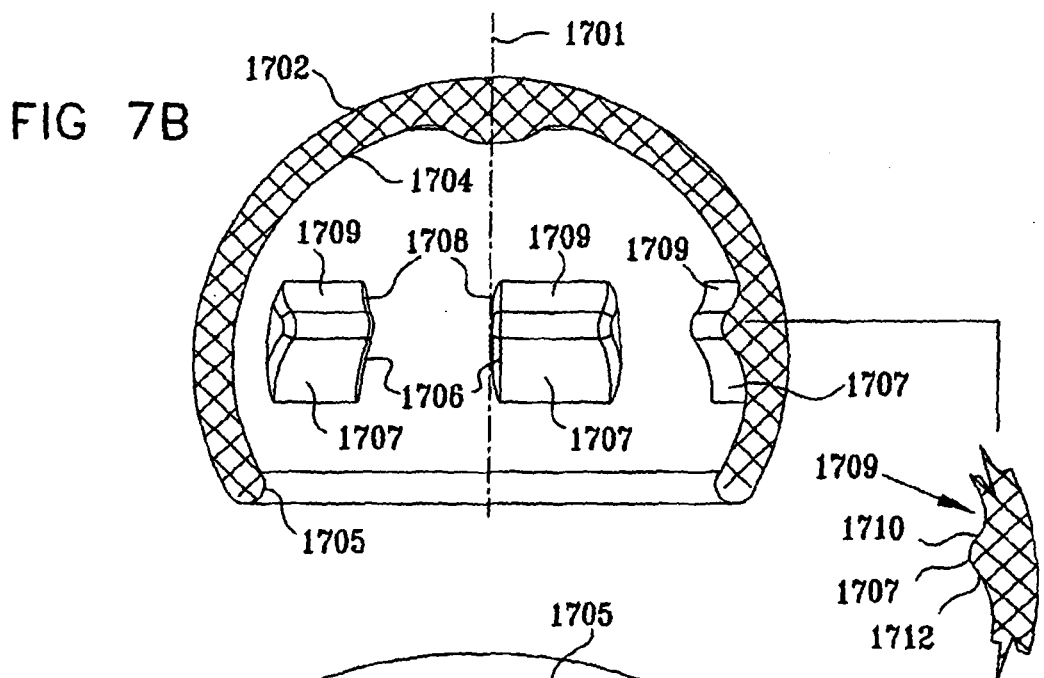
Figure 7C:
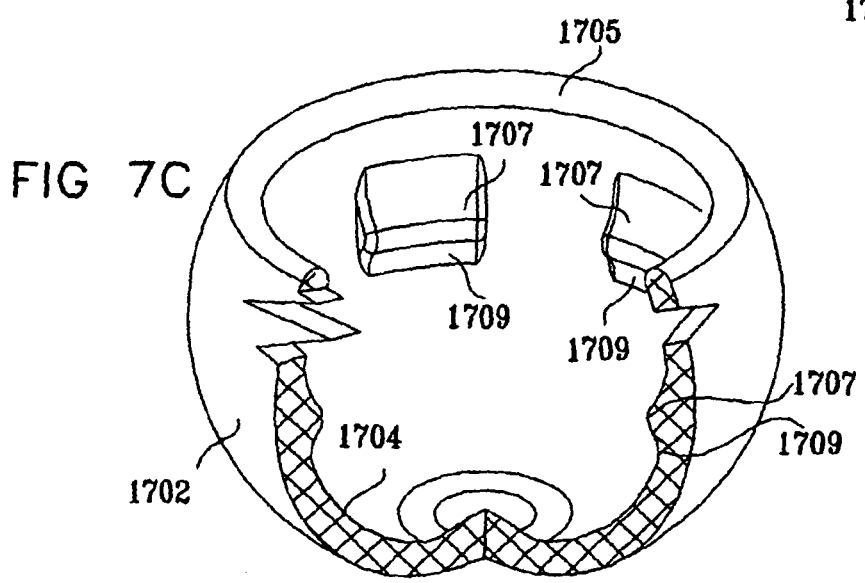

Reference is now made to FIGS. 7A, 7B and 7C, which are respective pictorial, sectional and partially cut away illustrations of an implantable artificial femoral head resurfacing element constructed and operative in accordance with another preferred embodiment of the present invention.

As seen in FIGS. 7A, 7B and 7C, an implantable artificial femoral head resurfacing element, designated by reference numeral 1700, is formed preferably by injection molding of polyurethane. Preferred polyurethane materials are described hereinbelow.

Preferably, implantable artificial femoral head resurfacing element 1700 is generally uniform thickness, other than at its apex which is thickened, is symmetric about an axis 1701 and defines an hemispherical outer articulation surface 1702 and a generally hemispherical inner bone engagement surface 1704, having a beveled edge 1705, which preferably has formed thereon, at any suitable location between its apex and its rim, a generally annular inwardly extending array 1706 of discrete protrusions 1707, preferably defining a generally annular array 1708 of undercuts 1709. Alternatively, the array 1706 may be any other suitable non-annular, open or closed, generally peripheral, array of protrusions. The array 1706 of protrusions 1707 is preferably arranged for snap-fit engagement with corresponding grooves formed inter alia by reaming of a femoral head.

Preferably, the protrusions 1707 have a cross-sectional configuration, as can be readily seen in FIG. 7B, which is characterized in that an underlying surface portion 1710 of each protrusion 1707, at the undercut 1709, defines a slope which is sharper than a corresponding slope of an overlying surface portion 1712 of the protrusion 1707.

It is appreciated that, even though the illustrated embodiment shows the non-uniform thickness portion of artificial femoral head resurfacing element 1700 at the apex thereof, any suitable portion thereof may be of non-uniform thickness.

Figure 8A:
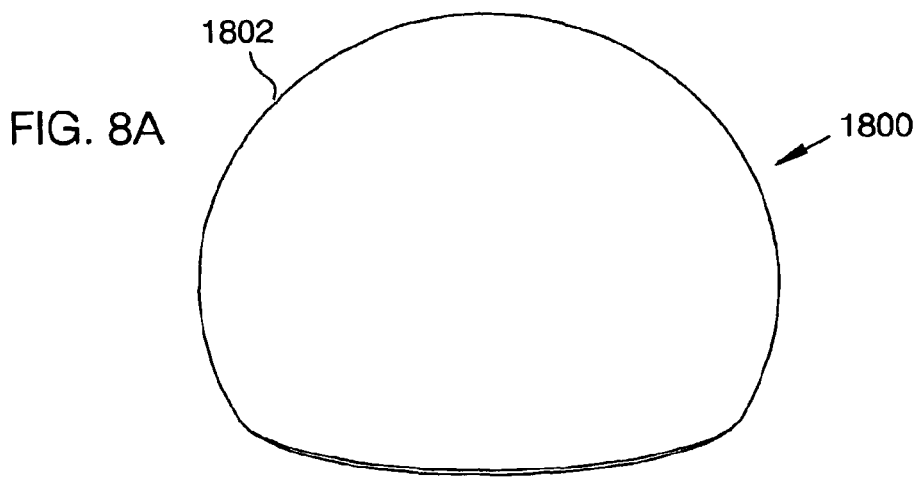
FIGS. 8A, 8B and 8C are respective pictorial, sectional and partially cut away illustrations of an implantable artificial femoral head resurfacing element constructed and operative in accordance with still another preferred embodiment of the present invention.
Figure 8B:
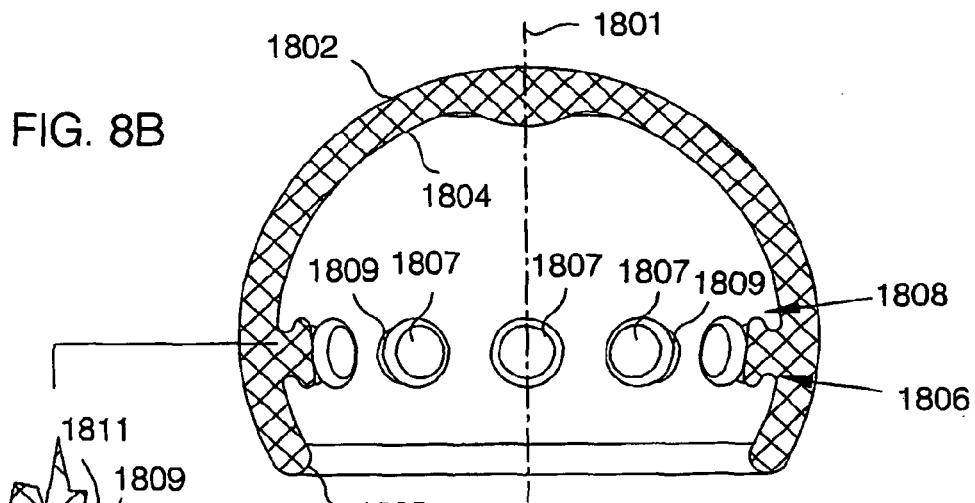
Figure 8C:
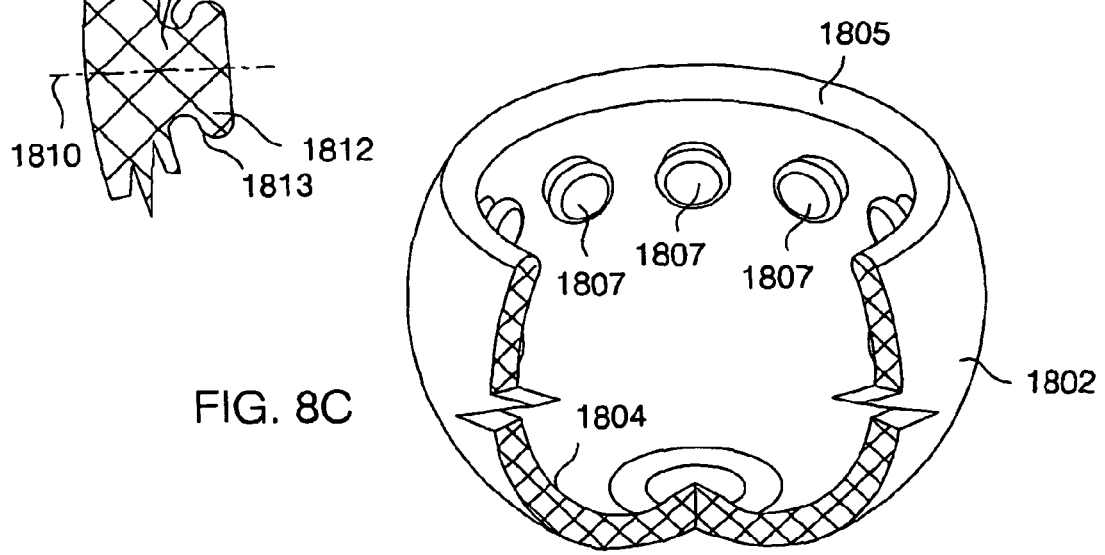

Reference is now made to FIGS. 8A, 8B and 8C, which are respective pictorial, sectional and partially cut away illustrations of an implantable artificial femoral head resurfacing element constructed and operative in accordance with still another preferred embodiment of the present invention.

As seen in FIGS. 8A, 8B and 8C, an implantable artificial femoral head resurfacing element, designated by reference numeral 1800, is formed preferably by injection molding of polyurethane. Preferred polyurethane materials are described hereinbelow.

Preferably, implantable artificial femoral head resurfacing element 1800 is or generally uniform thickness, other than at its apex which is thickened, is symmetric about an axis 1801 and defines an hemispherical outer articulation surface 1802 and a generally hemispherical inner bone engagement surface 1804, having a beveled edge 1805, which preferably has formed thereon, at any suitable location between its apex and its rim, a generally annular inwardly extending array 1806 of discrete protrusions 1807, preferably defining a generally annular array 1808 of undercuts 1809. Alternatively, the array 1806 may be any other suitable non-annular, open or closed, generally peripheral, array of protrusions. The array 1806 of protrusions 1807 is preferably arranged for snap-fit engagement with corresponding recesses formed inter alia by suitable machining of a femoral head.

Preferably, the protrusions 1807 have a generally button-like configuration which is symmetric about an axis 1810 and include a body portion 1811 and an enlarged head portion 1812, as can be readily seen in FIG. 8B. Protrusions 1807 are generally characterized in that an underlying surface portion 1813 of each protrusion 1807 defines the peripheral undercut 1809 with respect to axis 1810.

It is appreciated that, even though the illustrated embodiment shows the non-uniform thickness portion of artificial femoral head resurfacing element 1800 at the apex thereof, any suitable portion thereof may be of non-uniform thickness.

Figure 9A:
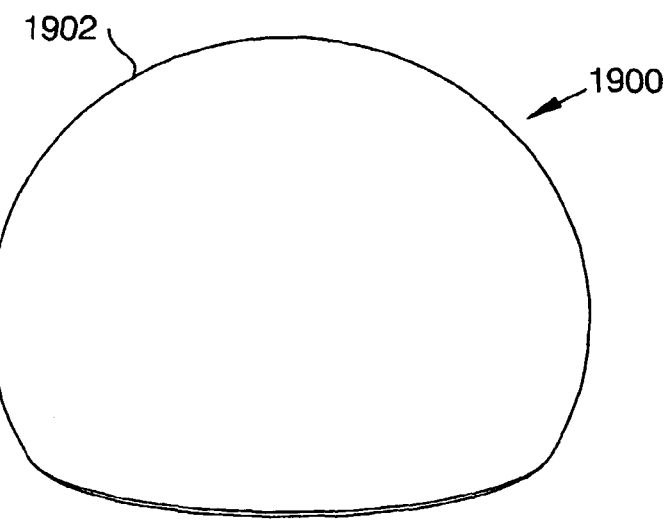
FIGS. 9A, 9B and 9C are respective pictorial, sectional and partially cut away illustrations of an implantable artificial femoral head resurfacing element constructed and operative in accordance with yet another preferred embodiment of the present invention.
Figure 9B:
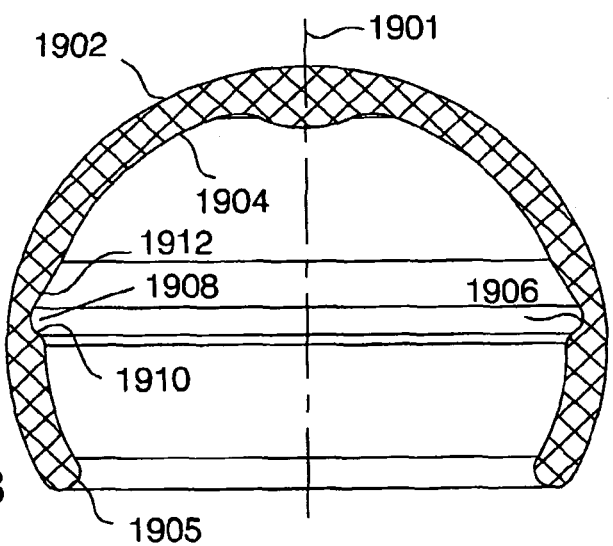
Figure 9C:
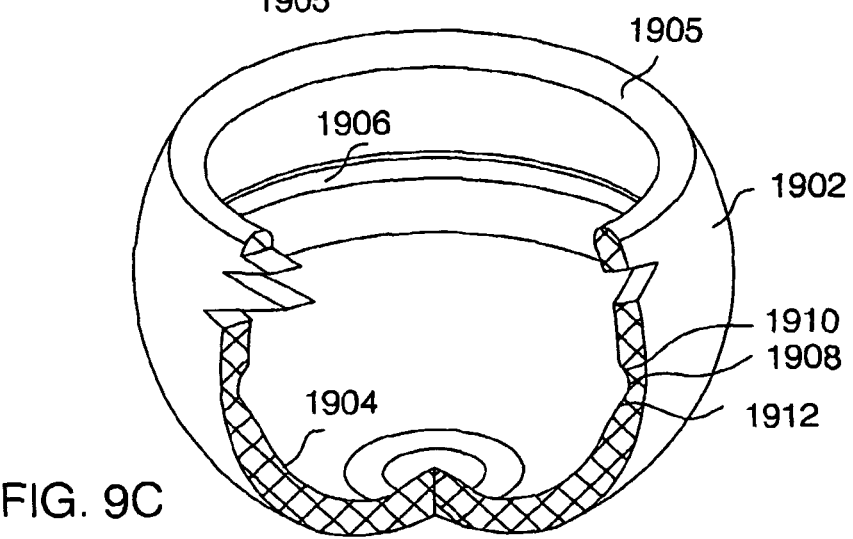

Reference is now made to FIGS. 9A, 9B and 9C, which are respective pictorial, sectional and partially cut away illustrations of an implantable artificial femoral head resurfacing element constructed and operative in accordance with yet another preferred embodiment of the present invention.

As seen in FIGS. 9A, 9B and 9C, an implantable artificial femoral head resurfacing, element, designated by reference numeral 1900, is formed preferably by injection molding of polyurethane. Preferred polyurethane materials are described hereinbelow.

Preferably, implantable artificial femoral head resurfacing element 1900 is of generally uniform thickness, other than at its apex which is thickened, is symmetric about an axis 1901 and defines an hemispherical outer articulation surface 1902 and a generally hemispherical inner bone engagement surface 1904, having a beveled edge 1905, which preferably has formed thereon, at any suitable location between its apex and its rim, a generally annular outwardly extending recess 1906, preferably defining a generally annular undercut 1908. Alternatively, the recess 1906 may be any other suitable non-annular, open or closed, generally peripheral, protrusion. The recess 1906 is preferably arranged for snap-fit engagement with a corresponding protrusion formed by reaming of a femoral head.

Preferably, the recess 1906 has a cross-sectional configuration, as can be readily seen in FIG. 9B, which is characterized in that an overlying surface portion 1910 of recess 1906, at the undercut 1908, defines a slope which is sharper than a corresponding slope of an underlying surface portion 1912 of recess 1906.

It is appreciated that, even though the illustrated embodiment shows the non-uniform thickness portion of artificial femoral head resurfacing element 1900 at the apex thereof, any suitable portion thereof may be of non-uniform thickness.

Figure 10A:
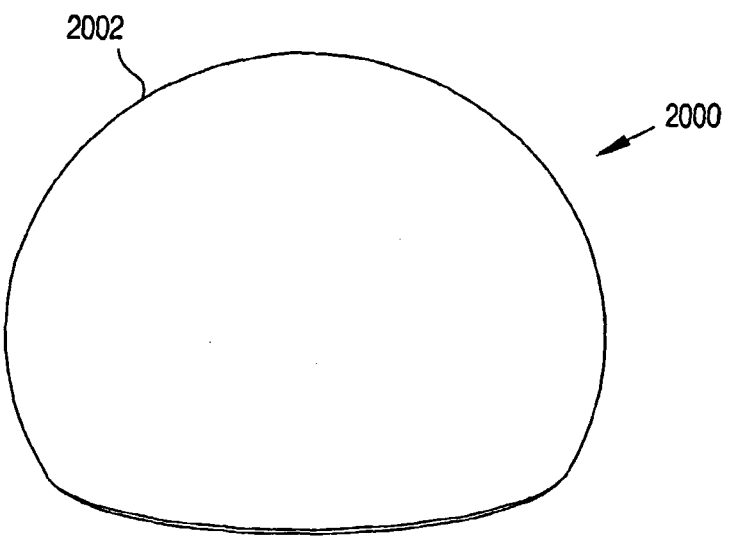
FIGS. 10A, 10B and 10C are respective pictorial, sectional and partially cut away illustrations of an implantable artificial femoral head resurfacing element constructed and operative in accordance with a further preferred embodiment of the present invention.
Figure 10B:
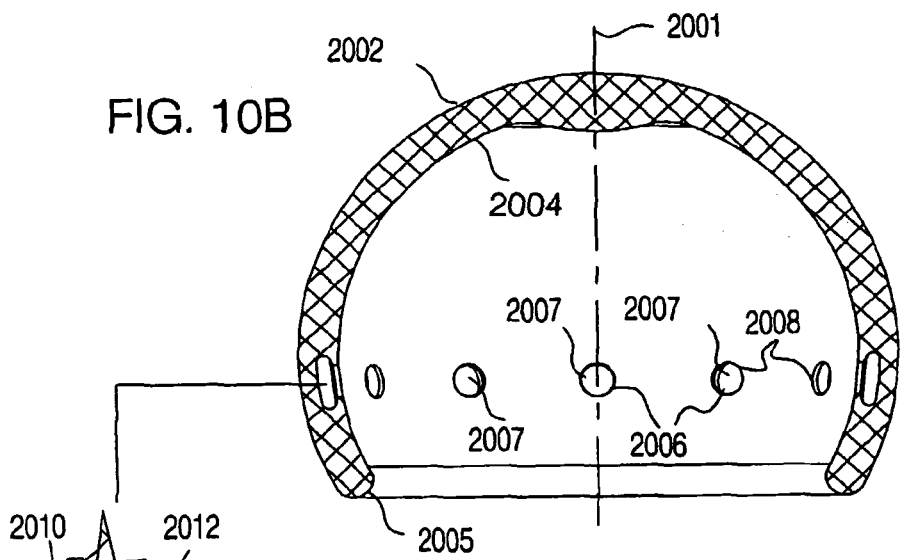
Figure 10C:
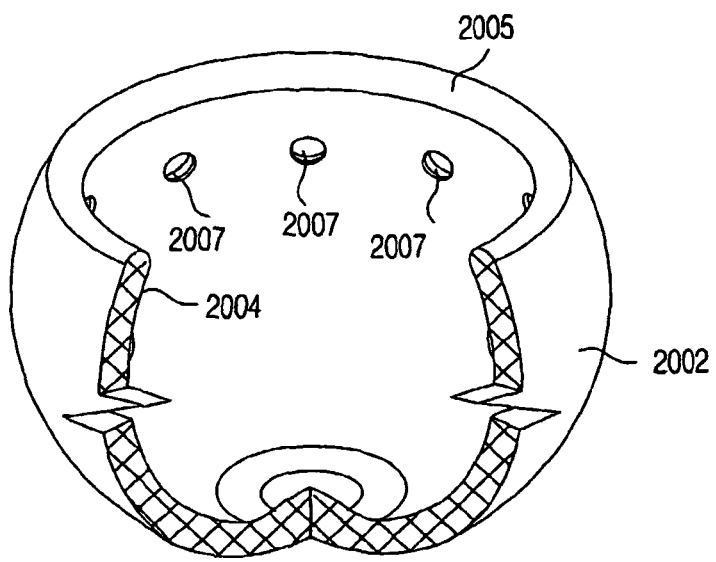

Reference is now made to FIGS. 10A, 10B and 10C, which are respective pictorial, sectional and partially cut away illustrations of an implantable artificial femoral head resurfacing element constructed and operative in accordance with still another preferred embodiment of the present invention.

As seen in FIGS. 10A, 10B and 10C, an implantable artificial femoral head resurfacing element, designated by reference numeral 2000, is formed preferably by injection molding of polyurethane. Preferred polyurethane materials are described hereinbelow.

Preferably, implantable artificial femoral head resurfacing element 2000 is of generally uniform thickness, other than at its apex which is thickened, is symmetric about an axis 2001 and defines an hemispherical outer articulation surface 2002 and a generally hemispherical inner bone engagement surface 2004, having a beveled edge 2005, which preferably has formed thereon, at any suitable location between its apex and its rim, a generally annular outwardly extending array 2006 of discrete recesses 2007, preferably defining a generally annular array 2008 of undercuts 2009. Alternatively, the array 2006 may be any other suitable non-annular, open or closed, generally peripheral, array of recesses. The array 2006 of recesses 2007 is preferably arranged for snap-fit engagement with corresponding protrusions formed inter alia by suitable machining of a femoral head.

Preferably, the recesses 2007 have a generally button-like configuration which is symmetric about an axis 2010 and include a body portion 2011 and an enlarged head portion 2012, as can be readily seen in FIG. 10B. Recesses 2007 are generally characterized in that an overlying surface portion 2013 of each recess 2007 defines peripheral undercut 2009 with respect to axis 2010.

It is appreciated that, even though the illustrated embodiment shows the non-uniform thickness portion of artificial femoral head resurfacing element 2000 at the apex thereof, any suitable portion thereof may be of non-uniform thickness.

Figure 11B:
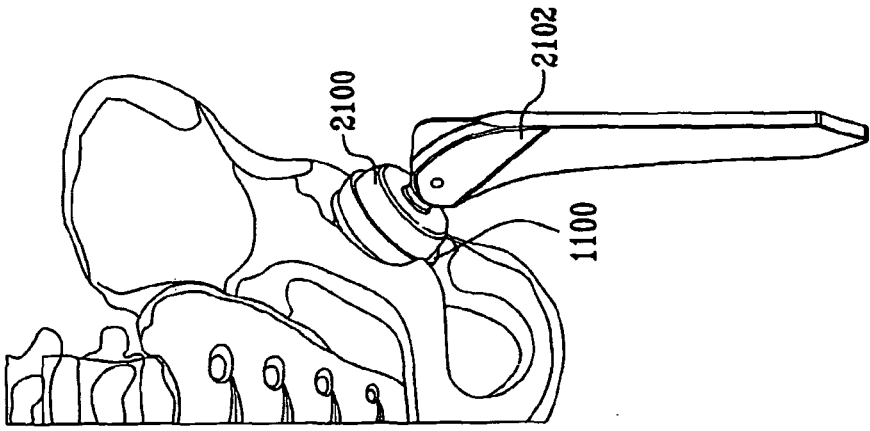
FIGS. 11A and 11B are respective exploded view and assembled view illustrations of the implantable artificial socket of FIGS. 1A-1C in a total hip replacement environment.
Figure 11A:
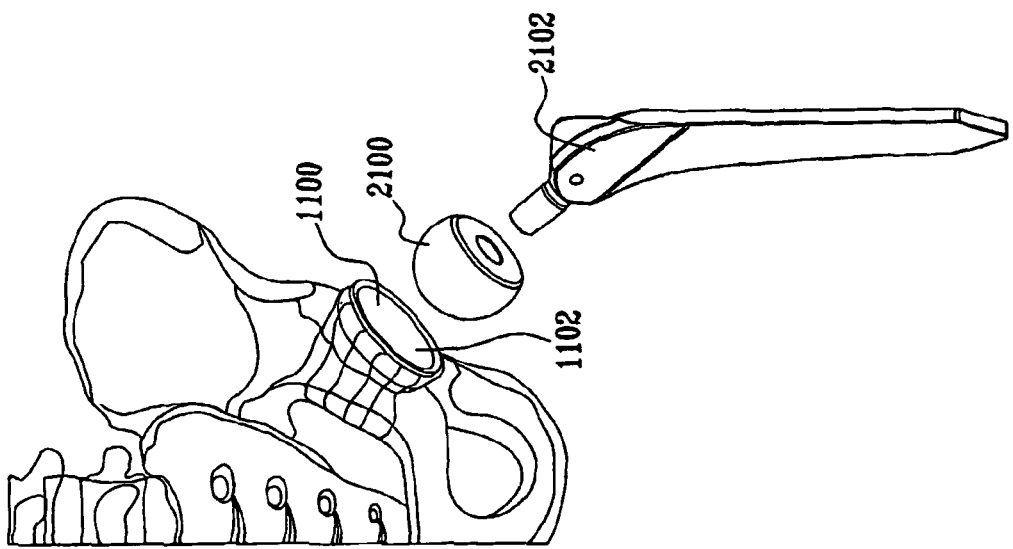

Reference is now made to FIGS. 11A and 11B, which are respective exploded view and assembled view illustrations of the implantable artificial acetabular socket of FIGS. 1A-1C in a total hip replacement environment. As seen in FIGS. 11A and 11B, implantable artificial acetabular socket 1100 (FIGS. 1A-1C) is snap-fitted into a suitably machined natural acetabulum of a patient. A conventional artificial femoral head 2100 is mounted onto a conventional femoral stem 2102 and is arranged for articulation with articulation surface 1102 of socket 1100.

Reference is now made to FIGS. 12A and 12B, which are respective exploded view and assembled view illustrations of the implantable artificial acetabular socket of FIGS. 1A-1C in a partial hip replacement environment. As seen in FIGS. 12A and 12B, implantable artificial acetabular socket 1100 (FIGS. 1A-1C) is snap-fitted into a suitably machined natural acetabulum of a patient. A natural femoral head 2200 is arranged for articulation with articulation surface 1102 of socket 1100.

It is a particular feature of the embodiment of FIGS. 12A and 12B that the size and configuration of articulation surface 1102 of artificial acetabular socket 1100 is made to be identical to that of the natural acetabular socket of the patient, in order that the natural femoral head 2200 may articulate therewith with desired dimensional clearances and without requiring machining of the femoral head. The ability of the articulation surface 1102 of socket 1100 to be identical to that of the natural femoral head 2200 is provided by the flexibility and resiliency of artificial acetabular socket 1100, which enables small adjustments in the size and configuration of the articulation surface 1102 to be realized by suitably exact machining of the natural acetabular socket.

Reference is now made to FIGS. 13A and 13B, which are respective exploded view and assembled view illustrations of the implantable artificial acetabular socket of FIGS. 1A-1C and the implantable artificial femoral head resurfacing element of FIGS. 6A-6C in a total hip resurfacing environment. As seen in FIGS. 13A and 13B, implantable artificial acetabular socket 1100 (FIGS. 1A-1C) is snap-fitted into a suitably machined natural acetabulum of a patient. A suitably machined natural femoral head 2300 having the implantable artificial femoral head resurfacing element 1600 of FIGS. 6A-6C snap-fit mounted thereon is arranged for articulation of articulation surface 1602 thereof with articulation surface 1102 of socket 1100.

Reference is now made to FIGS. 14A and 14B, which are respective exploded view and assembled view illustrations of the implantable artificial femoral head resurfacing element of FIGS. 6A-6C in a hemi hip resurfacing environment. As seen in FIGS. 14A and 14B, a suitably machined natural femoral head 2400 having the implantable artificial femoral head resurfacing element 1600 of FIGS. 6A-6C snap-fit mounted thereon is arranged for articulation of articulation surface 1602 thereof with a natural articulation surface of a natural acetabulum.

It is a particular feature of the embodiment of FIGS. 14A and 14B that the size and configuration of articulation surface 1602 of artificial femoral head resurfacing element 1600 is made to be identical to that of the natural acetabular socket of the patient, in order that the natural femoral head 2400 onto which artificial femoral head resurfacing element 1600 is mounted may articulate therewith with desired dimensional clearances and without requiring machining of the natural acetabulum. The ability of the articulation surface 1602 of femoral head resurfacing element 1600 to be identical to that of the natural acetabulum is provided by the flexibility and resiliency of artificial femoral head resurfacing element 1600, which enables small adjustments in the size and configuration of the articulation surface 1602 to be realized by suitably exact machining of the femoral head.

Figure 15A:
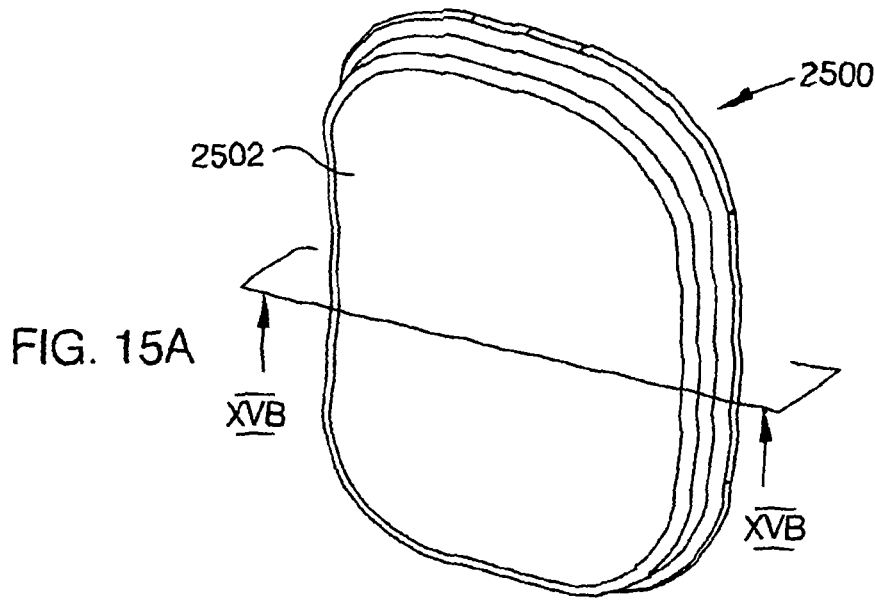
FIGS. 15A, 15B and 15C are respectively, an illustration of an articulation surface, a sectional illustration and an illustration of a bone engagement surface, of an implantable artificial socket for the glenoid constructed and operative in accordance with a preferred embodiment of the present invention.
Figure 15B:
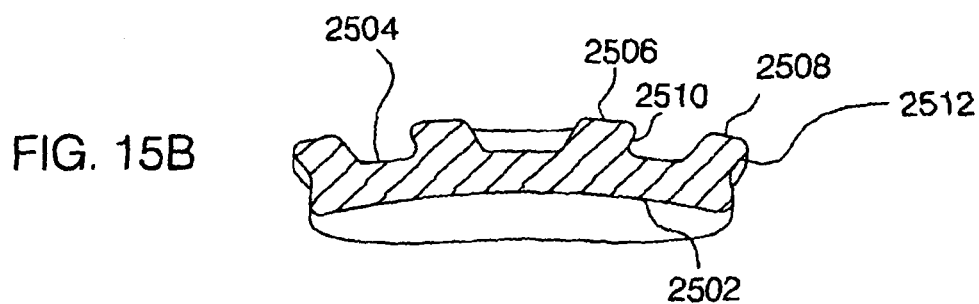
Figure 15C:
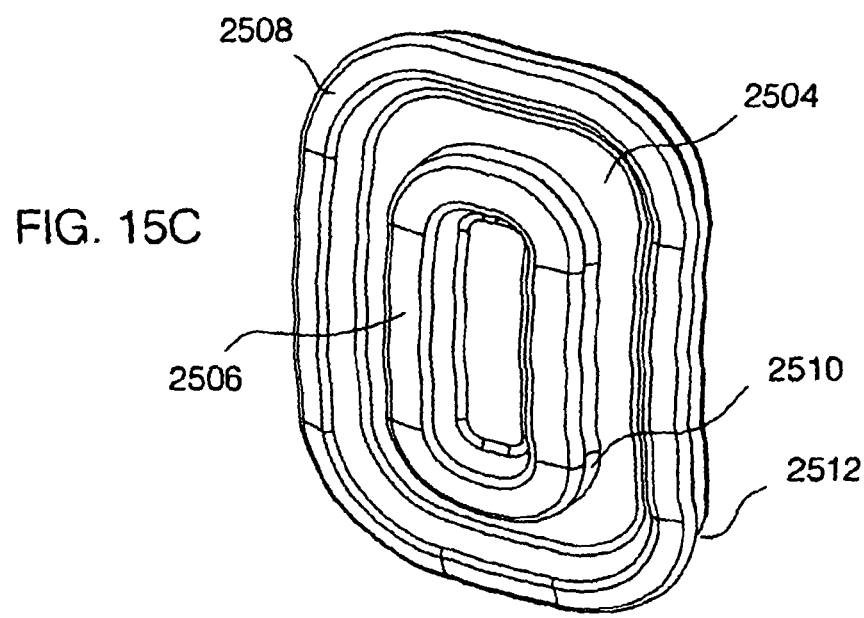

Reference is now made to FIGS. 15A, 15B and 15C, which are respectively, an illustration of an articulation surface, a sectional illustration and an illustration of a bone engagement surface, of an implantable artificial glenoid socket constructed and operative in accordance with a preferred embodiment of the present invention and which is particularly useful for a shoulder joint.

As seen in FIGS. 15A, 15B and 15C, an implantable artificial glenoid socket, designated by reference numeral 2500, is formed preferably by injection molding of polyurethane. Preferred polyurethane materials are described hereinbelow.

Preferably, implantable artificial glenoid socket 2500 is of generally uniform thickness and defines an articulation surface 2502, which defines a portion of a concave spherical surface, and a bone engagement surface 2504. Bone engagement surface 2504 preferably has formed thereon multiple protrusions. In the illustrated embodiment, there are provided inner and outer protrusions, respectively designated by reference numerals 2506 and 2508, defining respective undercuts 2510 and 2512. Alternatively, protrusions 2506 and 2508 may be any other suitable open or closed protrusions. Protrusions 2506 and 2508 are preferably arranged for snap-fit engagement with corresponding grooves formed by machining of the glenoid.

Figure 16A:
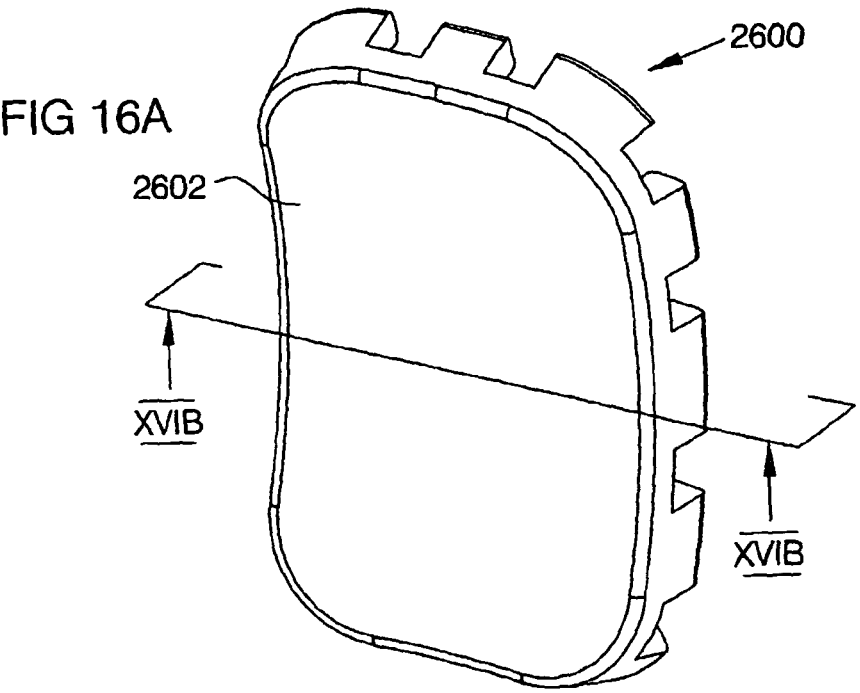
FIGS. 16A, 16B and 16C are respectively, an illustration of an articulation surface, a sectional illustration and an illustration of a bone engagement surface, of an implantable artificial socket for the glenoid constructed and operative in accordance with another preferred embodiment of the present invention.
Figure 16B:
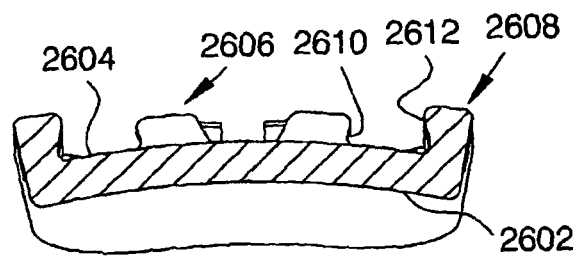
Figure 16C:
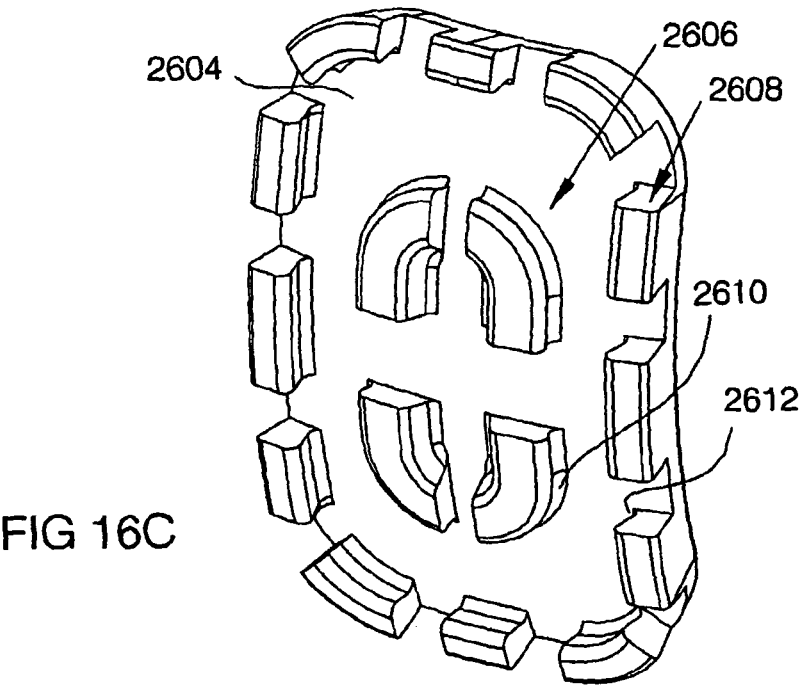

Reference is now made to FIGS. 16A, 16B and 16C, which are respectively, an illustration of an articulation surface, a sectional illustration and an illustration of a bone engagement surface, of an implantable artificial glenoid socket constructed and operative in accordance with another preferred embodiment of the present invention.

As seen in FIGS. 16A, 16B and 16C, an implantable artificial glenoid socket, designated by reference numeral 2600, is formed preferably by injection molding of polyurethane. Preferred polyurethane materials are described hereinbelow.

Preferably, implantable artificial glenoid socket 2600 is of generally uniform thickness and defines an articulation surface 2602, which defines a portion of a concave spherical surface, and a bone engagement surface 2604. Bone engagement surface 2604 preferably has formed thereon multiple protrusions. In the illustrated embodiment, there are provided inner and outer arrays of protrusions, the arrays being respectively designated by reference numerals 2606 and 2608, defining respective undercuts 2610 and 2612. Alternatively, protrusions of arrays 2606 and 2608 may be any other suitable open or closed protrusions. Protrusions 2606 and 2608 are preferably arranged for snap-fit engagement with corresponding grooves formed by machining of the glenoid.

Reference is now made to FIGS. 17A, 17B and 17C, which are respectively, an illustration of an articulation surface, a sectional illustration and an illustration of a bone engagement surface, of an implantable artificial glenoid socket constructed and operative in accordance with yet another preferred embodiment of the present invention.

As seen in FIGS. 17A, 17B and 17C, an implantable artificial glenoid socket, designated by reference numeral 2700, is formed preferably by injection molding of polyurethane. Preferred polyurethane materials are described hereinbelow.

Preferably, implantable artificial glenoid socket 2700 is of generally uniform thickness and defines an articulation surface 2702, which defines a portion of a concave spherical surface, and a bone engagement surface 2704. Bone engagement surface 2704 preferably has formed thereon multiple protrusions. In the illustrated embodiment, there are provided an inner array of protrusions 2706 and an outer peripheral protrusion 2708, defining respective undercuts 2710 and 2712. Alternatively, protrusions of array 2706 and protrusion 2708 may be any other suitable open or closed protrusions. Protrusions of array 2706 and protrusion 2708 are preferably arranged for snap-fit engagement with corresponding grooves formed by machining of the glenoid.

Preferably, at least some of the protrusions of array 2706, here designated as protrusions 2713 have a generally button-like configuration which is symmetric about an axis 2714 and include a body portion 2715 and an enlarged head portion 2716, as can be readily seen in FIG. 17B. Protrusions 2713 are generally characterized in that an underlying surface portion 2717 of each protrusion 2713 defines peripheral undercut 2710 with respect to axis 2714.

Figure 18A:
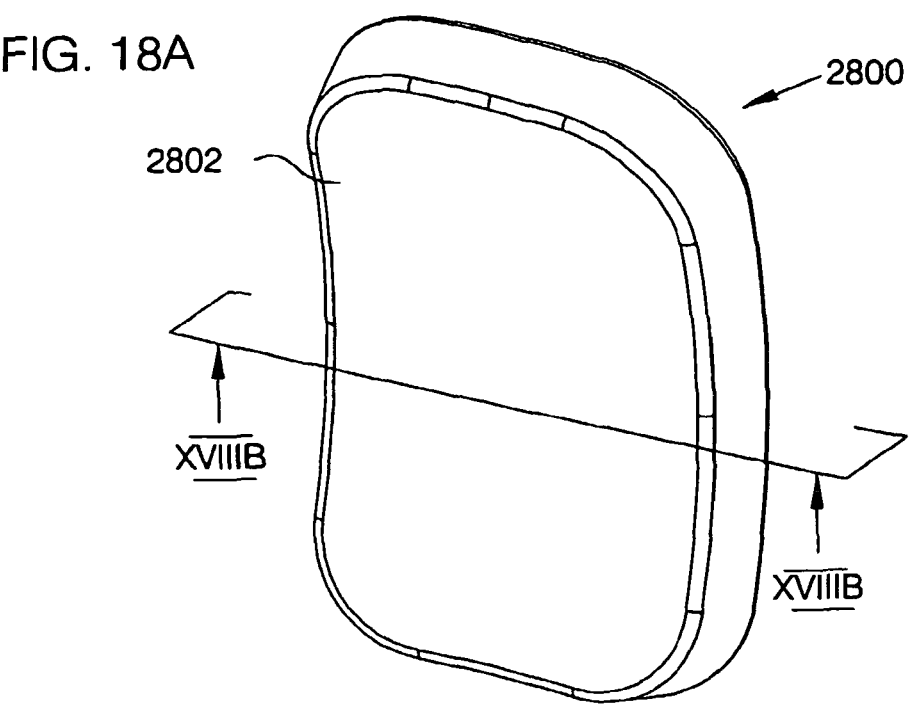
FIGS. 18A, 18B and 18C are respectively, an illustration of an articulation surface, a sectional illustration and an illustration of a bone engagement surface, of an implantable artificial socket for the glenoid constructed and operative in accordance with yet another preferred embodiment of the present invention.
Figure 18B:
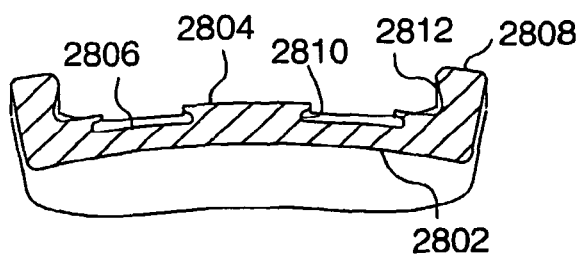
Figure 18C:
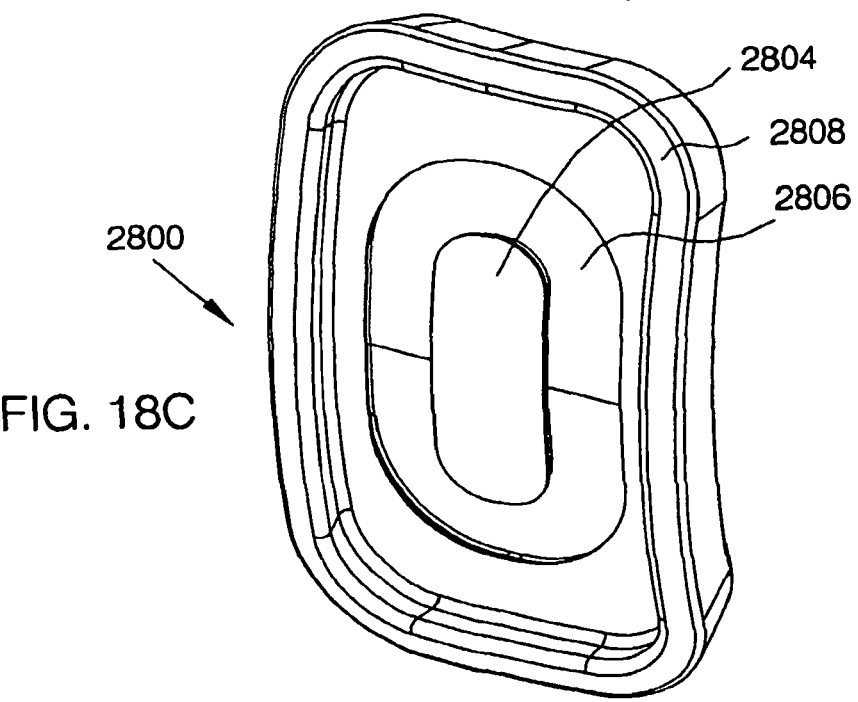

Reference is now made to FIGS. 18A, 18B and 18C, which are respectively, an illustration of an articulation surface, a sectional illustration and an illustration of a bone engagement surface, of an implantable artificial glenoid socket constructed and operative in accordance with still another preferred embodiment of the present invention.

As seen in FIGS. 18A, 18B and 18C, an implantable artificial glenoid socket, designated by reference numeral 2800, is formed preferably by injection molding of polyurethane. Preferred polyurethane materials are described hereinbelow.

Preferably, implantable artificial glenoid socket 2800 is of generally uniform thickness and defines an articulation surface 2802, which defines a portion of a concave spherical surface, and a bone engagement surface 2804. Bone engagement surface 2804 preferably has formed thereon an inner recess and an outer protrusion, respectively designated by reference numerals 2806 and 2808, defining respective undercuts 2810 and 2812. Alternatively, recess 2806 and protrusion 2808 may be any other suitable, open or closed, recesses or protrusions, respectively. Recess 2806 and protrusion 2808 are preferably arranged for snap-fit engagement with corresponding protrusions and grooves respectively formed by machining of the glenoid.

Figure 19A:
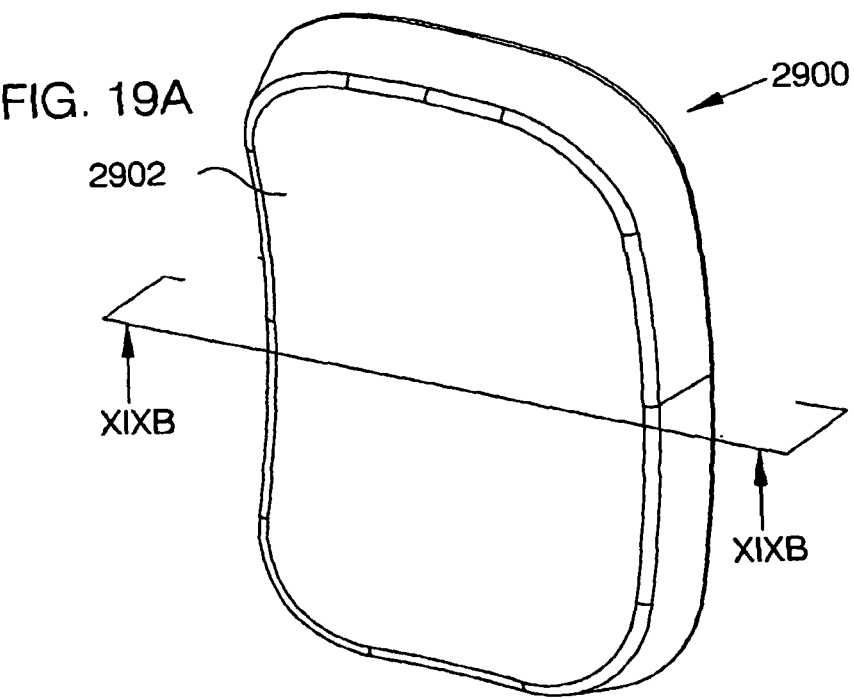
FIGS. 19A, 19B and 19C are respectively, an illustration of an articulation surface, a sectional illustration and an illustration of a bone engagement surface, of an implantable artificial socket for the glenoid constructed and operative in accordance with a further preferred embodiment of the present invention.
Figure 19B:
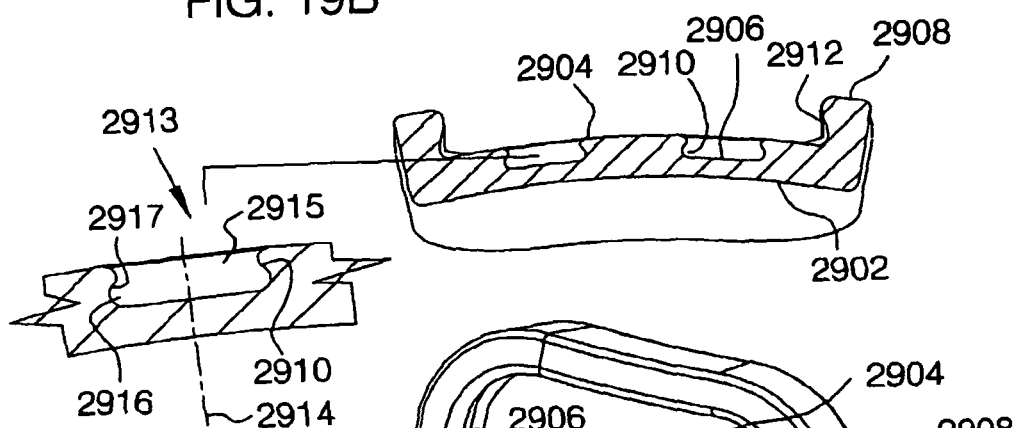
Figure 19C:
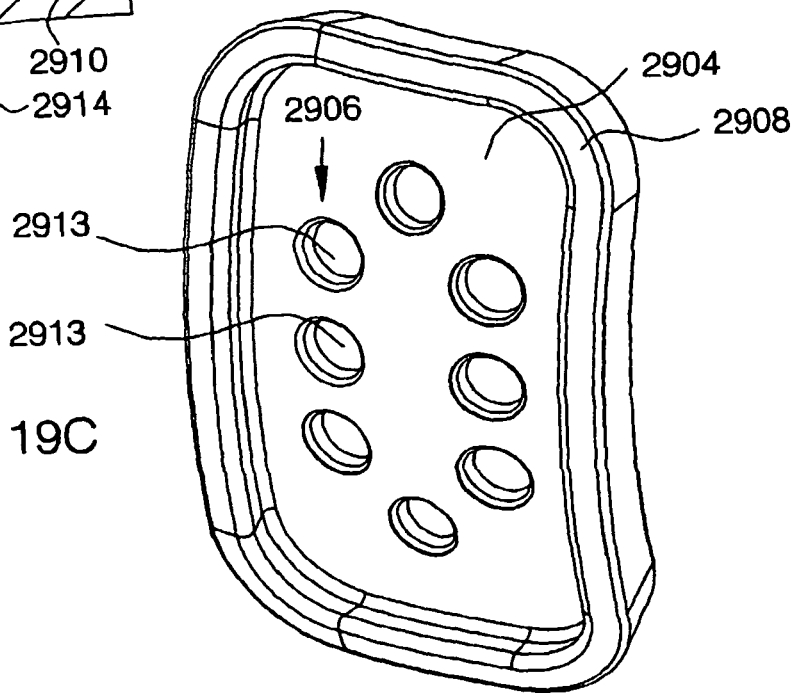

Reference is now made to FIGS. 19A, 19B and 19C, which are respectively, an illustration of an articulation surface, a sectional illustration and an illustration of a bone engagement surface, of an implantable artificial glenoid socket constructed and operative in accordance with yet another preferred embodiment of the present invention.

As seen in FIGS. 19A, 19B and 19C, an implantable artificial glenoid socket, designated by reference numeral 2900, is formed preferably by injection molding of polyurethane. Preferred polyurethane materials are described hereinbelow.

Preferably, implantable artificial glenoid socket 2900 is of generally uniform thickness and defines an articulation surface 2902, which defines a portion of a concave spherical surface, and a bone engagement surface 2904. Bone engagement surface 2904 preferably has formed thereon multiple recesses and/or protrusions. In the illustrated embodiment, there are provided an inner array of recesses 2906 and an outer peripheral protrusion 2908, defining respective undercuts 2910 and 2912. Alternatively, recesses of array 2906 and protrusion 2908 may be any other suitable, open or closed, recesses and protrusion, respectively. Recesses of array 2906 and protrusion 2908 are preferably arranged for snap-fit engagement with corresponding protrusions and grooves respectively, formed by machining of the glenoid.

Preferably, at least some of the recesses of array 2906, here designated as recesses 2913, have a generally button-like configuration which is symmetric about an axis 2914 and include a body portion 2915 and an enlarged head portion 2916, as can be readily seen in FIG. 19B. Recesses 2913 are generally characterized in that an underlying surface portion 2917 of each protrusion 2913 defines peripheral undercut 2910 with respect to axis 2914.

Reference is now made to FIGS. 20A, 20B and 20C, which are respective pictorial, sectional and partially cut away illustrations of an implantable artificial humeral head surface element constructed and operative in accordance with a preferred embodiment of the present invention. The implantable artificial humeral head surface element is intended for mounting onto a natural humeral head in accordance with a preferred embodiment of the present invention.

As seen in FIGS. 20A, 20B and 20C, an implantable artificial humeral head surface element, designated by reference numeral 3000, is formed preferably by injection molding of polyurethane. Preferred polyurethane materials are described hereinbelow.

Preferably, implantable artificial humeral head surface element 3000 is of generally uniform thickness, other than at its apex which is thickened, is symmetric about an axis 3001 and defines an articulation surface 3002, which defines a portion of a convex spherical surface, and a bone engagement surface 3004, having a beveled edge 3005, which preferably has formed thereon, at any suitable location between its apex and its rim, a generally annular inwardly extending protrusion 3006, preferably defining a generally annular undercut 3008. Alternatively, the protrusion 3006 may be any other suitable non-annular, open or closed, generally peripheral, protrusion. The protrusion 3006 is preferably arranged for snap-fit engagement with a corresponding groove formed by reaming of a humeral head.

Preferably, the protrusion 3006 has a cross-sectional configuration, as can be readily seen in FIG. 20B, which is characterized in that an underlying surface portion 3010 of protrusion 3006, at the undercut 3008, defines a slope which is sharper than a corresponding slope of an overlying surface portion 3012 of protrusion 3006.

It is appreciated that, even though the illustrated embodiment shows the non-uniform thickness portion of artificial humeral head surface element 3000 at the apex thereof, any suitable portion thereof may be of non-uniform thickness.

Reference is now made to FIGS. 21A, 21B and 21C, which are respective pictorial, sectional and partially cut away illustrations of an implantable artificial humeral head surface element constructed and operative in accordance with another preferred embodiment of the present invention.

As seen in FIGS. 21A, 21B and 21C, an implantable artificial humeral head surface element, designated by reference numeral 3100, is formed preferably by injection molding of polyurethane. Preferred polyurethane materials are described hereinbelow.

Preferably, implantable artificial humeral head surface element 3100 is of generally uniform thickness, other than at its apex which is thickened, is symmetric about an axis 3101 and defines an articulation surface 3102, which defines a portion of a convex spherical surface, and a bone engagement surface 3104, having a beveled edge 3105, which preferably has formed thereon, at any suitable location between its apex and its rim, a generally annular inwardly extending array 3106 of discrete protrusions 3107, preferably defining a generally annular array 3108 of undercuts 3109. Alternatively, the array 3106 may be any other suitable non-annular, open or closed, generally peripheral, array of protrusions. The array 3106 of protrusions 3107 is preferably arranged for snap-fit engagement with corresponding grooves formed inter alia by reaming of a humeral head.

Preferably, the protrusions 3107 have a cross-sectional configuration, as can be readily seen in FIG. 21B, which is characterized in that an underlying surface portion 3110 of each protrusion 3107, at the undercut 3109, defines a slope which is sharper than a corresponding slope of an overlying surface portion 3112 of the protrusion 3107

It is appreciated that, even though the illustrated embodiment shows the non-uniform thickness portion of artificial humeral head surface element 3100 at the apex thereof, any suitable portion thereof may be of non-uniform thickness.

Figure 22A:
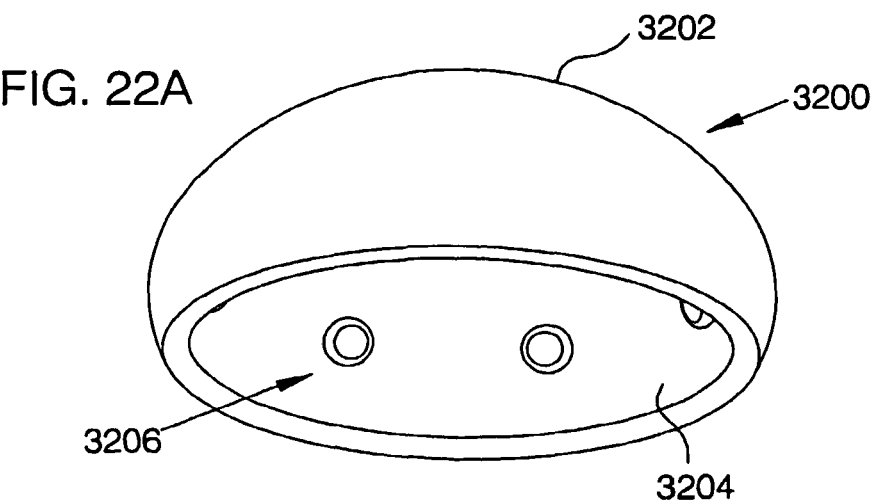
FIGS. 22A, 22B and 22C are respective pictorial, sectional and partially cut away illustrations of an implantable artificial humeral head surface element constructed and operative in accordance with still another preferred embodiment of the present invention.
Figure 22B:
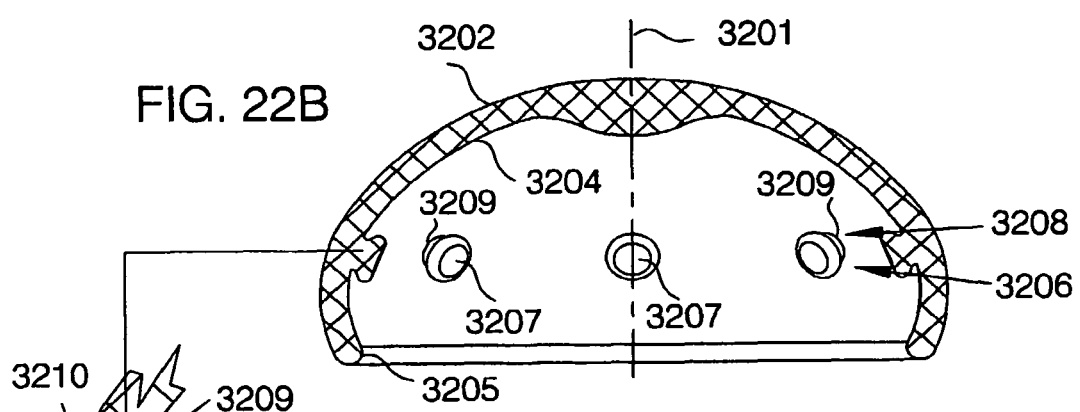
Figure 22C:
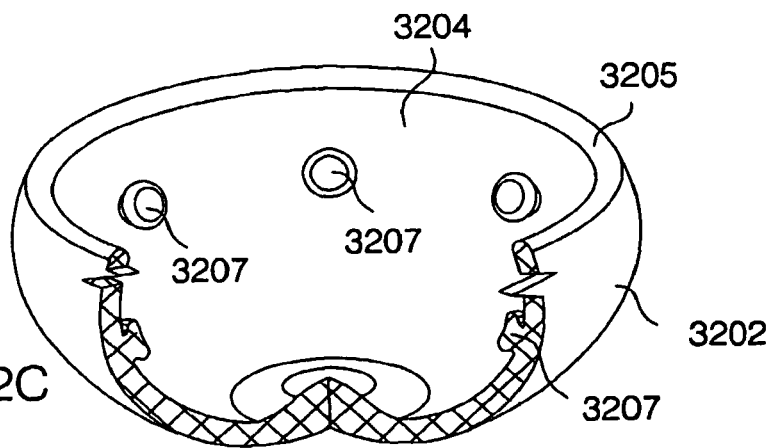

Reference is now made to FIGS. 22A, 22B and 22C, which are respective pictorial, sectional and partially cut away illustrations of an implantable artificial humeral head surface element constructed and operative in accordance with still another preferred embodiment of the present invention.

As seen in FIGS. 22A, 22B and 22C, an implantable artificial humeral head surface element, designated by reference numeral 3200, is formed preferably by injection molding of polyurethane. Preferred polyurethane materials are described hereinbelow.

Preferably, implantable artificial humeral head surface element 3200 is of generally uniform thickness, other than at its apex which is thickened, is symmetric about an axis 3201 and defines an articulation surface 3202, which defines a portion of a convex spherical surface, and a bone engagement surface 3204, having a beveled edge 3205, which preferably has formed thereon, at any suitable location between its apex and its rim, a generally annular inwardly extending array 3206 of discrete protrusions 3207, preferably defining a generally annular array 3208 of undercuts 3209. Alternatively, the array 3206 may be any other suitable non-annular, open or closed, generally peripheral, array of protrusions. The array 3206 of protrusions 3207 is preferably arranged for snap-fit engagement with corresponding recesses formed inter alia by suitable machining of a humeral head.

Preferably, the protrusions 3207 have a generally button-like configuration which is symmetric about an axis 3210 and include a body portion 3211 and an enlarged head portion 3212, as can be readily seen in FIG. 22B. Protrusions 3207 are generally characterized in that an underlying surface portion 3213 of each protrusion 3207 defines peripheral undercut 3209 with respect to axis 3210.

It is appreciated that, even though the illustrated embodiment shows the non-uniform thickness portion of artificial humeral head surface element 3200 at the apex thereof, any suitable portion thereof may be of non-uniform thickness.

Figure 23A:
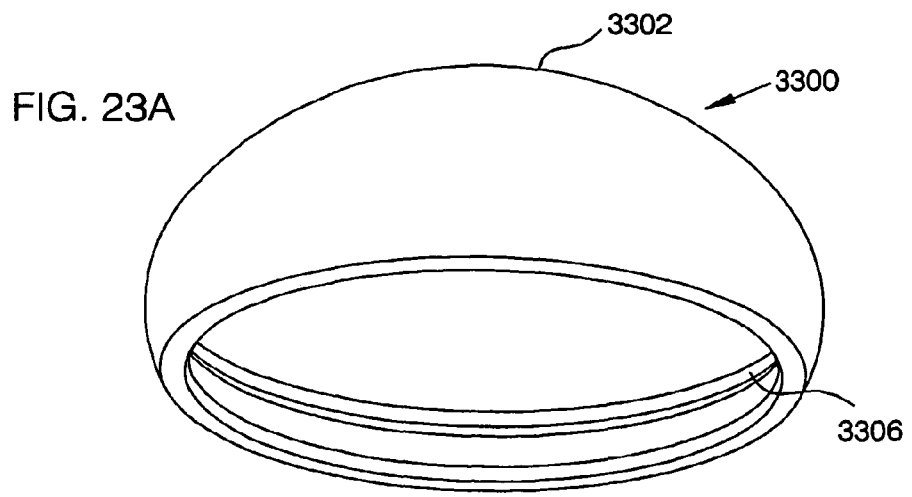
FIGS. 23A, 23B and 23C are respective pictorial, sectional and partially cut away illustrations of an implantable artificial humeral head surface element constructed and operative in accordance with yet another preferred embodiment of the present invention.
Figure 23B:
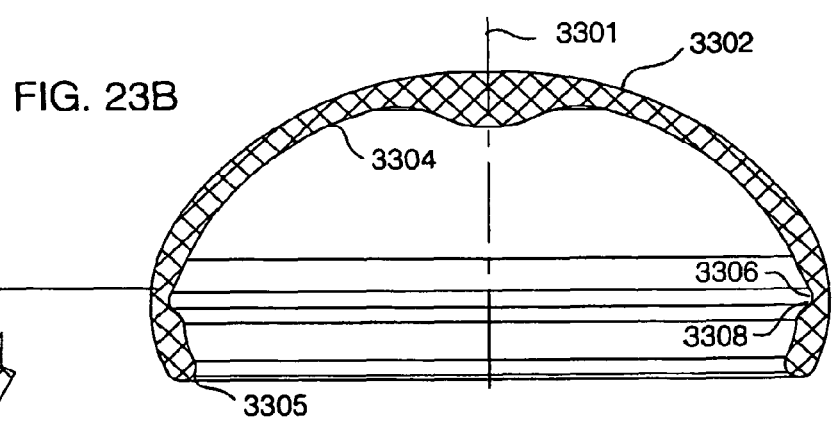
Figure 23C:
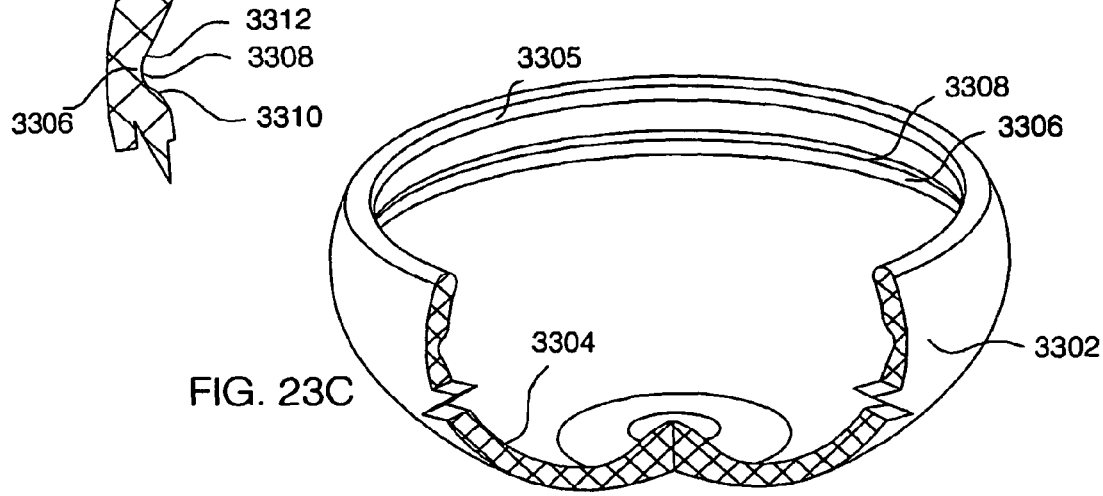

Reference is now made to FIGS. 23A, 23B and 23C, which are respective pictorial, sectional and partially cut away illustrations of an implantable artificial humeral head surface element constructed and operative in accordance with yet another preferred embodiment of the present invention.

As seen in FIGS. 23A, 23B and 23C, an implantable artificial humeral head surface element, designated by reference numeral 3300, is formed preferably by injection molding of polyurethane. Preferred polyurethane materials are described hereinbelow.

Preferably, implantable artificial humeral head surface element 3300 is of generally uniform thickness, other than at its apex which is thickened, is symmetric about an axis 3301 and defines an articulation surface 3302, which defines a portion of a convex spherical surface, and a bone engagement surface 3304, having a beveled edge 3305, which preferably has formed thereon, at any suitable location between its apex and its rim, a generally annular outwardly extending recess 3306, preferably defining a generally annular undercut 3308. Alternatively, the recess 3306 may be any other suitable non-annular, open or closed, generally peripheral, protrusion. The recess 3306 is preferably arranged for snap-fit engagement with a corresponding protrusion formed by reaming of a humeral head.

Preferably, the recess 3306 has a cross-sectional configuration, as can be readily seen in FIG. 23B, which is characterized in that an overlying surface portion 3310 of recess 3306, at the undercut 3308, defines a slope which is sharper than a corresponding slope of an underlying surface portion 3312 of recess 3306.

It is appreciated that, even though the illustrated embodiment shows the non-uniform thickness portion of artificial humeral head surface element 3300 at the apex thereof, any suitable portion thereof may be of non-uniform thickness.

Figure 24A:
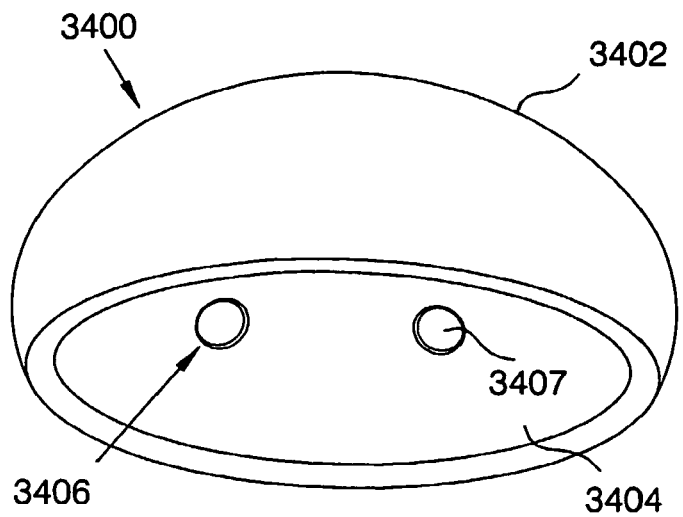
FIGS. 24A, 24B and 24C are respective pictorial, sectional and partially cut away illustrations of an implantable artificial humeral head surface element constructed and operative in accordance with a further preferred embodiment of the present invention.
Figure 24B:
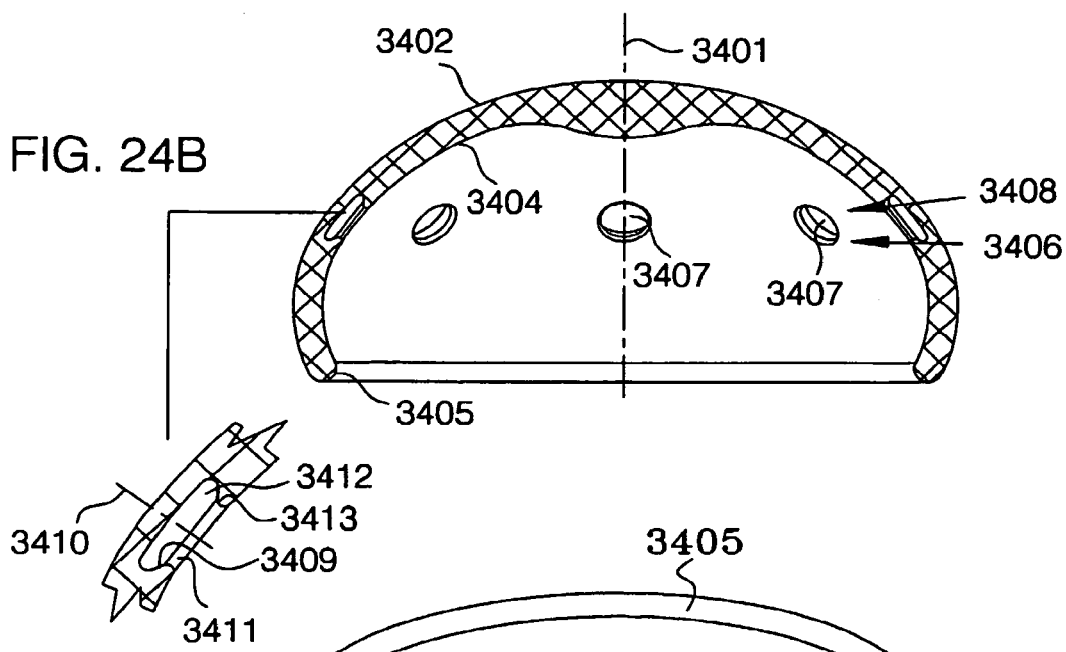
Figure 24C:
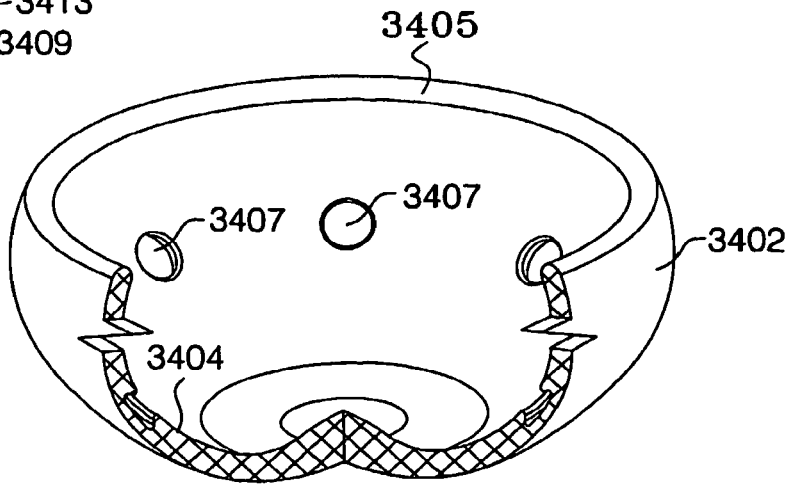

Reference is now made to FIGS. 24A, 24B and 24C, which are respective pictorial, sectional and partially cut away illustrations of an implantable artificial humeral head surface element constructed and operative in accordance with still another preferred embodiment of the present invention.

As seen in FIGS. 24A, 24B and 24C, an implantable artificial humeral head surface element, designated by reference numeral 3400, is formed preferably by injection molding of polyurethane. Preferred polyurethane materials are described hereinbelow.

Preferably, implantable artificial humeral head surface element 3400 is of generally uniform thickness, other than at its apex which is thickened, is symmetric about an axis 3401 and defines an articulation surface 3402, which defines a portion of a convex spherical surface, and a bone engagement surface 3404, having a beveled edge 3405, which preferably has formed thereon, at any suitable location between its apex and its rim, a generally annular outwardly extending array 3406 of discrete recesses 3407, preferably defining a generally annular array 3408 of undercuts 3409. Alternatively, the array 3406 may be any other suitable non-annular, open or closed, generally peripheral, array of recesses. The array 3406 of recesses 3407 is preferably arranged for snap-fit engagement with corresponding protrusions formed inter alia by suitable machining of a humeral head.

Preferably, the recesses 3407 have a generally button-like configuration which is symmetric about an axis 3410 and include a body portion 3411 and an enlarged head portion 3412, as can be readily seen in FIG. 24B. Recesses 3407 are generally characterized in that an overlying surface portion 3413 of each recess 3407 defines peripheral undercut 3409 with respect to axis 3410.

It is appreciated that, even though the illustrated embodiment shows the non-uniform thickness portion of artificial humeral head surface element 3400 at the apex thereof, any suitable portion thereof may be of non-uniform thickness.

Figure 25B:
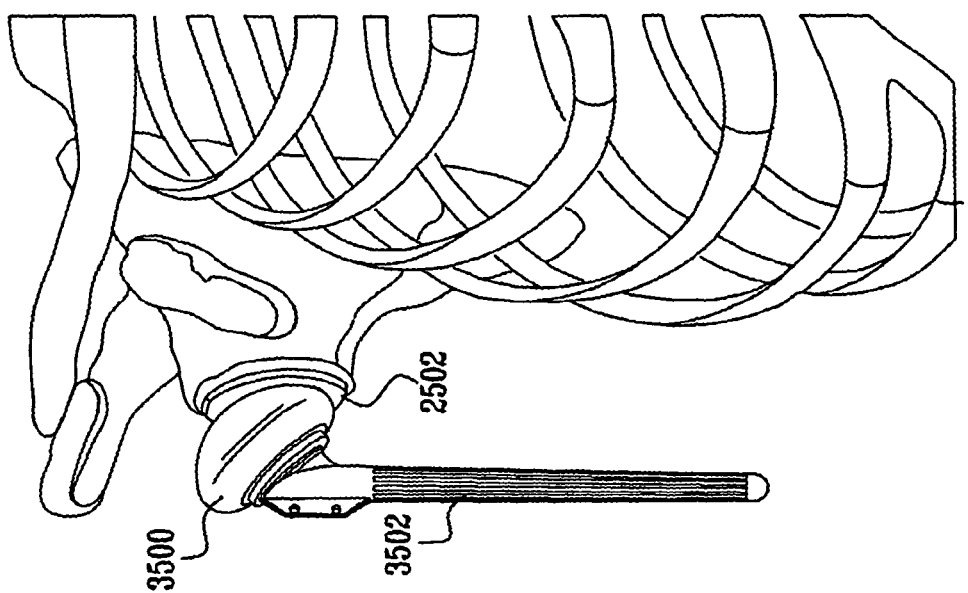
FIGS. 25A and 25B are respective exploded view and assembled view illustrations of the implantable artificial glenoid socket of FIGS. 15A-15C in a total shoulder replacement environment.
Figure 25A:
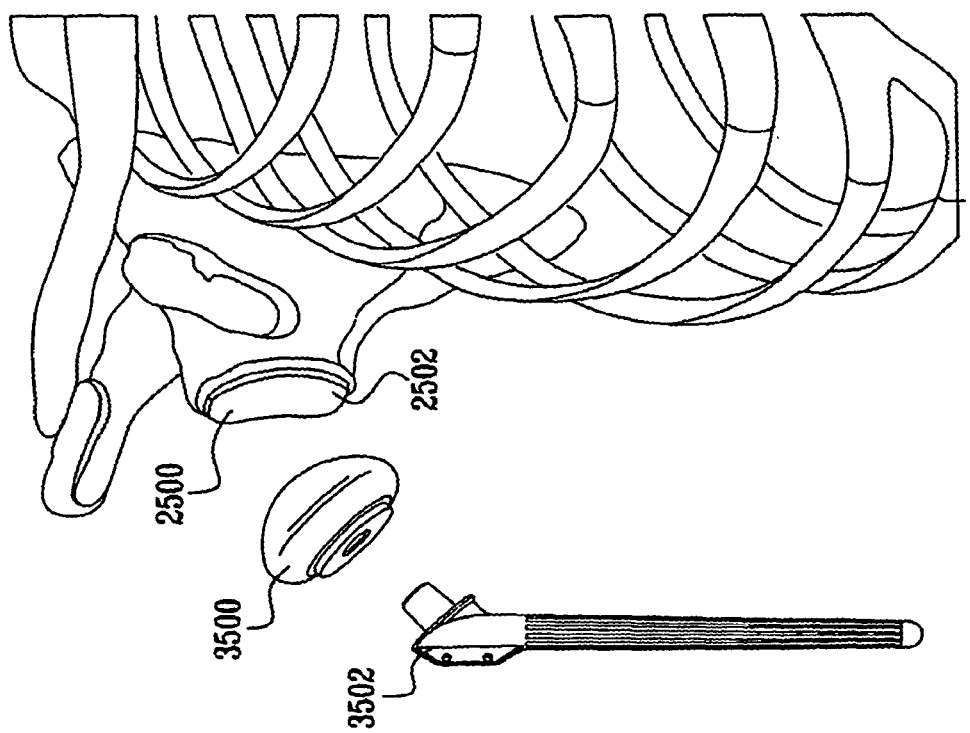

Reference is now made to FIGS. 25A and 25B, which are respective exploded view and assembled view illustrations of the implantable artificial glenoid socket of FIGS. 15A-15C in a total shoulder replacement environment. As seen in FIGS. 25A and 25B, implantable artificial glenoid socket 2500 (FIGS. 15A-15C) is snap-fitted into a suitably machined natural glenoid of a patient. A conventional artificial humeral head 3500 is mounted onto a conventional humeral stem 3502 and is arranged for articulation with articulation surface 2502 of socket 2500.

Figure 26A:
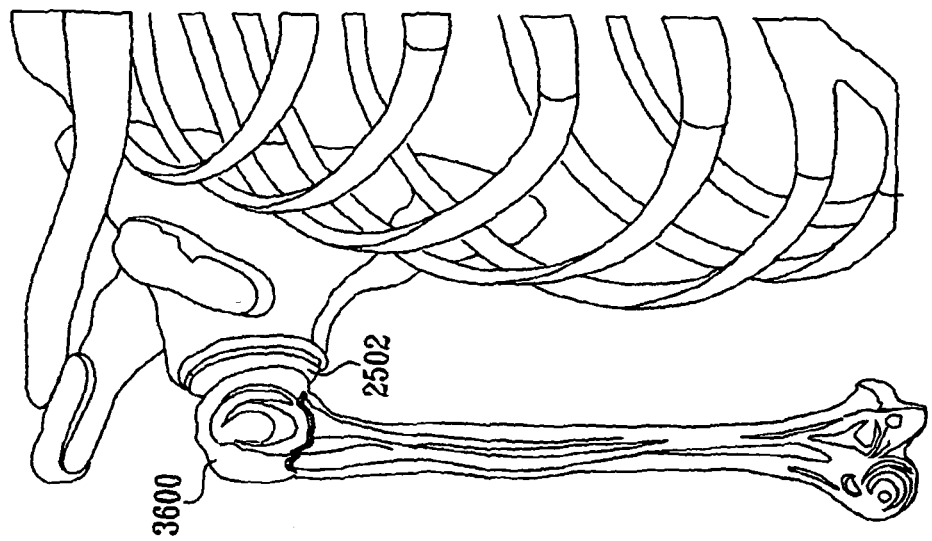
FIGS. 26A and 26B are respective exploded view and assembled view illustrations of the implantable artificial glenoid socket of FIGS. 15A-15C in a partial shoulder replacement environment.
Figure 26B:
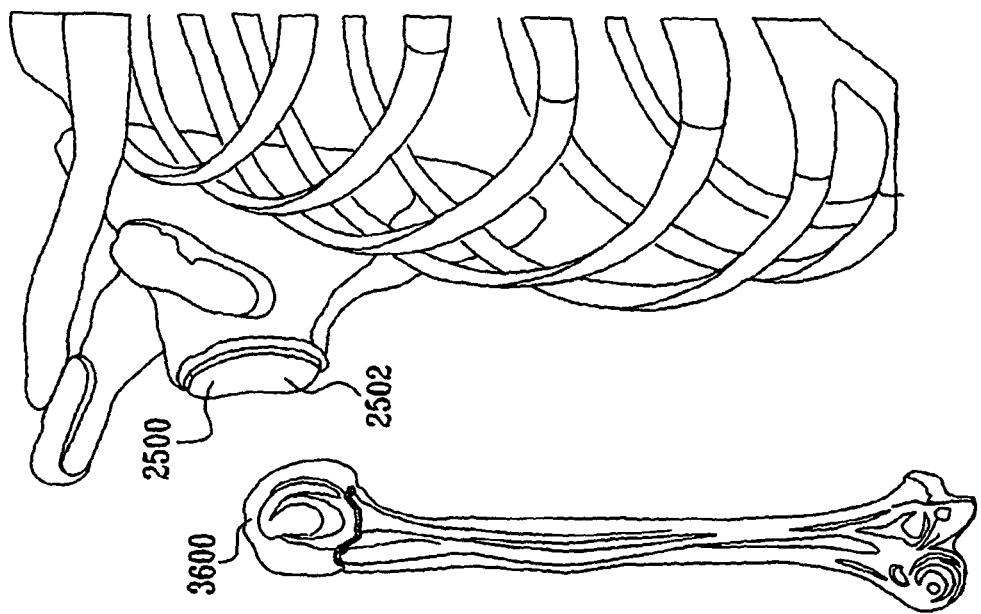

Reference is now made to FIGS. 26A and 26B, which are respective exploded view and assembled view illustrations of the implantable artificial glenoid socket of FIGS. 15A-15C in a partial shoulder replacement environment. As seen in FIGS. 26A and 26B, implantable artificial glenoid socket 2500 (FIGS. 15A-15C) is snap-fitted into a suitably machined natural glenoid of a patient. A natural humeral head 3600 is arranged for articulation with articulation surface 2502 of socket 2500.

It is a particular feature of the embodiment of FIGS. 26A and 26B that the size and configuration of articulation surface 2502 of artificial glenoid socket 2500 is made to be identical to that of the natural glenoid socket of the patient, in order that the natural humeral head 3600 may articulate therewith with desired dimensional clearances and without requiring machining of the humeral head. The ability of the articulation surface 2502 of socket 2500 to be identical to that of the natural humeral head is provided by the flexibility and resiliency of artificial glenoid socket 2500, which enables small adjustments in the size and configuration of the articulation surface 2502 to be realized by suitably exact machining of the natural glenoid socket.

Figure 27B:
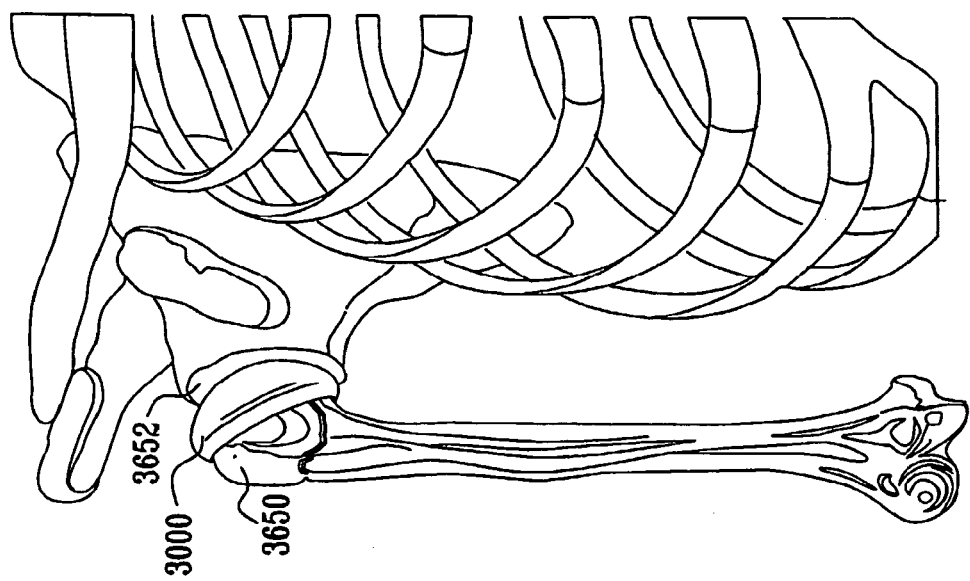
FIGS. 27A and 27B are respective exploded view and assembled view illustrations of the implantable artificial humeral head surface element of FIGS. 20A-20C in a hemi shoulder resurfacing environment.
Figure 27A:
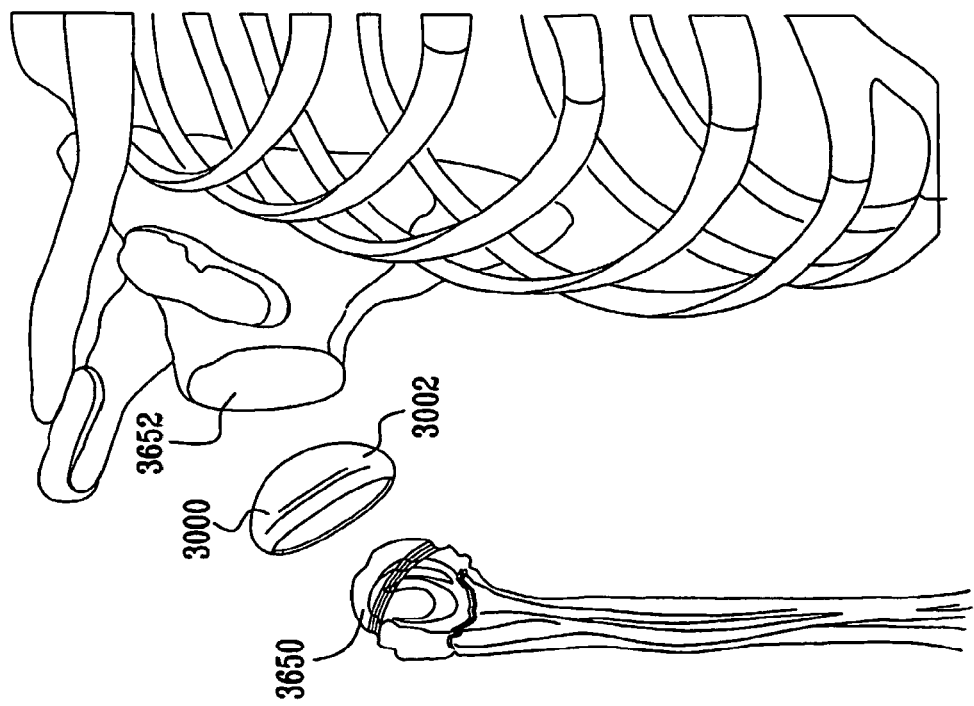

Reference is now made to FIGS. 27A and 27B, which are respective exploded view and assembled view illustrations of the implantable artificial humeral head surface element of FIGS. 20A-20C in a hemi shoulder resurfacing environment. As seen in FIGS. 27A and 27B, a suitably machined natural humeral head 3650 having she implantable artificial humeral head surface element 3000 of FIGS. 20A-20C snap-fit mounted thereon is arranged for articulation of articulation surface 3002 thereof with a natural articulation surface 3652 of a natural glenoid.

It is a particular feature of the embodiment of FIGS. 27A and 27B that the size and configuration of articulation surface 3002 of artificial humeral head surface element 3000 is made to be identical to that of the natural glenoid socket 3652 of the patient, in order that the natural humeral head 3650 onto which artificial humeral head surface element 3000 is mounted may articulate therewith with desired dimensional clearances and without requiring machining of the natural glenoid. The ability of the articulation surface 3002 of humeral head surface element 3000 to be identical to that of the natural glenoid is provided by the flexibility and resiliency of artificial humeral head surface element 3000, which enables small adjustments in the size and configuration of the articulation surface 3002 to be realized by suitably exact machining of the humeral head.

Figure 28B:
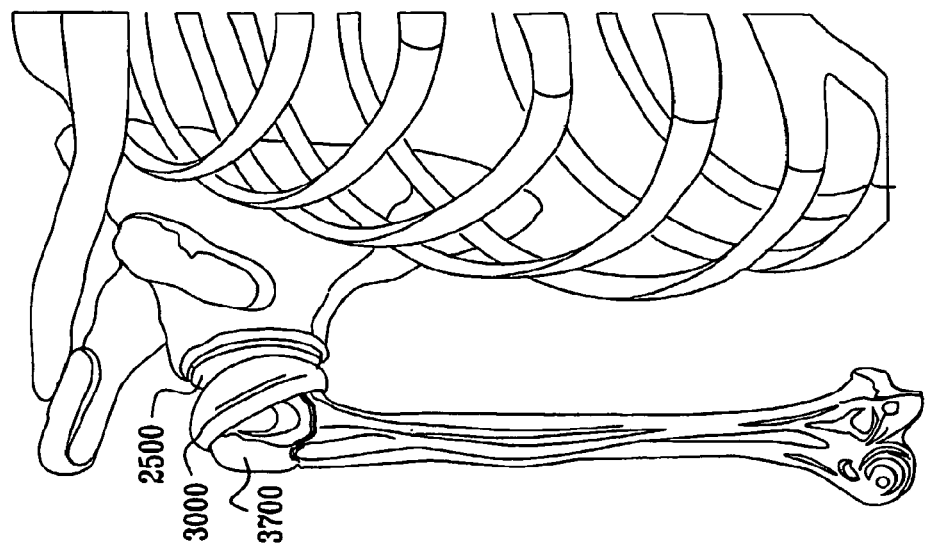
FIGS. 28A and 28B are respective exploded view and assembled view illustrations of the implantable artificial glenoid socket of FIGS. 15A-15C and the implantable artificial humeral head surface element of FIGS. 20A-20C in a total shoulder resurfacing environment.
Figure 28A:
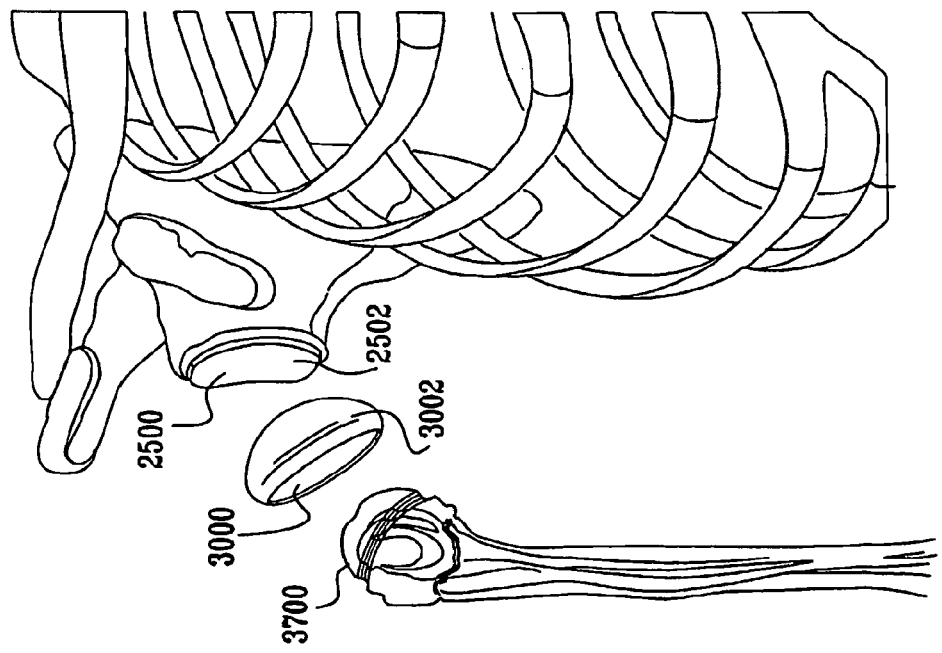

Reference is now made to FIGS. 28A and 28B, which are respective exploded view and assembled view illustrations of the implantable artificial glenoid socket of FIGS. 15A-15C and the implantable artificial humeral head surface element of FIGS. 20A-20C in a total shoulder resurfacing environment. As seen in FIGS. 28A and 28B, implantable artificial glenoid socket 2500 (FIGS. 15A-15C) is snap-fitted into a suitably machined natural glenoid of a patient. A suitably machined natural humeral head 3700 having the implantable artificial humeral head surface element 3000 of FIGS. 20A-20C snap-fit mounted thereon is arranged for articulation of articulation surface 3002 thereof with articulation surface 2502 of socket 2500.

Figure 29A:
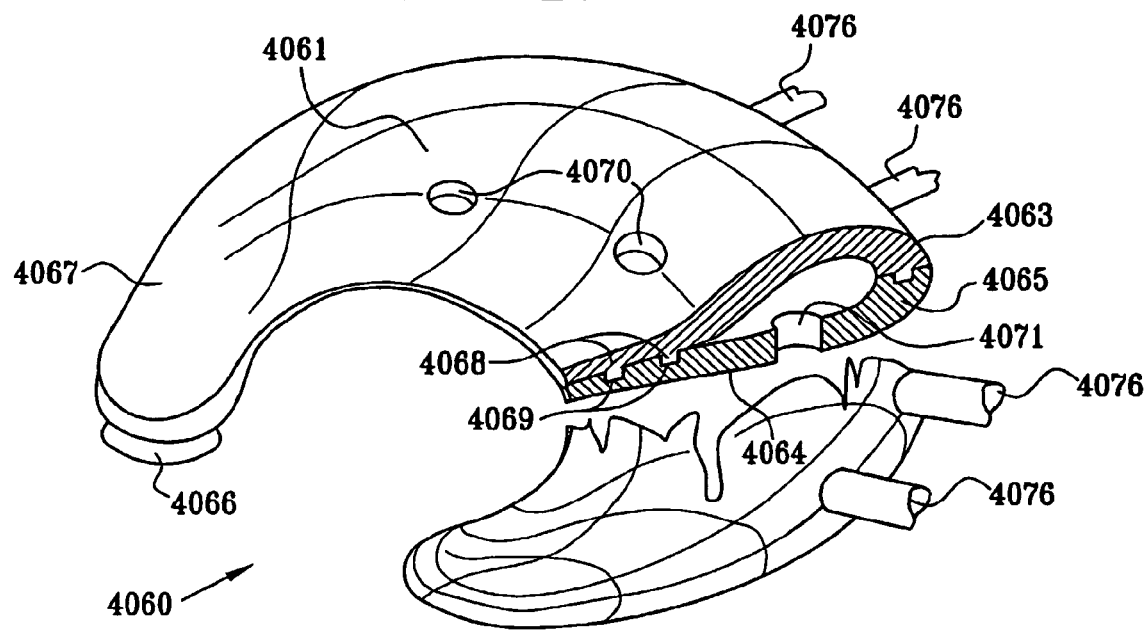
FIGS. 29A and 29B are pictorial illustrations showing an implantable artificial medial meniscus implant assembly constructed and operative in accordance with a preferred embodiment of the present invention.
Figure 29B:
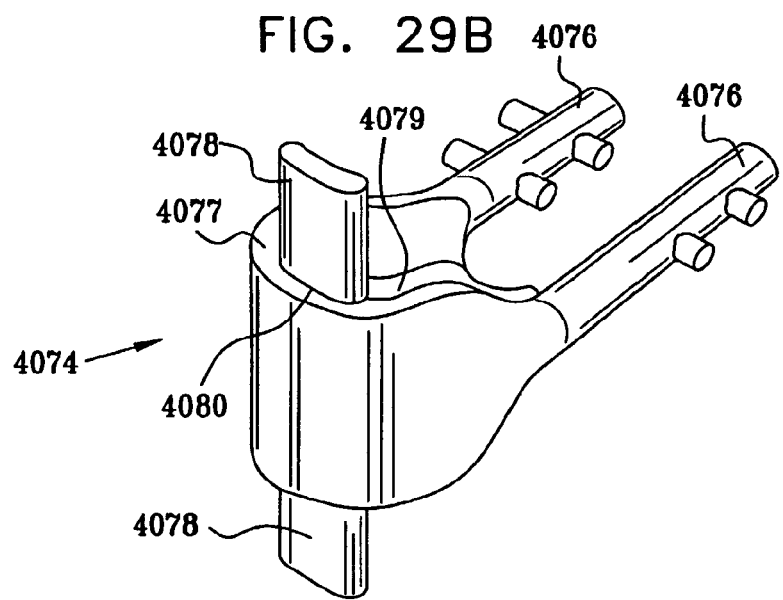

Reference is now made to FIGS. 29A and 29B, which are pictorial illustrations showing an implantable artificial medial meniscus implant assembly constructed and operative in accordance with a preferred embodiment of the present invention. As seen in FIGS. 29A and 29B, an implantable artificial medial meniscus implant assembly, designated by reference numeral 4060, is formed preferably by injection molding of polyurethane. Preferred polyurethane materials are described hereinbelow Preferably, implantable meniscus implant assembly 4060 defines a concave articulation surface 4061, which is defined on an articulation portion 4063, a convex articulation surface 4064, which is defined on an articulation portion 4065, and a bone snap-fit engagement element 4066 for locking engagement with a matching machined tibia recess (not shown) which is defined on a bone anchoring portion 4067. Articulation portion 4063 preferably has formed thereon multiple protrusions 4068 for snap-fit engagement with multiple recesses 4069 defined on articulation portion 4065.

Articulation portions 4063 and 4065 may alternatively be formed as one piece constructed to fold and snap-fit on itself, only in some portions of the snap-fit engagement regions provided in assembly 4060.

Articulation portion 4063 has formed, in articulation surface 4061, a plurality of thoroughgoing apertures 4070, which, as described hereinbelow, allow synovial fluid to pass therethrough for lubrication of the articulation surface 4061 when articulation portion 4063 articulates with the articulation surface of the femur. Articulation portion 4065 has formed in articulation surface 4064 a plurality of thoroughgoing apertures 4071, which, as described hereinbelow, allow synovial fluid to pass therethrough for lubrication of the articulation surface 4064 when articulation portion 4065 articulates with the articulation surface of the tibia.

The application of force on articulation surface 4061 or articulation surface 4064 causes the corresponding articulation portion 4063 or 4065 to be resiliently displaced inwardly, thus causing synovial fluid, located between the articulation portion 4063 and the articulation portion 4065 to be forced through apertures 4070 and 4071 so as to lie on and over articulation surfaces 4061 or 4064 and to provide enhanced lubrication for the articulation of articulation surfaces 4061 and 4064.

In accordance with a preferred embodiment of the present invention, in addition to the snap-fit anchoring to the tibia by element 4066, implantable meniscus implant assembly 4060 is also securely positioned into a sliding operational condition with respect to any of femur articulating surface and tibia articulating surface by multiple tissue secure assemblies 4074.

As seen in FIG. 29A, insert elements 4076 are securely assembled between articulation portion 4063 and articulation portion 4065. As seen in FIG. 29B, insert elements 4076 are formed on each end of clip 4077 shown gripping from the outside a connecting tissue fraction 4078 of the connecting tissue surrounding the knee joint Implantable meniscus implant assembly 4060 also comprises an inner grip element 4079, shown in FIG. 29B gripping the connecting tissue fraction 4078 from the inside. Tissue secure assembly 4074 defines a rounded edge seat 4080 provided for slidingly securing the tissue fraction 4078 with respect to the tissue secure assembly 4074. A first segment of seat 4080 is formed as a recess on the inside surface of clip 4077 and a second segment of seat 4080 is formed as a recess on the outside surface of grip 4079.

Figure 30A:
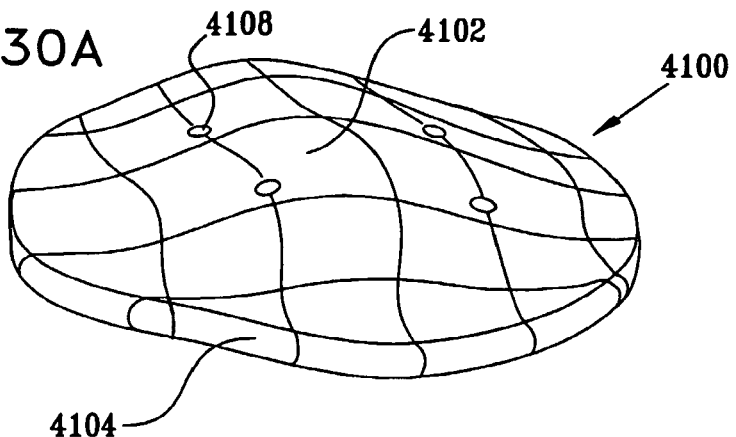
FIGS. 30A and 30B are first and second pictorial illustrations of an implantable artificial patella surface element constructed and operative in a pre installation stage in accordance with a preferred embodiment of the present invention.
Figure 30B:
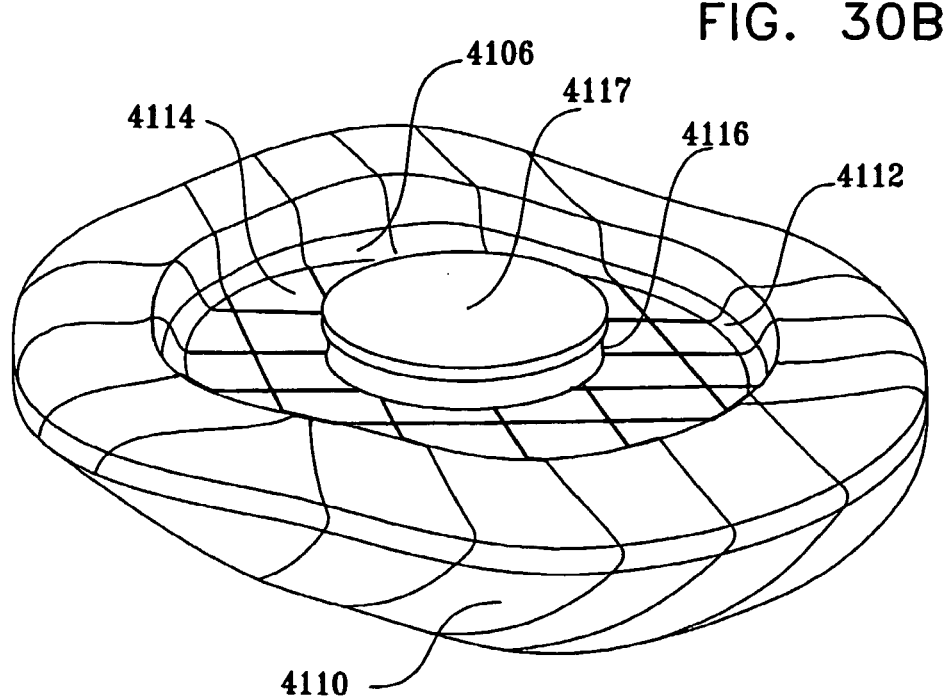

Reference is now made to FIGS. 30A and 30B, which are pictorial illustrations of a pre installation stage of an implantable artificial patella surface element, constructed and operative in accordance with a preferred embodiment of the present invention. FIG. 30A shows an implantable artificial patella surface element 4100, while FIG. 30B illustrates the preparation of the patella for implantation of implantable artificial patella surface element 4100. As seen in FIG. 30A, implantable artificial patella surface element 4100 is formed, preferably, by injection molding of polyurethane. Preferred polyurethane materials are described hereinbelow.

Preferably, implantable artificial patella surface element 4100 defines a concave articulation surface 4102 and an outer peripheral protrusion 4104 arranged for snap-fit engagement with a corresponding recess 4106 provided by machining of patella 4110. Implantable artificial patella surface element 4100 also preferably includes a plurality of thoroughgoing apertures 4108 to allow synovial fluid to pass therethrough for lubrication of the articulation surface 4102, as described hereinbelow with reference to FIG. 32B

As seen in FIG. 30B, recess 4106 is formed with an inner circumferential undercut 4112. A planar surface 4114, an undercut closed circumferential groove 4116 and an additional planar surface 4117 are provided by machining of the patella 4110.

Figure 31A:
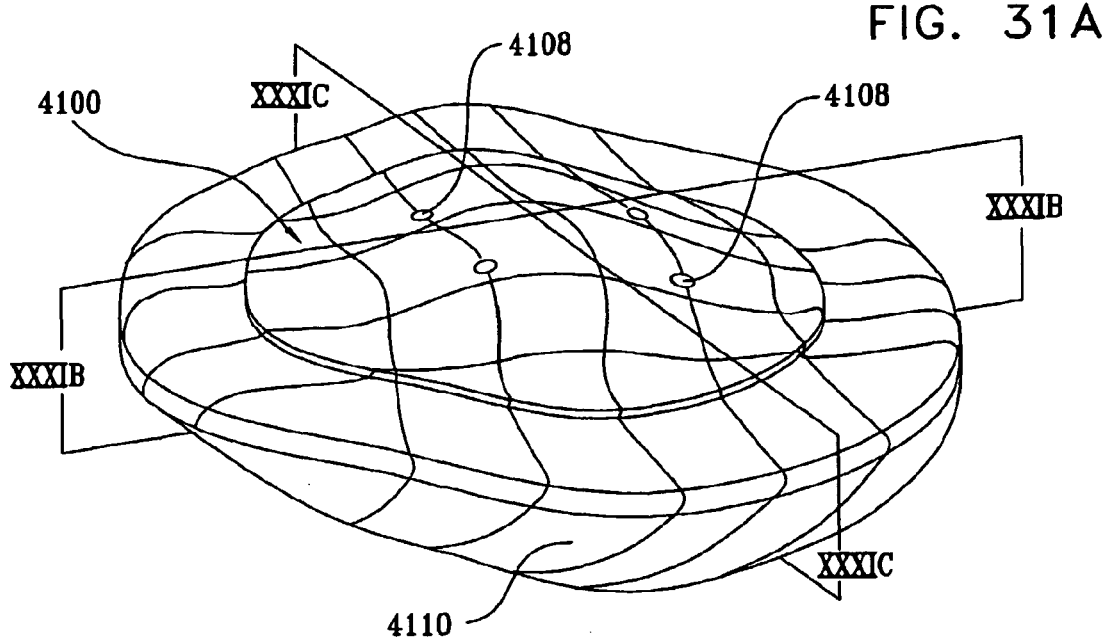
FIGS. 31A, 31B and 31C are, respectively, a pictorial illustration and sectional illustrations of the implantable artificial patella surface element of FIGS. 30A and 30B installed in patella.
Figure 31B:
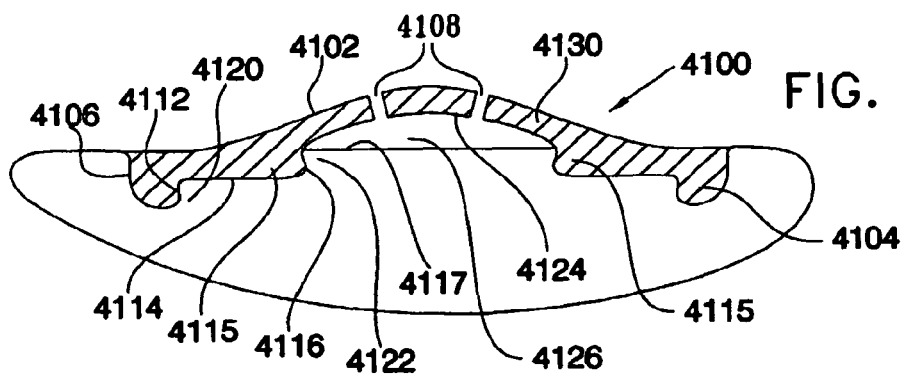
Figure 31C:
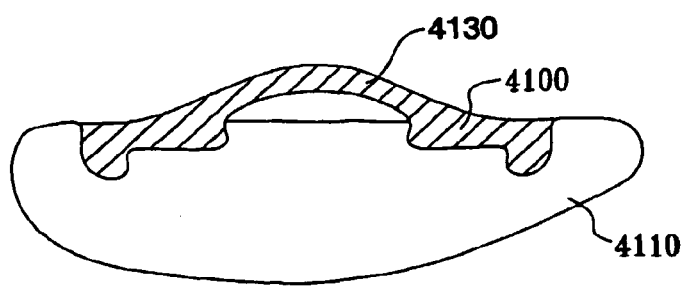

Reference is now made to FIGS. 31A, 31B and 31C, which show artificial patella surface element 4100 of FIG. 30A installed in a patella 4110, prepared as shown in FIG. 30B, in accordance with a preferred embodiment of the present invention. As seen in FIG. 31B, outer peripheral protrusion 4104 of implantable artificial patella surface element 4100 defines an undercut 4120 configured for a snap-fit engagement with undercut 4112 machined in recess 4106 in patella 4110. In addition, artificial patella surface element 4100 defines an inner snap-fit circumferential locking portion 4115 comprising undercut 4122 configured for a snap-fit engagement with groove 4116 machined in patella 4110. It is appreciated that artificial patella surface element 4100 is configured with an inner free surface 4124 positioned remote from planar surface 4117 creating a void 4126. Articulating portion 4130 of artificial patella surface element 4100 is external to inner free surface 4124 and is defined by circumferential snap-fit locking portion 4115. Articulating portion 4130 of artificial patella surface element 4100 also preferably includes apertures 4108 to allow synovial fluid to pass therethrough for lubrication of the articulation surface 4102, as described hereinbelow with reference to FIG. 32B.

Figure 32A:
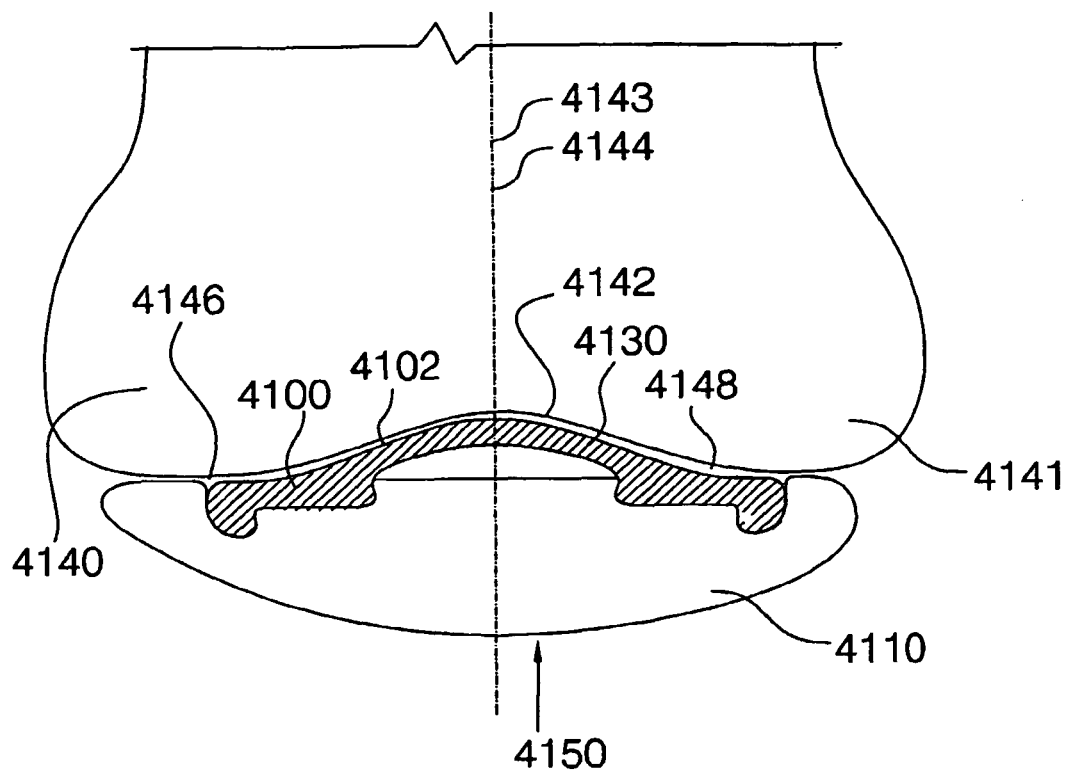
FIGS. 32A and 32B are sectional illustrations of an implantable artificial patella surface element of FIGS. 30A and 30B in a patella replacement environment.
Figure 32B:
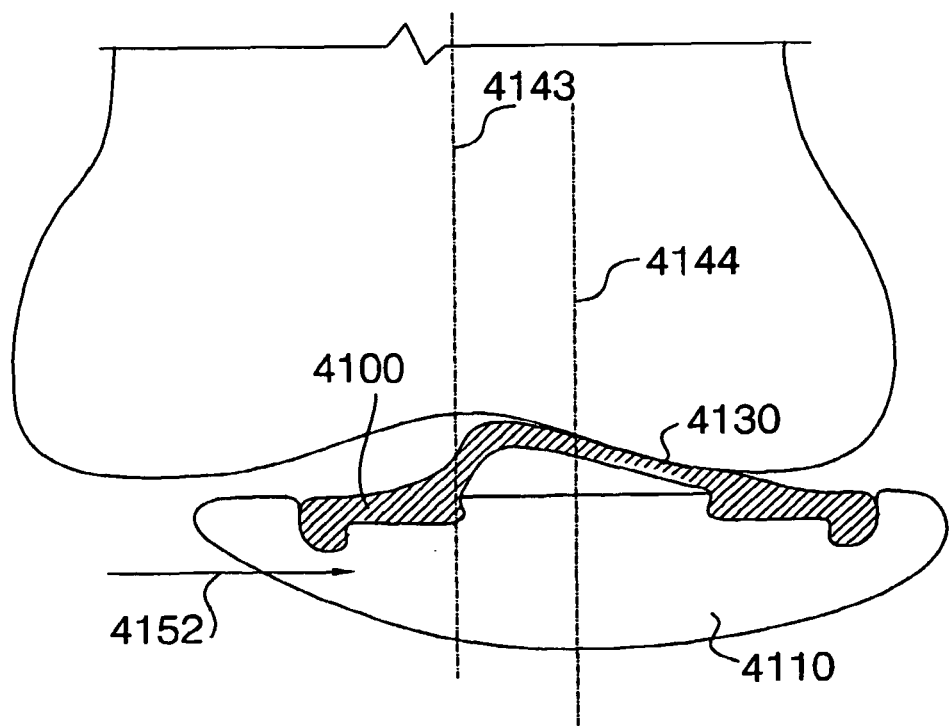

Reference is now made to FIGS. 32A and 32B, which are sectional illustrations of the implantable artificial patella surface element 4100 of FIG. 30A in a patella replacement environment in operative orientations where the joint is un-impacted and wherein the joint is impacted.

In FIG. 32A, which shows an un-impacted joint, patella 4110 and artificial patella surface element 4100 are installed in an articulating arrangement with lateral condyle 4140, medial condyle 4141 and trochlear groove 4142. The approximate center of articulation of the femur is shown as an axis 4143, and the approximate center of articulation of the articulating portion 4130 of artificial patella surface element 4100 is shown as an axis 4144. Most of the articulating contact of artificial patella surface element 4100 is performed by articulation portion 4130, providing a space 4146 between patella 4110 and lateral condyle 4140 and a space 4148 between patella 4110 and medial condyle 4141.

Articulating portion 4130 may undergo deformation when frontal impact force is exerted on patella 4110. An example of such impact force is the impact force here designated by arrow 4150. This frontal impact force results in an inward deformation of articulation portion 4130, thus providing a shock-absorbing effect protecting the joint from being damaged by the impact force.

FIG. 32B shows the joint being impacted by a lateral impact force, designated here by arrow 4152, exerted on artificial patella surface element 4100. The lateral impact force deflects patella 4110 sideways in relation to the femoral condyles as can be seen from the shifted position of axis 4144 in relation to axis 4143. The flexible construction of articulating portion 4130 allows a considerable deformation from its original form without dislodgment of artificial patella surface element 4100 from its anchoring engagement with patella 4110. The deformation of articulating portion 4130 results in recoil energy which returns the patella 4110 to its original orientation after the impact force dissipates.

In accordance with a preferred embodiment of the present invention, articulating portion 4130 includes apertures 4108 (FIG. 31A) to allow synovial fluid to pass therethrough for lubrication of the articulation surface 4102.

At least part of articulation portion 4130 is forced to be resiliently displaced toward any of lateral condyle 4140, medial condyle 4141 and trochlear groove 4142, laterally by any of frontal impact force, lateral impact force, flexation action of the knee joint and extension action of the knee joint. Such resilient displacement causes synovial fluid, located in void 4126, to be forced through apertures 4108 (FIG. 31A) so as to lie on and over articulation surface 4102 and to provide enhanced lubrication for the articulation of articulation surface 4102 of articulation portion 4130 with the femoral condyles 4140 and 4141 and trochlear groove 4142.

Reference is now made to FIGS. 33A, 33B, 33C, 33D, 33E and 33F, which are simplified illustrations of first and second implantable artificial humeral elbow surface elements, constructed and operative in accordance with another preferred embodiment of the present invention, which are particularly useful for an elbow joint.

As seen in FIGS. 33A, 33B, 33D and 33E, an artificial humeral elbow surface element 4180 is constructed for articulation with the ulna and an artificial humeral surface element 4182 is constructed for articulation with the radius. Implantable artificial humeral surface elements 4180 and 4182 are formed, preferably, by injection molding of polyurethane. Preferred polyurethane materials are described hereinbelow.

Preferably, implantable artificial humeral surface elements 4180 and 4182 are of generally uniform thickness, and define, respectively, an articulation surface 4184, which defines a portion of a concave saddle shape surface, and an articulation surface 4186, which defines a portion of a convex generally spherical surface, and respective bone engagement surfaces 4188 and 4190. Bone engagement surfaces 4188 and 4190 preferably have formed thereon respective peripheral protrusion elements 4192 and 4194.

As seen in FIGS. 33C and 33F, peripheral protrusion elements 4192 and 4194 define respective undercuts 4196 and 4198. Alternatively, protrusions elements 4192 and 4194 may be any other suitable open or closed protrusions. Protrusions 4192 and 4194 are preferably arranged for snap-fit engagement with corresponding grooves formed by machining of the humerus.

Reference is now made to FIGS. 34A, 34B, 34C, 34D, 34E and 34F, which are simplified illustrations of an implantable artificial ulna surface element and an implantable radius surface element, constructed and operative in accordance with another preferred embodiment of the present invention, which are particularly useful for an elbow joint. As seen in FIGS. 34A, 34B, 34C, 34D, 34E and 34F, artificial ulna surface element 4210 and artificial radius surface elements 4212 are constructed for articulation with the humerus. Implantable artificial ulna surface element 4210 and artificial radius surface element 4212 are formed preferably by injection molding of polyurethane. Preferred polyurethane materials are described hereinbelow.

Preferably, implantable artificial ulna surface element 4210 and artificial radius surface elements 4212 are of generally uniform thickness and respectively define an articulation surface 4214, which defines a portion of a concave saddle shape surface, and an articulation surface 4216, which defines a portion of a concave generally spherical surface, and respective bone engagement surfaces 4218 and 4220. Bone engagement surfaces 4218 and 4220 preferably have formed thereon respective peripheral protrusion elements 4226 and 4228. Peripheral protrusion elements 4226 and 4228 define respective undercuts 4232 and 4234. Alternatively, protrusions elements 4226 and 4228 may be any other suitable, open or closed protrusions. Protrusions 4226 and 4228 are preferably arranged for snap-fit engagement with corresponding grooves formed by machining of the ulna and radius, respectively.

Figure 35A:
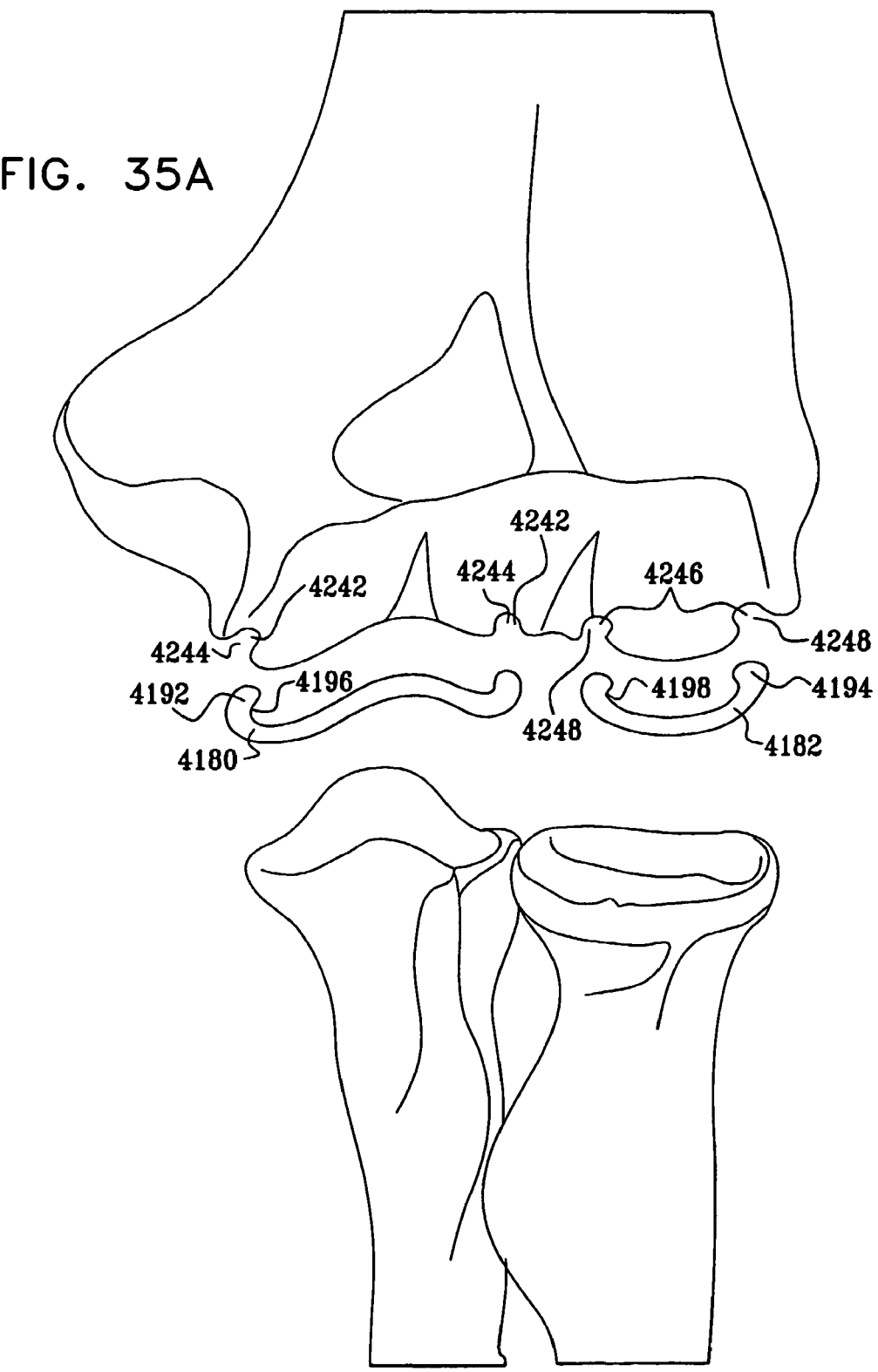

Reference is now made to FIGS. 35A and 35B, which are respective exploded view and assembled view illustrations of the implantable artificial humeral elbow elements of FIGS. 33A-33F in a partial elbow replacement environment. FIG. 35A shows a pre installation stage, while FIG. 35B shows the elements installed.

As seen in FIG. 35A, protrusion 4192 of implantable artificial humeral elbow element 4180 is preferably arranged for snap-fit engagement with corresponding groove 4242 firmed by machining of the humerus. Groove 4242 is preferably formed with an undercut 4244 matching undercut 4196 of protrusion 4192.

Protrusion 4194 of implantable artificial humeral elbow element 4182 is preferably arranged for snap-fit engagement with corresponding groove 4246 formed by machining of the humerus. Groove 4246 is preferably formed with an undercut 4248 matching undercut 4198 of protrusion 4194.

FIG. 35B shows implantable artificial humeral elbow element 4180 and implantable artificial humeral elbow element 4182 mounted onto a humerus.

Figure 36A:
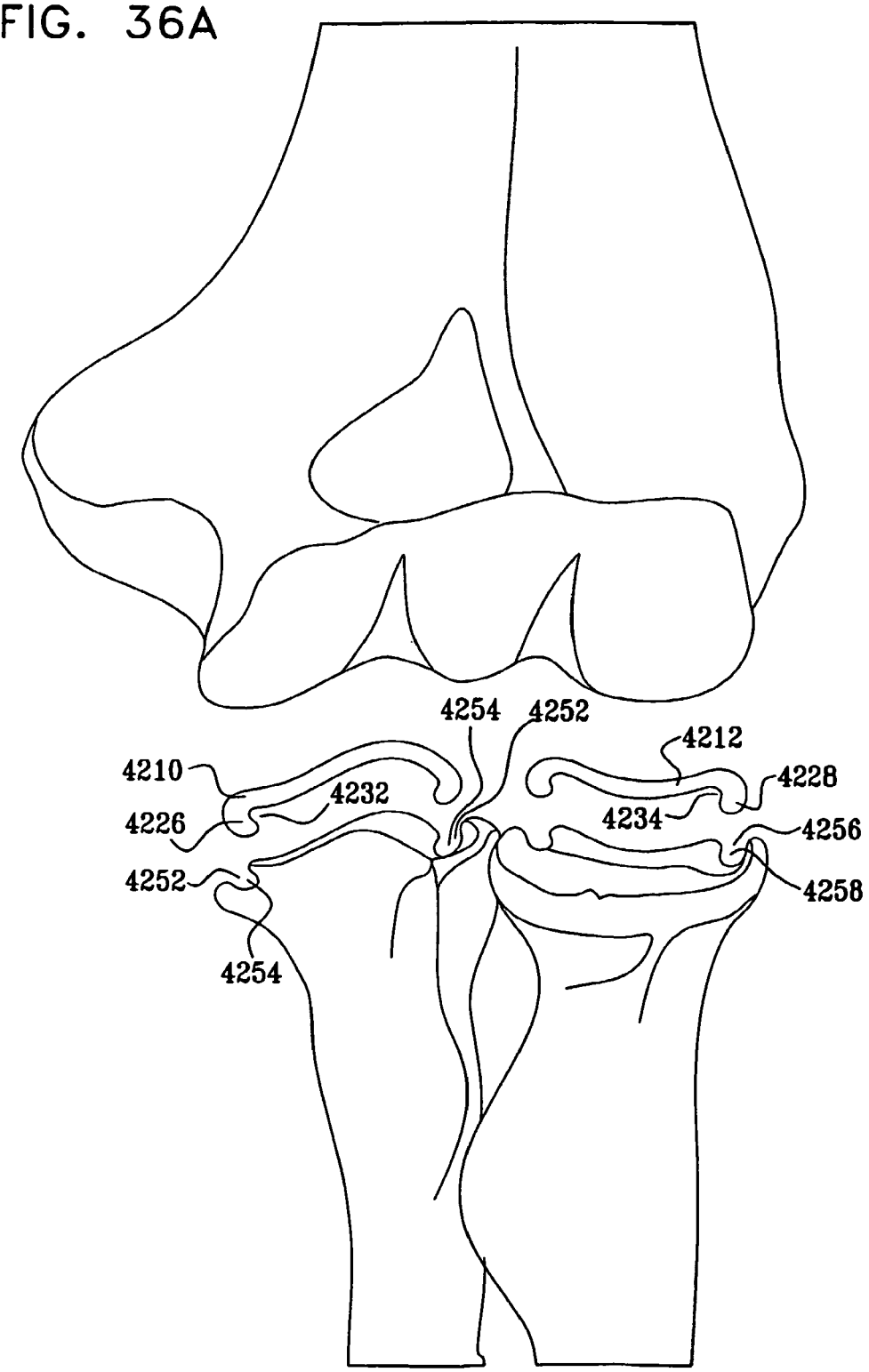

Reference is now made to FIGS. 36A and 36B, which are respective exploded view and assembled view illustrations of the implantable artificial ulna surface element 4210 and artificial radius surface elements 4212 of FIGS. 34A-34F in a partial elbow replacement environment. FIG. 36A shows a pre installation stage, while FIG. 36B shows the elements installed.

As seen in FIG. 36A, protrusion 4226 of implantable artificial ulna surface element 4210 is preferably arranged for snap-fit engagement with a corresponding groove 4252 formed by machining of the ulna. Groove 4252 is preferably formed with an undercut 4254 matching undercut 4232 of protrusion 4226.

Protrusion 4228 of artificial radius surface element 4212 is preferably arranged for snap-fit engagement with a corresponding groove 4256 formed by machining of the radius. Groove 4256 is preferably formed with an undercut 4258 matching undercut 4234 of protrusion 4228.

Figure 37:
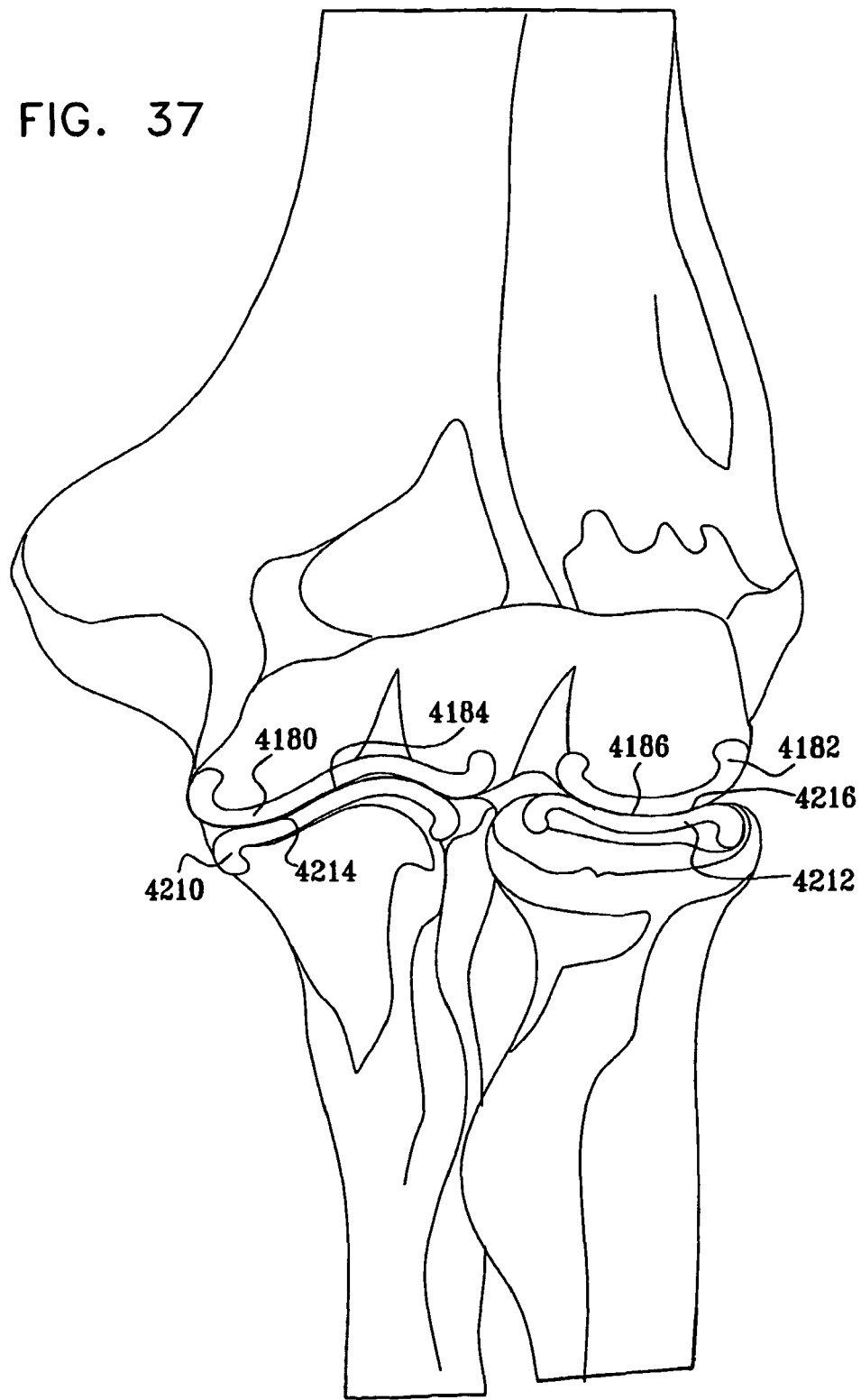
FIG. 37 is an assembled view illustration of the implantable humeral elbow elements of FIGS. 33A-33F and the implantable artificial ulna and radius elements of FIGS. 34A-34F in a total elbow replacement environment.

FIG. 36B shows implantable artificial ulna elbow element 4210 mounted onto an ulna and implantable artificial radius elbow element 4212 mounted onto a radius Reference is now made to FIG. 37, which is a simplified illustration of the implantable humeral elbow elements of FIGS. 33A-33F and the implantable artificial ulna and radius elements of FIGS. 34A-34F in a total elbow replacement environment.

As seen in FIG. 37, implantable artificial humeral elbow element 4180 and implantable artificial humeral elbow element 4182 are shown mounted onto a humerus. Implantable artificial ulna elbow element 4210 is shown mounted onto an ulna and implantable artificial radius elbow element 4212 is shown mounted onto a radius.

Articulation surface 4184 of artificial humeral elbow element 4180 articulates with articulation surface 4214 of artificial ulna elbow element 4210. Articulation surface 4186 of artificial humeral elbow element 4182 articulates with Articulation surface 4216 of artificial radius elbow element 4212.

Figure 38A:
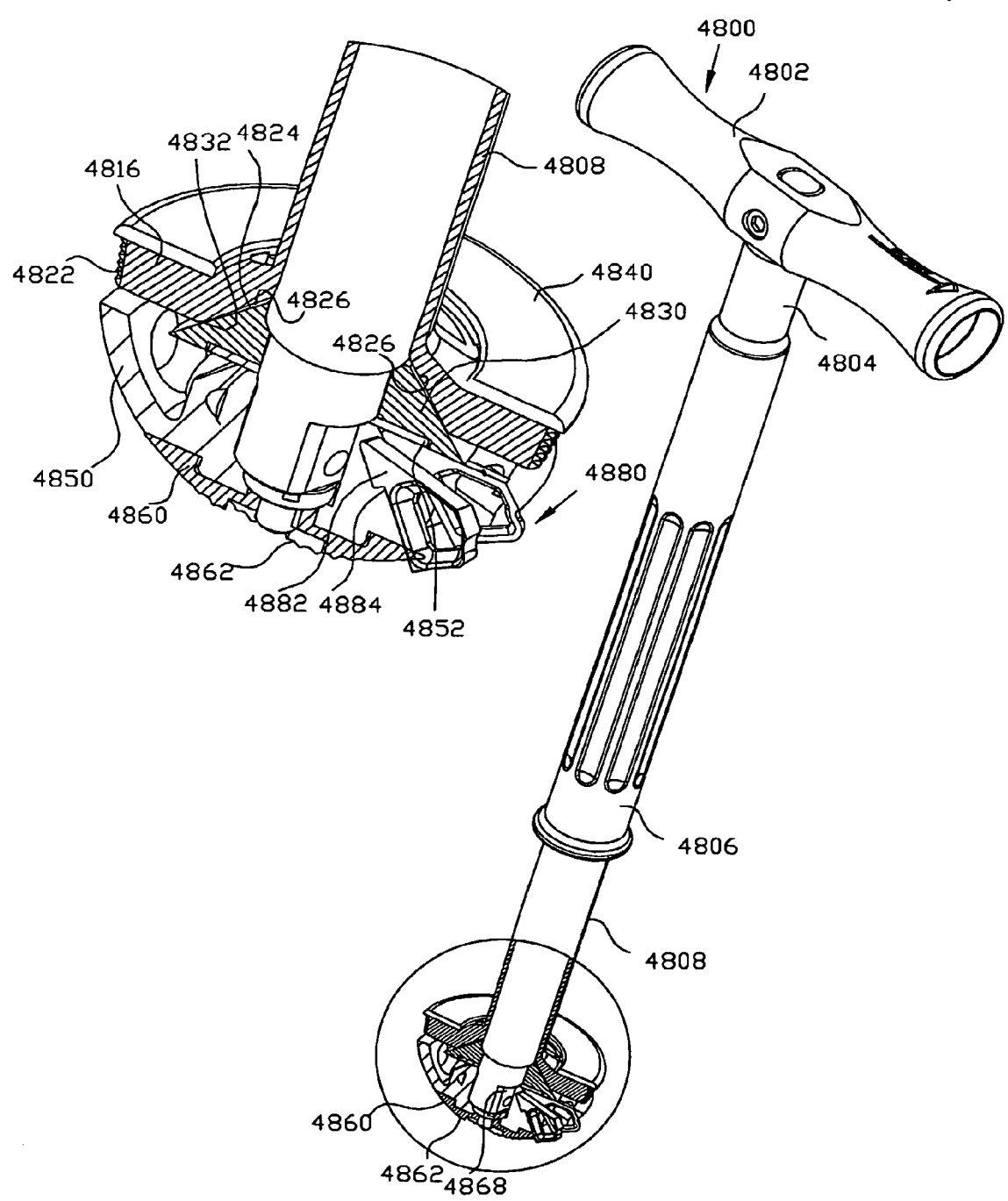
FIGS. 38A, 38B, 38C and 38D are, respectively, a partially cut away illustration and an exploded view illustration of a groove reaming tool, and exploded and assembled view illustrations of a portion of the groove reaming tool, constructed and operative in accordance with a preferred embodiment of the present invention.
Figure 38B:
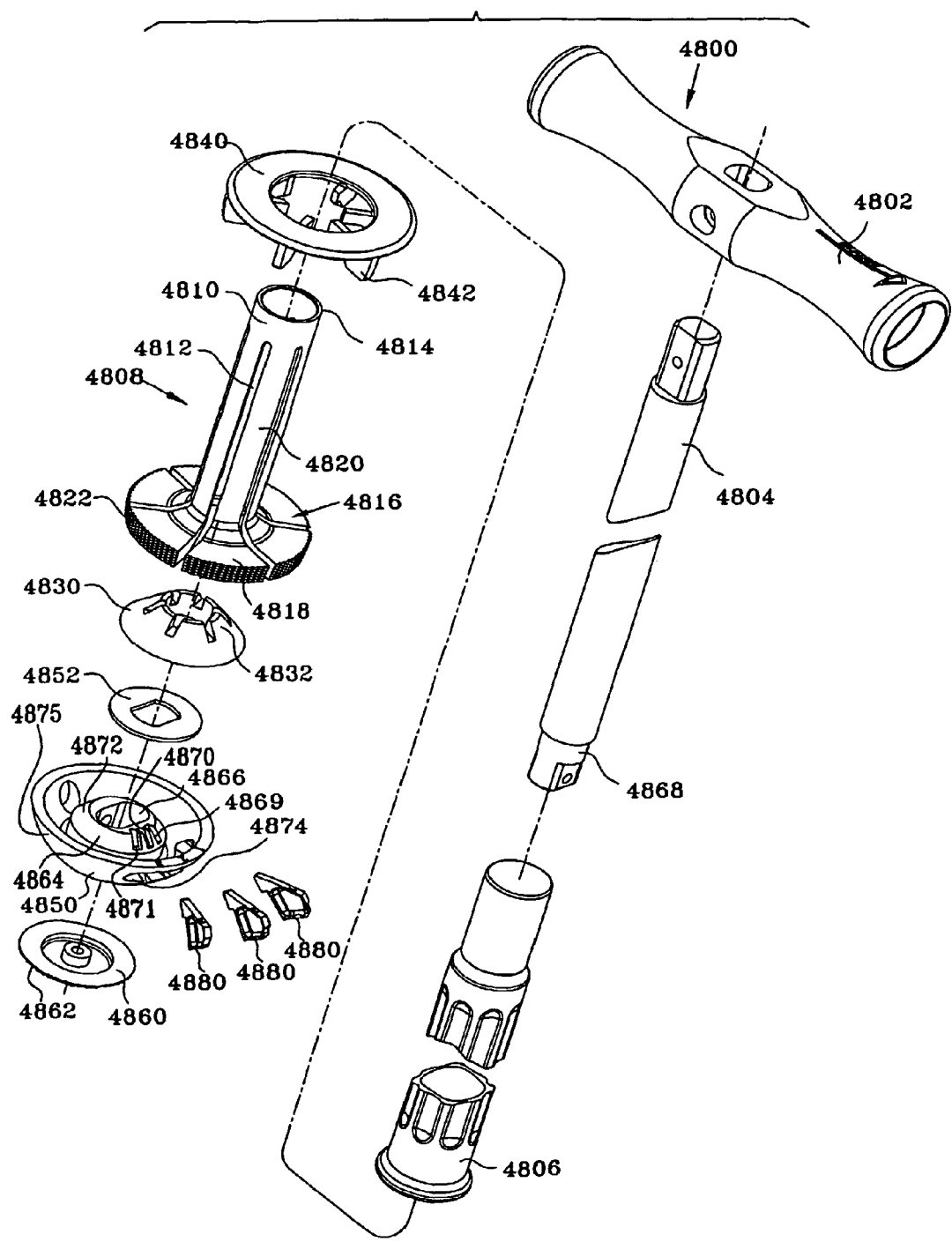
Figure 38C:
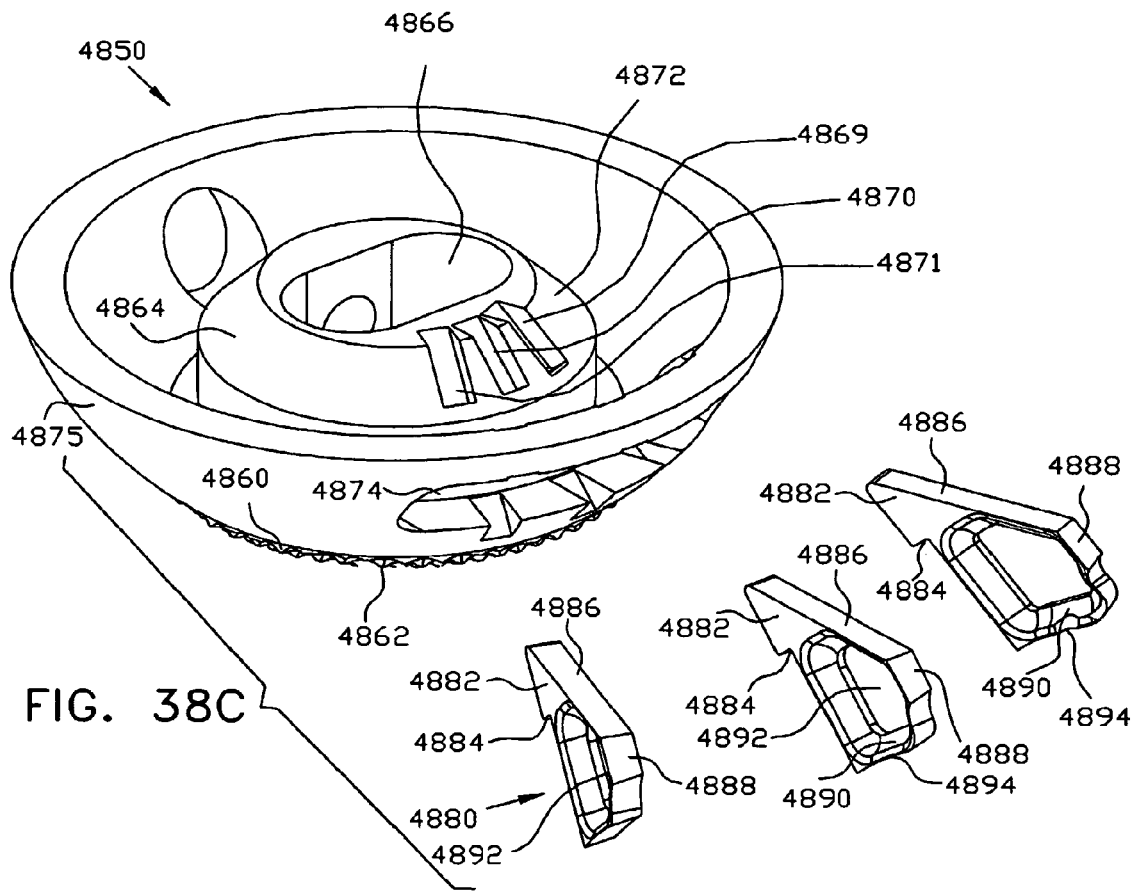

Reference is now made to FIGS. 38A, 38B, 38C and 38D, which illustrate a groove reaming tool constructed and operative in accordance with a preferred embodiment of the present invention. As seen in FIGS. 38A and 38B, a hand operated reaming tool 4800 is provided with a handle 4802, fixedly coupled to a shaft 4804. An elongate grip 4806 is rotatably and slidably mounted over shaft 4804 and axially engages an outwardly extendible recess engagement element 4808, which is also rotatably and slidably mounted with respect to shaft 4804.

Outwardly extendible recess engagement element 4808 is preferably an integrally formed element made of metal, such as spring steel, and includes a generally hollow cylindrical portion 4810 formed with a plurality of axially extending slots 4812, which extend from a location spaced from a top edge 4814 of the cylindrical portion 4810 towards and through a generally radially outwardly extending disk-like portion 4816.

It is appreciated that disk-like portion 4816 thus includes a plurality of azimuthally separated segments 4818, each of which defines a continuation of a corresponding azimuthally separated segment 4820 of cylindrical portion 4810. Preferably, an outer edge 4822 of disk-like portion 4816 is formed with a high friction engagement surface, such as a toothed surface.

It is seen that preferably disk-like portion 4816 is formed with a central generally conical recess 4824 on an underside surface 4826 thereof.

A generally solid, centrally apertured conical element 4830 is rotatably mounted onto shaft 4804 such that a conical surface 4832 thereof is adapted to operatively engage conical recess 4824 in a manner that such engagement produces radially outward displacement of segments 4818 of disk-like portion 4816.

Preferably, there is provided a retainer element 4840 which is rotatably mounted with respect to shaft 4804 and overlies disk-like portion 4816. Preferably retainer element 4840 includes depending plates 4842 which engage interstices between segments 4818.

In accordance with a preferred embodiment of the invention, a groove cutter mounting element 4850 is fixedly mounted to shaft 4804 for rotation together therewith in response to rotation of handle 4802. Groove cutter mounting element 4850 preferably underlies conical element 4830 and is separated therefrom by a washer 4852, to enable groove cutter mounting element 4850 to easily rotate with respect to conical element 4830.

An end element 4860 is rotatably mounted onto an end of shaft 4804, underlying groove cutter mounting element 4850 such that groove cutter mounting element 4850 is rotatable with respect thereto. End element 4860 is preferably formed with a high friction engagement surface 4862, such as a toothed surface, on the underside thereof.

Groove cutter mounting element 4850 is preferably a generally hollow hemispherical element having a central hub 4864 which defines a rectangular thoroughgoing aperture 4866 for receiving an end 4868 of shaft 4804. Three extending recesses 4869, 4870 and 4871, respectively, are formed in an outer facing wall 4872 of hub 4864. A corresponding generally elongate aperture 4874 is formed in a wall 4875 of groove cutter mounting element 4850 opposite recesses 4869, 4870 and 4871. Aperture 4874 extends azimuthally beyond recesses 4869, 4870 and 4871.

A plurality of cutter elements 4880, preferably three in number, are together removably retained in groove cutter mounting element 4850. As seen clearly in FIGS. 38C and 38D, the cutter elements 4880 are preferably of similar configuration, but have at least one differing dimension. Each cutter element 4880 preferably is formed of a flat piece or metal and includes a hook portion 4882, defining an undercut 4884, a central portion 4886 and a cutting portion 4888, which defines a curved cutting edge 4890 inwardly of which is defined an aperture 4892 having a beveled peripheral edge 4894.

Figure 38D:
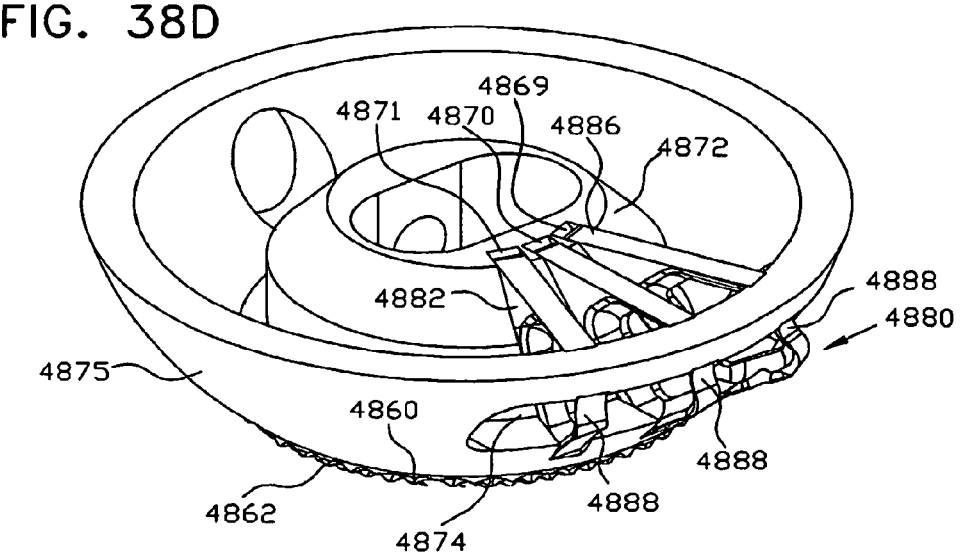

Preferably, as seen clearly in FIG. 38D, the cutter elements 4880 are arranged such that their hook portions 4882 engage recesses 4869, 4870 and 4871 and their cutting portions 4888 extend outwardly of wall 4875 through aperture 4874. Preferably the extent of central portions 4886 of cutter elements 4880 varies such that the amount that cutting portions 4888 extend outwardly of wall 4875 varies as illustrated in FIG. 38D. Preferably, the cutting elements 4880 are arranged to provide a stepped increase in the extent that the cutting portions 4888 extend outwardly, in the direction of operational rotation of the tool 4800.

Figure 39A:
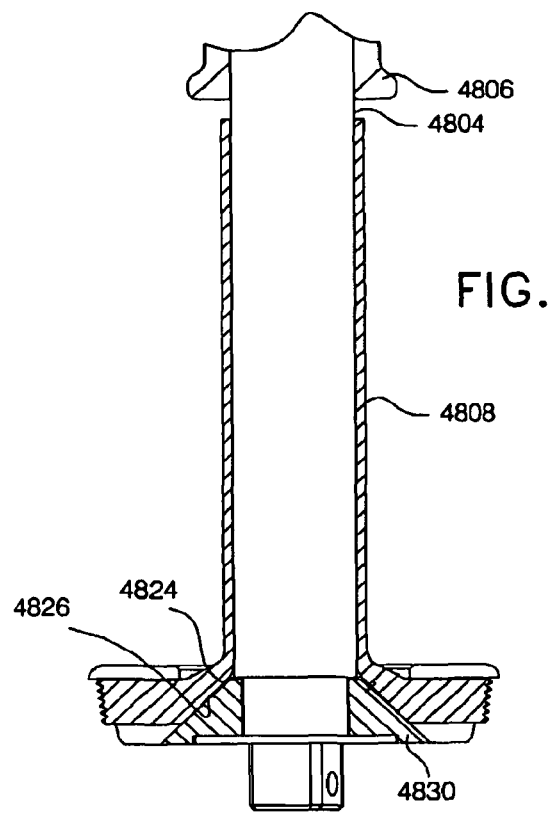
FIGS. 39A and 39B are illustrations of another portion of the groove reaming tool of FIGS. 38A, 38B, 38C and 38D in first and second operative orientations.
Figure 39B:
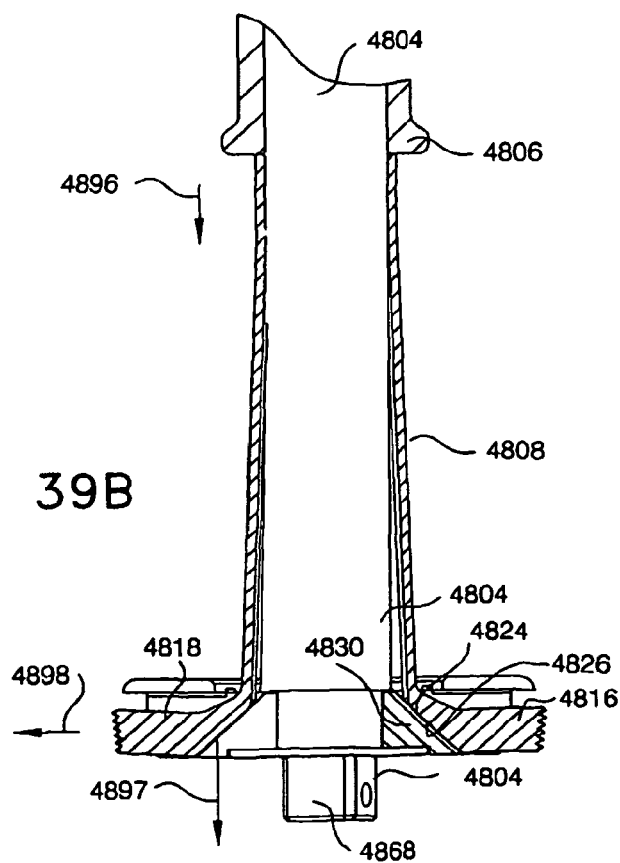

Reference is now made to FIGS. 39A and 39B, which are illustrations of another portion of the groove reaming tool of FIGS. 38A and 38B in first and second operative orientations. In a first, non-engagement orientation shown in FIG. 39A, when grip 4806 is not pushed downward along shaft 4804 towards groove cutter mounting element 4850 (FIGS. 38A and 38B), outwardly extendible recess engagement element 4808 is not subject to downward axial force and thus no axial force is applied between recess 4824, on the underside surface 4826 thereof, and conical element 4830.

In a second, bone recess engagement orientation shown in FIG. 39B, grip 480h is pushed downward along shaft 4804 towards groove cutter mounting element 4850 (FIGS. 38A and 38B), as indicated by an arrow 4896 and engages outwardly extendible recess engagement element 4808, forcing recess 4824 on the underside surface 4826 thereof axially against conical element 4830, as indicated by arrow 4897. This axial force causes radially outward displacement of segments 4818 of disk-like portion 4816, as indicated by arrow 4898.

Reference is now made to FIGS. 40A-40G, which illustrate various stages in groove reaming of an acetabulum in accordance with a preferred embodiment of the present invention preferably employing the apparatus of FIGS. 38A-38D.

Figure 40A:
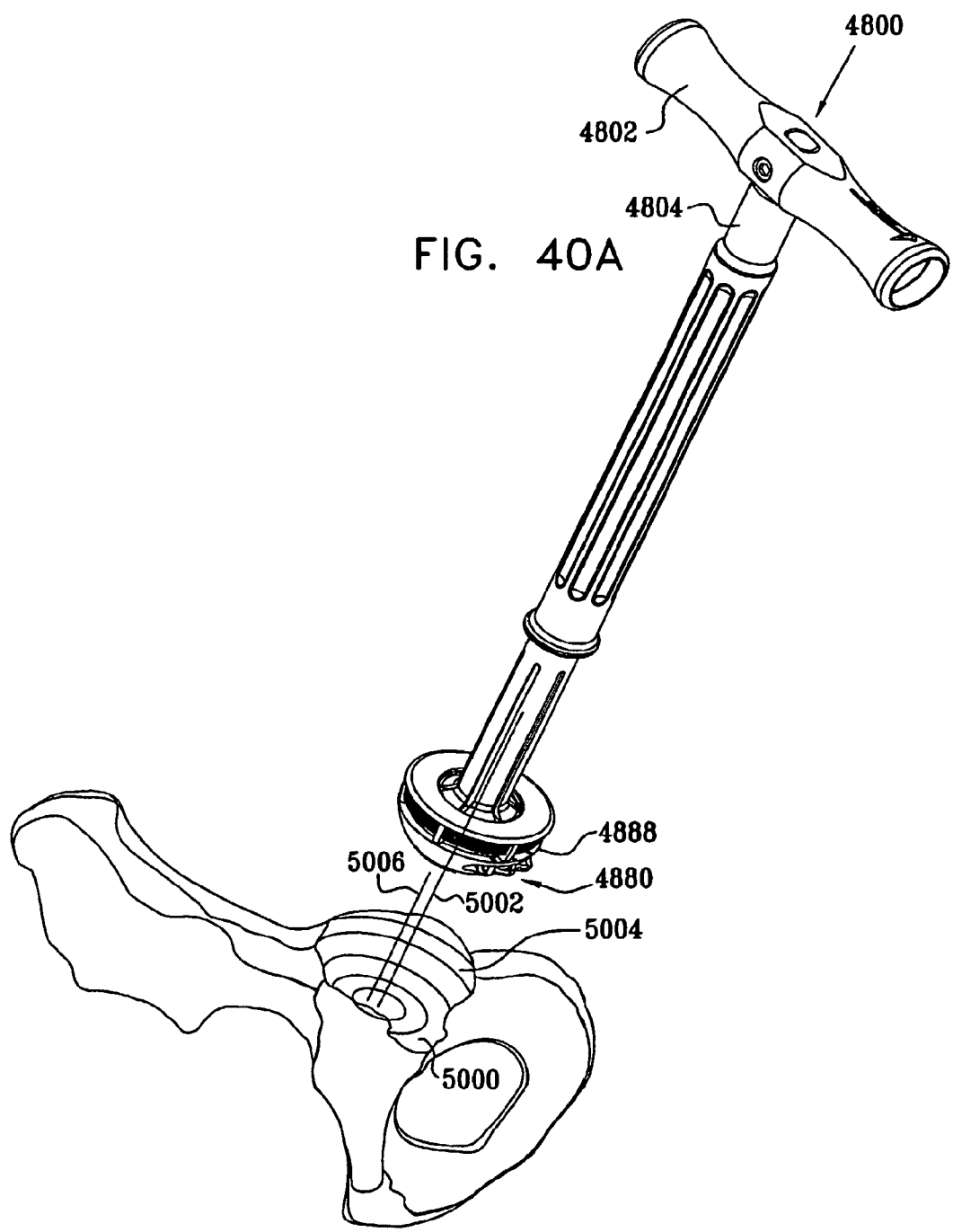

FIG. 40A illustrates groove reaming tool 4800 prior to engagement with an acetabulum which has been previously reamed. It is seen that the cutting portions 4888 of cutter elements 4880 are aligned with an acetabulum notch 5000 and that the shall 4804 is arranged along an axis 5002 which is approximately coaxial with the axis of symmetry of the reamed acetabulum 5004, which axis of symmetry is designated by reference numeral 5006.

Figure 40B:
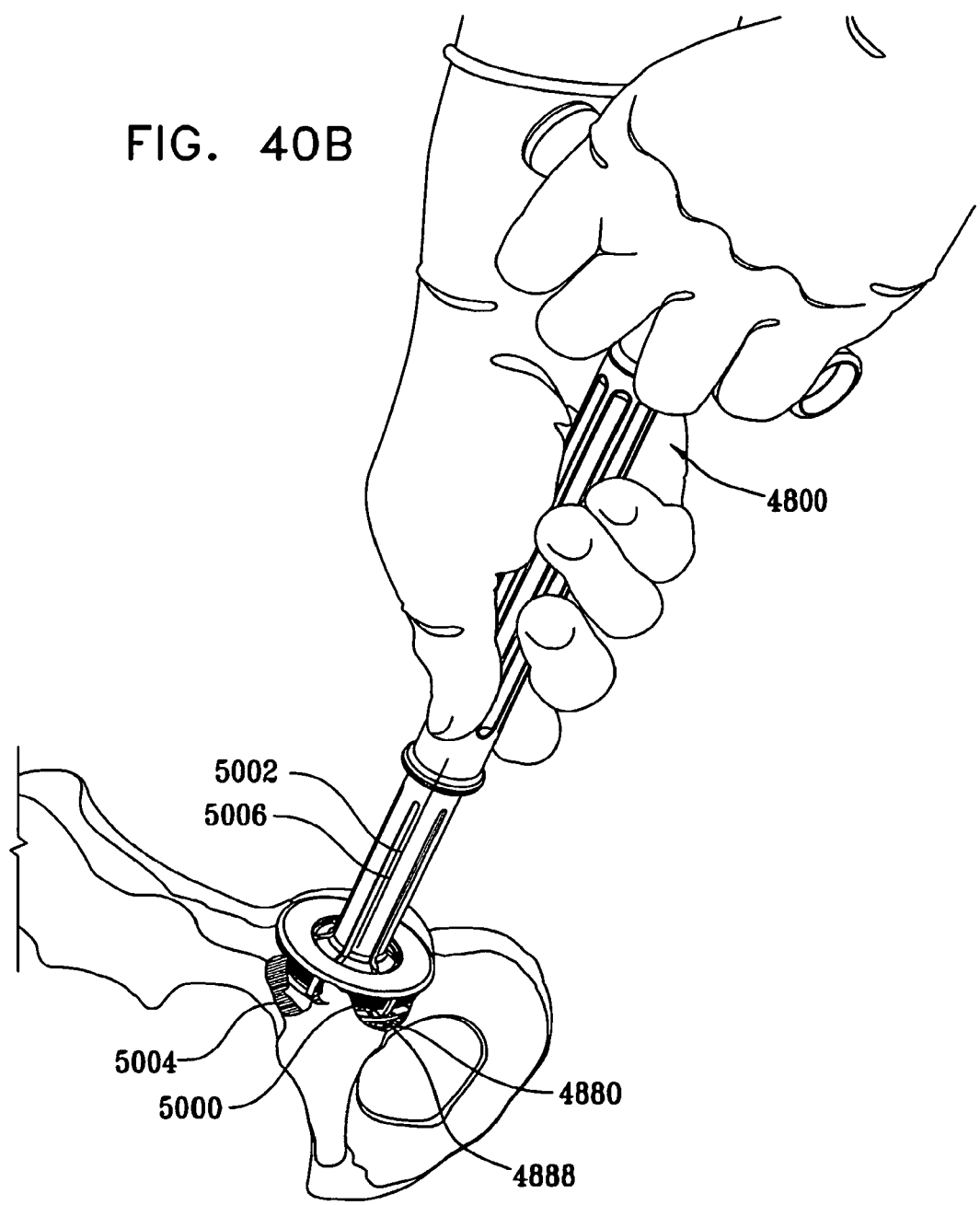

FIG. 40B illustrates the groove reaming tool 4800 following insertion thereof via notch 5000, wherein cutting portions 4888 of cutter elements 4880 are still located within acetabulum notch 5000. The groove reaming tool 4800 is also shown fully aligned with axis of symmetry 5006.

Figure 40C:
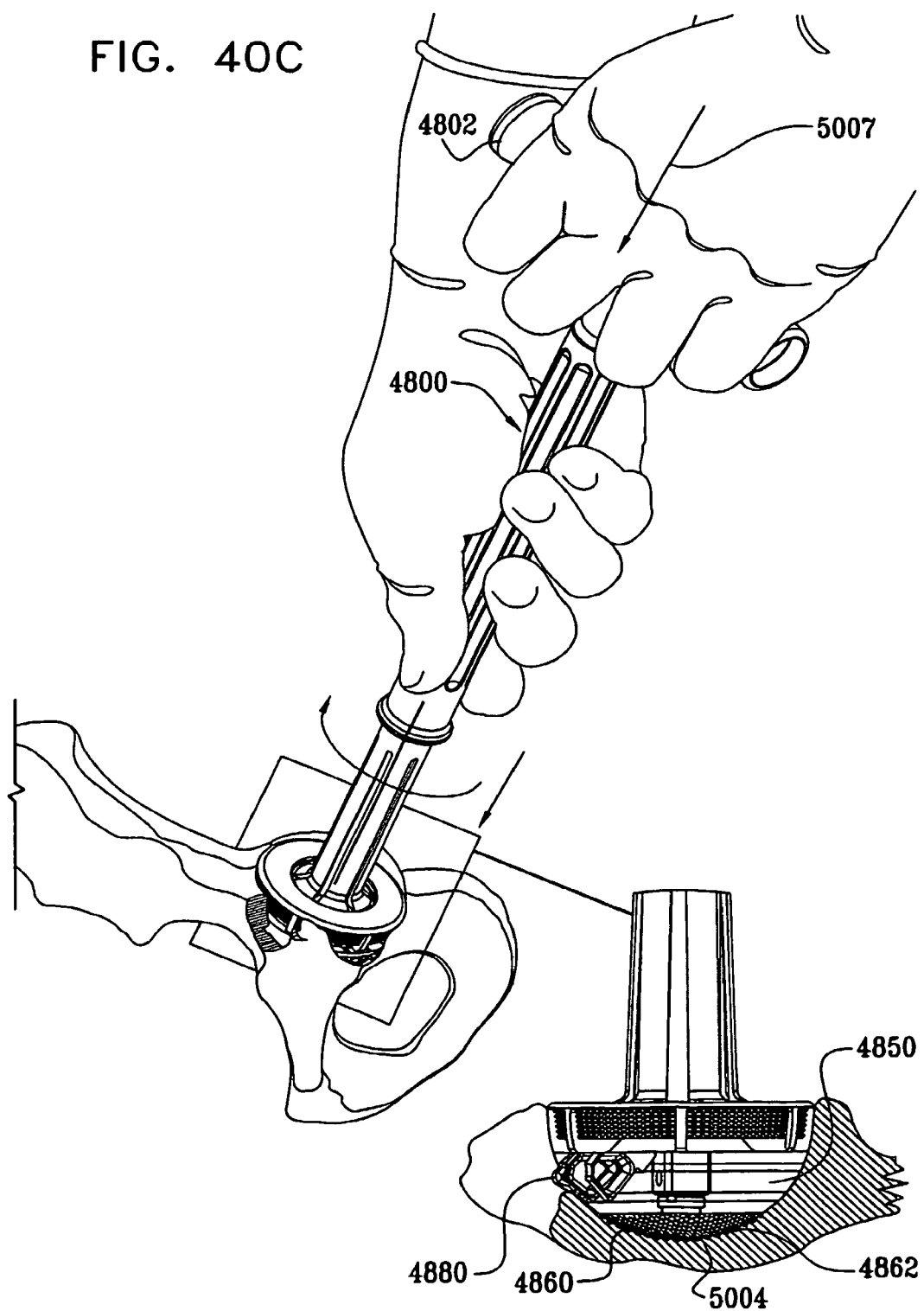

FIG. 40C illustrates the groove reaming tool 4800 following application of axial downward force, as indicated by an arrow 5007 on handle 4802, causing high friction engagement surface 4862 of end element 4860 to frictionally engage the reamed acetabulum 5004.

Figure 40D:
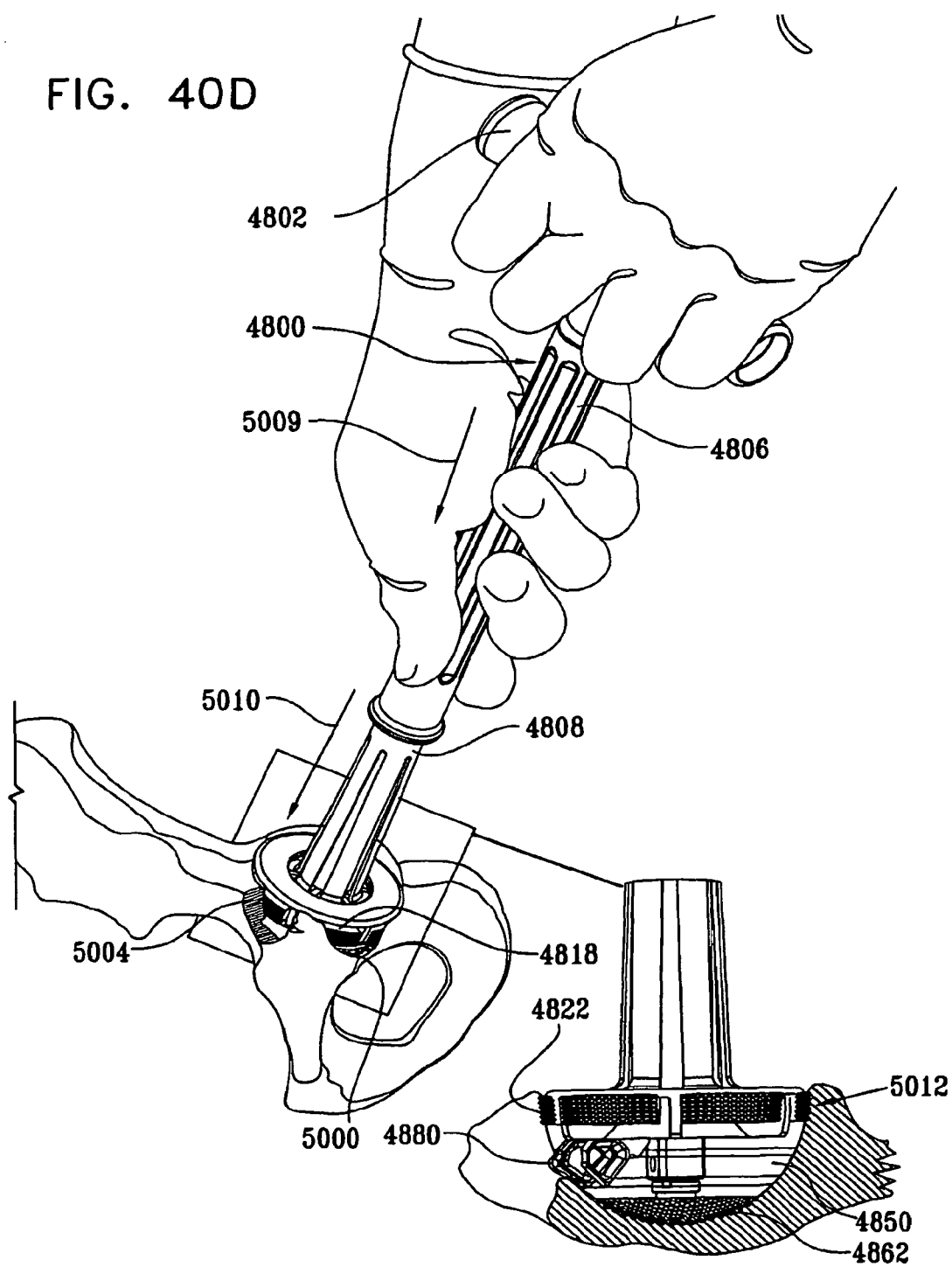

FIG. 40D shows the groove reaming tool 4800 following application of axial downward force, as indicated by an arrow 5009 on grip 4806, causing grip 4806 to engage outwardly extendible recess engagement element 4808 with linear force 5010, thereby forcing the recess on the underside surface thereof axially against the conical element, as illustrated in FIG. 39B at arrow 4897. This axial force causes radially outward displacement of segments 4818 and causes the high friction surface on the outer edge 4822 of segments 4818 into frictional engagement with the reamed acetabulum 5004, as indicated by arrow 5012.

Figure 40E:
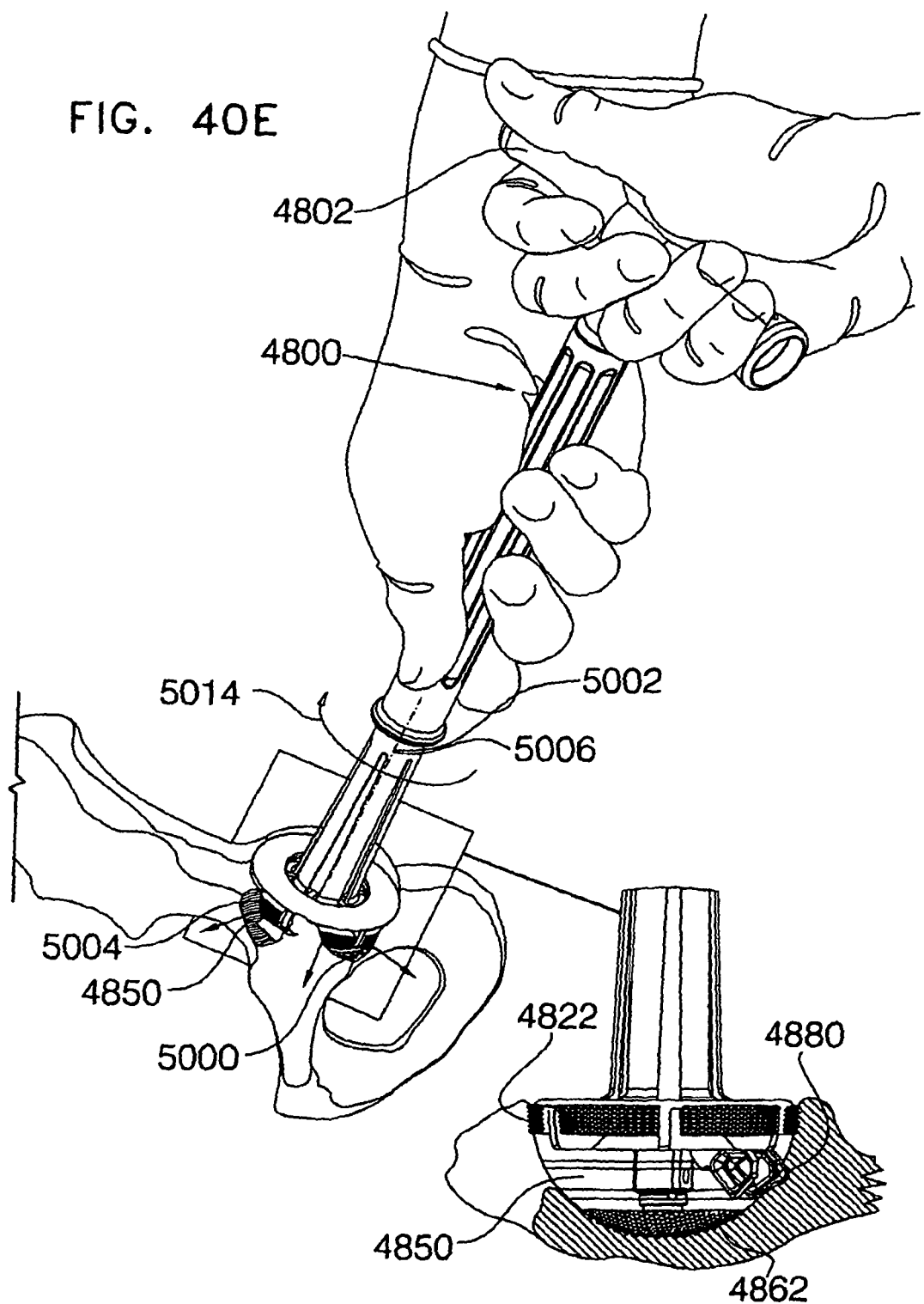

FIG. 40E shows the groove reaming tool 4800 following an approximately 180 degree rotation of handle 4802, groove cutter mounting element 4850 and cutter elements 4880 about coaxial axes 5002 and 5006, as indicated by arrow 5014, thereby producing an approximately 180 degree groove 5016 (seen in FIG. 40G) in reamed acetabulum 5004.

Figure 40F:
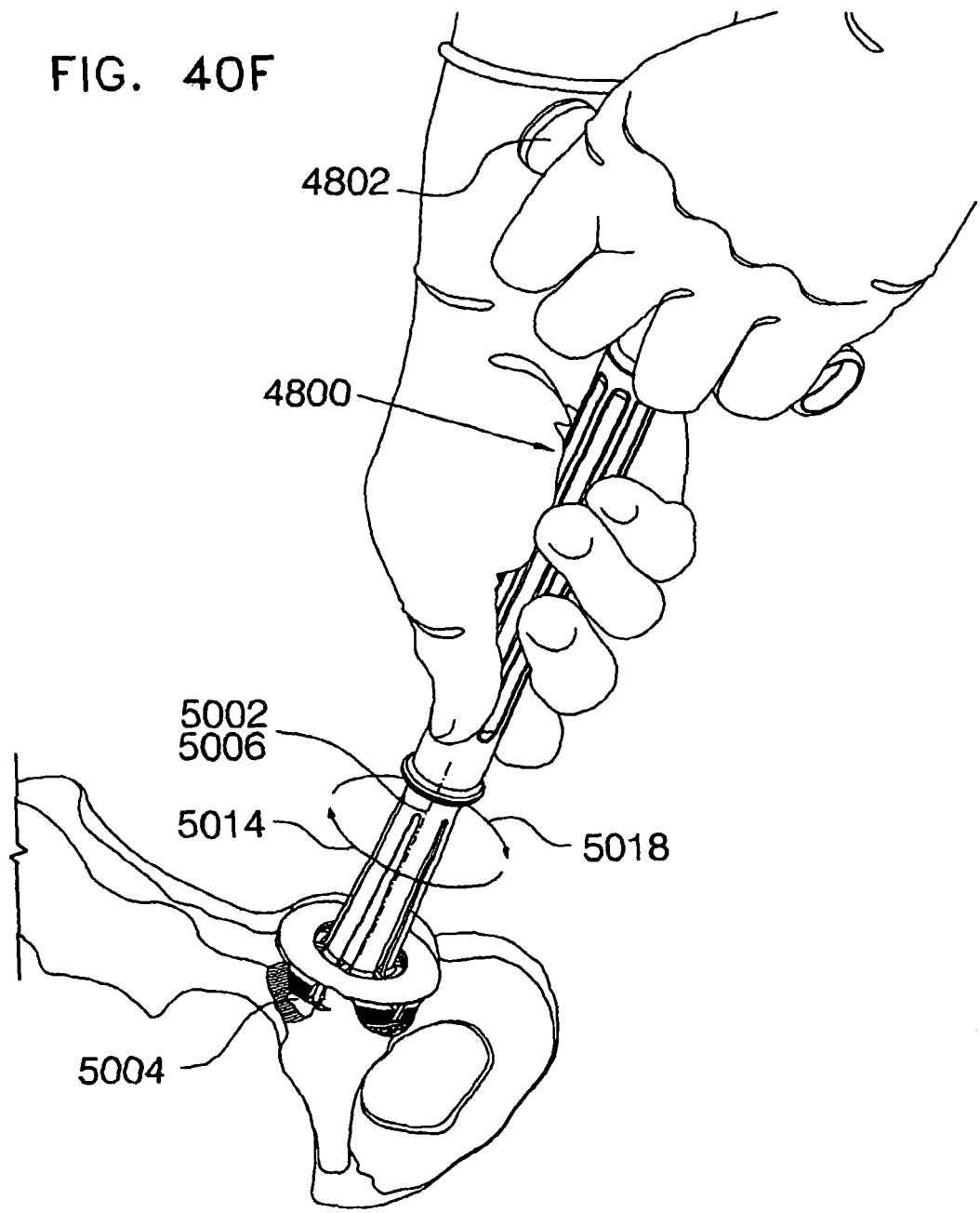

FIG. 40F shows the groove reaming tool 4800 following a further approximately 180 degree rotation of handle 4802, groove cutter mounting element 4850 and cutter elements 4880 about coaxial axes 5002 and 5006, as indicated by arrow 5018, thereby extending groove 5016, producing a 360 degree groove in reamed acetabulum 5004.

FIG. 40G illustrates the groove reaming tool 4800 following removal thereof via notch 5000, wherein cutting portions 4888 of cutter elements 4880 are still aligned with the acetabulum notch 5000, showing groove 5016 produced in the steps described in FIGS. 40E and 40F.

Reference is now made to FIGS. 41A, 41B, 41C and 41D, which are sectional illustrations, showing alternative reamed acetabulum configurations.

Figure 41A:
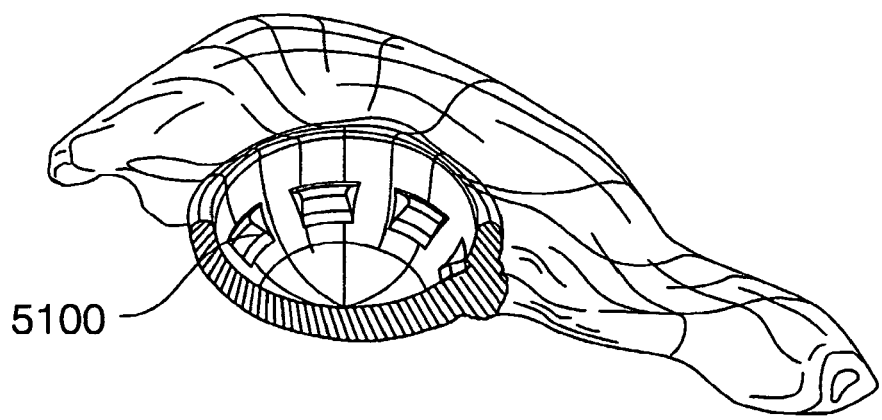
FIGS. 41A, 41B, 41C and 41D are sectional illustrations showing alternative reamed acetabulum configurations.

FIG. 41A illustrates a modification of the machined acetabulum shown in FIG. 40G, wherein a discontinuous groove array 5100 is shown. This groove array is preferably configured to correspond with the protrusion array shown in FIG. 2A.

Figure 41B:
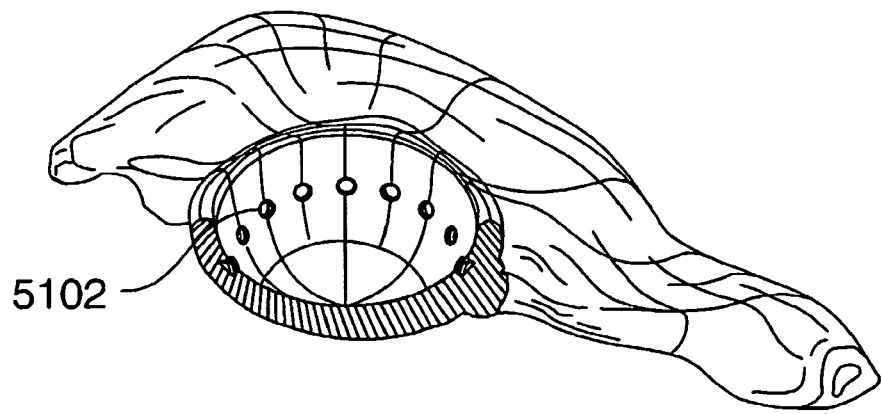

FIG. 41B illustrates another modification of the machined acetabulum shown in FIG. 40G, wherein another type of discontinuous recess array 5102 is shown. This groove array is preferably configured to correspond with the protrusion array shown in FIG. 3A.

Figure 41C:
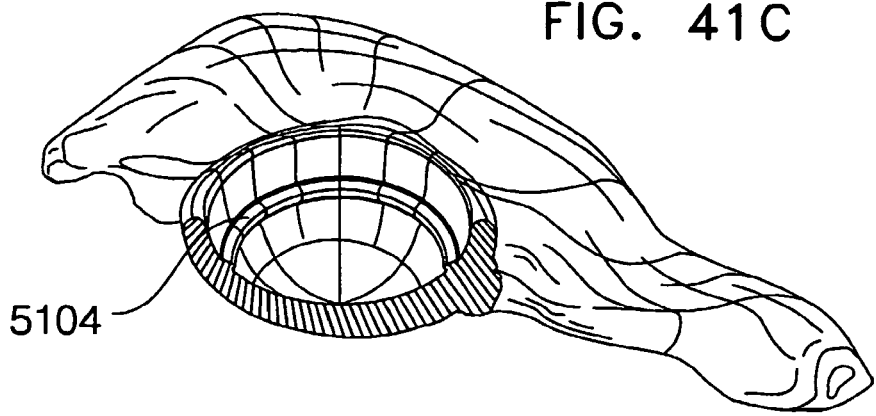

FIG. 41C illustrates another modification of the machined acetabulum shown in FIG. 40G, wherein a circumferential protrusion 5104 is shown. This circumferential protrusion is preferably configured to correspond with the circumferential recess shown in FIG. 4A.

Figure 41D:
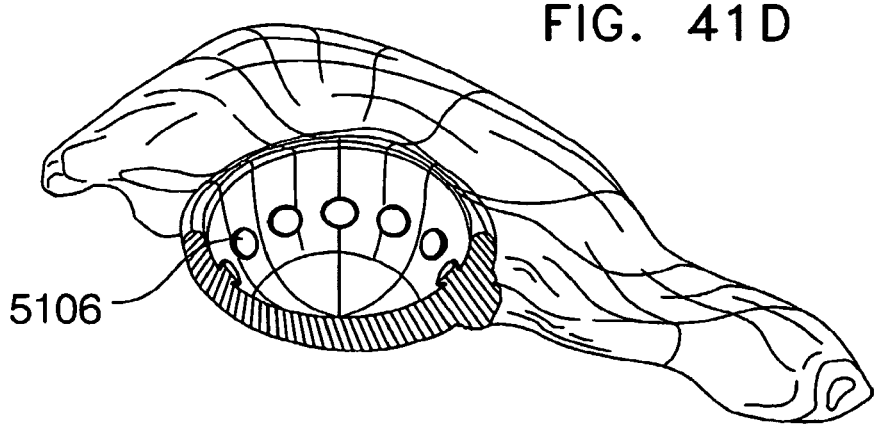

FIG. 41D illustrates another modification of the machined acetabulum shown in FIG. 40G, wherein a discontinuous protrusion array 5106 is shown. This discontinuous protrusion array 5106 is preferably configured to correspond with recess array shown in FIG. 5A.

Figure 42A:
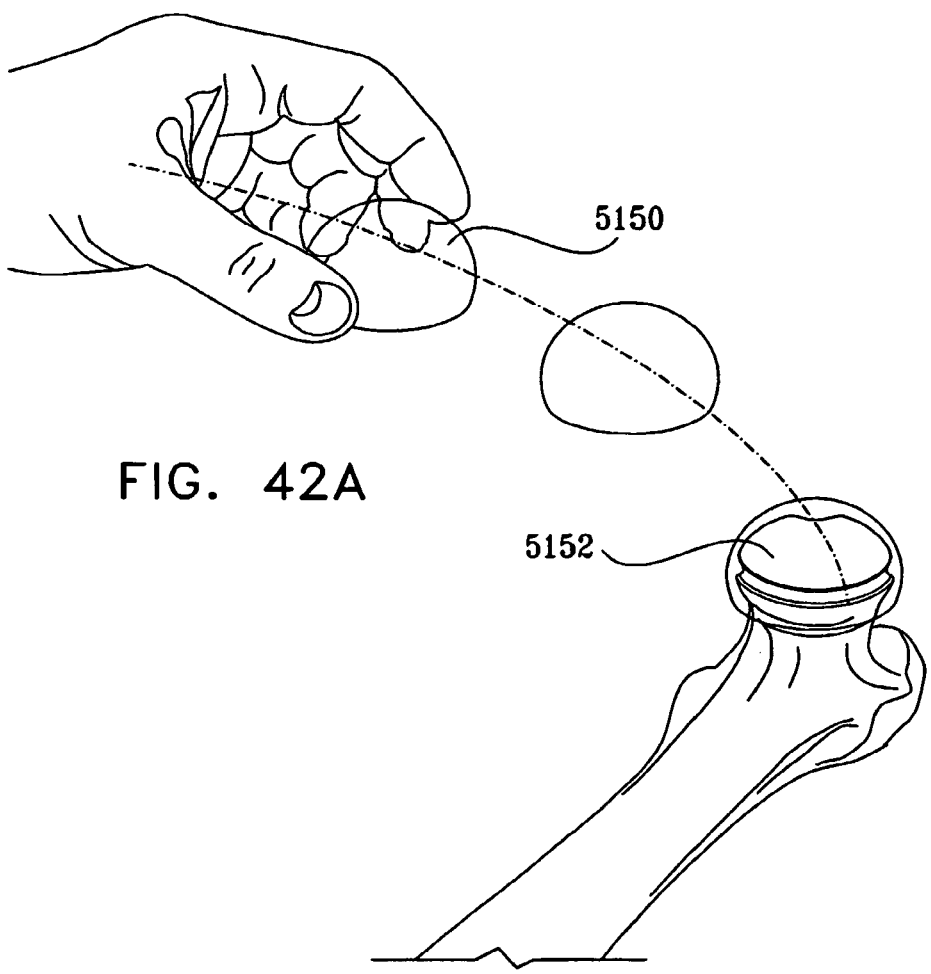
FIGS. 42A and 42B are simplified pictorial illustrations of introduction and pre-snap fit placement of an implantable artificial femoral head resurfacing element adjacent a reamed femoral head in accordance with two alternative embodiments of the present invention.
Figure 42B:
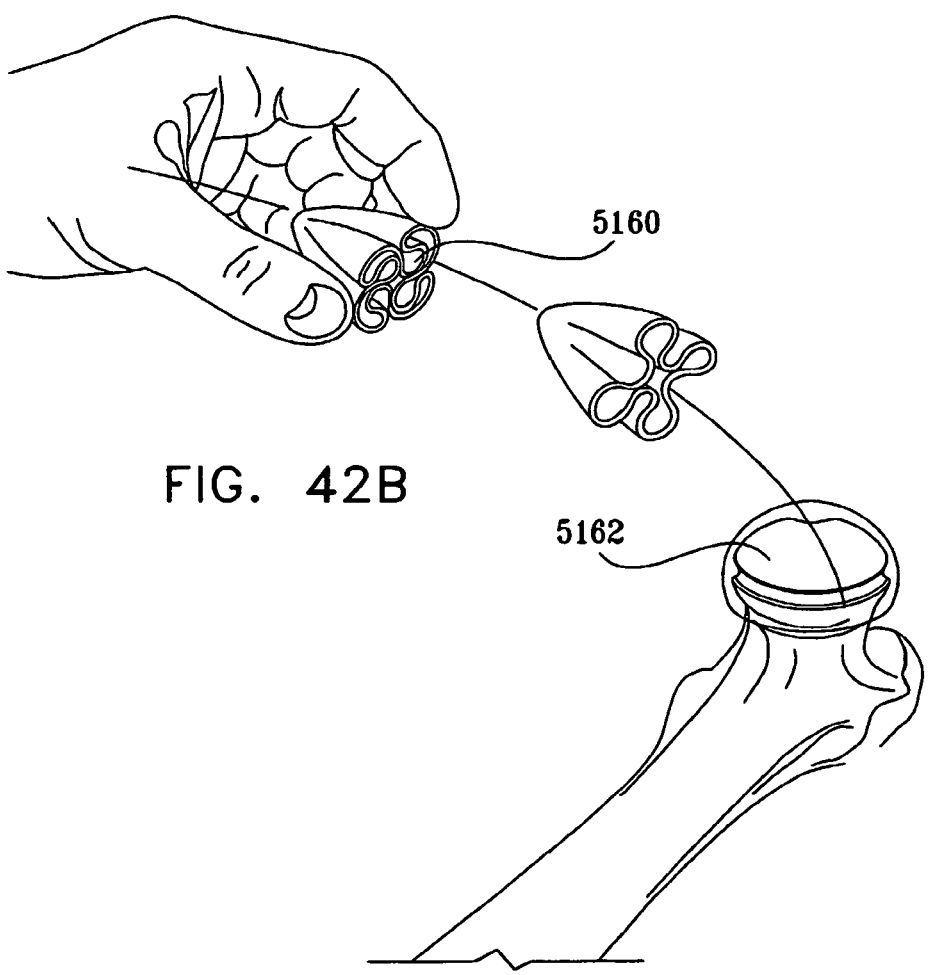

Reference is now made to FIGS. 42A and 42B, which are simplified pictorial illustrations of introduction and pre-snap fit placement of an implantable artificial femoral head resurfacing element adjacent a reamed femoral head in accordance with two alternative embodiments of the present invention. FIG. 42A shows introduction and placement of an implantable artificial femoral head resurfacing element 5150 adjacent a reamed femoral head 5152. Implantable artificial femoral head resurfacing element 5150 may be any suitable implantable artificial femoral head resurfacing element such as those shown and described herein, for example, in any of FIGS. 6A-10C.

FIG. 42B shows introduction and placement of a folded implantable artificial femoral head resurfacing element 5160 adjacent a reamed femoral head 5162. Implantable artificial femoral head resurfacing element 5160 may be any suitable implantable artificial femoral head resurfacing element such as those shown and described herein, for example in any of FIGS. 6A-10C. The embodiment of FIG. 42B is particularly suitable for minimally invasive surgery.

Reference is now made to FIGS. 43A and 43B, which are simplified pictorial illustrations of introduction and pre-snap fit placement of an implantable artificial acetabular socket adjacent a reamed acetabulum in accordance with two alternative embodiments of the present invention. FIG. 43A shows introduction and placement of an implantable artificial acetabular socket 5170 adjacent a reamed acetabulum 5172. Implantable artificial acetabular socket 5170 may be any suitable implantable artificial acetabular socket such as those shown and described herein, for example in any of FIGS. 1A-5C.

FIG. 43B shows introduction and placement of a folded implantable artificial acetabular socket 5180 adjacent a reamed acetabulum 5182. Implantable artificial acetabular socket 5180 may be any suitable implantable artificial acetabular socket such as those shown and described herein, for example in any of FIGS. 1A-5C. The embodiment of FIG. 43B is particularly suitable for minimally invasive surgery.

Figure 44B:
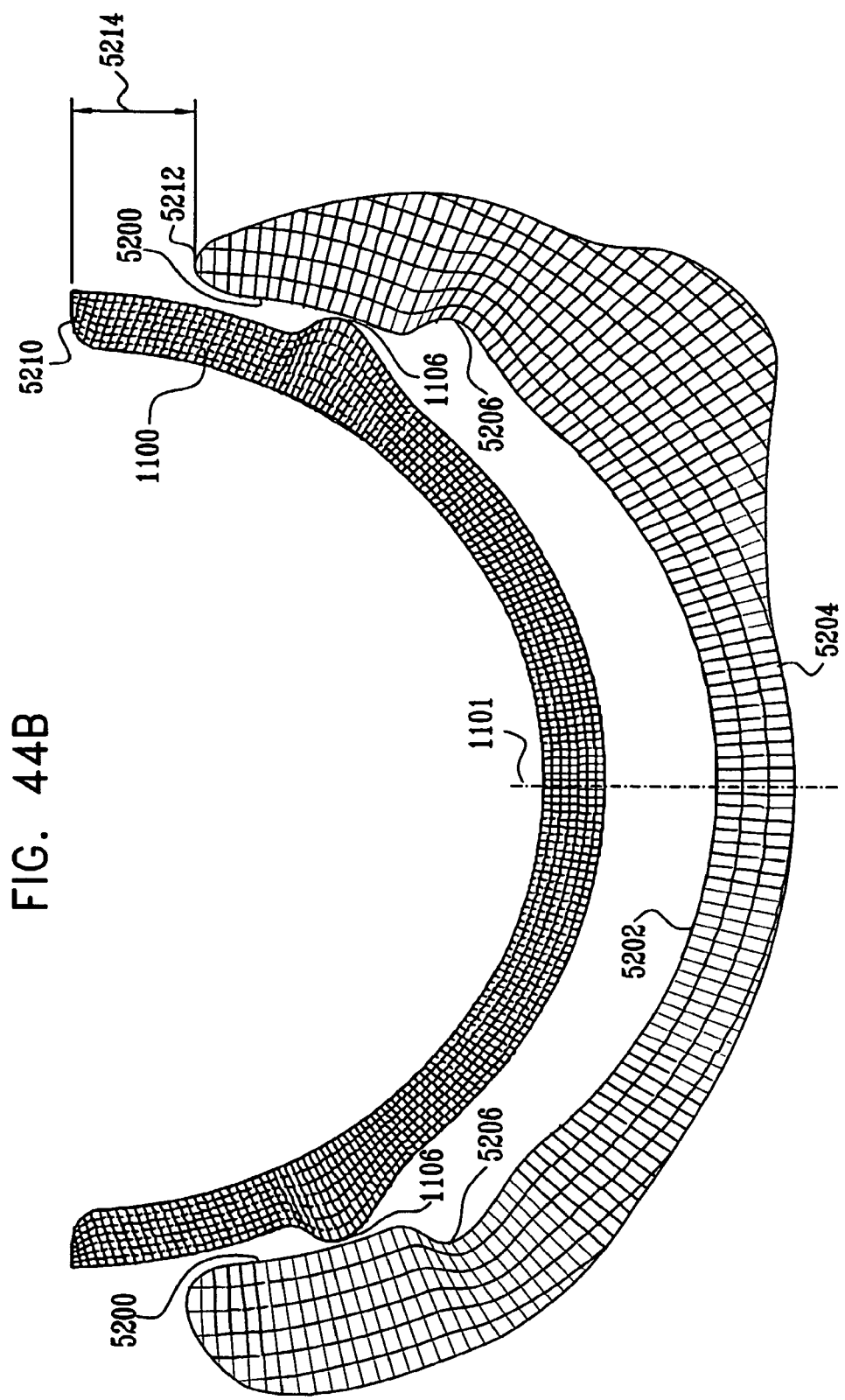

Reference is now made to FIGS. 44A, 44B, 44C and 44D, which are, respectively, a simplified pictorial illustration and sectional illustrations of a snap-fit installation of an implantable artificial acetabular socket in a reamed acetabulum in accordance with a preferred embodiment of the present invention. As shown in FIG. 44A, following introduction and placement of an implantable artificial acetabular socket adjacent a reamed acetabulum, a surgeon, using his fingers, gently introduces the artificial acetabular socket into position for snap-fit engagement with the reamed acetabulum. This position is shown clearly in FIG. 44B, which is a sectional illustration of the reamed acetabulum of FIG. 44A.

For the sake of conciseness and clarity, the implantable artificial acetabular socket 1100 of FIGS. 1A-1C and the description thereof are employed in the explanation which follows, unless specifically indicated otherwise. It is appreciated, however, that where suitable, any other type of acetabular socket described herein may be installed in a manner employing features described hereinbelow.

At the positioning stage shown in FIGS. 44A and 44B, annular outwardly extending protrusion 1106 lies in touching, generally non-compressive engagement with an annular portion 5200 of a generally spherical inner concave surface 5202 of a machined acetabulum 5204. Annular portion 5200 lies above a groove 5206, formed in generally spherical inner concave surface 5202, which is designed to receive protrusion 1106. Accordingly, engagement of protrusion 1106 with annular portion 5200 causes the implantable artificial acetabular socket 1100 to rest at a position wherein an outer edge thereof, designated by reference numeral 5210, lies above a corresponding outer edge 5212 of machined acetabulum 5204. The separation between the planes of outer edge 5210 of implantable artificial acetabular socket 1100 and of outer edge 5212, along axis 1101, is indicated by arrows 5214.

As can be seen from FIG. 44B, substantially no stress is applied to the implantable artificial acetabular socket 1100 and to machined acetabulum 5204 by the engagement thereof shown in FIGS. 44A and 44B.

Figure 44C:
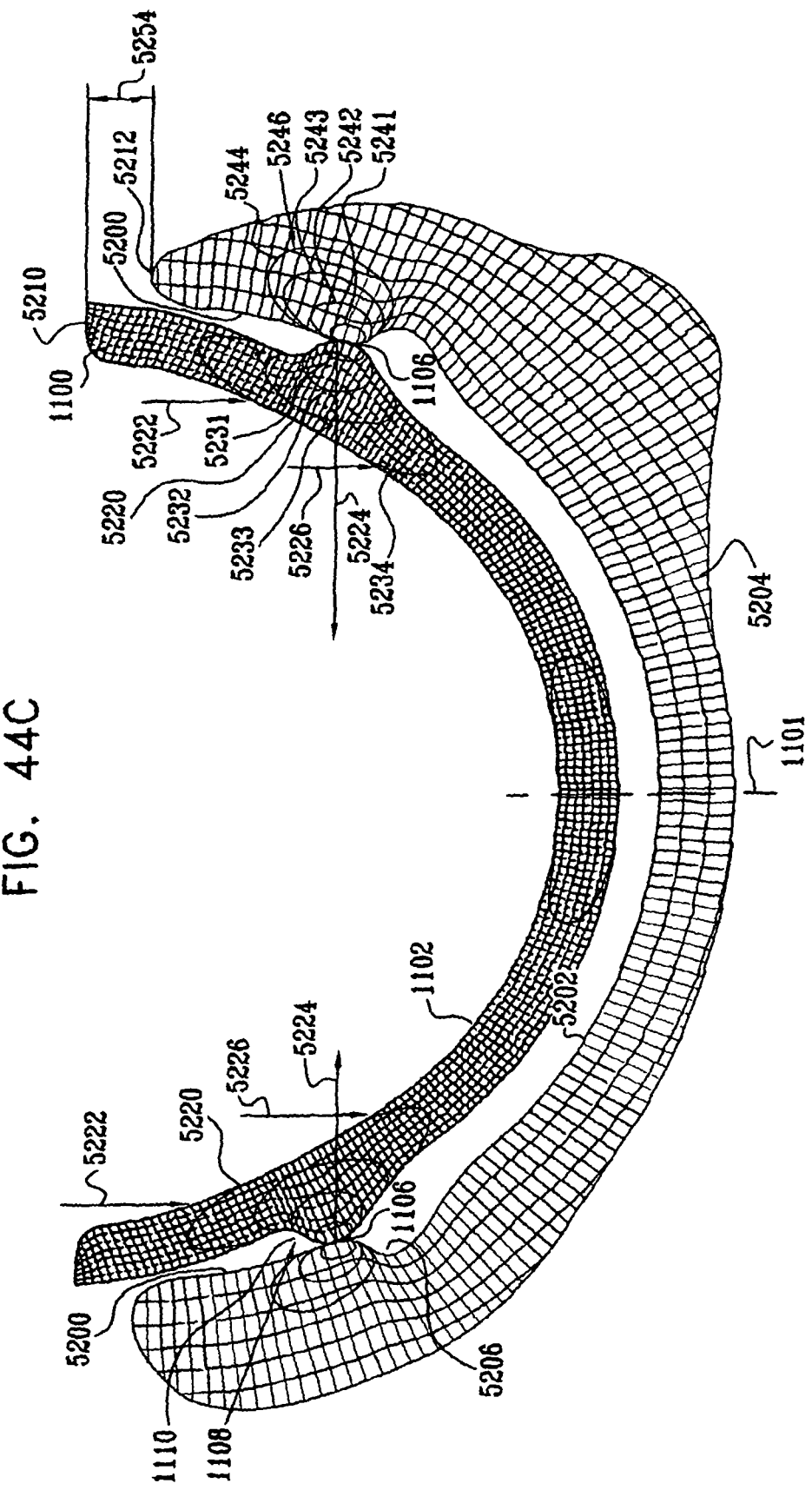

FIG. 44C illustrates a second stage in snap-fit installation of an implantable artificial acetabular socket in a reamed acetabulum in accordance with a preferred embodiment of the present invention. As shown in FIG. 44C, following placement of implantable artificial acetabular socket 1100 into position for snap-fit engagement with the reamed acetabulum, as shown in FIGS. 44A and 44B, the surgeon, using his fingers, gently engages the artificial acetabular socket 1100, preferably at locations, designated by reference numeral 5220, on inner concave surface 1102 thereof, and presses thereon in a direction indicated by arrows 5222, which direction lies generally along axis 1101. The application of this pressure causes displacement of artificial acetabular socket 1100 in direction 5222. Due to the concave configuration of surface 5202 at annular surface portion 5200, this displacement produces radially inward compression of artificial acetabular socket 1100 at protrusion 1106, as indicated by arrows 5224 This radially inward compression results in deformation of the artificial acetabular socket 1100 at protrusion 1106 and in the general region thereof, as indicated, inter alia by arrows 5226.

The radially inward compression and the resulting deformation of artificial acetabular socket 1100 produces stresses in the acetabular socket 1100, as illustrated, inter alia, by stress contour lines 5231, 5232, 5233 and 5234. The above-described engagement of artificial acetabular socket 1100 with the machined acetabulum 5204 causes forces to be applied to the machined acetabulum 5204, producing compression stresses therein, as illustrated, inter alia, by stress contour lines 5241, 5242, 5243 and 5244, in a region designated by reference numeral 5246, in the vicinity of annular surface portion 5200. It is appreciated that the stresses thus produced in machined acetabular socket 5204 produce corresponding strains therein. Both the stresses and the strains have positive medical implications, as will be discussed hereinbelow.

Displacement of artificial acetabular socket 1100 in direction 5222 is seen to reduce the separation between the planes of outer edge 5210 of implantable artificial acetabular socket 1100 and of outer edge 5212 along axis 1101, indicated by arrows 5254.

Figure 44D:
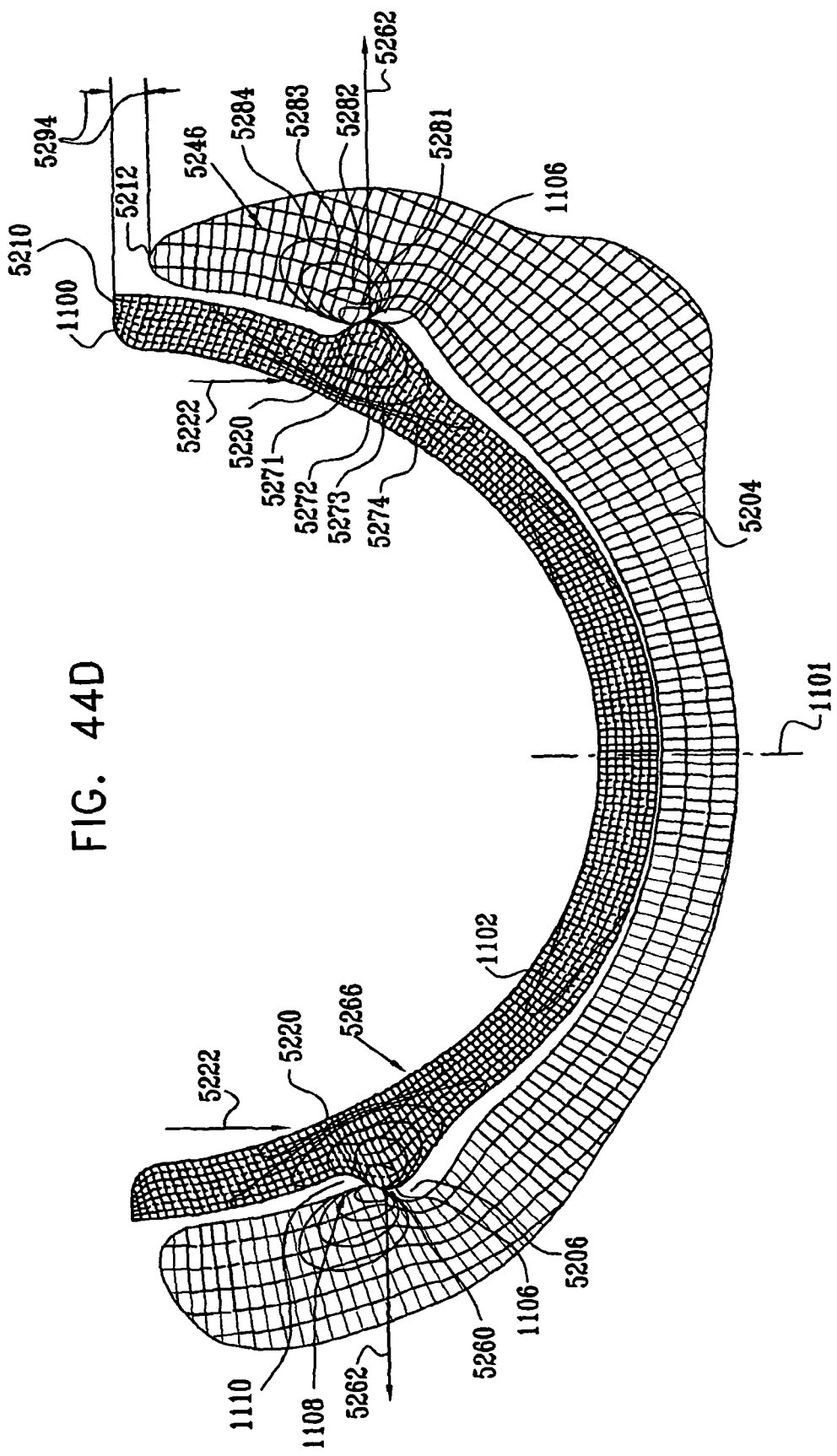

FIG. 44D illustrates a third stage in snap-fit installation of an implantable artificial socket in a reamed acetabulum in accordance with a preferred embodiment of the present invention. As shown in FIG. 44D, the surgeon, using his fingers, presses further on the artificial acetabular socket 1100 preferably at locations, designated by reference numeral 5220 on inner concave surface 1102 thereof in the direction indicated by arrows 5222. The application of this further pressure, causes further displacement of artificial acetabular socket 1100 in direction 5222. This further displacement produces sliding pressure engagement between underlying surface portion 1110 of protrusion 1106 at the undercut 1108 and a radially outward extending surface portion 5260 of groove 5206. It is noted that the resiliency of the artificial acetabular socket 1100 causes radially outward displacement of protrusion 1106, as indicated by arrows 5262. The resulting radially outward decompression results in different deformation of the artificial acetabular socket 1100 at protrusion 1106 and in the general region thereof, as indicated, inter aha by arrow 5266.

This results in reduced and changed stress patterns in both the artificial acetabular socket 1100 and in the machined acetabulum 5204 at region 5246 thereof, as indicated by stress contour lines 5271, 5272, 5273 and 5274 in artificial acetabular socket 1100 and by stress contour lines 5281, 5282, 5283 and 5284 in machined acetabulum 5204.

The further displacement of artificial acetabular socket 1100 in direction 5222 is seen to further reduce the separation between the planes of outer edge 5210 of implantable artificial acetabular socket 1100 and of outer edge 5212 along axis 1101, indicated by arrows 5294.

Figure 45B:
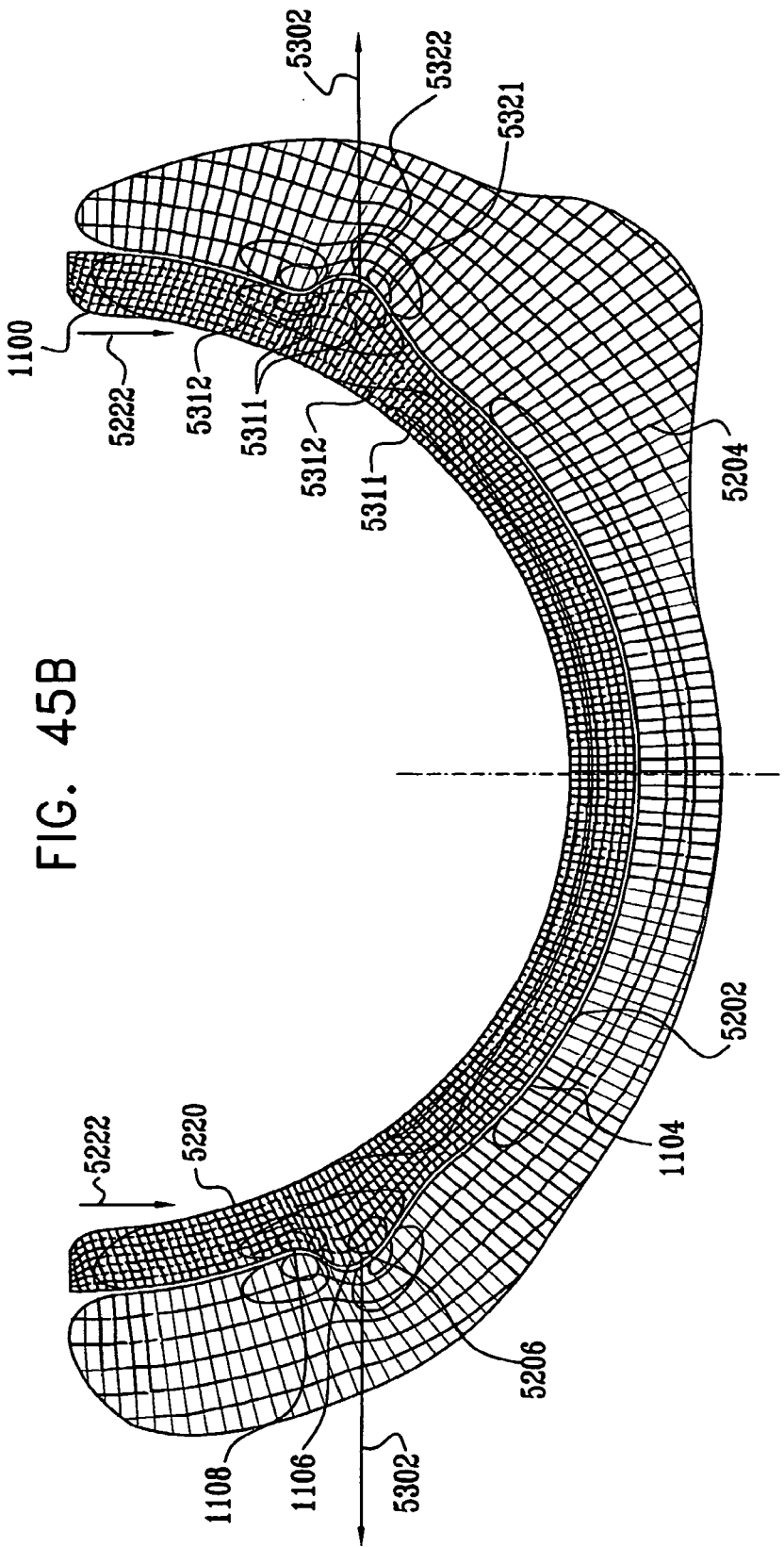

Reference is now made to FIGS. 45A and 45B, which are a simplified pictorial illustration and sectional illustration of a fourth stage in snap-fit installation of an implantable artificial acetabular socket in a reamed acetabulum in accordance with a preferred embodiment of the present invention. As shown in FIG. 45A, the surgeon, using his fingers, now presses on the artificial acetabular socket 1100, preferably at locations, designated by reference numeral 5300, on edges 5210 thereof, in the direction indicated by arrow 5222.

As seen in FIG. 45B, the application of this further pressure causes further displacement of artificial acetabular socket 1100 in direction 5222. This further displacement produces sliding snap-fit engagement between protrusion 1106 and groove 5206.

It is noted that the resiliency of the artificial acetabular socket 1100 causes radially outward displacement of protrusion 1106, as indicated by arrows 5302. The resulting radially outward decompression generally eliminates deformation of the artificial acetabular socket 1100 at protrusion 1106 and in the general region thereof designated by reference numeral 5220.

It is noted that the snap-fit engagement shown in FIG. 45B is a generally non-press fit engagement. Touching engagement between the artificial acetabular socket 1100 and the machined acetabulum 5204 typically takes place at surface 1104 of artificial acetabular socket 1100 and surface 5202 of the machined acetabulum. Accordingly the stresses in both the acetabular socket 1100 and in the machined acetabulum 5204 are generally small and localized in the region of the snap fit engagement therebetween, as indicated by stress contour lines 5311 and 5312 in artificial acetabular socket 1100 and by stress contour lines 5321 and 5322 in machined acetabulum 5204.

It is also appreciated that the snap-fit engagement of the artificial acetabular socket 1100 with the machined acetabulum 5204 produces locking of the artificial acetabular socket 1100 in groove 5206, wherein undercut 1108 prevents disengagement of protrusion 1106 from groove 5206.

Reference is now made to FIGS. 46A, 46B, 46C and 46D, which are illustrations of an implantable artificial acetabular socket, constructed and operative in accordance with a further preferred embodiment of the present invention, which is particularly suitable for use in a hip joint.

As seen in FIGS. 46A, 46B, 46C and 46D, an implantable artificial acetabular socket, designated by reference numeral 5600, is formed preferably by injection molding of polyurethane. Preferred polyurethane materials are described hereinbelow.

Preferably, implantable artificial acetabular socket 5600 is of an uneven thickness, and defines a concave hemispherical inner articulation surface 5602 which is symmetric about an axis 5601, having a beveled edge 5603, and a generally hemispherical outer bone engagement surface 5604 which preferably has formed thereon at any suitable location between its apex and its rim a generally annular outwardly extending protrusion 5606, preferably defining a generally annular undercut 5608. Alternatively, the protrusion 5606 may be any other suitable non-annular, open or closed, generally peripheral, protrusion. The protrusion 5606 is preferably arranged for snap-fit engagement with a corresponding groove formed by reaming of a bone, examples of which are described hereinabove.

Figure 46A:
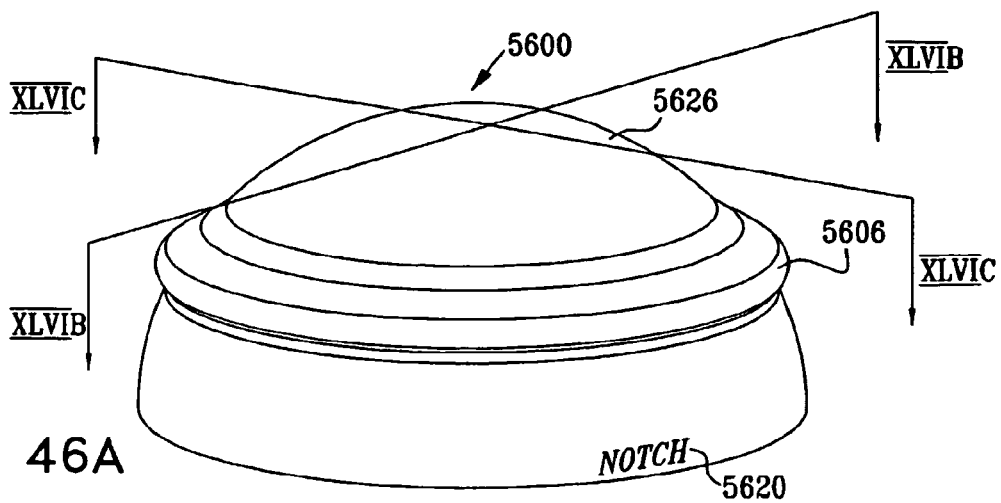
FIGS. 46A, 46B, 46C and 46D are respectively, a pictorial illustration, two different sectional views and a partially cut away pictorial illustration of an implantable artificial acetabular socket constructed and operative in accordance with a further preferred embodiment of the present invention.
Figure 46B:
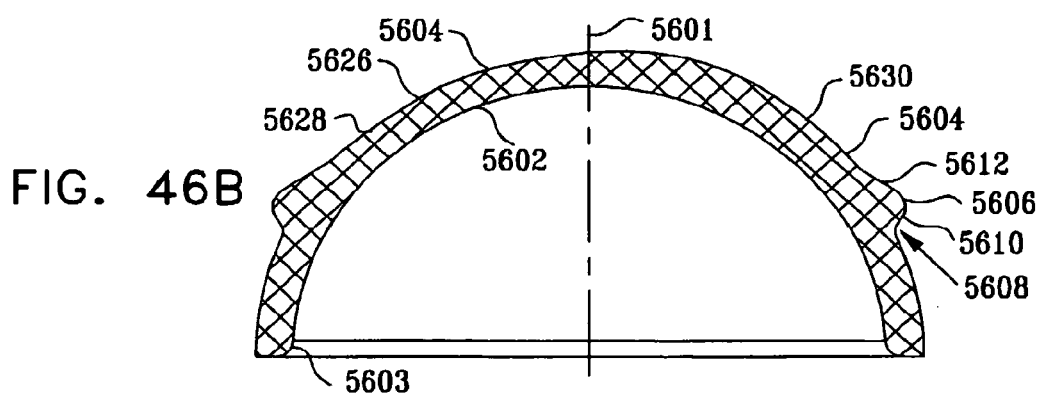

Preferably, the protrusion 5606 has a cross-sectional configuration, as can be readily seen in FIG. 46B, which is characterized in that an underlying surface portion 5610 of protrusion 5606, at the undercut 5608, defines a slope which is sharper than a corresponding slope of an overlying surface portion 5612 of protrusion 5606.

It is a particular feature of the implantable artificial acetabular socket 5600 that its thickness varies at various regions, corresponding to various portions of the hone engagement surface 5604, which gives it an asymmetric configuration requiring a definition of the implanting orientation with regard to the acetabulum. Preferably, a marking 5620, such as a writing "notch" corresponding to the acetabulum notch, is used to position implantable artificial acetabular socket 5600 in its designed orientation by placing the marking 5620 at the acetabulum notch.

Preferably, implantable artificial acetabular socket 5600 defines an uneven thickness portion 5626 between its apex and the annular outwardly extending protrusion 5606. Alternatively, other uneven thickness portions may be defined, such as a protrusion similar to protrusion 5606 constructed of a varied cross section. Alternatively, the portion defined between annular outwardly extending protrusion 5606 and the rim may be of an uneven thickness.

As seen in FIG. 46B, which is a sectional illustration taken along lines XLVIB-XLVIB of FIG. 46A, preferably, uneven thickness portion 5626 includes a region 5628 of a thickness less than the average thickness of uneven thickness portion 5620, which is located opposite marking 5620, which is at the bottom part of implantable artificial acetabular socket 5600, and a region 5630 of a thickness greater than the average thickness of uneven thickness portion 5626, located towards marking 5620 in the bottom part of the implantable artificial acetabular socket 5600.

Figure 46C:
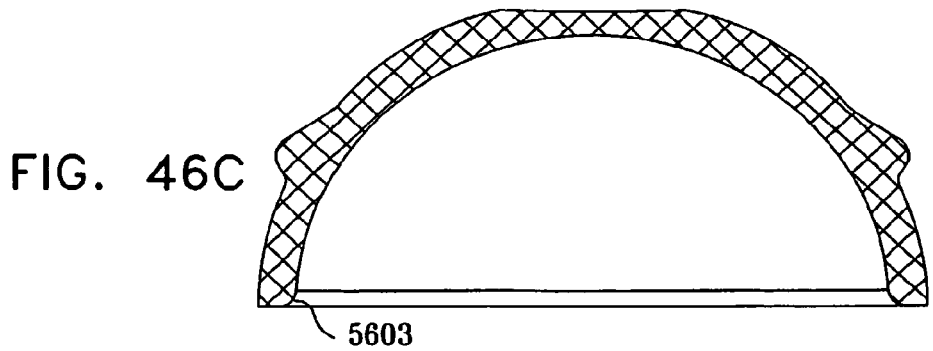
Figure 46D:
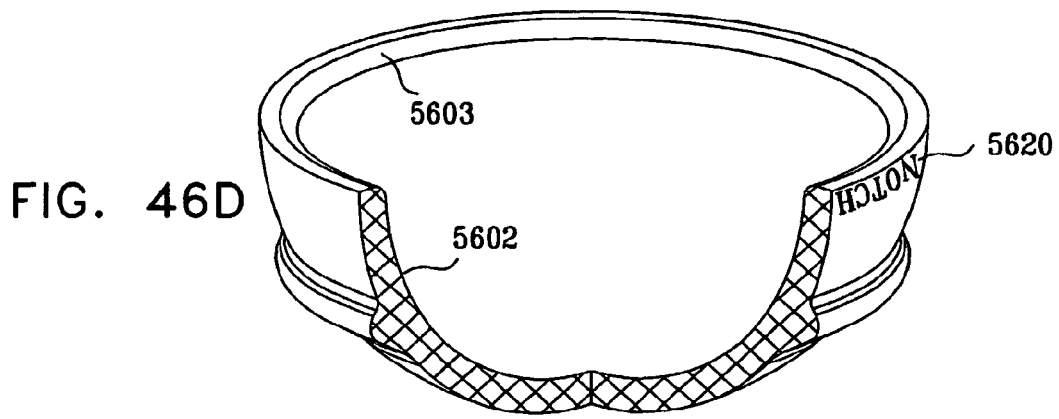

As seen in FIG. 46C, which is a sectional illustration taken along lines XLVIC-XLVIC of FIG. 46A, uneven thickness portion 5626 may include other variations of thickness across uneven thickness portion 5626.

Figure 47A:
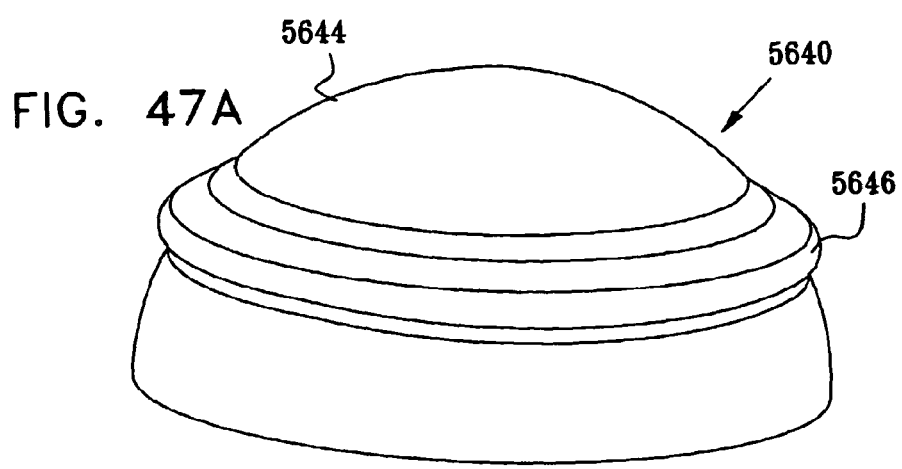
FIGS. 47A, 47B and 47C are respectively, a pictorial and two partially cut away illustrations of an implantable artificial acetabular socket constructed and operative in accordance with another preferred embodiment of the present invention.
Figure 47B:
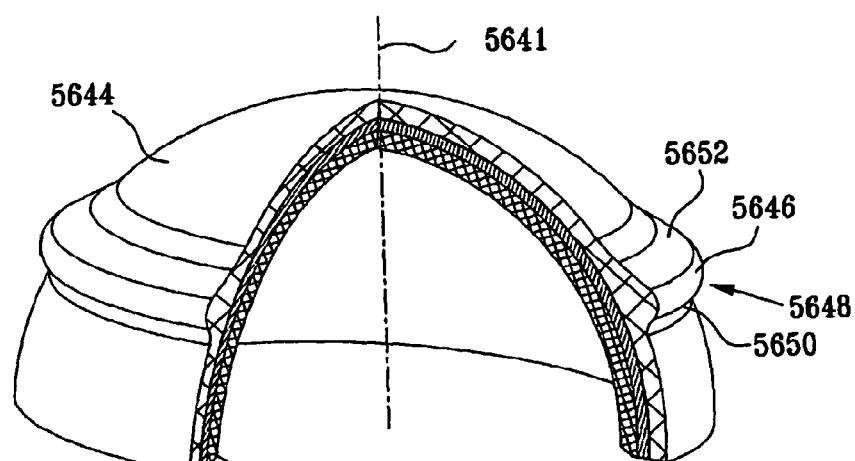
Figure 47C:
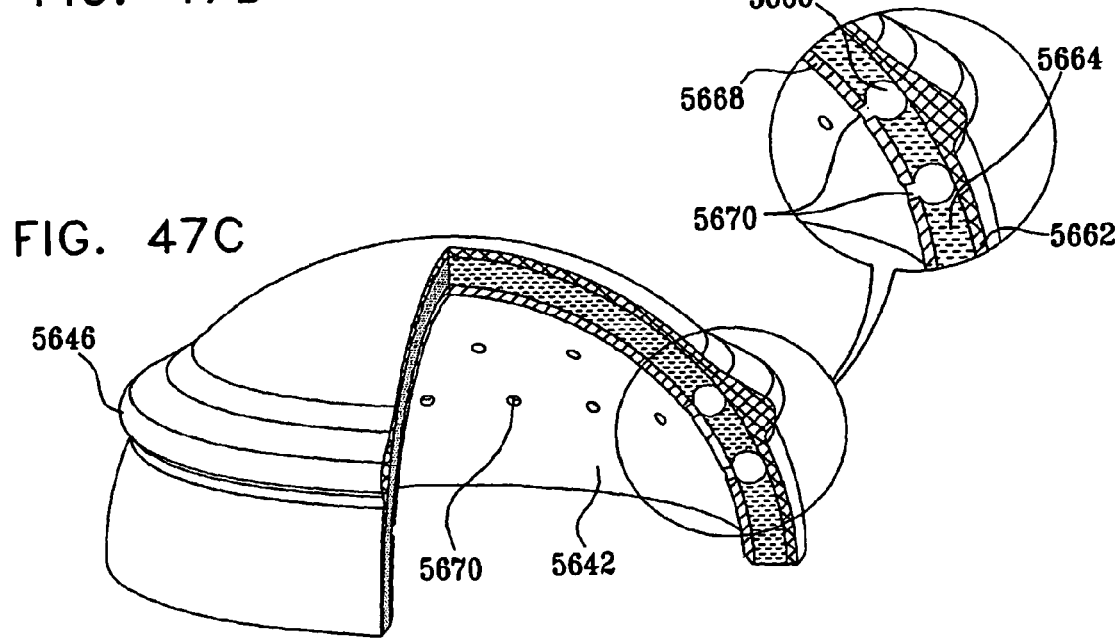

Reference is now made to FIGS. 47A, 47B and 47C, which are illustrations of an implantable artificial acetabular socket constructed and operative in accordance with another preferred embodiment of the present invention, which is particularly suitable for use in a hip joint.

As seen in FIGS. 47A, 47B and 47C, an implantable artificial acetabular socket, designated by reference numeral 5640, is formed preferably by injection molding of polyurethane. Preferred polyurethane materials are described hereinbelow.

Preferably, implantable artificial acetabular socket 5640 is of generally uniform thickness, is symmetric about an axis 5641 and defines an hemispherical concave inner articulation surface 5642, having a beveled edge 5643, and a generally hemispherical outer bone engagement surface 5644 which preferably has formed thereon at any suitable location between its apex and its rim a generally annular outwardly extending protrusion 5646, preferably defining a generally annular undercut 5648. Alternatively, the protrusion 5646 may be any other suitable non-annular, open or closed, generally peripheral, protrusion. The protrusion 5646 is preferably arranged for snap-fit engagement with a corresponding groove formed by reaming of a bone, examples of which are described hereinabove.

Preferably, the protrusion 5646 has a cross-sectional configuration, as can be readily seen in FIG. 47B, which is characterized in that an underlying surface portion 5650 of protrusion 5646, at the undercut 5648, defines a slope which is sharper than a corresponding slope of an overlying surface portion 5652 of protrusion 5646.

Implantable artificial acetabular socket 5640 is constructed from an outer layer 5662, an intermediate layer 5664, preferably, including a plurality of voids 5666, and an inner layer 5668. Outer layer 5662 is preferably molded of a polyurethane of durometer number 55 shore D, intermediate layer 5664 is preferably molded of a polyurethane or durometer number 70 shore D, and inner layer 5668 is preferably molded of a polyurethane of durometer number 80 shore A. Intermediate layer 5664 preferably includes carbon whiskers.

In another preferred embodiment of the present invention, implantable artificial acetabular socket 5640 is constructed from an outer layer 5662, an intermediate layer 5664, preferably, including a plurality of voids 5666, and an inner layer 5668. Outer layer 5662 is preferably molded of a polyurethane of durometer number 55 shore D, inner layer 5668 is preferably molded of a polyurethane of durometer number S0 shore A and intermediate layer 5664 is preferably molded of a polyurethane having a fluid absorption property, such as HydroThane™, manufactured by CardioTech International, Inc., 78E Olympia Ave., Woburn, Mass., USA. Inner layer 5668 has formed in articulation surface 5642 a plurality of thoroughgoing apertures 5670 connecting to voids 5666.

Reference is now made to FIGS. 48A, 48B, 48C and 48D which are partially cut away pictorial illustrations of an implantable artificial acetabular socket constructed and operative in accordance with still another preferred embodiment of the present invention and which is particularly suitable for use in a hip joint.

As seen in FIGS. 48A, 48B, 48C and 48D, an implantable artificial acetabular socket, designated by reference numeral 5680, is formed preferably by injection molding of polyurethane. Preferred polyurethane materials are described hereinbelow.

Preferably, implantable artificial acetabular socket 5680 is of generally uniform thickness, is symmetric about an axis 5681 and defines an hemispherical concave inner articulation surface 5682, having a beveled edge 5683, and a generally hemispherical outer bone engagement surface 5684 which preferably has formed thereon at any suitable location between its apex and its rim a generally annular outwardly extending protrusion 5686, preferably defining a generally annular undercut 5688. Alternatively, the protrusion 5686 may be any other suitable non-annular, open or closed, generally peripheral, protrusion. The protrusion 5686 is preferably arranged for snap-lit engagement with a corresponding groove formed by reaming of a bone, examples of which are described hereinabove.

Preferably, the protrusion 5686 has a cross-sectional configuration, which is characterized in that an underlying surface portion 5690 of protrusion 5686, at the undercut 5688, defines a slope which is sharper than a corresponding slope of an overlying surface portion 5692 of protrusion 5686.

Figure 48A:
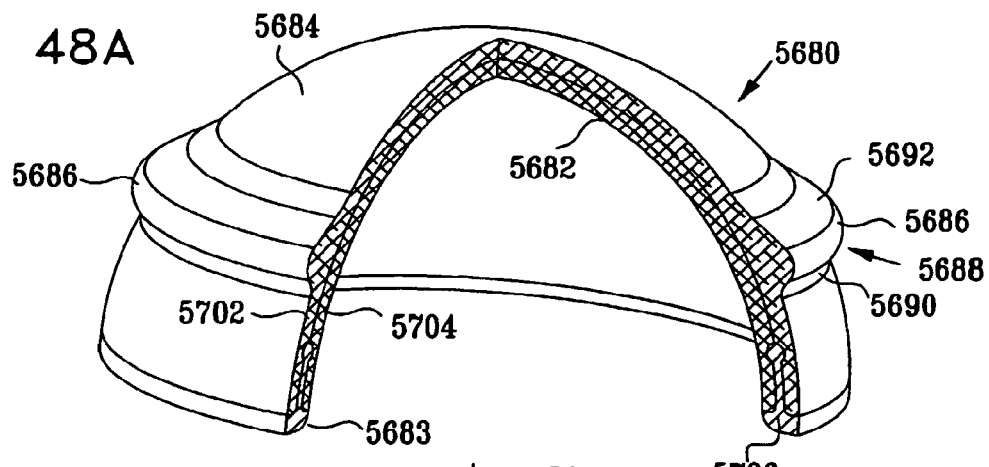
FIGS. 48A, 48B, 48C and 48D are partially cut away pictorial illustrations of an implantable artificial acetabular socket constructed and operative in accordance with still another preferred embodiment of the present invention.
Figure 48B:
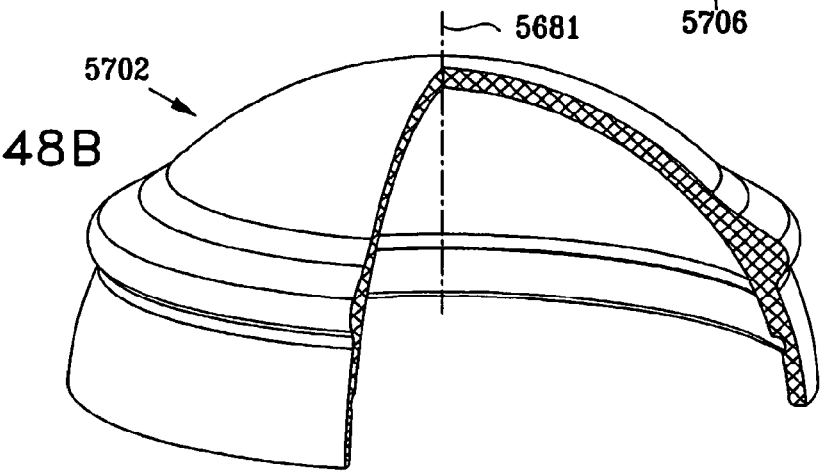
Figure 48C:
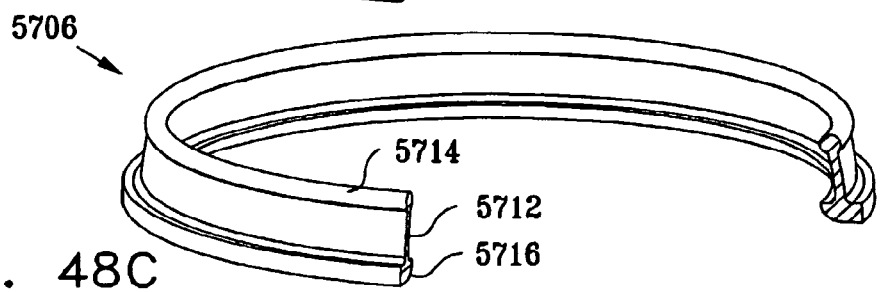
Figure 48D:
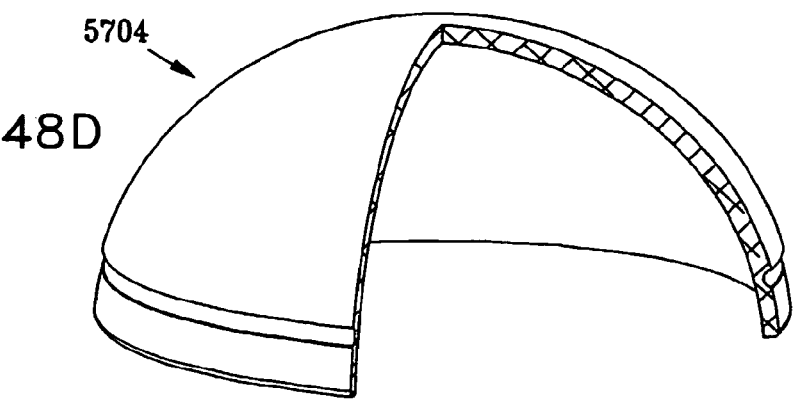

Implantable artificial acetabular socket 5680 is constructed from an outer layer 5702, as shown in FIG. 48B, and an inner layer 5704, as shown in FIG. 48D, and includes an inserted internal deformation control element 5706, as shown in FIG. 48C. Outer layer 5702 is preferably molded of a polyurethane of durometer number 55 shore D and inner layer 5704 is preferably molded of a polyurethane having a durometer number 80 shore A. Internal deformation control element 5706 is preferably molded of a relatively rigid polyurethane, typically one having a Shore hardness of approximately 70 D and may have carbon whiskers embedded therein. The deformation control element 570n preferably has an overall generally annular configuration, defined by a web portion 5712, a first thickened portion 5714, having a circular cross section, and a second thickened portion 5716 having a rectangular cross section.

Preferably, deformation control element 5706 is configured and insertably positioned within implantable artificial acetabular socket 5680 with portions of outer layer 5702 covering it outwardly and with portions of inner layer 5704 covering it inwardly.

Figure 49A:
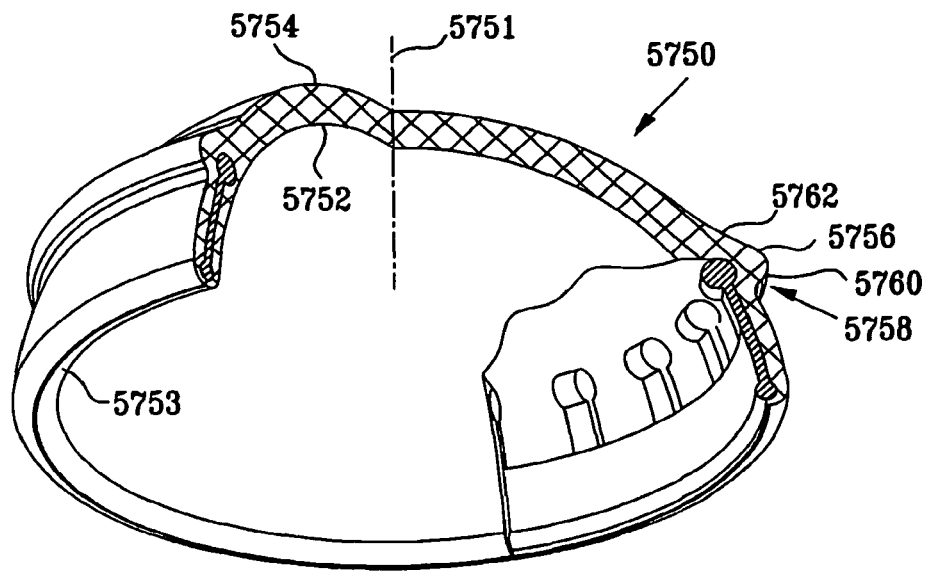
FIGS. 49A and 49B are respective pictorial and partially cut away illustrations of an implantable artificial acetabular socket constructed and operative in accordance with yet another preferred embodiment of the present invention.
Figure 49B:
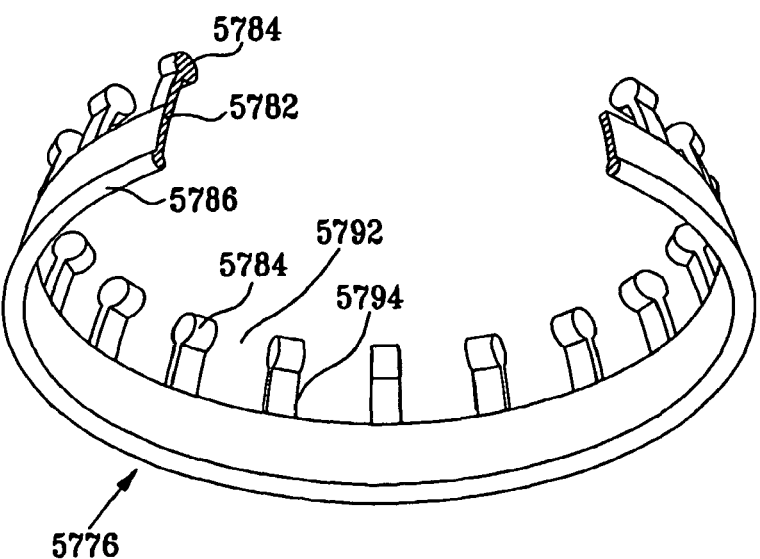

Reference is now made to FIGS. 49A and 49B, which are respective pictorial and partially cut away illustrations of an implantable artificial acetabular socket, constructed and operative in accordance with still another preferred embodiment of the present invention, which is particularly suitable for use in a hip joint As seen in FIGS. 49A and 49B, an implantable artificial acetabular socket, designated by reference numeral 5750, is formed preferably by injection molding of polyurethane. Preferred polyurethane materials are described hereinbelow.

Preferably, implantable artificial acetabular socket 5750 is of generally uniform thickness, is symmetric about an axis 5751 and defines an hemispherical concave inner articulation surface 5752, having a beveled edge 5753, and a generally hemispherical outer bone engagement surface 5754 which preferably has formed thereon at any suitable location between its apex and its rim a generally annular outwardly extending protrusion 5756, preferably defining a generally annular undercut 5758 Alternatively, the protrusion 5756 may be any other suitable non-annular, open or closed, generally peripheral protrusion. The protrusion 5756 is preferably arranged for snap-fit engagement with a corresponding groove formed by reaming of a bone, examples of which are described hereinabove.

Preferably, the protrusion 5756 has a cross-sectional configuration, which is characterized in that an underlying surface portion 5760 of protrusion 5756, at the undercut 5758, defines a slope which is sharper than a corresponding slope of an overlying surface portion 5762 of protrusion 5756.

It is a particular feature of the artificial implantable artificial acetabular socket 5750 that it is constructed from a single layer, preferably, molded of a polyurethane of durometer number 80 shore A, and includes an inserted internal deformation control element 5776, illustrated pictorially in FIG. 49B. The deformation control element 5776 is preferably molded of a relatively rigid polyurethane, typically one having a Shore hardness of approximately 70 D, and may have carbon whiskers embedded therein.

Preferably, deformation control element 5776 is configured and insertably positioned within implantable artificial acetabular socket 5750 with portions of PU material of the single molded layer covering it outwardly, inwardly and towards the rim of implantable artificial acetabular socket 5750.

The deformation control element 5776 preferably has an overall generally annular configuration defined by a web portion 5782, a first thickened portion 5784, having a circular cross section, and a second thickened portion 5786, having a circular cross section. Deformation control element 5776 is further defined by rectangular cut-outs 5792 separated by flaps 5794 which terminate in thickened portions 5784 which are also separated by cut-outs 5792.

Figure 50A:
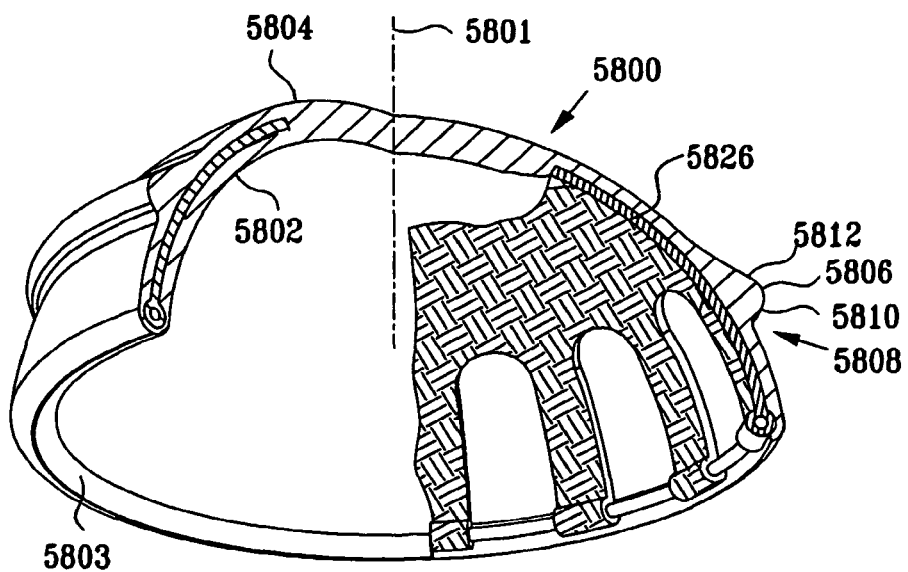
FIGS. 50A and 50B are respective pictorial and partially cut away illustrations of an implantable artificial acetabular socket constructed and operative in accordance with a further preferred embodiment of the present invention.
Figure 50B:
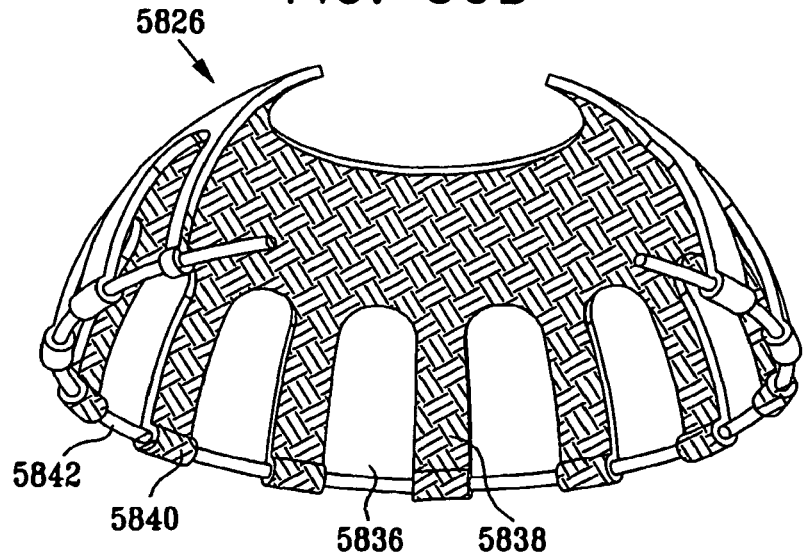

Reference is now made to FIGS. 50A and 50B, which are respective pictorial and partially cut away illustrations of an implantable artificial acetabular socket, constructed and operative in accordance with still another preferred embodiment of the present invention, which is particularly suitable for use in a hip joint.

As seen in FIGS. 50A and 50B, an implantable artificial acetabular socket, designated by reference numeral 5800, is formed preferably by injection molding of polyurethane over a reinforcing deformation control element. Preferred polyurethane materials are described hereinbelow.

Preferably, implantable artificial acetabular socket 5800 is of generally uniform thickness, is symmetric about an axis 5801 and defines art hemispherical concave inner articulation surface 5802, having a beveled edge 5803, and a generally hemispherical outer bone engagement surface 5804 which preferably has formed thereon at any suitable location between its apex and its rim a generally annular outwardly extending protrusion 5806, preferably defining a generally annular undercut 5808. Alternatively, the protrusion 5806 may be any other suitable non-annular, open or closed, generally peripheral, protrusion. The protrusion 5806 is preferably arranged for snap-fit engagement with a corresponding groove formed by reaming of a bone, examples of which are described hereinabove.

Preferably, the protrusion 5806 has a cross-sectional configuration, as can be readily seen in FIG. 50A, which is characterized in that an underlying surface portion 5810 of protrusion 5806, at the undercut 5808, defines a slope which is sharper than a corresponding slope of an overlying surface portion 5812 of protrusion 5806.

Implantable artificial acetabular socket 5800 is constructed from a single layer, preferably, molded of a polyurethane of durometer number 80 shore A over internal deformation control element 5826, illustrated pictorially in FIG. 50B. The deformation control element 5826 is preferably formed of woven high performance fibers, such as carbon fibers, KEVLAR®, DYNEEMA®, and glass fibers, and has an overall generally truncated spherical configuration defined by arched cut-outs 5836 separated by flaps 5838 which terminate in transverse cylindrical portions 5840 in which are fixedly disposed rigid rod element 5842 which extends circumferentially as an open or closed ring.

It is seen that deformation control element 5826 is preferably molded entirely within artificial implantable artificial acetabular socket 5800.

Figure 51A:
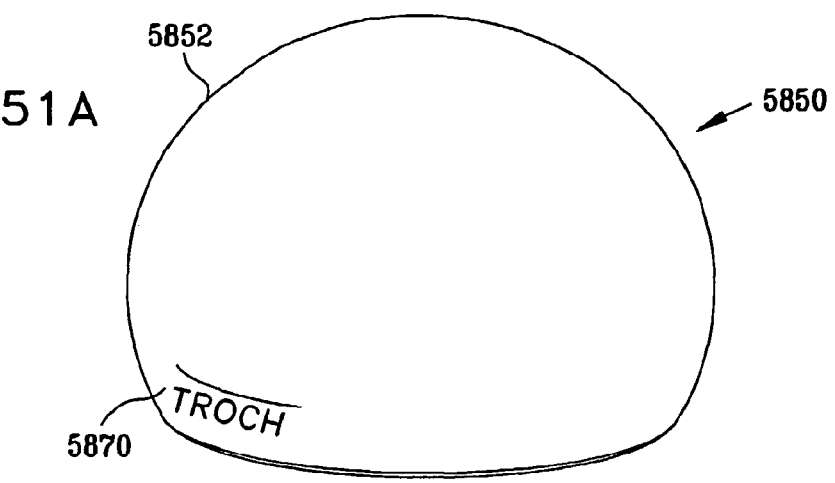
FIGS. 51A, 51B and 51C are respective pictorial, sectional and partially cut away illustrations of an implantable artificial femoral head resurfacing element constructed and operative in accordance with a further preferred embodiment of the present invention.
Figure 51B:
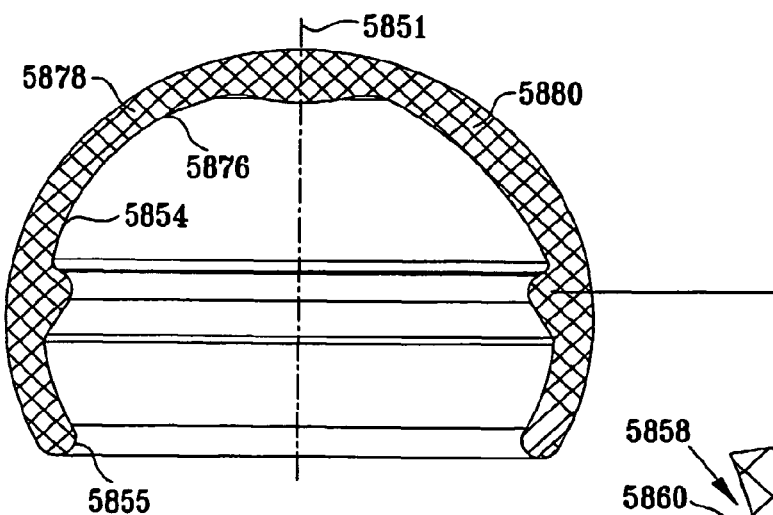
Figure 51C:
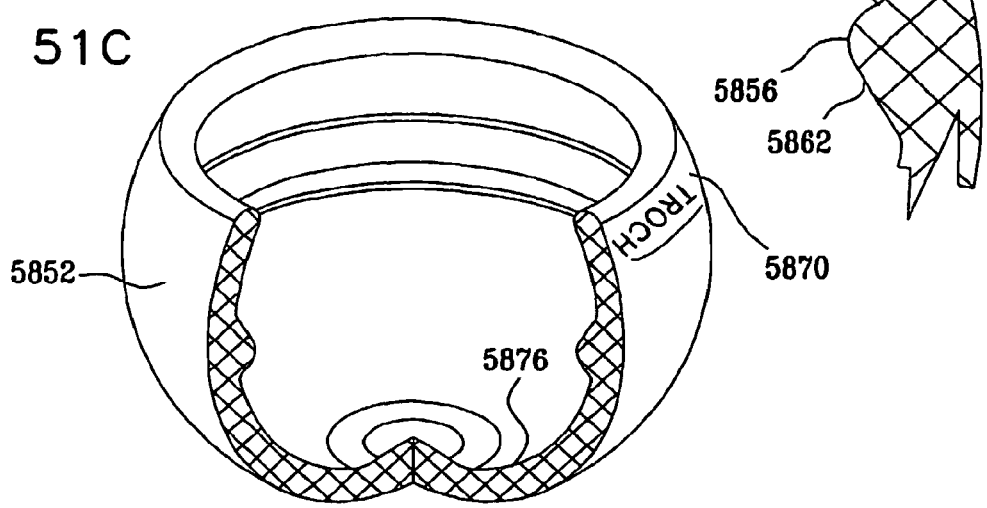

Reference is now made to FIGS. 51A, 51B and 51C, which are respective pictorial sectional and partially cut away illustrations of an implantable artificial femoral head resurfacing element constructed and operative in accordance with a further preferred embodiment of the present invention. The implantable artificial femoral head resurfacing element is intended for mounting onto a natural femoral head in accordance with a preferred embodiment of the present invention.

As seen in FIGS. 51A, 51B and 51C, an implantable artificial femoral head resurfacing element, designated by reference numeral 5850, is formed preferably by injection molding of polyurethane. Preferred polyurethane materials are described hereinbelow.

Preferably, implantable artificial femoral head resurfacing element 5850 is of generally uneven thickness, with a distinct thickened portion at its apex. Artificial femoral head resurfacing element 5850 defines a hemispherical outer articulation surface 5852 and an inner bone engagement surface 5854, having a beveled edge 5855, which preferably has formed thereon at any suitable location between its apex and its rim a generally annular inwardly extending protrusion 5856, preferably defining a generally annular undercut 5858. Alternatively, the protrusion 5856 may be any other suitable non-annular, open or closed, generally peripheral, protrusion. The protrusion 5850 is preferably arranged for snap-fit engagement with a corresponding groove formed by reaming of a femoral head.

Preferably, the protrusion 5856 has a cross-sectional configuration, as can be readily seen in FIG. 51B, which is characterized in that an underlying surface portion 5860 of protrusion 5856, at the undercut 5858, defines a slope which is sharper than a corresponding slope of an overlying surface portion 5862 of protrusion 5856.

Implantable artificial femoral head resurfacing element 5850 defines an uneven thickness portion 5876 extending between thickened apex portion and the protrusion 5856. The thickness of uneven thickness portion 5876 varies at various regions, corresponding to various portions of the bone engagement surface 5854, which renders it an asymmetric configuration requiring a definition of the implanting orientation with regard to the femoral head. Preferably, a marking numeral 5870, such as the writing trochanter, designating and corresponding to the great trochanter, is used to position implantable artificial femoral head resurfacing element 5850 in its designed orientation by placing the marking 5870 facing the great trochanter.

As can be seen in FIG. 51B, preferably, uneven thickness portion 5876 comprises a region 5878 of a thickness less than the average thickness of uneven thickness portion 5876, located facing marking 5870, and a region 5880 of a thickness greater than the average thickness of uneven thickness portion 5876, located away from marking 5870.

As can be seen in FIG. 51C, preferably, uneven thickness portion 5876 may include other variations of thickness across uneven thickness portion 5876.

Reference is now made to FIGS. 52A, 52B and 52C, which are respective pictorial, sectional and partially cut away illustrations of an implantable artificial femoral head resurfacing element constructed and operative in accordance with another preferred embodiment of the present invention.

As seen in FIGS. 52A, 52B, and 52C, an implantable artificial femoral head resurfacing element, designated by reference numeral 5900, is formed preferably by injection molding of multi layers of polyurethane including a fluid absorbing layer. Preferred polyurethane materials are described hereinbelow.

Preferably, implantable artificial femoral head resurfacing element 5900 is of generally uniform thickness, other than at its apex which is thickened, is symmetric about an axis 5901 and defines an hemispherical outer articulation surface 5902 and a generally hemispherical inner bone engagement surface 5904, having a beveled edge 5905, which preferably has formed thereon at any suitable location between its apex and its rim a generally annular inwardly extending protrusion 5906, preferably defining a generally annular undercut 5908. Alternatively, the protrusion 5906 may be any other suitable non-annular, open or closed, generally peripheral, protrusion. The protrusion 5906 is preferably arranged for snap-fit engagement with a corresponding groove formed by reaming of a femoral head.

Preferably, the protrusion 5906 has a cross-sectional configuration, as can be readily seen in FIG. 52B, which is characterized in that an underlying surface portion 5910 of protrusion 5906, at the undercut 5908, defines a slope which is sharper than a corresponding slope of an overlying surface portion 5912 of protrusion 5906.

Implantable artificial femoral head resurfacing element 5900 is constructed from an inner layer 5922, an intermediate layer 5924, which preferably includes a plurality of voids 5926, and an outer layer 5928. Inner layer 5922 is, preferably, molded of a polyurethane of durometer number 55 shore D, outer layer 5928 is, preferably, molded of a polyurethane of durometer number 80 shore A and intermediate layer 5924 is, preferably, molded of a polyurethane having a fluid absorption property, such as HydroThane™, manufactured by CardioTech International, Inc., 78E Olympia Ave., Woburn, Mass., USA. Outer layer 5928 has formed in articulation surface 5902 a plurality of thoroughgoing apertures 5929 connecting to voids 5926.

It is appreciated that, even though the illustrated embodiment shows the non-uniform thickness portion of artificial femoral head resurfacing element 5900 at the apex thereof, any suitable portion thereof may be of non-uniform thickness.

Figure 53A:
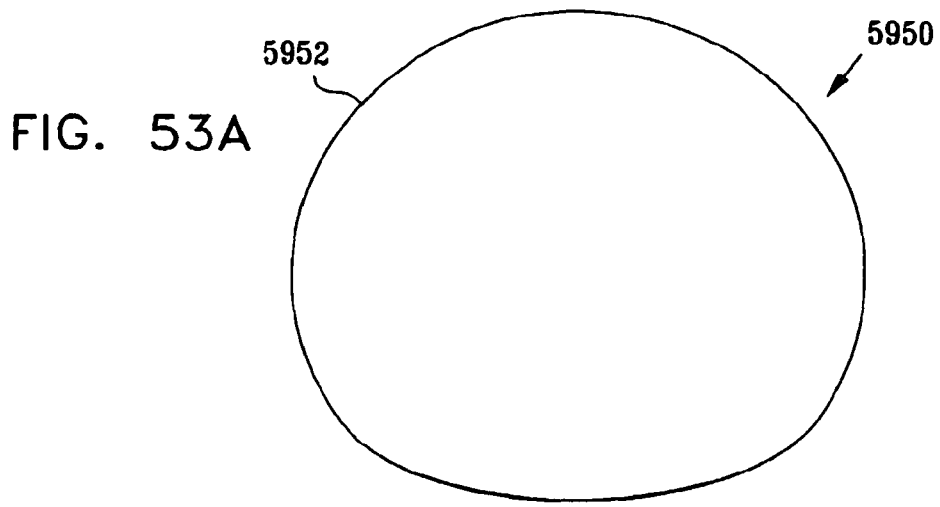
FIGS. 53A, 53B and 53C are respective pictorial, sectional and partially cut away illustrations of an implantable artificial femoral head resurfacing element constructed and operative in accordance with still another preferred embodiment of the present invention.
Figure 53B:
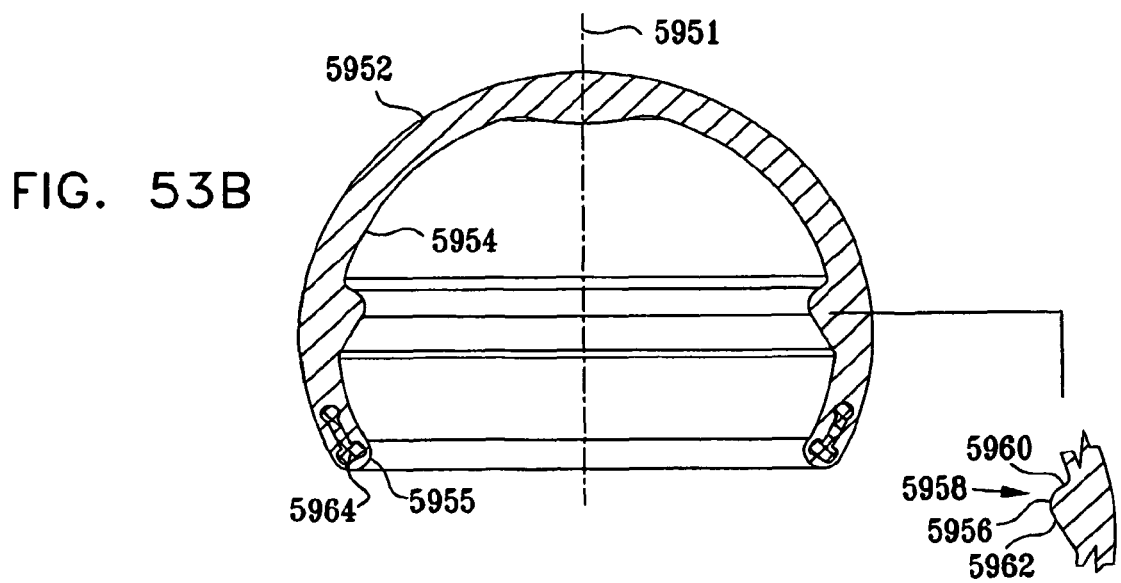
Figure 53C:
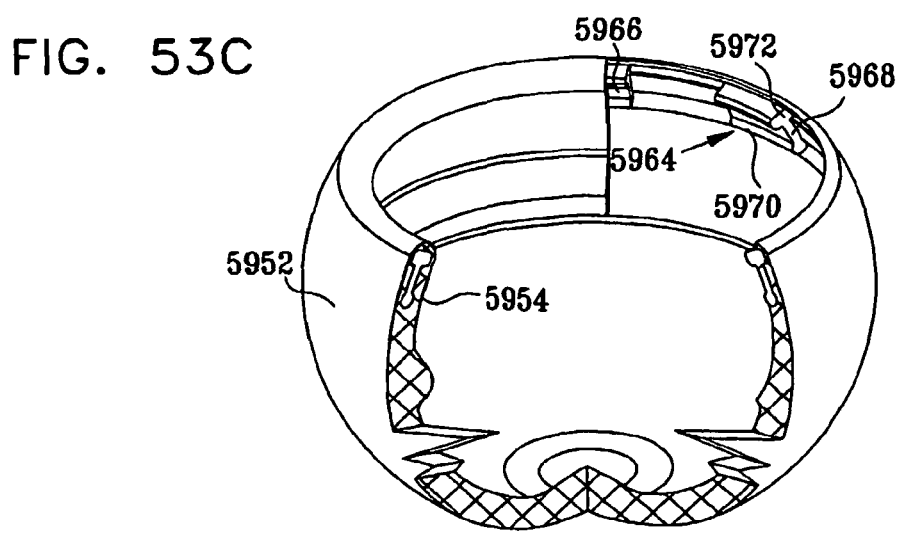

Reference is now made to FIGS. 53A, 53B and 53C, which are respective pictorial, sectional and partially cut away illustrations of an implantable artificial femoral head resurfacing element, intended for mounting onto a natural femoral head, in accordance with still another preferred embodiment of the present invention.

As seen in FIGS. 53A, 53B, and 53C, an implantable artificial femoral head resurfacing element, designated by reference numeral 5950, is formed preferably by injection molding of polyurethane formed over a deformation control element. Preferred polyurethane materials are described hereinbelow.

Preferably, implantable artificial femoral head resurfacing element 5950 is of generally uniform thickness, other than at its apex which is thickened, is symmetric about an axis 5951 and defines an hemispherical outer articulation surface 5952 and a generally hemispherical inner bone engagement surface 5954, having a beveled edge 5955, which preferably has formed thereon at any suitable location between its apex and its rim a generally annular inwardly extending protrusion 5956, preferably defining a generally annular undercut 5958. Alternatively, the protrusion 5956 may be any other suitable non-annular, open or closed, generally peripheral, protrusion. The protrusion 5956 is preferably arranged for snap-fit engagement with a corresponding groove formed by reaming of a femoral head.

Preferably, the protrusion 5956 has a cross-sectional configuration, as can be readily seen in FIG. 53B, which is characterized in that an underlying surface portion 5960 of protrusion 5956, at the undercut 5958, defines a slope which is sharper than a corresponding slope of an overlying surface portion 5962 of protrusion 5956.

Implantable artificial femoral head resurfacing element 5950 is constructed from a single layer molded of a polyurethane of durometer number 80 shore A, and includes an inserted array 5964 of internal deformation control elements 5966, as seen in FIG. 53C. The deformation control elements 5966 are preferably molded of a relatively rigid polyurethane, typically one having a Shore hardness of approximately 70 D and may have carbon whiskers embedded therein.

The deformation control elements 5966, preferably, have an overall generally partial annular configuration including a web portion 5968, a first thickened portion 5970, having a circular cross section, and a second thickened portion 5972 having a rectangular cross section. Preferably, deformation control elements 5966 are configured and insertably positioned within implantable artificial femoral head resurfacing element 5950 with portions of PU material of the single molded layer covering them outwardly, inwardly and towards the rim of implantable artificial head resurfacing element 5950.

Reference is now made to FIGS. 54A, 54B and 54C, which are respective pictorial, sectional and partially cut away illustrations of an implantable artificial femoral head resurfacing element, intended for mounting onto a natural femoral head, in accordance with yet another preferred embodiment of the present invention.

As seen in FIGS. 54A, 54B, and 54C, an implantable artificial femoral head resurfacing element, designated by reference numeral 6000, is formed preferably by injection molding of multi layers of polyurethane formed over a deformation control element. Preferred polyurethane materials are described hereinbelow.

Preferably, implantable artificial femoral head resurfacing element 6000 is of generally uniform thickness, other than at its apex which is thickened, is symmetric about an axis 6001 and defines an hemispherical outer articulation surface 6002 and a generally hemispherical inner bone engagement surface 6004, having a beveled edge 6005, which preferably has formed thereon at any suitable location between its apex and its rim a generally annular inwardly extending protrusion 6006, preferably defining a generally annular undercut 6008. Alternatively, the protrusion 6006 may be any other suitable non-annular, open or closed, generally peripheral, protrusion. The protrusion 6006 is preferably arranged for snap-fit engagement with a corresponding groove formed by reaming of a femoral head.

Preferably, the protrusion 6006 has a cross-sectional configuration, as can be readily seen in FIG. 54B, which is characterized in that an underlying surface portion 6010 of protrusion 6006, at the undercut 6008, defines a slope which is sharper than a corresponding slope of an overlying surface portion 6012 of protrusion 6006.

Implantable artificial femoral head resurfacing element 6000 is constructed from an outer layer 6022 and an inner layer 6024 and includes an inserted array 6026 of internal deformation control elements 6028, as seen in FIG. 54C. Outer layer 6022 is, preferably, molded of a polyurethane of durometer number 80 shore A, and inner layer 6024 is, preferably, molded of a polyurethane having a durometer number 55 shore D. The deformation control elements 6028 are preferably molded of a relatively rigid polyurethane, typically one having a Shore hardness of approximately 70 D and may have carbon whiskers embedded therein.

The deformation control elements 6028 preferably have an overall generally partial annular configuration including a web portion 6032, a first thickened portion 6034, having a circular cross section, and a second thickened portion 6036, having a rectangular cross section. Preferably, deformation control elements 6028 are configured and insertably positioned within implantable artificial femoral head resurfacing element 6000 with portions of outer layer 6022 covering them outwardly and with portions of inner layer 6024 covering them inwardly and towards the rim of implantable artificial femoral head resurfacing element 6000.

It is appreciated that, even though the illustrated embodiment shows the non-uniform thickness portion of artificial femoral head resurfacing element 6000 at the apex thereof, any suitable portion thereof may be of non-uniform thickness.

Figures 55A, 55B, 55C:
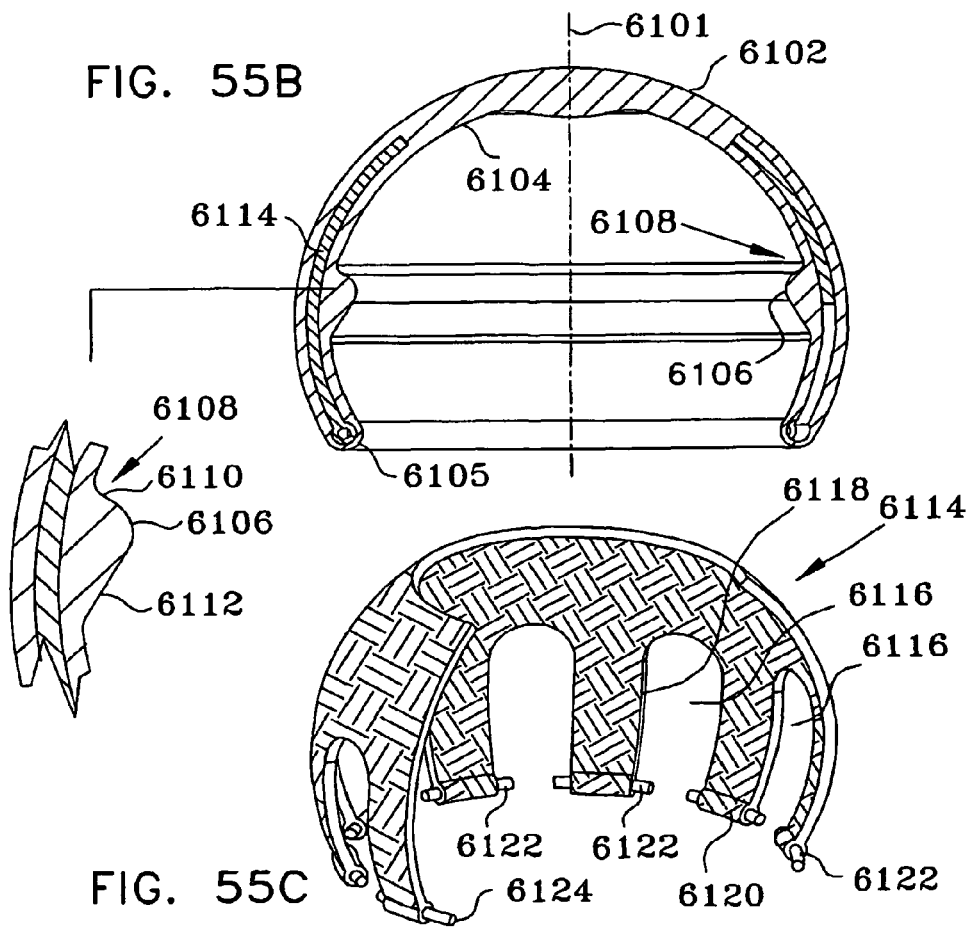
FIGS. 55A, 55B and 55C are respective pictorial, sectional and partially cut away illustrations of an implantable artificial femoral head resurfacing element constructed and operative in accordance with a further preferred embodiment of the present invention.

Reference is now made to FIGS. 55A, 55B and 55C, which are respective pictorial, sectional and partially cut away illustrations of an implantable artificial femoral head resurfacing element constructed and operative in accordance with a further preferred embodiment of the present invention. The implantable artificial femoral head resurfacing element is intended for mounting onto a natural femoral head in accordance with a preferred embodiment of the present invention.

As seen in FIGS. 55A, 55B and 55C, an implantable artificial femoral head resurfacing element, designated by reference numeral 6100, is formed preferably by injection molding of polyurethane over a reinforcing deformation control element. Preferred polyurethane materials are described hereinbelow.

Preferably, implantable artificial femoral head resurfacing element 6100 is of generally uniform thickness, other than at its apex which is thickened, is symmetric about an axis 6101 and defines an hemispherical outer articulation surface 6102 and a generally hemispherical inner bone engagement surface 6104, having a beveled edge 6105, which preferably has formed thereon, at any suitable location between its apex and its rim, a generally annular inwardly extending protrusion 6106, preferably defining a generally annular undercut 6108. Alternatively, the protrusion 6106 may be any other suitable non-annular, open or closed, generally peripheral, protrusion. The protrusion 6106 is preferably arranged for snap-fit engagement with a corresponding groove formed by reaming of a femoral head.

Preferably, the protrusion 6106 has a cross-sectional configuration, as can be readily seen in FIG. 55B, which is characterized in that an underlying surface portion 6110 or protrusion 6106, at the undercut 6108, defines a slope which is sharper than a corresponding slope of an overlying surface portion 6112 of protrusion 6106.

It is a particular feature of the artificial femoral head resurfacing element 6100 that it includes an internal reinforcing deformation control element, which is designated by reference numeral 6114 and illustrated pictorially in FIG. 55C. The deformation control element 6114 is preferably formed of woven high performance fibers, such as carbon fibers, KEVLAR®, DYNEEMA®, and glass fibers, and has an overall generally truncated spherical configuration defined by arched cut-outs 6116 separated by flaps 6118 which terminate in transverse cylindrical portions 6120 in which are fixedly disposed rigid rod elements 6122, ends 6124 of which extend beyond flaps 6118, as shown.

It is seen that insert 6114 is preferably molded entirely within artificial femoral head resurfacing element 6100.

Figure 56A:
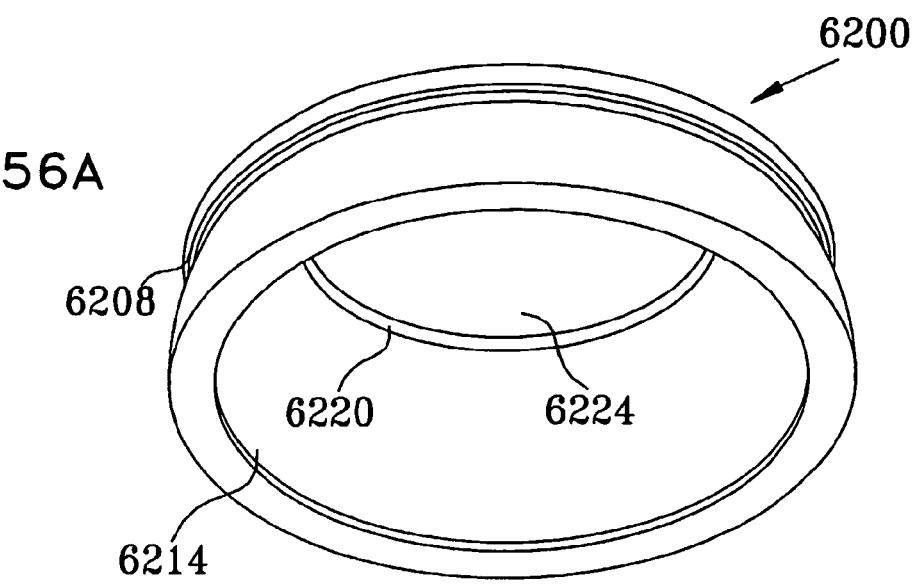
FIGS. 56A, 56B and 56C are respective pictorial, sectional and partially cut away illustrations of an implantable artificial acetabular socket constructed and operative in accordance with a further preferred embodiment of the present invention.
Figure 56B:
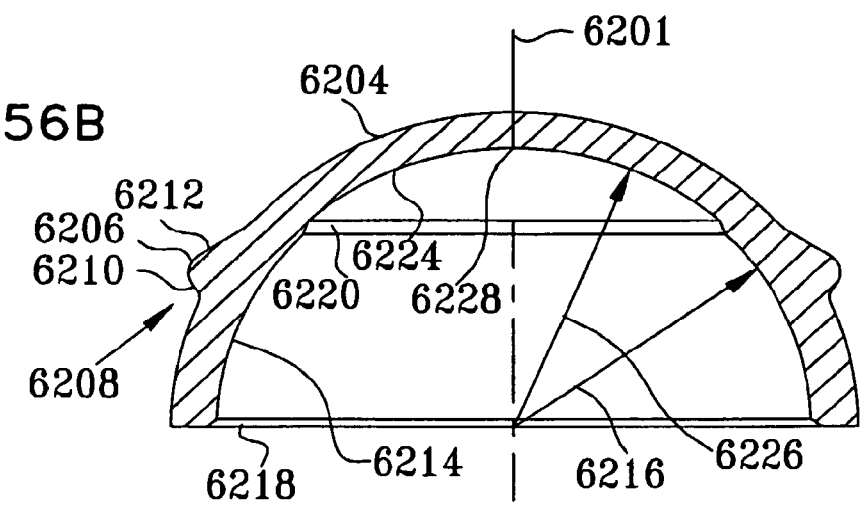
Figure 56C:
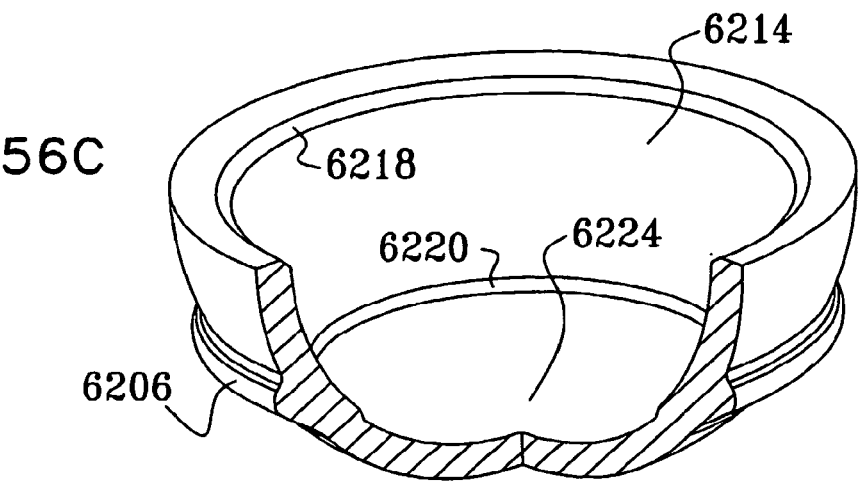

Reference is now made to FIGS. 56A, 56B and 56C, which are respective pictorial, sectional and partially cut away illustrations of an implantable artificial acetabular socket constructed and operative in accordance with a further preferred embodiment of the present invention and which is particularly suitable for use in a hip joint.

As seen in FIGS. 56A, 56B and 56C, an implantable artificial acetabular socket, designated by reference numeral 6200, is formed preferably by injection molding of polyurethane. Preferred polyurethane materials are described hereinbelow.

Preferably, implantable artificial acetabular socket 6200 comprises a surface of rotation which is symmetric about an axis 6201 and defines a generally hemispherical outer bone engagement surface 6204 which preferably has formed thereon, at any suitable location between its apex and its rim, a generally annular outwardly extending protrusion 6206, preferably defining a generally annular undercut 6208. Alternatively, the protrusion 6206 may be any other suitable non-annular, open or closed, generally peripheral, protrusion. The protrusion 6206 is preferably arranged for snap-fit engagement with a corresponding groove formed by reaming of a bone, examples of which are described hereinabove.

Preferably, the protrusion 6206 has a cross-sectional configuration, as can be readily seen in FIG. 56B, which is characterized in that an underlying surface portion 6210 of protrusion 6206, at the undercut 6208, defines a slope which is sharper than a corresponding slope of an overlying surface portion 6212 of protrusion 6206.

It is a particular feature of the implantable artificial acetabular socket 6200 that an inner surface thereof defines two portions of spherical surfaces of rotation having different radii. A first portion, designated by reference numeral 6214, having a radius designated by reference numeral 6216, extends from a beveled edge 6218 to a peripheral step 6220. A second portion, designated by reference numeral 6224, and having a radius designated by reference numeral 6226, which radius is larger than radius 6216, extends from step 6220 to the apex, here designated by reference numeral 6228.

It is appreciated that surface 6224 need not be spherical, provided that it does not extend to a location within the spherical volume partially defined by surface portion 6214 and thus defines a recess extending beyond that spherical volume.

Figure 57A:
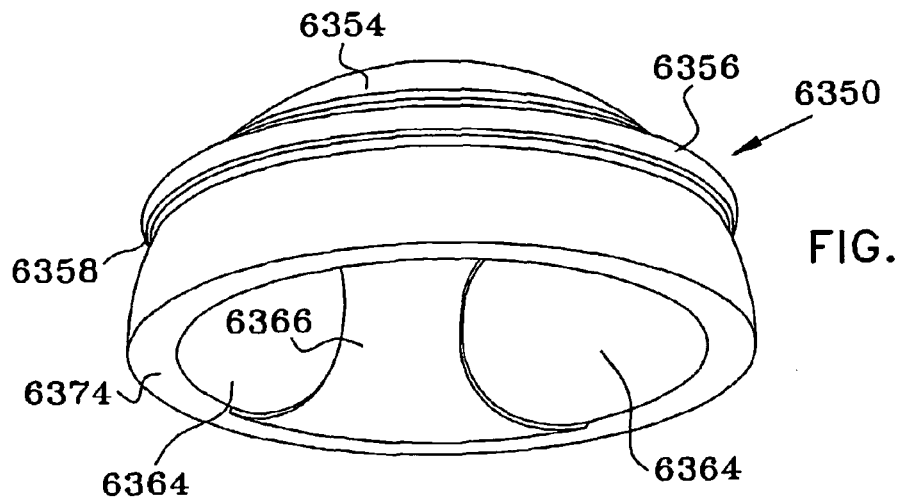
FIGS. 57A, 57B and 57C are respective pictorial, sectional and partially cut away illustrations of an implantable artificial acetabular socket constructed and operative in accordance with another preferred embodiment of the present invention.
Figure 57B:
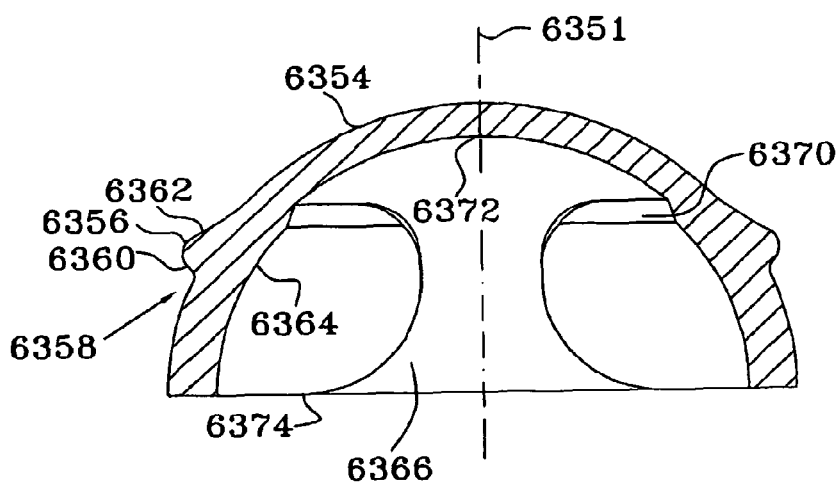
Figure 57C:
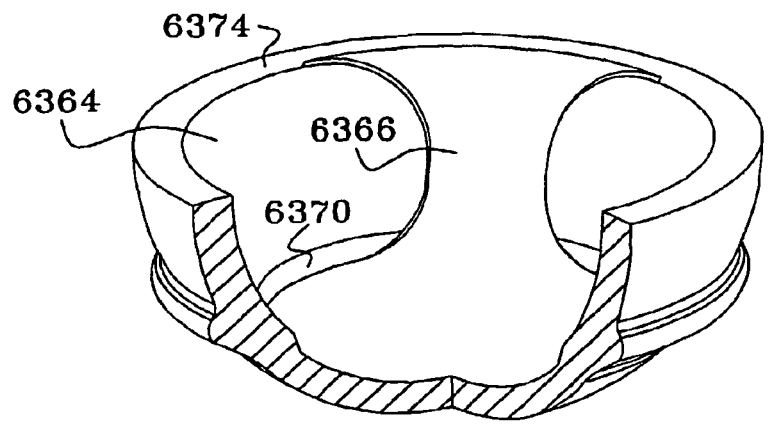

Reference is now made to FIGS. 57A, 57B and 57C, which are respective pictorial, sectional and partially cut away illustrations of an implantable artificial acetabular socket constructed and operative in accordance with a further preferred embodiment of the present invention and which is particularly suitable for use in a hip joint.

As seen in FIGS. 57A, 57B and 57C, an implantable artificial acetabular socket, designated by reference numeral 6350, is formed preferably by injection molding of polyurethane. Preferred polyurethane materials are described hereinbelow.

Preferably, implantable artificial acetabular socket 6350 comprises a surface of rotation which is symmetric about an axis 6351 and defines a generally hemispherical outer bone engagement surface 6354 which preferably has formed thereon, at any suitable location between its apex and its rim, a generally annular outwardly extending protrusion 6356, preferably defining a generally annular undercut 6358. Alternatively, the protrusion 6356 may be any other suitable non-annular, open or closed, generally peripheral, protrusion. The protrusion 6356 is preferably arranged for snap-lit engagement with a corresponding groove formed by reaming of a bone, examples of which are described hereinabove.

Preferably, the protrusion 6356 has a cross-sectional configuration, as can be readily seen in FIG. 57B, which is characterized in that an underlying surface portion 6360 of protrusion 6356, at the undercut 6358, defines a slope which is sharper than a corresponding slope of an overlying surface portion 6362 of protrusion 6356.

Artificial acetabular socket 6350 is similar to artificial acetabular socket 1100 shown is FIGS. 1A-1C, except that an inner articulation surface 6364 defines an additional hemispherical concave layer 6366 along a portion thereof. Additional concave layer 6366 is defined by a peripheral step 6370 and extends from peripheral step 6370 to the apex 6372 of acetabular socket 6350. Additional concave layer 6366 also continues below peripheral step 6370, underlying a portion of inner surface 6364 and continuing until a lower edge 6374, and defines a recess provided to allow for the accumulation of synovial fluid for lubrication of the articulation surface 6364.

It is appreciated that the provision of layer 6366 further defines inner articulation surface 6364 as having a horseshoe shaped portion to more closely approximate the acetabular articular surface of the natural acetabulum. This provides for an articulation surface that more closely approximates the natural articulation surface.

Figure 58A:
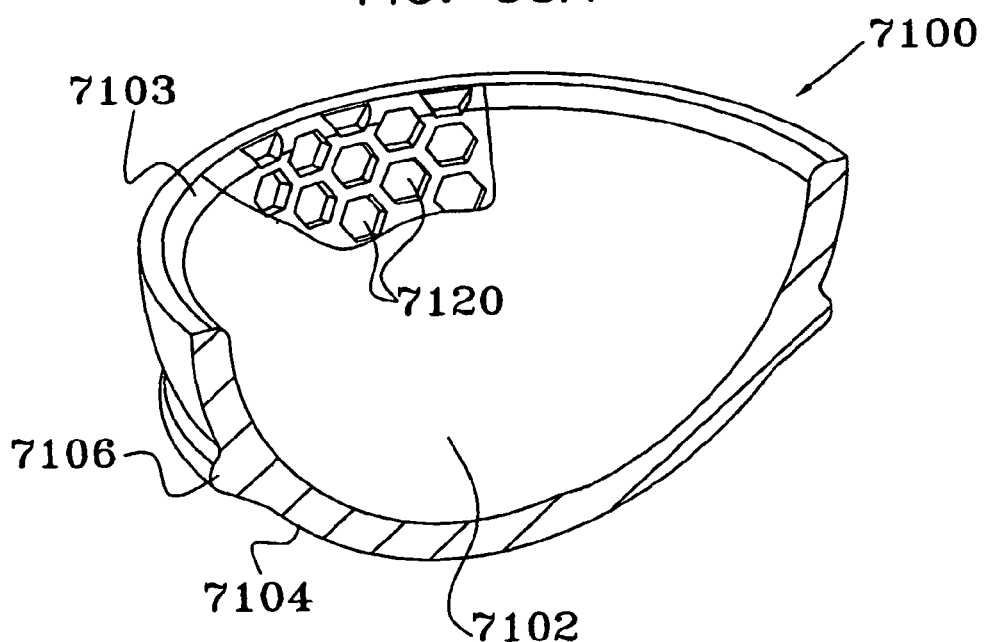
FIGS. 58A and 58B are respective partially cut away pictorial and sectional illustrations of an implantable artificial acetabular socket constructed and operative in accordance with still another preferred embodiment of the present invention.
Figure 58B:
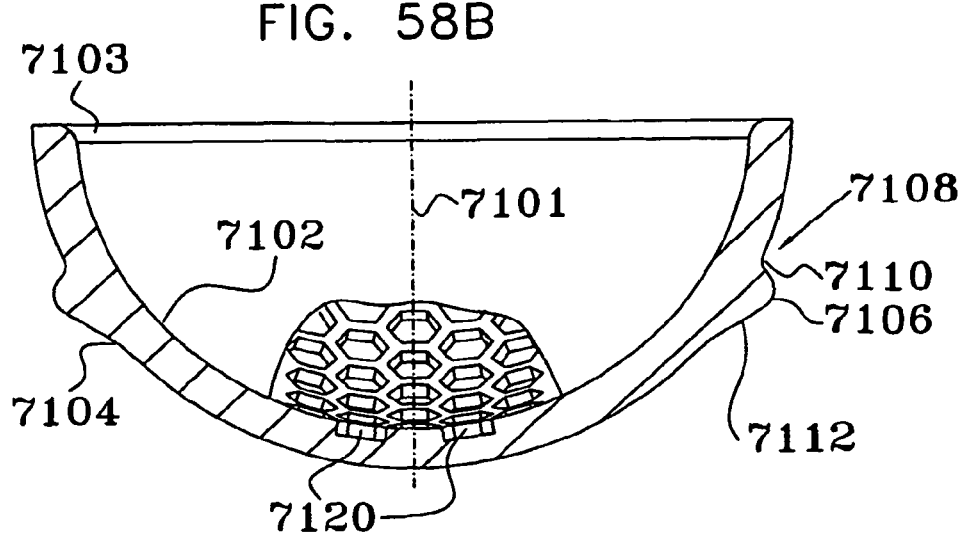

Reference is now made to FIGS. 58A and 58B, which are respective partially cut away pictorial and sectional illustrations of an implantable artificial acetabular socket constructed and operative in accordance with a further preferred embodiment of the present invention and which is particularly suitable for use in a hip joint.

As seen in FIGS. 58A and 58B, an implantable artificial acetabular socket, designated by reference numeral 7100, is formed preferably by injection molding of polyurethane. Preferred polyurethane materials are described hereinbelow.

Preferably, implantable artificial acetabular socket 7100 is of generally uniform thickness, is symmetric about an axis 7101 and defines an hemispherical concave inner articulation surface 7102, having a beveled edge 7103, and a generally hemispherical outer bone engagement surface 7104, which preferably has formed thereon, at any suitable location between its apex and its rim, a generally annular outwardly extending protrusion 7106, preferably defining a generally annular undercut 7108. Alternatively, the protrusion 7106 may be any other suitable non-annular, open or closed, generally peripheral, protrusion. The protrusion 7106 is preferably arranged for snap-fit engagement with a corresponding groove formed by reaming of a bone, examples of which are described hereinabove.

Preferably, the protrusion 7106 has a cross-sectional configuration, as can be readily seen in FIG. 58B, which is characterized in that an underlying surface portion 7110 of protrusion 7106, at the undercut 7108, defines a slope which is sharper than a corresponding slope of an overlying surface portion 7112 of protrusion 7106.

Artificial acetabular socket 7100 is similar to artificial acetabular socket 1100 shown is FIGS. 1A-1C, except that inner articulation surface 7102 is further defined by a hexagonal configuration pattern, which includes hexagonal recessed surface portions 7120. Recessed surface portions 7120 may be connected or isolated from each other and are provided to allow for the accumulation of synovial fluid for lubrication of the articulation surface 7102. Additionally, the hexagonal recessed configuration provides for reduced surface contact area, which reduces friction. It is appreciated that, even though the illustrated embodiment shows a hexagonal configuration, any suitable configuration of recessed surface portions may be provided.

Figure 59A:
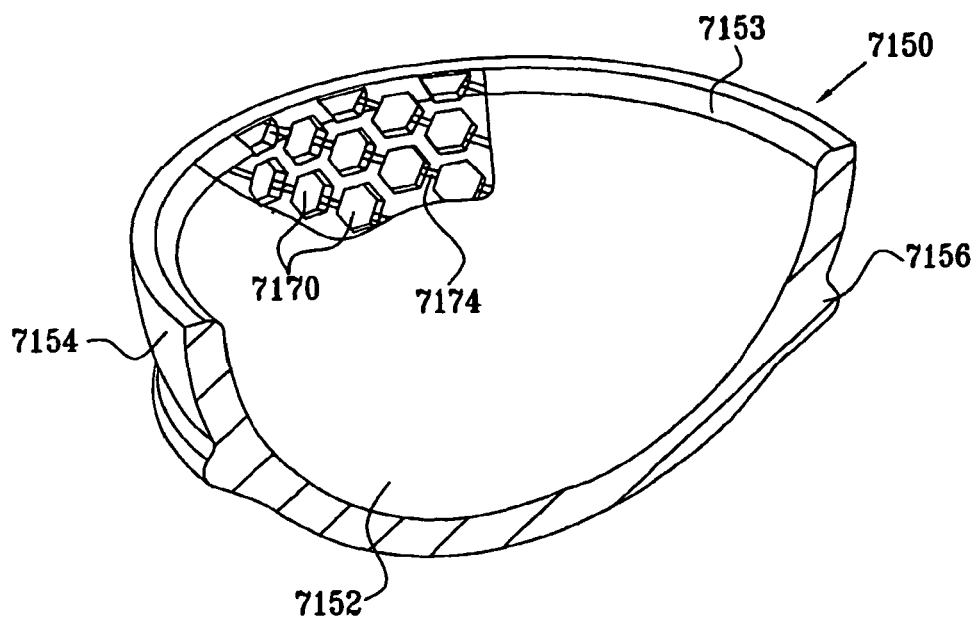
FIGS. 59A and 59B are respective partially cut away pictorial and sectional illustrations of an implantable artificial acetabular socket constructed and operative in accordance with yet another preferred embodiment of the present invention.
Figure 59B:
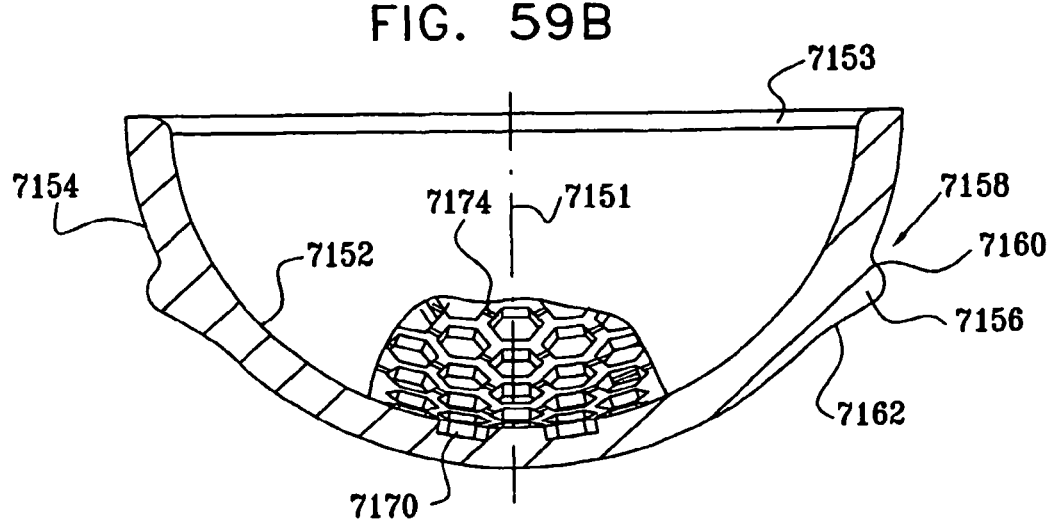

Reference is now made to FIGS. 59A and 59B, which are respective partially cut away pictorial and sectional illustrations of an implantable artificial acetabular socket constructed and operative in accordance with a further preferred embodiment of the present invention and which is particularly suitable for use in a hip joint.

As seen in FIGS. 59A and 59B, an implantable artificial acetabular socket, designated by reference numeral 7150, is formed preferably by injection molding of polyurethane. Preferred polyurethane materials are described hereinbelow.

Preferably, implantable artificial acetabular socket 7150 is of generally uniform thickness, is symmetric about an axis 7151 and defines an hemispherical concave inner articulation surface 7152, having a beveled edge 7153, and a generally hemispherical outer bone engagement surface 7154, which preferably has formed thereon, at any suitable location between its apex and its rim, a generally annular outwardly extending protrusion 7156, preferably defining a generally annular undercut 7158. Alternatively, the protrusion 7156 may be any other suitable non-annular, open or closed, generally peripheral, protrusion. The protrusion 7156 is preferably arranged for snap-fit engagement with a corresponding groove formed by reaming of a bone, examples of which are described hereinabove.

Preferably, the protrusion 7156 has a cross-sectional configuration, as can be readily seen in FIG. 59B, which is characterized in that an underlying surface portion 7160 of protrusion 7156, at the undercut 7158, defines a slope which is sharper than a corresponding slope of an overlying surface portion 7162 of protrusion 7156.

Artificial acetabular socket 7150 is similar to artificial acetabular socket 7100 shown is FIGS. 58A-58B, except that inner surface 7152 is further defined by a hexagonal configuration pattern, which includes hexagonal recessed surface portions 7170 connected by peripheral channels 7174. Peripheral channels 7174 are preferably interconnected and continuous and are provided to allow synovial fluid to pass through for lubrication of the articulation surface 7152. Additionally, the hexagonal recessed configuration provides for reduced surface contact area, which reduces friction. It is appreciated that, even though the illustrated embodiment shows a hexagonal configuration, any suitable configuration of recessed surface portions may be provided.

Figure 60A:
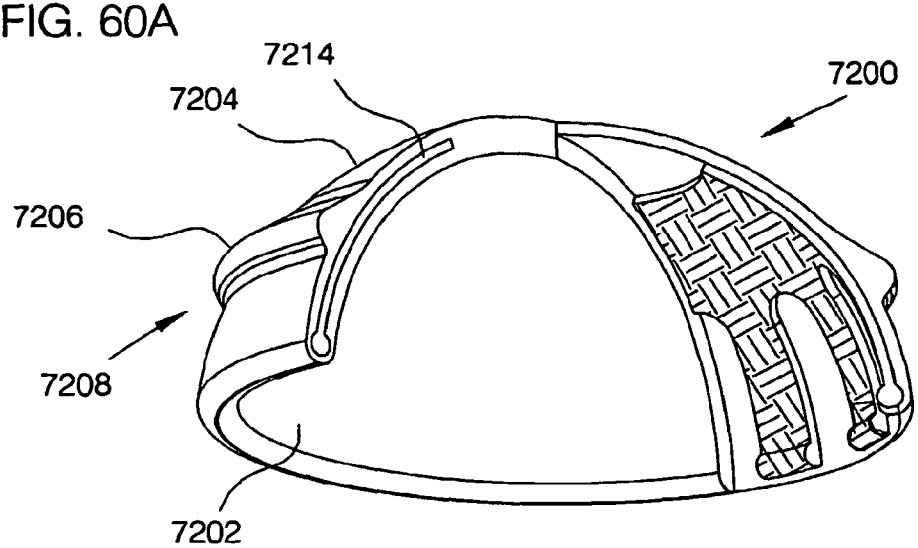
FIGS. 60A, 60B and 60C are respective pictorial, sectional and partially cut away illustrations of an implantable artificial acetabular socket constructed and operative in accordance with a further preferred embodiment of the present invention.
Figure 60B:
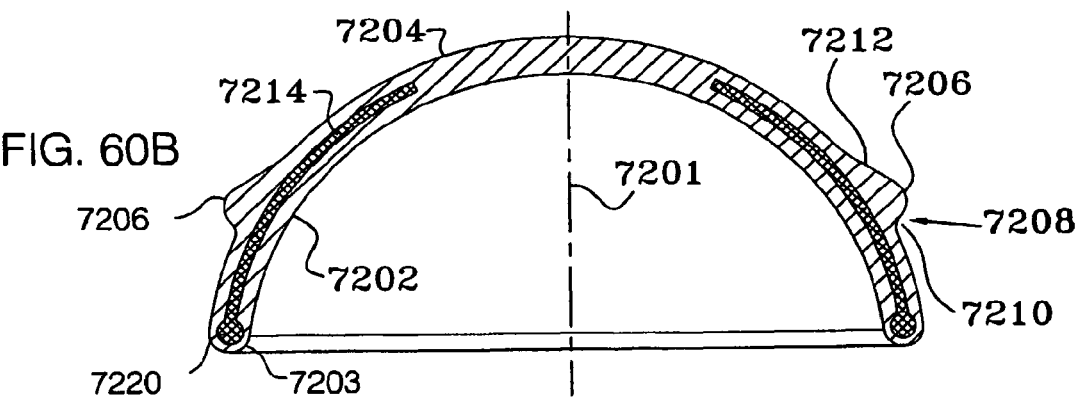
Figure 60C:
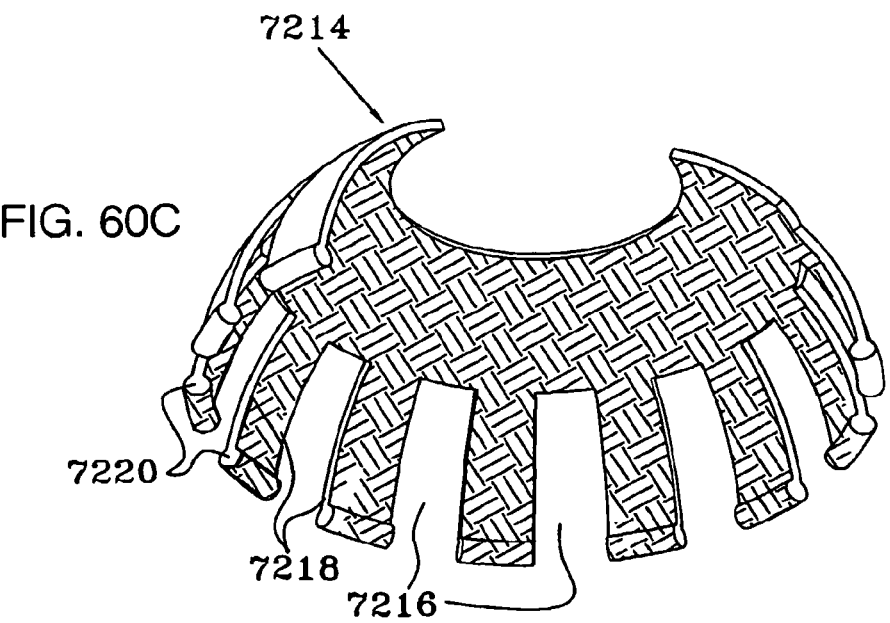

Reference is now made to FIGS. 60A, 60B and 60C, which are respective pictorial, sectional and partially cut away illustrations of an implantable artificial acetabular socket constructed and operative in accordance with a further preferred embodiment of the present invention and which is particularly suitable for use in a hip joint.

As seen in FIGS. 60A, 60B and 60C, an implantable artificial acetabular socket, designated by reference numeral 7200, is formed preferably by injection molding of polyurethane. Preferred polyurethane materials are described hereinbelow.

Preferably, implantable artificial acetabular socket 7200 is of generally uniform thickness, is symmetric about an axis 7201 and defines an hemispherical concave inner articulation surface 7202, having a beveled edge 7203, and a generally hemispherical outer bone engagement surface 7204 which preferably has formed thereon, at any suitable location between its apex and its rim, a generally annular outwardly extending protrusion 7206, preferably defining a generally annular undercut 7208. Alternatively, the protrusion 7206 may be any other suitable non-annular, open or closed, generally peripheral, protrusion. The protrusion 7206 is preferably arranged for snap-lit engagement with a corresponding groove formed by reaming of a bone, examples of which are described hereinabove.

Preferably, the protrusion 7206 has a cross-sectional configuration, as can be readily seen in FIG. 60B, which is characterized in that an underlying surface portion 7210 of protrusion 7206, at the undercut 7208, defines a slope which is sharper than a corresponding slope of an overlying surface portion 7212 of protrusion 7206.

It is a particular feature of the implantable artificial acetabular socket 7200 that it includes an internal reinforcing deformation control element, which is designated by reference numeral 7214 and illustrated pictorially in FIG. 60C. The deformation control element 7214 is preferably molded of a relatively rigid polyurethane, typically one having a Shore hardness of approximately 70 D and may have carbon whiskers embedded therein. The deformation control element 7214 preferably has an overall generally truncated spherical configuration defined by rectangular cut-outs 7216 separated by flaps 7218 which terminate in thickened portions 7220. It is seen that deformation control element 7214 is preferably molded entirely within artificial acetabular socket 7200.

Figure 61A:
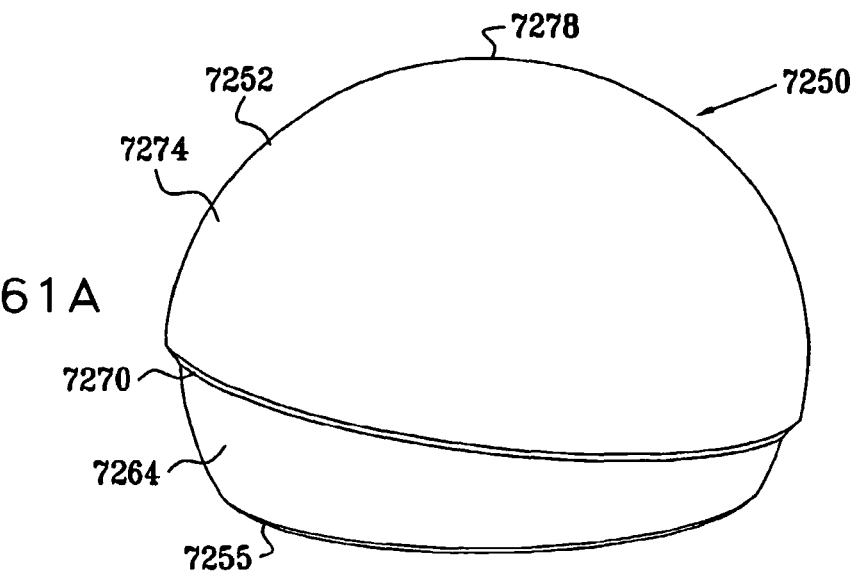
FIGS. 61A, 61B and 61C are respective pictorial, sectional and partially cut away illustrations of an implantable artificial femoral head resurfacing element constructed and operative in accordance with a further preferred embodiment of the present invention.
Figure 61B:
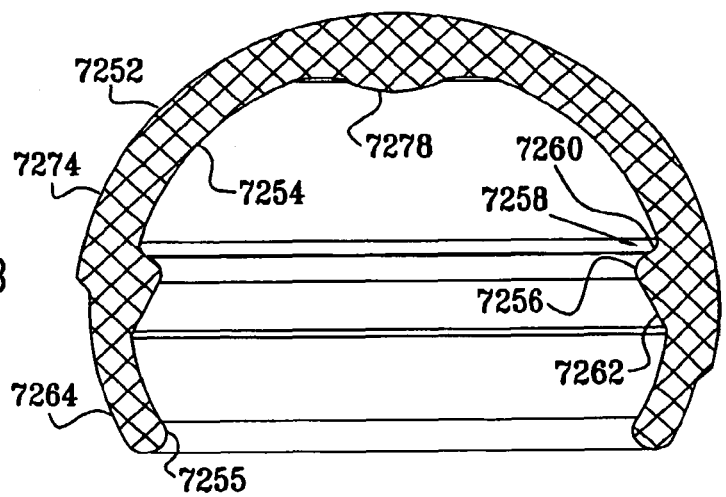
Figure 61C:
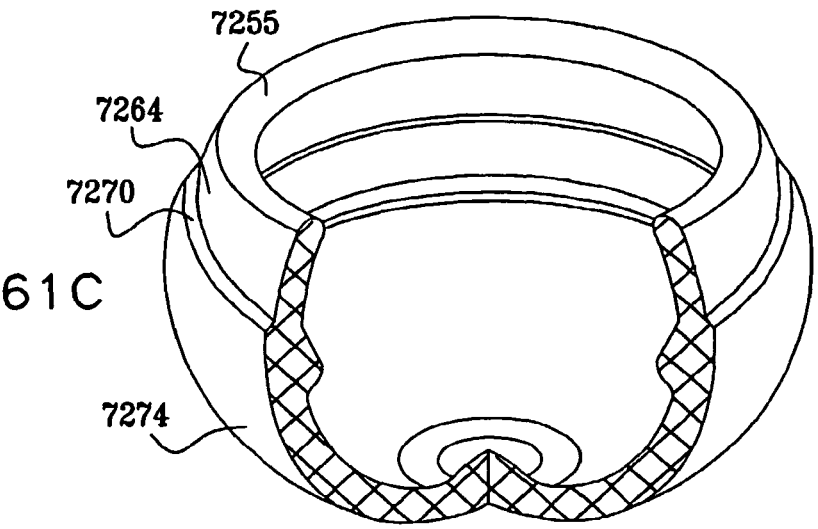

Reference is now made to FIGS. 61A, 61B and 61C, which are respective pictorial, sectional and partially cut away illustrations of an implantable artificial femoral head resurfacing element constructed and operative in accordance with a further preferred embodiment of the present invention. The implantable artificial femoral head resurfacing element is intended for mounting onto a natural femoral head in accordance with a preferred embodiment of the present invention.

As seen in FIGS. 61A, 61B and 61C, an implantable artificial femoral head resurfacing element, designated by reference numeral 7250, is formed preferably by injection molding of polyurethane. Preferred polyurethane materials are described hereinbelow.

Preferably, implantable artificial femoral head resurfacing element 7250 is of generally uneven thickness, with a distinct thickened portion at its apex. Artificial femoral head resurfacing element 7250 defines a hemispherical outer articulation surface 7252 and an inner bone engagement surface 7254, having a beveled edge 7255, which preferably has formed thereon at any suitable location between its apex and its rim a generally annular inwardly extending protrusion 7256, preferably defining a generally annular undercut 7258. Alternatively, the protrusion 7256 may be any other suitable non-annular, open or closed, generally peripheral, protrusion. The protrusion 7256 is preferably arranged for snap-fit engagement with a corresponding groove formed by reaming of a femoral head.

Preferably, the protrusion 7256 has a cross-sectional configuration, as can be readily seen in FIG. 61B, which is characterized in that an underlying surface portion 7260 of protrusion 7256, at the undercut 7258, defines a slope which is sharper than a corresponding slope of an overlying surface portion 7262 of protrusion 7256.

It is a particular feature of the implantable artificial femoral head resurfacing element 7250 that outer articulation surface 7252 further defines two portions of spherical surfaces of rotation. A first portion, designated by reference numeral 7264, extends from beveled edge 7255 to a generally circular rim 7270. A second portion, designated by reference numeral 7274, extends from rim 7270 to the apex, here designated by reference numeral 7278. As seen in FIG. 61A, rim 7270 is not at a uniform distance from beveled edge 7255. The provision of rim 7270 allows artificial femoral head resurfacing element 7250 to more closely approximate a natural femoral head, which reduces friction and provides a thicker portion aligned with the area of greatest stress applied to the surface element during articulation. It is appreciated that, even though, in the illustrated embodiment of FIGS. 61A-61C, rim 7270 is circular, any suitable configuration of rim 7270, may be provided. One such alternate configuration of rim 7270 is shown hereinbelow in FIGS. 62A-62C.

As shown in FIGS. 61A-61C, artificial femoral head resurfacing element 7250 need not have a uniform outer articulation surface, but is thickened asymmetrically to provide a thicker portion where required by the specific joint reaction force of the joint with which it is articulating.

Figure 62A:
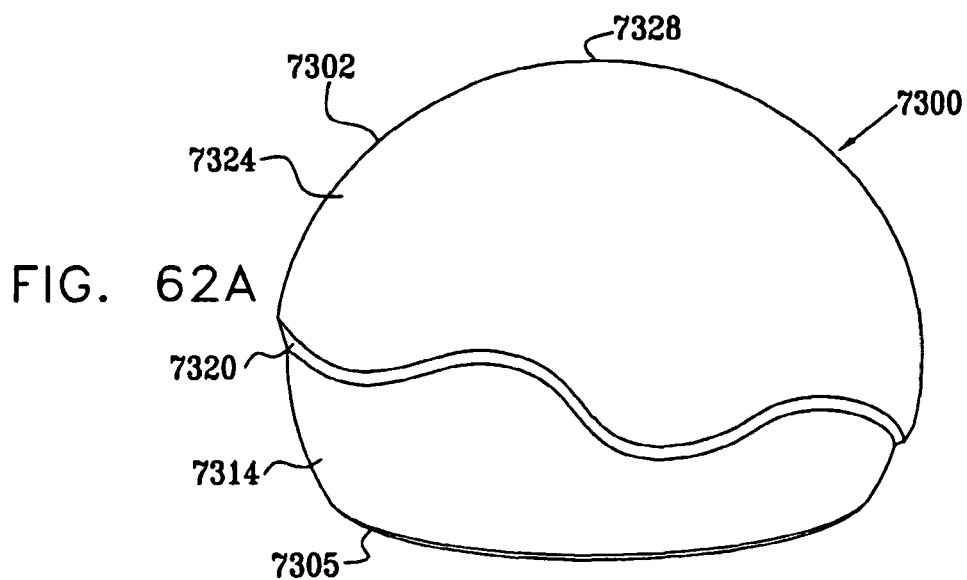
FIGS. 62A, 62B and 62C are respective pictorial, sectional and partially cut away illustrations of an implantable artificial femoral head resurfacing element constructed and operative in accordance with another preferred embodiment of the present invention.
Figure 62B:
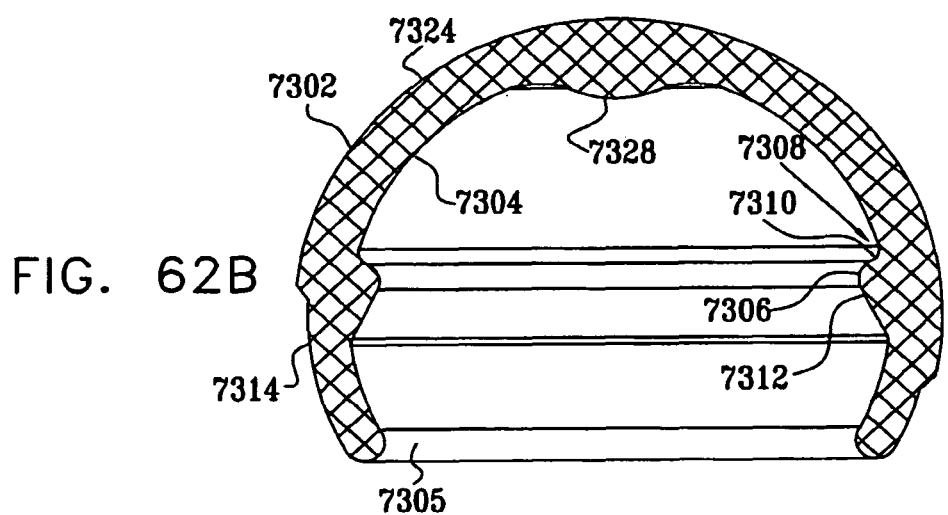
Figure 62C:
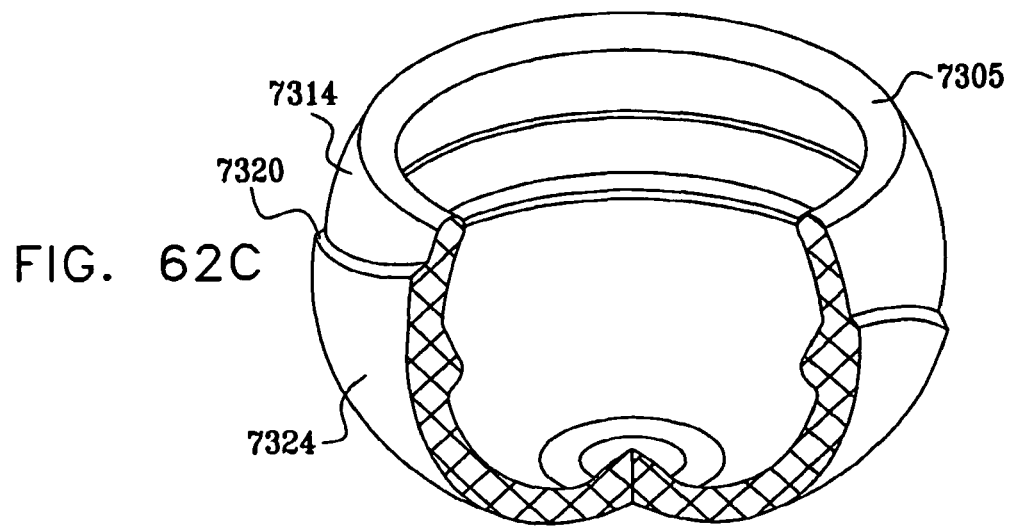

Reference is now made to FIGS. 62A, 62B and 62C, which are respective pictorial, sectional and partially cut away illustrations of an implantable artificial femoral head resurfacing element constructed and operative in accordance with a further preferred embodiment of the present invention. The implantable artificial femoral head resurfacing element is intended for mounting onto a natural femoral head in accordance with a preferred embodiment of the present invention.

As seen in FIGS. 62A, 62B and 62C, an implantable artificial femoral head resurfacing element, designated by reference numeral 7300, is formed preferably by injection molding of polyurethane. Preferred polyurethane materials are described hereinbelow.

Preferably, implantable artificial femoral head resurfacing element 7300 is of generally uneven thickness, with a distinct thickened portion at its apex. Artificial femoral head resurfacing element 7300 defines a hemispherical outer articulation surface 7302 and an inner bone engagement surface 7304, having a beveled edge 7305, which preferably has formed thereon at any suitable location between its apex and its rim a generally annular inwardly extending protrusion 7306, preferably defining a generally annular undercut 7308. Alternatively, the protrusion 7306 may be any other suitable non-annular, open or closed, generally peripheral, protrusion. The protrusion 7306 is preferably arranged for snap-fit engagement with a corresponding groove formed by reaming of a femoral head.

Preferably, the protrusion 7306 has a cross-sectional configuration, as can be readily seen in FIG. 62B, which is characterized in that an underlying surface portion 7310 of protrusion 7306, at the undercut 7308, defines a slope which is sharper than a corresponding slope of an overlying surface portion 7312 of protrusion 7306.

It is a particular feature of the implantable artificial femoral head resurfacing element 7300 that outer articulation surface 7302 further defines two portions of spherical surfaces of rotation. A first portion, designated by reference numeral 7314, extends from beveled edge 7305 to a rim 7320. A second portion, designated by reference numeral 7324, extends from rim 7320 to the apex, here designated by reference numeral 7328. As seen in FIG. 62A, rim 7320 is not at a uniform distance from beveled edge 7305. The provision of rim 7320 allows artificial femoral head resurfacing element 7300 to more closely approximate a natural femoral head, which reduces friction and provides a thicker portion aligned with the area of greatest stress applied to the surface element during articulation.

As shown in FIGS. 62A-62C, artificial femoral head resurfacing element 7300 need not have a uniform outer articulation surface, but is thickened asymmetrically to provide a thicker portion where required by the specific joint reaction force of the joint with which it is articulating.

Figure 63A:
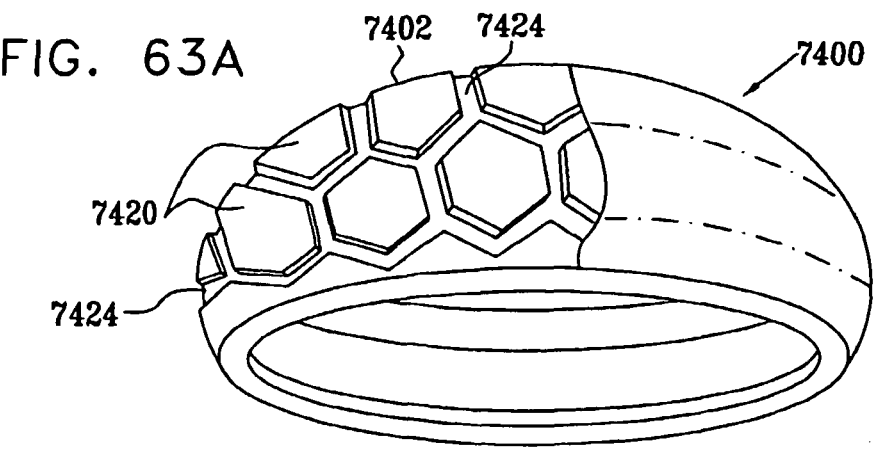
FIGS. 63A and 63B are respective pictorial, sectional and partially cut away illustrations of an implantable artificial femoral or humeral head resurfacing element constructed and operative in accordance with still another preferred embodiment of the present invention.
Figure 63B:
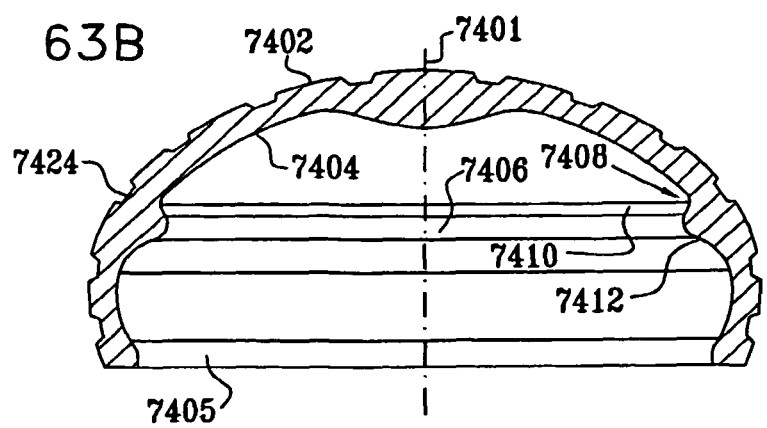

Reference is now made to FIGS. 63A and 63B, which are respective pictorial and sectional illustrations of an implantable artificial femoral or humeral head resurfacing element constructed and operative in accordance with still another preferred embodiment of the present invention. The implantable artificial femoral or humeral head resurfacing element is intended for mounting onto a natural femoral or humeral head in accordance with a preferred embodiment of the present invention.

As seen in FIGS. 63A and 63B, an implantable artificial femoral or humeral head resurfacing element, designated by reference numeral 7400, is formed preferably by injection molding of polyurethane. Preferred polyurethane materials are described hereinbelow.

Preferably, implantable artificial femoral or humeral head resurfacing element 7400 is of generally uniform thickness, other than at its apex which is thickened, is symmetric about an axis 7401 and defines an hemispherical outer articulation surface 7402 and a generally hemispherical inner bone engagement surface 7404, having a beveled edge 7405, which preferably has formed thereon, at any suitable location between its apex and its rim, a generally annular inwardly extending protrusion 7406, preferably defining a generally annular undercut 7408. Alternatively, the protrusion 7406 may be any other suitable non-annular, open or closed, generally peripheral, protrusion. The protrusion 7406 is preferably arranged for snap-fit engagement with a corresponding groove formed by reaming of a femoral or humeral head.

Preferably, the protrusion 7406 has a cross-sectional configuration, as can be readily seen in FIG. 63B, which is characterized in that an underlying surface portion 7410 of protrusion 7406, at the undercut 7408, defines a slope which is sharper than a corresponding slope of an overlying surface portion 7412 of protrusion 7406.

The outer articulation surface 7402 of implantable artificial femoral or humeral head resurfacing element 7400 preferably comprises a hexagonal configuration pattern, which includes hexagonal articulating surface portions 7420 defined by peripheral channels 7424. Peripheral channels 7424 are preferably interconnected and continuous and are provided to allow synovial fluid to pass through for lubrication of the articulation surface 7402. Additionally, the hexagonal recessed configuration provides for reduced surface contact area, which reduces friction. It is appreciated that, even though the illustrated embodiment shows a hexagonal configuration, any suitable configuration of channels and surface portions may be provided.

It is appreciated that, even though the illustrated embodiment shows the non-uniform thickness portion of artificial femoral head resurfacing element 7400 at the apex thereof, any suitable portion thereof may be of non-uniform thickness.

Figure 64A:
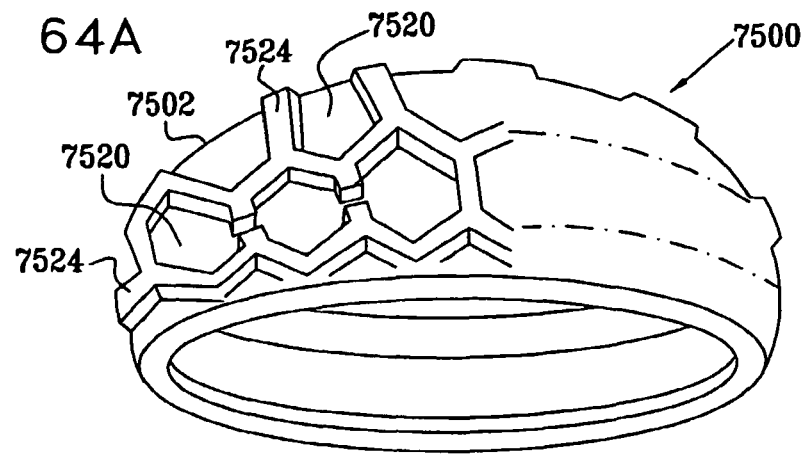
FIGS. 64A and 64B are respective pictorial and sectional illustrations of an implantable artificial femoral or humeral head resurfacing element constructed and operative in accordance with yet another preferred embodiment of the present invention.
Figure 64B:
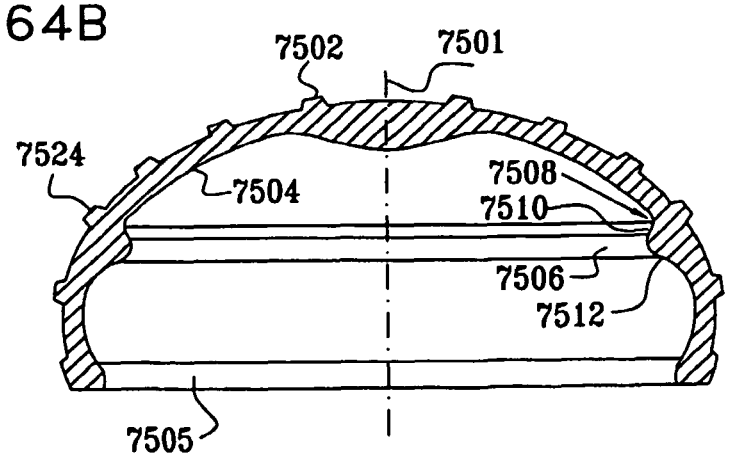

Reference is now made to FIGS. 64A and 64B, which are respective pictorial and sectional illustrations of an implantable artificial femoral or humeral head resurfacing element constructed and operative in accordance with still another preferred embodiment of the present invention. The implantable artificial femoral or humeral head resurfacing element is intended for mounting onto a natural femoral or humeral head in accordance with a preferred embodiment of the present invention.

As seen in FIGS. 64A and 64B, an implantable artificial femoral or humeral head resurfacing element, designated by reference numeral 7500, is formed preferably by injection molding of polyurethane. Preferred polyurethane materials are described hereinbelow.

Preferably, implantable artificial femoral or humeral head resurfacing element 7500 is of generally uniform thickness, other than at its apex which is thickened, is symmetric about an axis 7501 and defines an hemispherical outer articulation surface 7502 and a generally hemispherical inner bone engagement surface 7504, having a beveled edge 7505, which preferably has formed thereon, at any suitable location between its apex and its rim, a generally annular inwardly extending protrusion 7506, preferably defining a generally annular undercut 7508. Alternatively, the protrusion 7506 may be any other suitable non-annular, open or closed, generally peripheral, protrusion. The protrusion 7506 is preferably arranged for snap-fit engagement with a corresponding groove formed by reaming of a femoral or humeral head.

Preferably, the protrusion 7506 has a cross-sectional configuration, as can be readily seen in FIG. 64B, which is characterized in that an underlying surface portion 7510 of protrusion 7506, at the undercut 7508, defines a slope which is sharper than a corresponding slope of an overlying surface portion 7512 of protrusion 7506.

The outer articulation surface 7502 of implantable artificial femoral or humeral head resurfacing element 7500 preferably comprises a hexagonal configuration pattern, which includes hexagonal recessed surface portions 7520 defined by peripheral articulating surface elements 7524. Recessed surface portions 7520 may be connected or isolated from each other and are provided to allow for the accumulation of synovial fluid for lubrication of the articulation surface 7502. Additionally, the hexagonal recessed configuration provides for reduced surface contact area, which reduces friction. It is appreciated that, even though the illustrated embodiment shows a hexagonal configuration, any suitable configuration of articulating surface elements and recessed surface portions may be provided.

It is appreciated that, even though the illustrated embodiment shows the non-uniform thickness portion of artificial femoral head resurfacing element 7500 at the apex thereof, any suitable portion thereof may be of non-uniform thickness.

Figure 65A:
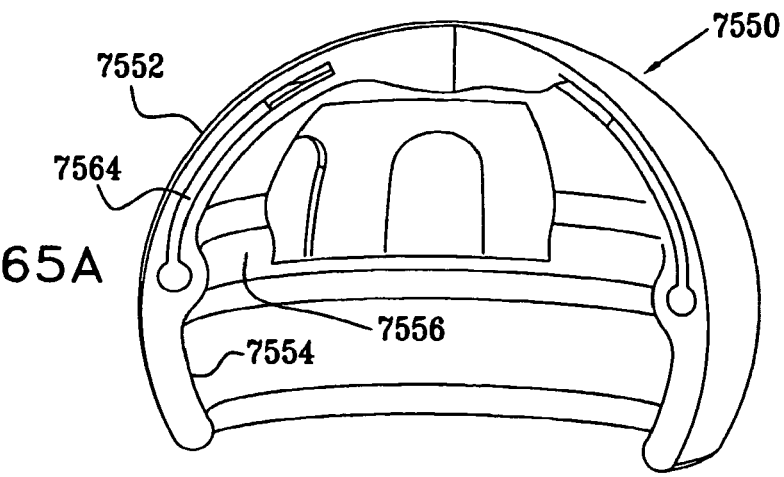
FIGS. 65A, 65B and 65C are respective pictorial, sectional and partially cut away illustrations of an implantable artificial femoral or humeral head resurfacing element constructed and operative in accordance with a further preferred embodiment of the present invention.
Figure 65B:
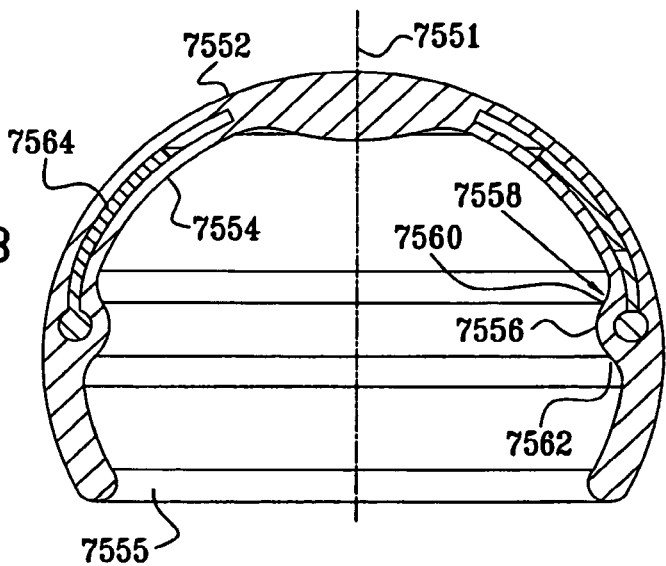
Figure 65C:
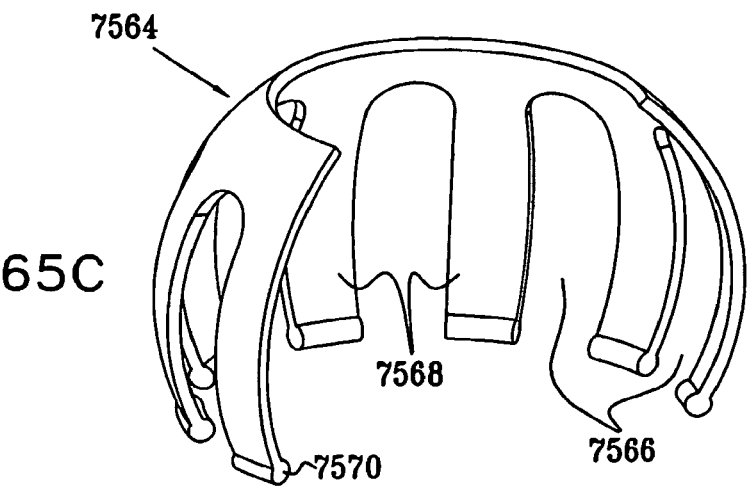

Reference is now made to FIGS. 65A, 65B and 65C, which are respective pictorial, sectional and partially cut away illustrations of an implantable artificial femoral head resurfacing element constructed and operative in accordance with a further preferred embodiment of the present invention. The implantable artificial femoral head resurfacing element is intended for mounting onto a natural femoral head in accordance with a preferred embodiment of the present invention.

As seen in FIGS. 65A, 65B and 65C, an implantable artificial femoral head resurfacing element, designated by reference numeral 7550; is formed preferably by injection molding of polyurethane over a reinforcing deformation control element. Preferred polyurethane materials are described hereinbelow.

Preferably, implantable artificial femoral head resurfacing element 7550 is of generally uniform thickness, other than at its apex which is thickened, is symmetric about an axis 7551 and defines an hemispherical outer articulation surface 7552 and a generally hemispherical inner bone engagement surface 7554, having a beveled edge 7555, which preferably has formed thereon, at any suitable location between its apex and its rim, a generally annular inwardly extending protrusion 7556, preferably defining a generally annular undercut 7558. Alternatively, the protrusion 7556 may be any other suitable non-annular, open or closed, generally peripheral, protrusion. The protrusion 7556 is preferably arranged for snap-fit engagement with a corresponding groove formed by reaming of a femoral head.

Preferably, the protrusion 7556 has a cross-sectional configuration, as can be readily seen in FIG. 65B, which is characterized in that an underlying surface portion 7560 of protrusion 7556, at the undercut 7558, defines a slope which is sharper than a corresponding slope of an overlying surface portion 7562 of protrusion 7556.

It is a particular feature of the artificial femoral head resurfacing element 7550 that it includes an internal reinforcing deformation control element, which is designated by reference numeral 7564 and illustrated pictorially in FIG. 65C. The deformation control element 7564 is preferably, formed of woven high performance fibers, such as carbon fibers, KEVLAR®, DYNEEMA®, and glass fibers, and has an overall generally truncated spherical configuration defined by arched cut-outs 7566 separated by flaps 7568 which terminate in thickened portions 7570. It is seen that insert 7564 is preferably molded entirely within artificial femoral head resurfacing element 7550.

It is appreciated that, even though the illustrated embodiment shows the non-uniform thickness portion of artificial femoral head resurfacing element 7550 at the apes thereof, any suitable portion thereof may be of non-uniform thickness.

Figure 66A:
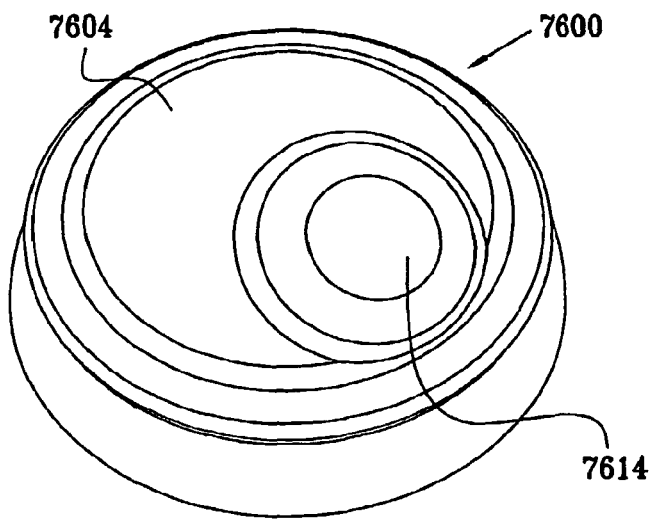
FIGS. 66A, 66B, and 66C are respective pictorial, sectional and partially cut away illustrations of an implantable artificial acetabular socket constructed and operative in accordance with a further preferred embodiment of the present invention.
Figure 66B:
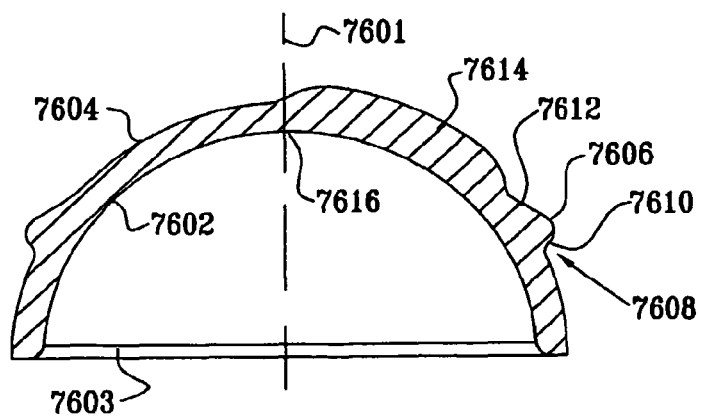
Figure 66C:
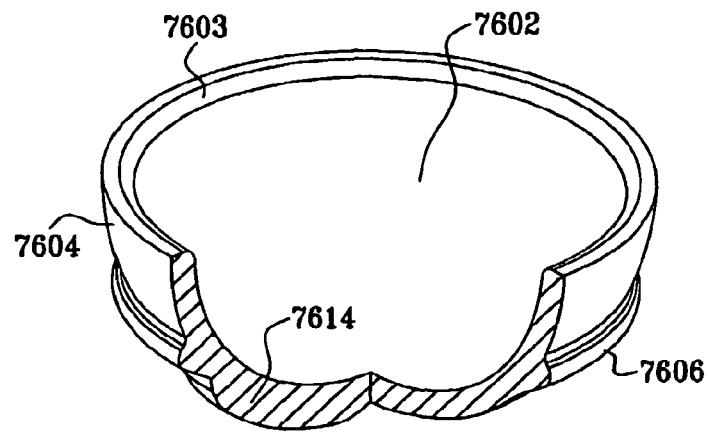

Reference is now made to FIGS. 66A, 66B, and 66C, which are respective pictorial, sectional and partially cut away illustrations of an implantable artificial acetabular socket constructed and operative in accordance with a further preferred embodiment of the present invention and which is particularly suitable for use in a hip joint.

As seen in FIGS. 66A, 66B, and 66C, an implantable artificial acetabular socket, designated by reference numeral 7600, is formed preferably by injection molding of polyurethane. Preferred polyurethane materials are described hereinbelow.

Preferably, implantable artificial acetabular socket 7600 defines an inner surface 7602 which is symmetric about an axis 7601. Acetabular socket 7600 also preferably has a beveled edge 7603 and defines a generally hemispherical outer bone engagement surface 7604 which preferably has formed thereon, at any suitable location between its apex and its rim, a generally annular outwardly extending protrusion 7606, preferably defining a generally annular undercut 7608. Alternatively, the protrusion 7606 may be any other suitable non-annular, open or closed, generally peripheral, protrusion. The protrusion 7606 is preferably arranged for snap-fit engagement with a corresponding groove formed by reaming of a bone, examples of which are described hereinabove.

Preferably, the protrusion 7606 has a cross-sectional configuration, as can be readily seen in FIG. 66B, which is characterized in that an underlying surface portion 7610 of protrusion 7606, at the undercut 7608, defines a slope which is sharper than a corresponding slope of an overlying surface portion 7612 of protrusion 7606.

It is a particular feature of the implantable artificial acetabular socket 7600 that a portion of outer bone engagement surface 7604 thereof defines a thickened portion 7614, preferably extending from a location generally atop inner apex 7616 of acetabular socket 7600 to the protrusion 7606. Thickened portion 7614 is preferably aligned with the natural acetabular recess, and is provided to allow a proper fit with a reamed acetabulum, without requiring reaming of the entire surface of the acetabulum down to the level of the acetabular recess, as described hereinbelow with reference to FIG. 69A. The thickened portion 7614 preferably allows for a less invasive procedure and also provides a thicker shock absorbing surface. It is appreciated that, even though the illustrated embodiment shows a circular configuration, any suitable configuration of thickened portion 7614 may be provided.

It is appreciated that thickened portion 7614 of acetabular socket 7600 may alternatively be oriented, as described hereinbelow with reference to FIG. 69B, so as to align thickened portion 7614 with the area of greatest applied force.

Figure 67A:
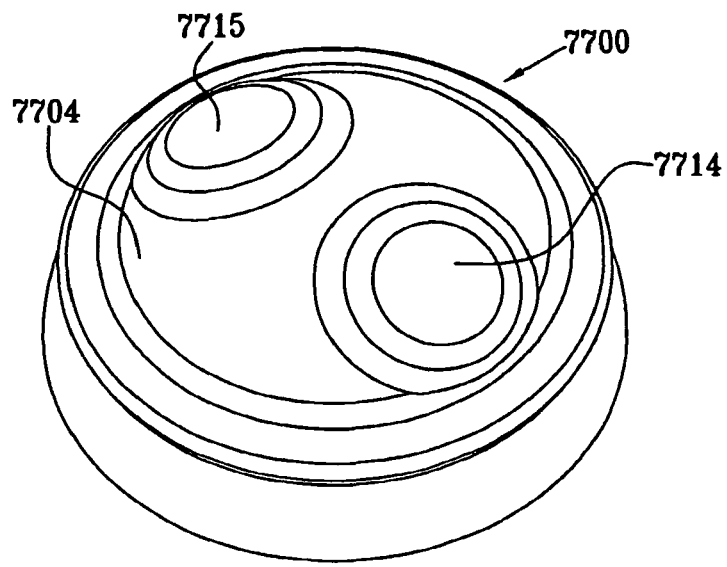
FIGS. 67A, 67B, and 67C are respective pictorial, sectional and partially cut away illustrations of an implantable artificial acetabular socket constructed and operative in accordance with another preferred embodiment of the present invention.
Figure 67B:
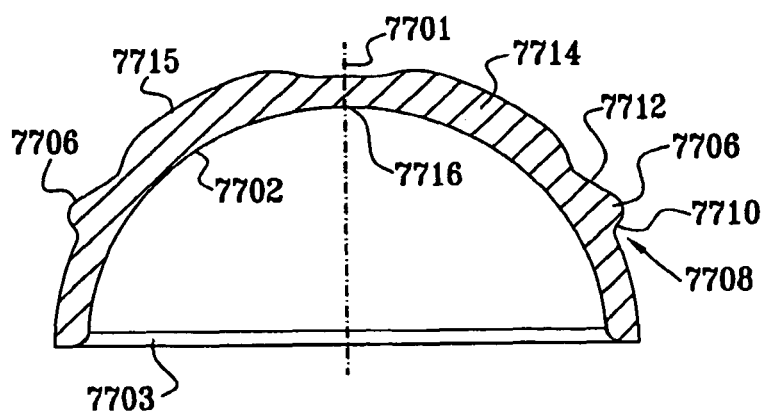
Figure 67C:
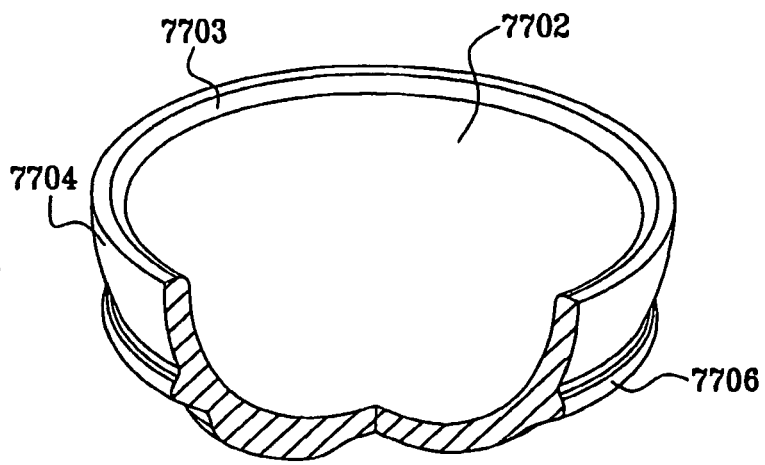

Reference is now made to FIGS. 67A, 67B, and 67C, which are respective pictorial, sectional and partially cut away illustrations of an implantable artificial acetabular socket constructed and operative in accordance with a further preferred embodiment of the present invention and which is particularly suitable for use in a hip joint.

As seen in FIGS. 67A, 67B, and 67C, an implantable artificial acetabular socket, designated by reference numeral 7700, is formed preferably by injection molding of polyurethane. Preferred polyurethane materials are described hereinbelow.

Preferably, implantable artificial acetabular socket 7700 defines an inner surface 7702 which is symmetric about an axis 7701. Acetabular socket 7700 also preferably has a beveled edge 7703 and defines a generally hemispherical outer bone engagement surface 7704 which preferably has formed thereon, at any suitable location between its apex and its rim, a generally annular outwardly extending protrusion 7706, preferably defining a generally annular undercut 7708. Alternatively, the protrusion 7706 may be any other suitable non-annular, open or closed, generally peripheral, protrusion. The protrusion 7706 is preferably arranged for snap-fit engagement with a corresponding groove formed by reaming of a bone, examples of which are described hereinabove.

Preferably, the protrusion 7706 has a cross-sectional configuration, as can be readily seen in FIG. 67B, which is characterized in that an underlying surface portion 7710 of protrusion 7706, at the undercut 7708, defines a slope which is sharper than a corresponding slope of an overlying surface portion 7712 of protrusion 7706.

It is a particular feature of the implantable artificial acetabular socket 7700 that a portion of outer bone engagement surface 7704 thereof defines multiple thickened portions 7714 and 7715, preferably extending from a location generally atop inner apex 7716 of acetabular socket 7700 to the protrusion 7706. Thickened portion 7714 is preferably aligned with the natural acetabular recess, and is provided to allow a proper fit with a reamed acetabulum, without requiring reaming of the entire surface of the acetabulum down to the level of the acetabular recess, as described hereinbelow with reference to FIG. 69C. The thickened portion 7714 preferably allows for a less invasive procedure and also provides a thicker shock absorbing surface. It is appreciated that even though the illustrated embodiment shows a circular configuration, any suitable configuration of thickened portion 7714 may be provided. Thickened portion 7715 or acetabular socket 7600 is oriented, as described hereinbelow with reference to FIG. 69C, so as to be aligned with the area of greatest applied force.

Figure 68A:
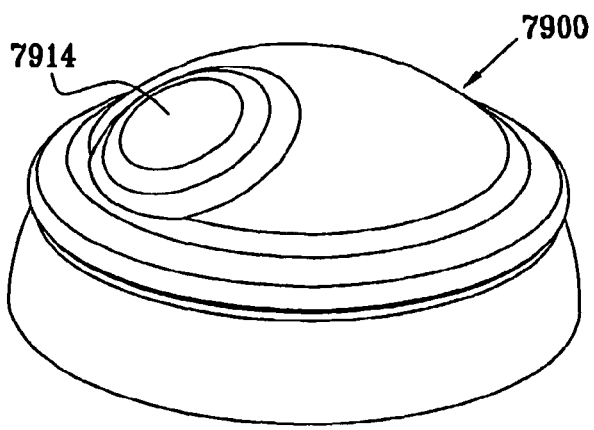
FIGS. 68A, 68B, and 68C are respective pictorial, sectional and partially cut away illustrations of an implantable artificial acetabular socket constructed and operative in accordance with yet another preferred embodiment of the present invention.
Figure 68B:
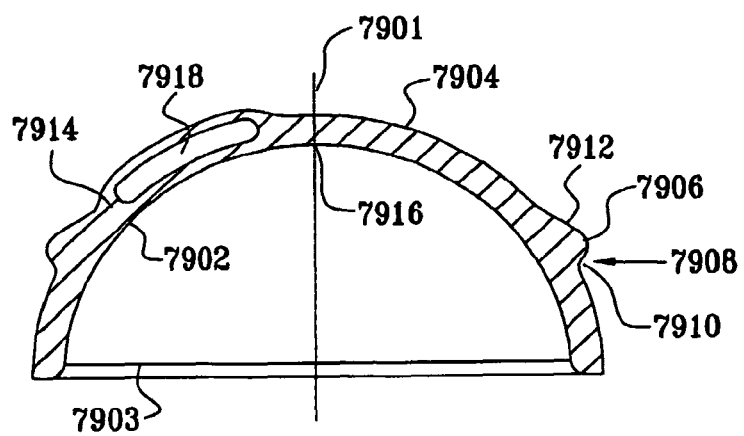
Figure 68C:
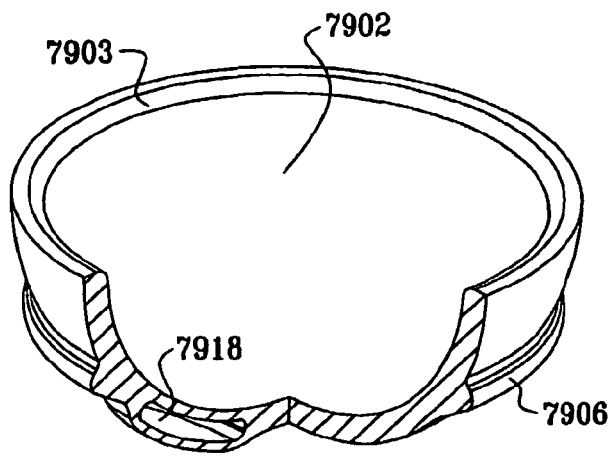

Reference is now made to FIGS. 68A, 68B, and 68C, which are respective pictorial, sectional and partially cut away illustrations of an implantable artificial acetabular socket constructed and operative in accordance with a further preferred embodiment of the present invention and which is particularly suitable for use in a hip joint As seen in FIGS. 68A, 68B, and 68C, an implantable artificial acetabular socket, designated by reference numeral 7900, is formed preferably by injection molding of polyurethane. Preferred polyurethane materials are described hereinbelow.

Preferably, implantable artificial acetabular socket 7900 defines an inner surface 7902 which is symmetric about an axis 7901. Acetabular socket 7900 also preferably has a beveled edge 7903 and defines a generally hemispherical outer bone engagement surface 7904 which preferably has formed thereon, at any suitable location between its apex and its rim, a generally annular outwardly extending protrusion 7906, preferably defining a generally annular undercut 7908. Alternatively, the protrusion 7900 may be any other suitable non-annular, open or closed, generally peripheral, protrusion. The protrusion 7906 is preferably arranged for snap-fit engagement with a corresponding groove formed by reaming of a bone, examples of which are described hereinabove.

Preferably, the protrusion 7906 has a cross-sectional configuration, as can be readily seen in FIG. 68B, which is characterized in that an underlying surface portion 7910 of protrusion 7906, at the undercut 7908, defines a slope which is sharper than a corresponding slope of an overlying surface portion 7912 of protrusion 7906.

It is a particular feature of the implantable artificial acetabular socket 7000 that a portion of outer bone engagement surface 7904 thereof defines a thickened portion 7914, preferably extending from a location generally atop inner apex 7916 of acetabular socket 7900 to the protrusion 7906. Thickened portion 7914 is preferably aligned with the peak direction of the joint reaction force of the joint with which it is articulating. Thickened portion 7914 also preferably includes hollow portion 7918, which provides for attenuation of the stresses incurred at the joint. It is appreciated that, even though the illustrated embodiment shows a generally circular configuration, any suitable configuration of thickened portion 7914 and hollow portion 7918 may be provided.

Reference is now made to FIGS. 69A, 69B, 69C and 69D, which are sectional illustrations of a hip joint employing the implantable artificial acetabular sockets of FIGS. 66A-68C implanted in a reamed acetabulum.

Figure 69A:
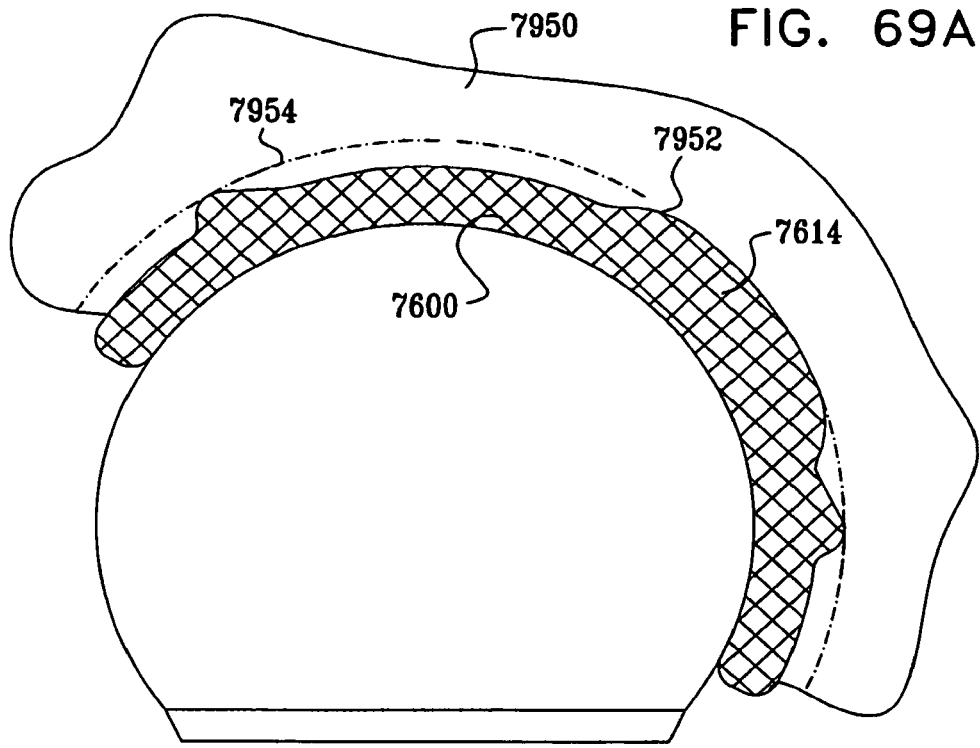
FIGS. 69A, 69B, 69C and 69D are sectional illustrations of a hip joint employing the implantable artificial acetabular sockets of FIGS. 66A-68C implanted in a reamed acetabulum.

As seen in FIG. 69A, implantable artificial acetabular socket 7600 of FIGS. 66A-66C is shown implanted in acetabulum 7950 in a first orientation, where thickened portion 7614 is aligned with the natural acetabular recess 7952. Provision of thickened portion 7614 allows acetabular socket 7600 to fit into acetabulum 7950 without requiring reaming of a hemispherical portion thereof, as indicated by dotted lines 7954. This allows for a less invasive procedure and also provides a thicker shock absorbing surface.

Figure 69B:
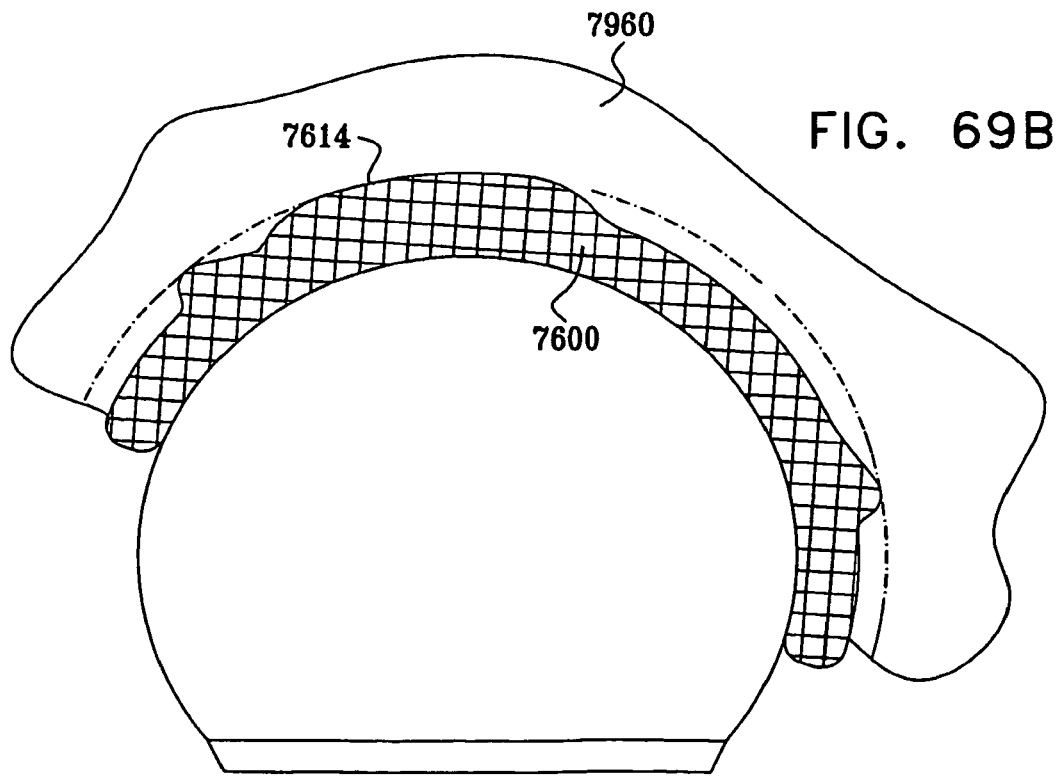

FIG. 69B illustrates implantable artificial acetabular socket 7600 of FIGS. 66A-66C implanted in acetabulum 7960 in a second orientation, where thickened portion 7614 is oriented so as to align thickened portion 7614 with the area of greatest applied force.

Figure 69C:
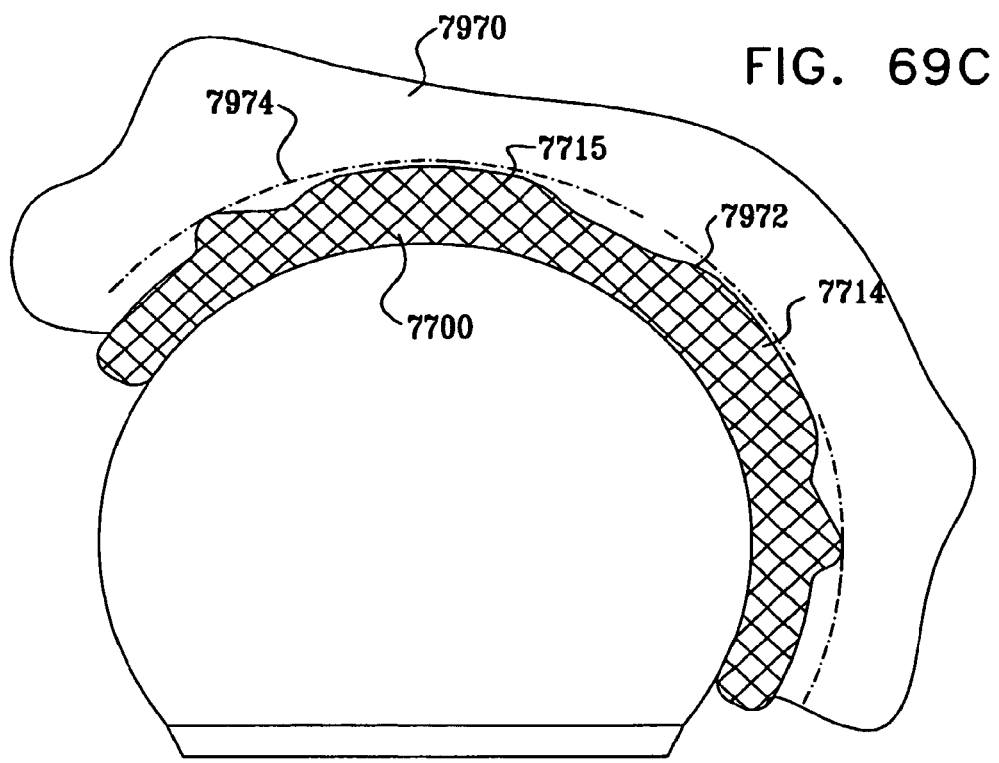

FIG. 69C illustrates implantable artificial acetabular socket 7700 of FIGS. 67A-67C implanted in acetabulum 7970. Thickened portion 7714 is aligned with the natural acetabular recess 7972. Provision of thickened portion 7714 allows acetabular socket 7700 to it into acetabulum 7970 without requiring reaming of a hemispherical portion thereof, as indicated by dotted lines 7974. This allows for a less invasive procedure and also provides a thicker shock absorbing surface. This embodiment requires additional reaming over that shown in FIG. 69A, to allow for the placement of thickened portion 7715 in the area of greatest applied force.

Figure 69D:
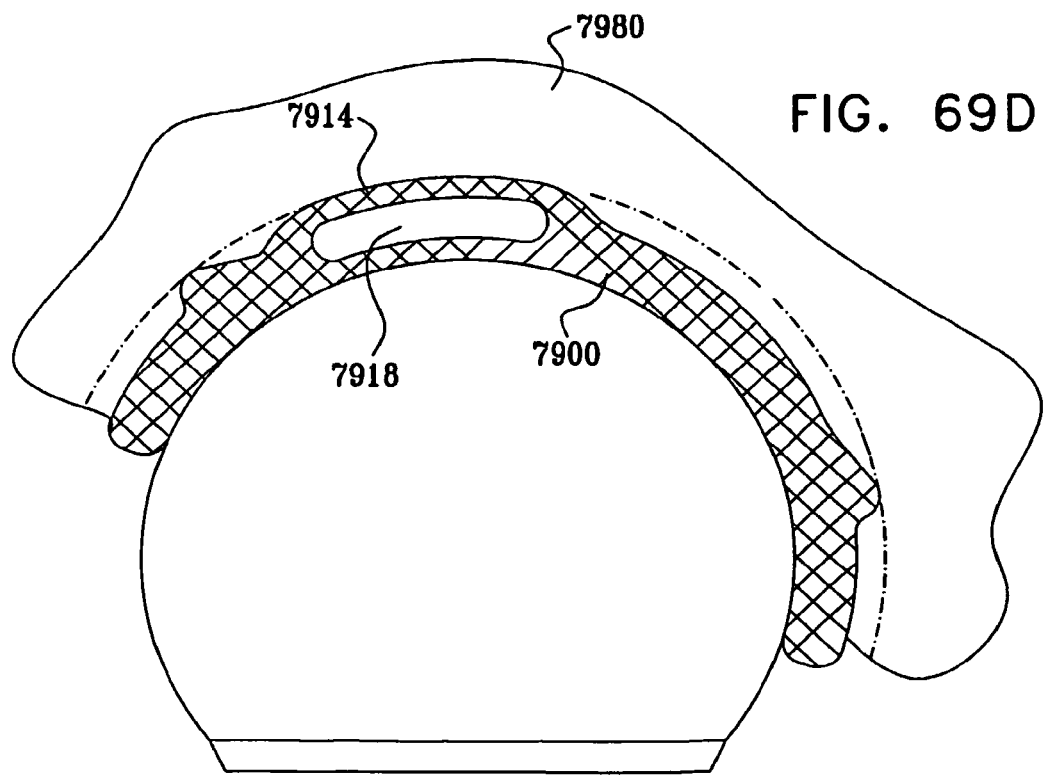

FIG. 69D shows implantable artificial acetabular socket 7900 of FIGS. 68A-68C implanted in acetabulum 7980, where thickened portion 7914 is oriented so as to align thickened portion 7914 with the area of greatest applied force. As seen in FIG. 69D, hollow portion 7918 is provided for attenuation of the stresses incurred at the joint.

Figure 70A:
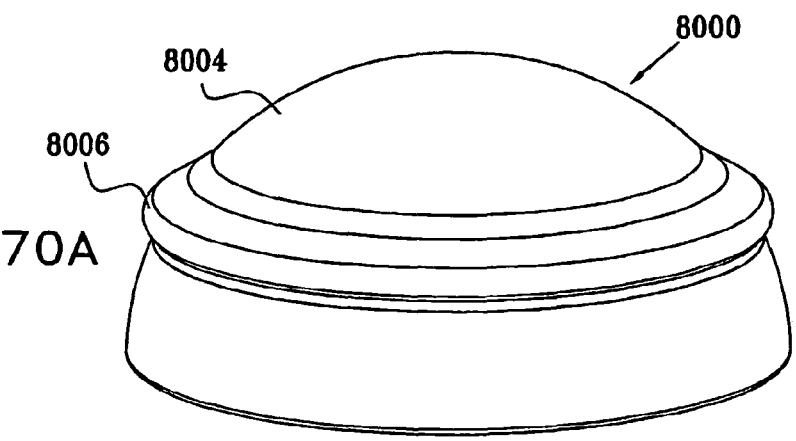
FIGS. 70A, 70B, and 70C are respective pictorial, sectional and partially cut away illustrations of an implantable artificial acetabular socket constructed and operative in accordance with a further preferred embodiment of the present invention.
Figure 70B:
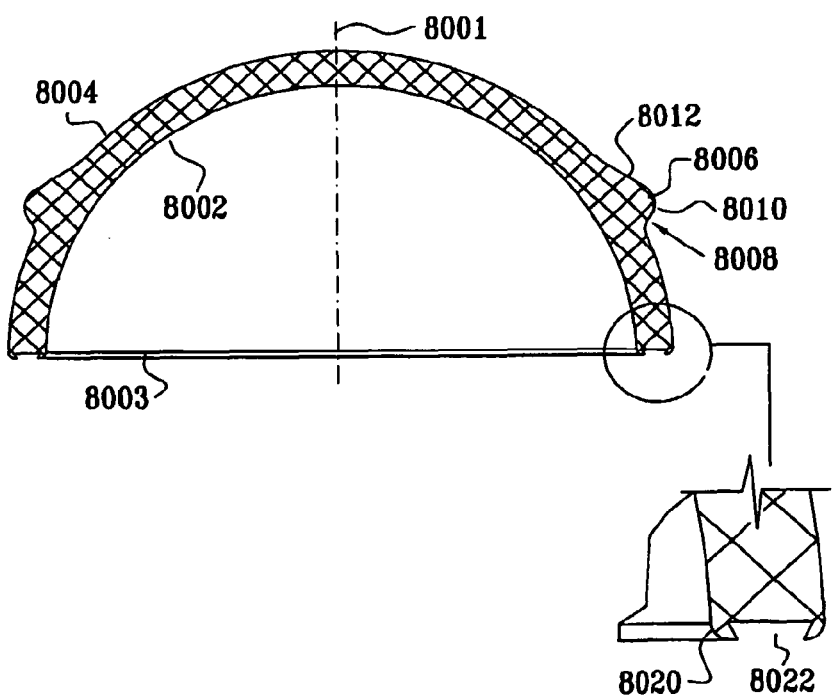
Figure 70C:
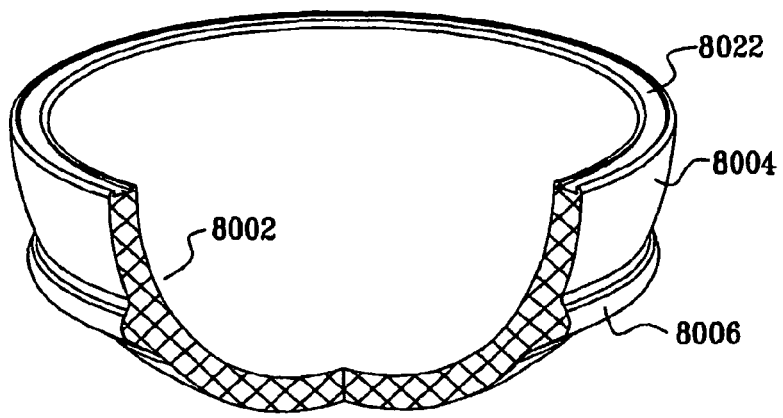

Reference is now made to FIGS. 70A, 70B, and 70C, which are respective pictorial, sectional and partially cut away illustrations of an implantable artificial acetabular socket constructed and operative in accordance with a further preferred embodiment of the present invention.

Preferably, implantable artificial acetabular socket 8000 is of generally uniform thickness, is symmetric about an axis 8001 and defines an hemispherical concave inner articulation surface 8002, having a beveled edge 8003, and a generally hemispherical outer bone engagement surface 8004, which preferably has formed thereon, at any suitable location between its apex and its rim, a generally annular outwardly extending protrusion 8006, preferably defining a generally annular undercut 8008. Alternatively, the protrusion 8006 may be any other suitable non-annular, open or closed, generally peripheral, protrusion. The protrusion 8006 is preferably arranged for snap-lit engagement with a corresponding groove formed by reaming of a bone, examples of which are described hereinabove.

Preferably, the protrusion 8006 has a cross-sectional configuration, as can be readily seen in FIG. 70B, which is characterized in that an underlying surface portion 8010 of protrusion 8006, at the undercut 8008, defines a slope which is sharper than a corresponding slope of an overlying surface portion 8012 of protrusion 8006.

It is a particular feature of the implantable artificial acetabular socket 8000 that an edge portion 8020 thereof is formed with an inward groove 8022. Inward groove 8022 is provided to allow for the growth of bone or fibrous tissue following the implantation of acetabular socket 8000 and to promote biological fixation of acetabular socket 8000.

Figure 71A:
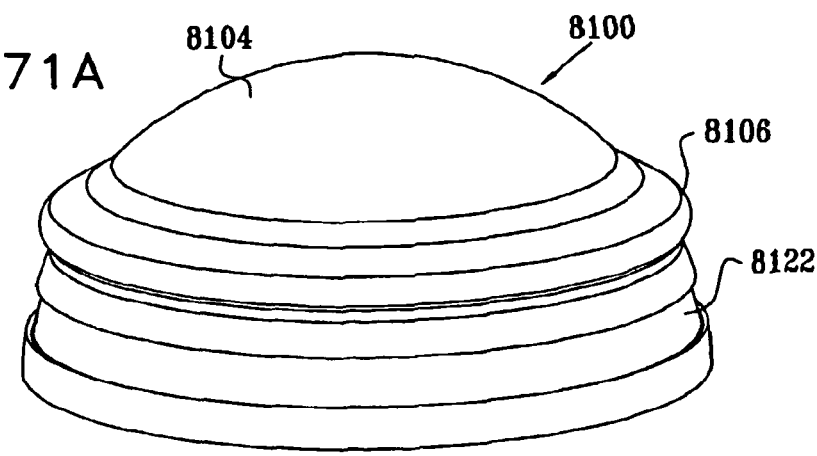
FIGS. 71A, 71B, and 71C are respective pictorial, sectional and partially cut away illustrations of an implantable artificial acetabular socket constructed and operative in accordance with another preferred embodiment of the present invention.
Figure 71B:
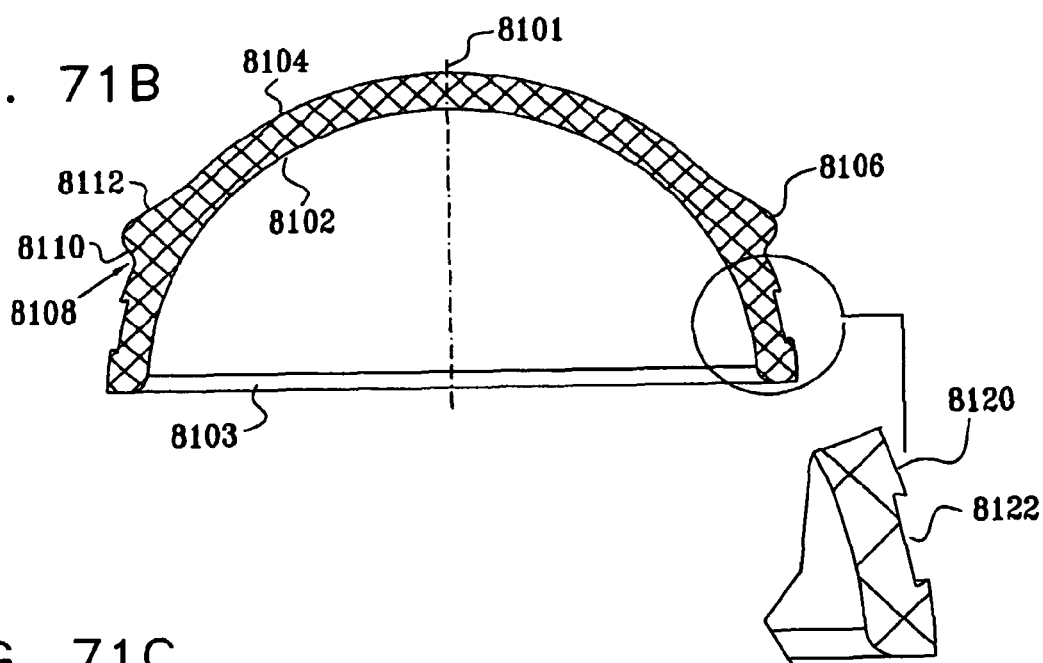
Figure 71C:
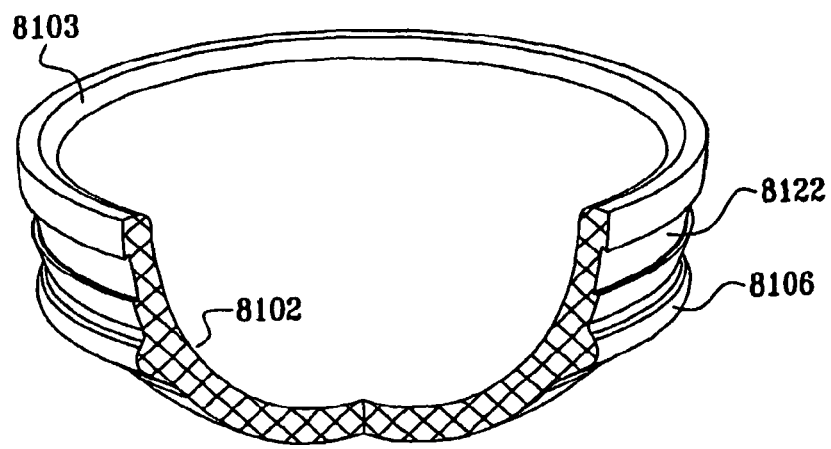

Reference is now made to FIGS. 71A, 71B, and 71C, which are respective pictorial, sectional and partially cut away illustrations of an implantable artificial acetabular socket constructed and operative in accordance with a further preferred embodiment or the present invention.

Preferably, implantable artificial acetabular socket 8100 is of generally uniform thickness, is symmetric about an axis 8101 and defines an hemispherical concave inner articulation surface 8102, having a beveled edge 8103, and a generally hemispherical outer bone engagement surface 8104, which preferably has formed thereon, at any suitable location between its apex and its rim, a generally annular outwardly extending protrusion 8106, preferably defining a generally annular undercut 8108. Alternatively, the protrusion 8106 may be any other suitable non-annular, open or closed, generally peripheral, protrusion. The protrusion 8106 is preferably arranged for snap-lit engagement with a corresponding groove formed by reaming of a bone, examples of which are described hereinabove.

Preferably, the protrusion 8106 has a cross-sectional configuration, as can be readily seen in FIG. 71B, which is characterized in that an underlying surface portion 8110 of protrusion 8106, at the undercut 8108, defines a slope which is sharper than a corresponding slope of an overlying surface portion 8112 of protrusion 8106.

It is a particular feature of the implantable artificial acetabular socket 8100 that a lower portion 8120 of outer bone engagement surface 8104 is formed with an inward groove 8122. Inward groove 8122 is provided to allow for the growth of bone or fibrous tissue following the implantation of acetabular socket 8100 and to promote biological fixation of acetabular socket 8100.

Reference is now made to FIGS. 72A, 72B, and 72C, which are respective pictorial, sectional and partially cut away illustrations of an implantable artificial acetabular socket constructed and operative in accordance with a further preferred embodiment of the present invention.

Preferably, implantable artificial acetabular socket 8200 is of generally uniform thickness, is symmetric about an axis 8201 and defines an hemispherical concave inner articulation surface 8202, having a beveled edge 8203, and a generally hemispherical outer bone engagement surface 8204, which preferably has formed thereon, at any suitable location between its apex and its rim, a generally annular outwardly extending protrusion 8206, preferably defining a generally annular undercut 8208. Alternatively, the protrusion 8206 may be any other suitable non-annular, open or closed, generally peripheral, protrusion. The protrusion 8206 is preferably arranged for snap-fit engagement with a corresponding groove formed by reaming of a bone, examples of which are described hereinabove.

Preferably, the protrusion 8206 has a cross-sectional configuration, as can be readily seen in FIG. 72B, which is characterized in that an underlying surface portion 8210 of protrusion 8206, at the undercut 8208, defines a slope which is sharper than a corresponding slope of an overlying surface portion 8212 of protrusion 8206.

It is a particular feature of the implantable artificial acetabular socket 8200 that a lower portion 8220 of outer bone engagement surface 8204 is formed with multiple inward grooves 8222. Multiple inward grooves 8222 are provided to allow for the growth of bone or fibrous tissue following the implantation of acetabular socket 8200 and to promote biological fixation of acetabular socket 8200.

Figure 73A:
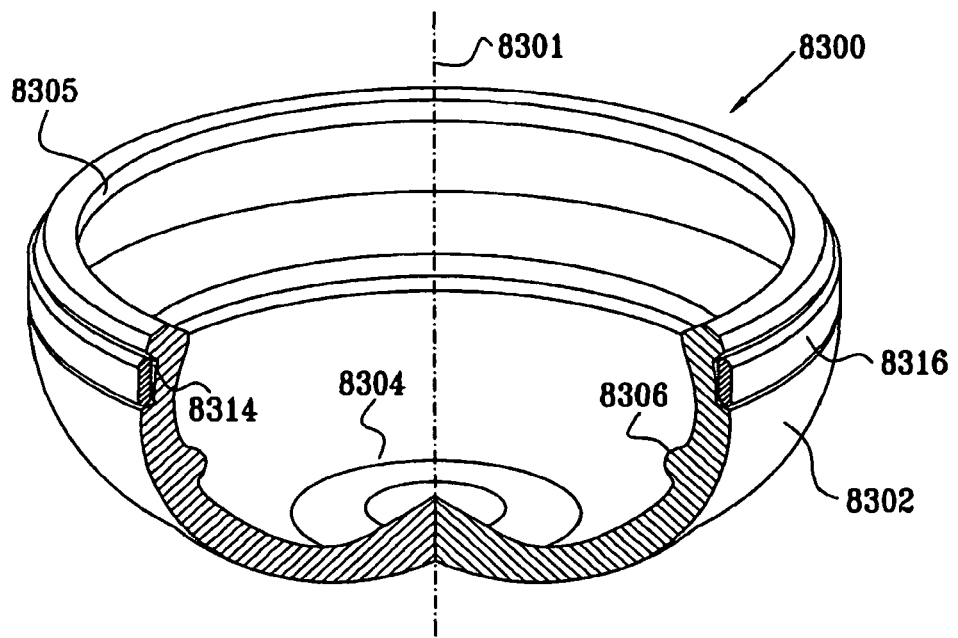
FIGS. 73A and 73B are respective pictorial and sectional illustrations of an implantable artificial femoral or humeral head resurfacing element constructed and operative in accordance with a further preferred embodiment of the present invention.
Figure 73B:
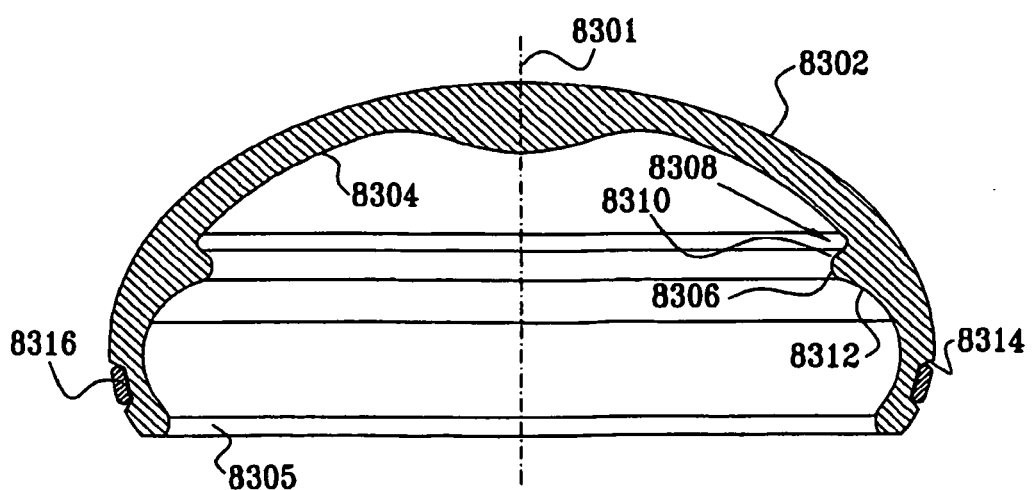

Reference is now made to FIGS. 73A and 73B, which are respective pictorial and sectional illustrations of an implantable artificial femoral or humeral head resurfacing element constructed and operative in accordance with still another preferred embodiment of the present invention. The implantable artificial femoral or humeral head resurfacing element is intended for mounting onto a natural femoral or humeral head in accordance with a preferred embodiment of the present invention.

As seen in FIGS. 73A and 73B, an implantable artificial femoral or humeral head resurfacing element, designated by reference numeral 8300, is formed preferably by injection molding of polyurethane. Preferred polyurethane materials are described hereinbelow.

Preferably, implantable artificial femoral or humeral head resurfacing element 8300 is of generally uniform thickness, other than at its apex which is thickened, is symmetric about an axis 8301 and defines an hemispherical outer articulation surface 8302 and a generally hemispherical inner bone engagement surface 8304, having a beveled edge 8305, which preferably has formed thereon, at any suitable location between its apex and its rim, a generally annular inwardly extending protrusion 8306, preferably defining a generally annular undercut 8308. Alternatively, the protrusion 8306 may be any other suitable non-annular, open or closed, generally peripheral, protrusion. The protrusion 8306 is preferably arranged for snap-fit engagement with a corresponding groove formed by reaming of a femoral or humeral head.

Preferably, the protrusion 8306 has a cross-sectional configuration, as can be readily seen in FIG. 73B, which is characterized in that an underlying surface portion 8310 of protrusion 8306, at the undercut 8308, defines a slope which is sharper than a corresponding slope of an overlying surface portion 8312 of protrusion 8306.

The outer articulation surface 8302 of implantable artificial femoral or humeral head resurfacing element 8300 preferably includes a peripheral recess 8314, generally located proximate to the edge of outer articulation surface 8302. Preferably, radio opaque ring element 8316 is embedded in peripheral recess 8314. Provision of radio opaque ring element 8316 provides the ability to monitor the position of artificial femoral or humeral head resurfacing element 8300 after it has been implanted. Radio opaque ring element 8316 is preferably comprised of metal, barium sulfate, zirconium oxide or any other suitable radio opaque material, and may be molded and inserted into artificial femoral or humeral head resurfacing element 8300 or integrally formed therewith.

It is appreciated that, even though the illustrated embodiment shows the non-uniform thickness portion of artificial femoral or humeral head resurfacing element 8300 at the apex thereof, any suitable portion thereof may be of non-uniform thickness.

It is appreciated that, even though the illustrated embodiment shows the provision of a radio opaque ring element in a femoral or humeral head, the provision of a radio opaque ring element is not limited to a femoral or humeral head, but may be included with any of the artificial implants described in this application.

Figure 74A:
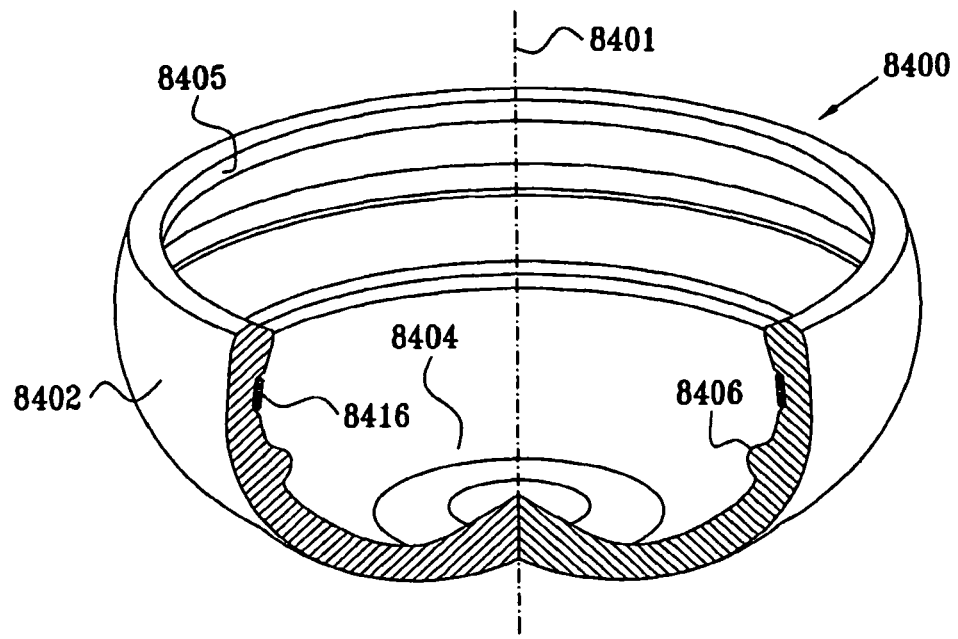
FIGS. 74A and 74B are respective pictorial and sectional illustrations of an implantable artificial femoral or humeral head resurfacing element constructed and operative in accordance with another preferred embodiment of the present invention.
Figure 74B:
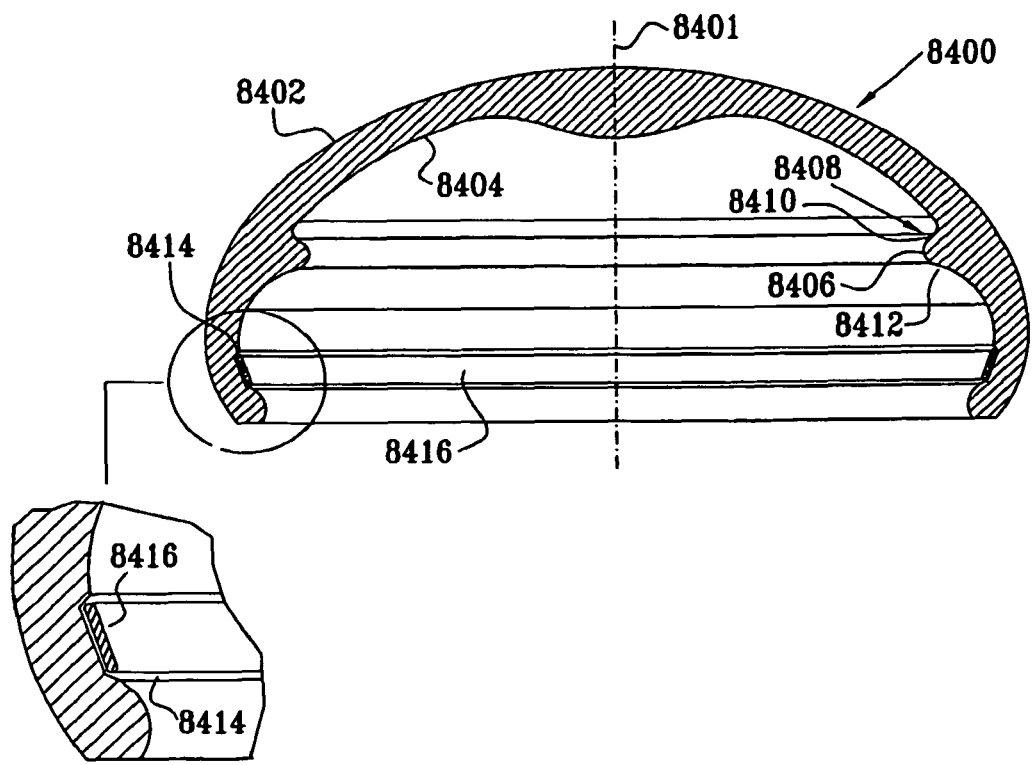

Reference is now made to FIGS. 74A and 74B, which are respective pictorial and sectional illustrations of an implantable artificial femoral or humeral head resurfacing element constructed and operative in accordance with still another preferred embodiment of the present invention. The implantable artificial femoral or humeral head resurfacing element is intended for mounting onto a natural femoral or humeral head in accordance with a preferred embodiment of the present invention.

As seen in FIGS. 74A and 74B, an implantable artificial femoral or humeral head resurfacing element, designated by reference numeral 8400, is formed preferably by injection molding of polyurethane. Preferred polyurethane materials are described hereinbelow.

Preferably, implantable artificial femoral or humeral head resurfacing element 8400 is of generally uniform thickness, other than at its apex which is thickened, is symmetric about an axis 8401 and defines an hemispherical outer articulation surface 8402 and a generally hemispherical inner bone engagement surface 8404, having a beveled edge 8405, which preferably has formed thereon, at any suitable location between its apex and its rim, a generally annular inwardly extending protrusion 8406, preferably defining a generally annular undercut 8408. Alternatively, the protrusion 8406 may be any other suitable non-annular, open or closed, generally peripheral, protrusion. The protrusion 8406 is preferably arranged for snap-fit engagement with a corresponding groove formed by reaming of a femoral or humeral head.

Preferably, the protrusion 8406 has a cross-sectional configuration, as can be readily seen in FIG. 74B, which is characterized in that an underlying surface portion 8410 of protrusion 8406, at the undercut 8408, defines a slope which is sharper than a corresponding slope of an overlying surface portion 8412 of protrusion 8406.

The inner bone engagement surface 8404 of implantable artificial femoral or humeral head resurfacing element 8400 preferably includes a peripheral recess 8414, generally located proximate to the edge of inner bone engagement surface 8404. Preferably, radio opaque ring element 8416 is embedded in peripheral recess 8414. Provision of radio opaque ring element 8416 provides the ability to monitor the position of artificial femoral or humeral head resurfacing element 8400 after it has been implanted. Radio opaque ring element 8416 is preferably comprised of metal, barium sulfate, zirconium oxide or any other suitable radio opaque material, and may be molded and inserted into artificial femoral or humeral head resurfacing element 8400 or integrally formed therewith.

It is appreciated that, even though the illustrated embodiment shows the non-uniform thickness portion of artificial femoral or humeral head resurfacing element 8400 at the apex thereof, any suitable portion thereof may be of non-uniform thickness.

Figure 75A:
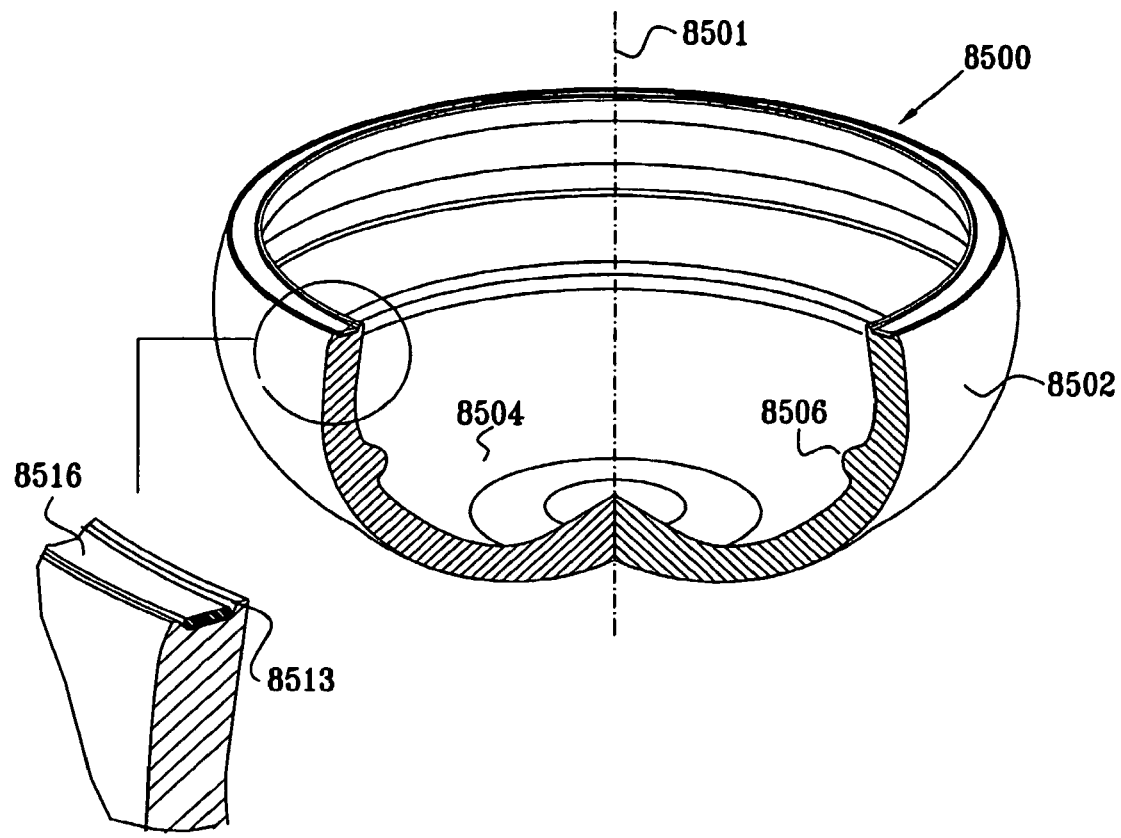
FIGS. 75A and 75B are respective pictorial and sectional illustrations of an implantable artificial femoral or humeral head resurfacing element constructed and operative in accordance with still another preferred embodiment of the present invention.
Figure 75B:
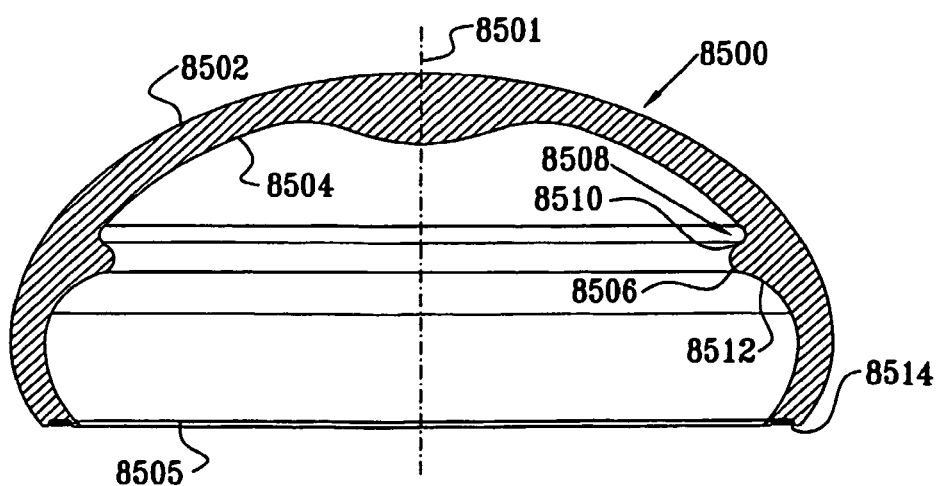

Reference is now made to FIGS. 75A and 75B, which are respective pictorial and sectional illustrations of an implantable artificial femoral or humeral head resurfacing element constructed and operative in accordance with still another preferred embodiment of the present invention. The implantable artificial femoral or humeral head resurfacing element is intended for mounting onto a natural femoral or humeral head in accordance with a preferred embodiment of the present invention.

As seen in FIGS. 75A and 75B, an implantable artificial femoral or humeral head resurfacing element, designated by reference numeral 8500, is formed preferably by injection molding of polyurethane. Preferred polyurethane materials are described hereinbelow.

Preferably, implantable artificial femoral or humeral head resurfacing element 8500 is of generally uniform thickness, other than at its apex which is thickened, is symmetric about an axis 8501 and defines an hemispherical outer articulation surface 8502 and a generally hemispherical inner bone engagement surface 8504, having a beveled edge 8505, which preferably has formed thereon, at any suitable location between its apex and its rim, a generally annular inwardly extending protrusion 8506, preferably defining a generally annular undercut 8508. Alternatively, the protrusion 8506 may be any other suitable non-annular, open or closed, generally peripheral, protrusion. The protrusion 8506 is preferably arranged for snap-fit engagement with a corresponding groove formed by reaming of a femoral or humeral head.

Preferably, the protrusion 8506 has a cross-sectional configuration, as can be readily seen in FIG. 75B, which is characterized in that an underlying surface portion 8510 of protrusion 8506, at the undercut 8508, defines a slope which is sharper than a corresponding slope of an overlying surface portion 8512 of protrusion 8506.

An edge surface 8513 of implantable artificial femoral or humeral head resurfacing element 8500 preferably includes a peripheral recess 8514. Preferably, radio opaque ring element 8516 is embedded in peripheral recess 8514. Provision of radio opaque ring element 8516 provides the ability to monitor the position of artificial femoral or humeral head resurfacing element 8500 after it has been implanted. Radio opaque ring element 8516 is preferably comprised of metal, barium sulfate, zirconium oxide or any other suitable radio opaque material, and may be molded and inserted into artificial femoral or humeral head resurfacing element 8500 or integrally formed therewith.

Figure 76A:
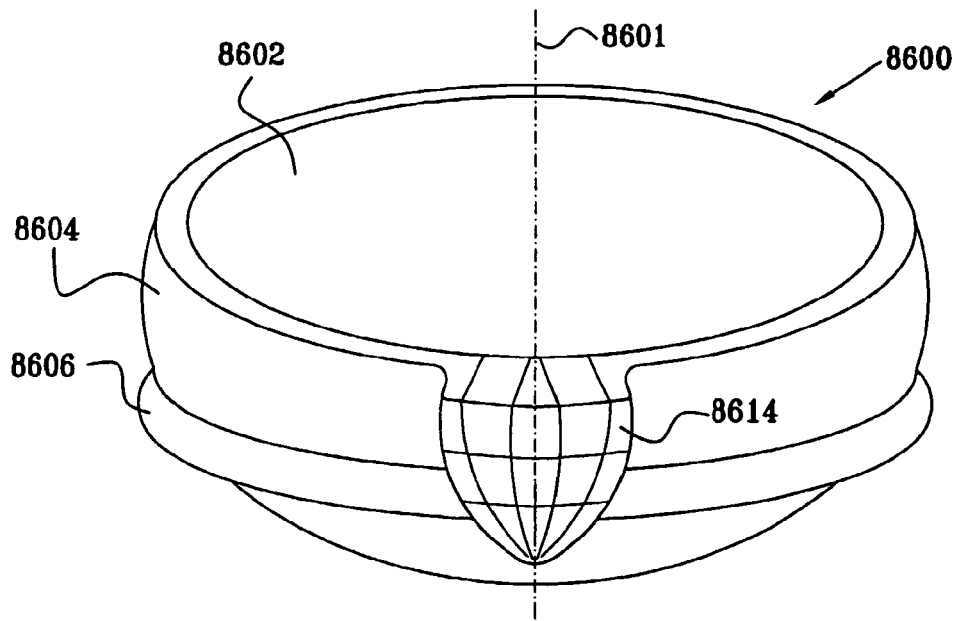
FIGS. 76A and 76B are respective pictorial and sectional illustrations of an implantable artificial acetabular socket constructed and operative in accordance with a further preferred embodiment of the present invention.
Figure 76B:
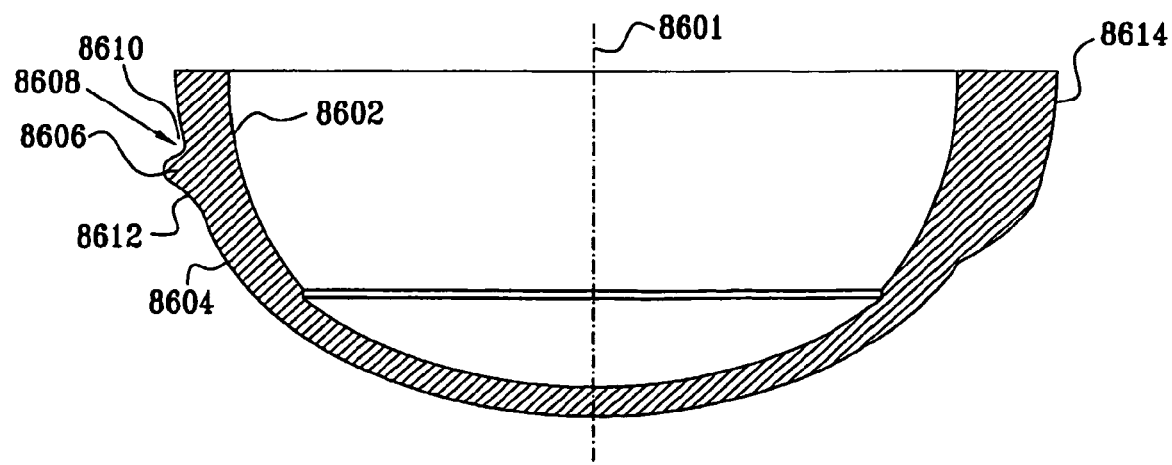

Reference is now made to FIGS. 76A and 76B, which are respective pictorial and sectional illustrations of an implantable artificial acetabular socket constructed and operative in accordance with a preferred embodiment of the present invention and which is particularly suitable for use in a hip joint.

As seen in FIGS. 76A and 76B, an implantable artificial acetabular socket, designated by reference numeral 8600, is formed preferably by injection molding of polyurethane. Preferred polyurethane materials are described hereinbelow.

Preferably, implantable artificial acetabular socket 8600 is of generally uniform thickness, is symmetric about an axis 8601 and defines an hemispherical concave inner articulation surface 8602 and a generally hemispherical outer bone engagement surface 8604, which preferably has formed thereon, at any suitable location between its apex and its rim, a generally annular outwardly extending protrusion 8606, preferably defining a generally annular undercut 8608. Alternatively, the protrusion 8606 may be any other suitable non-annular, open or closed, generally peripheral, protrusion. The protrusion 8606 is preferably arranged for snap-fit engagement with a corresponding groove formed by reaming of a bone, examples of which are described hereinabove.

Preferably, the protrusion 8606 has a cross-sectional configuration, as can be readily seen in FIG. 76B, which is characterized in that an underlying surface portion 8610 of protrusion 8606, at the undercut 8608, defines a slope which is sharper than a corresponding slope of an overlying surface portion 8612 of protrusion 8606.

It is a particular feature of the implantable artificial acetabular socket 8600 that a portion of outer bone engagement surface 8604 thereof defines a thickened portion 8614, preferably extending from a location generally adjacent protrusion 8606. Thickened portion 8614 is preferably molded to correspond with the shape of the acetabular notch. Thickened portion 8614 is provided to add stability to acetabular socket 8600 once implanted, by minimizing rotational movement and preventing rotational dislodgment.

Figure 77A:
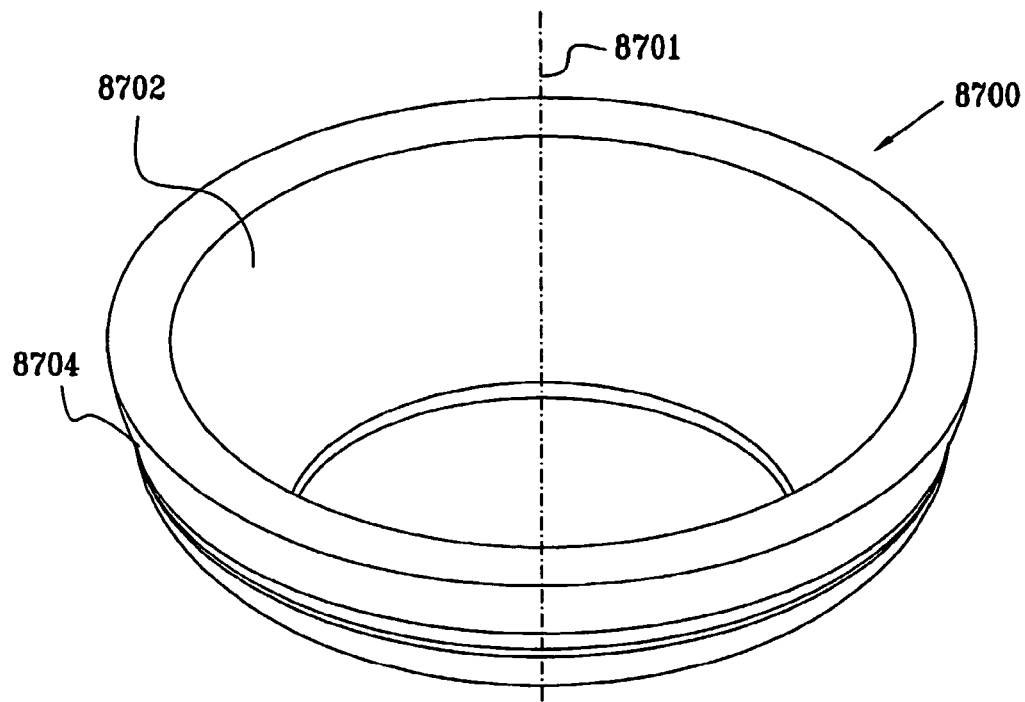
FIGS. 77A and 77B are respective pictorial and sectional illustrations of an implantable artificial acetabular socket constructed and operative in accordance with another preferred embodiment of the present invention.
Figure 77B:
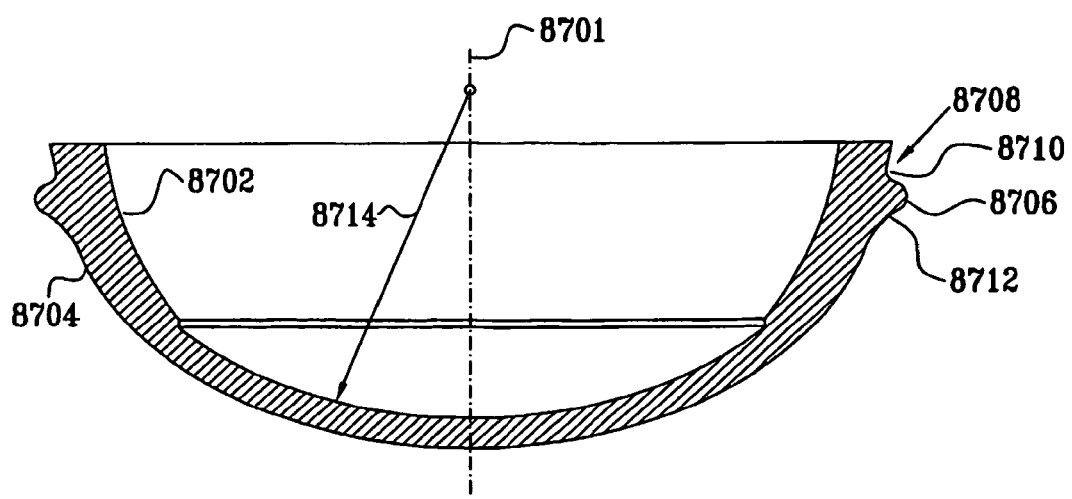

Reference is now made to FIGS. 77A and 77B, which are respective pictorial and sectional illustrations of an implantable artificial acetabular socket constructed and operative in accordance with a preferred embodiment of the present invention and which is particularly suitable for use in a hip joint.

As seen in FIGS. 77A and 77B, an implantable artificial acetabular socket, designated by reference numeral 8700, is formed preferably by injection molding of polyurethane. Preferred polyurethane materials are described hereinbelow.

Preferably, implantable artificial acetabular socket 8700 is of generally uniform thickness, is symmetric about an axis 8701 and defines an hemispherical concave inner articulation surface 8702 and a generally hemispherical outer bone engagement surface 8704, which preferably has formed thereon, at any suitable location between its apex and its rim, a generally annular outwardly extending protrusion 8706, preferably defining a generally annular undercut 8708. Alternatively, the protrusion 8706 may be any other suitable non-annular, open or closed, generally peripheral, protrusion. The protrusion 8706 is preferably arranged for snap-fit engagement with a corresponding groove formed by reaming of a bone, examples of which are described hereinabove.

Preferably, the protrusion 8706 has a cross-sectional configuration, as can be readily seen in FIG. 77B, which is characterized in that an underlying surface portion 8710 of protrusion 8706, at the undercut 8708, defines a slope which is sharper than a corresponding slope of an overlying surface portion 8712 of protrusion 8706.

As seen in FIGS. 77A and 77B, implantable artificial acetabular socket 8700 is a less than full hemispherical, low profile acetabular socket, as can be readily seen from radius 8714, which shows a radius of the full hemispherical socket that acetabular socket 8700 is similar to. Acetabular socket 8700 thus provides for implantation with less reaming of bone required.

Figure 78A:
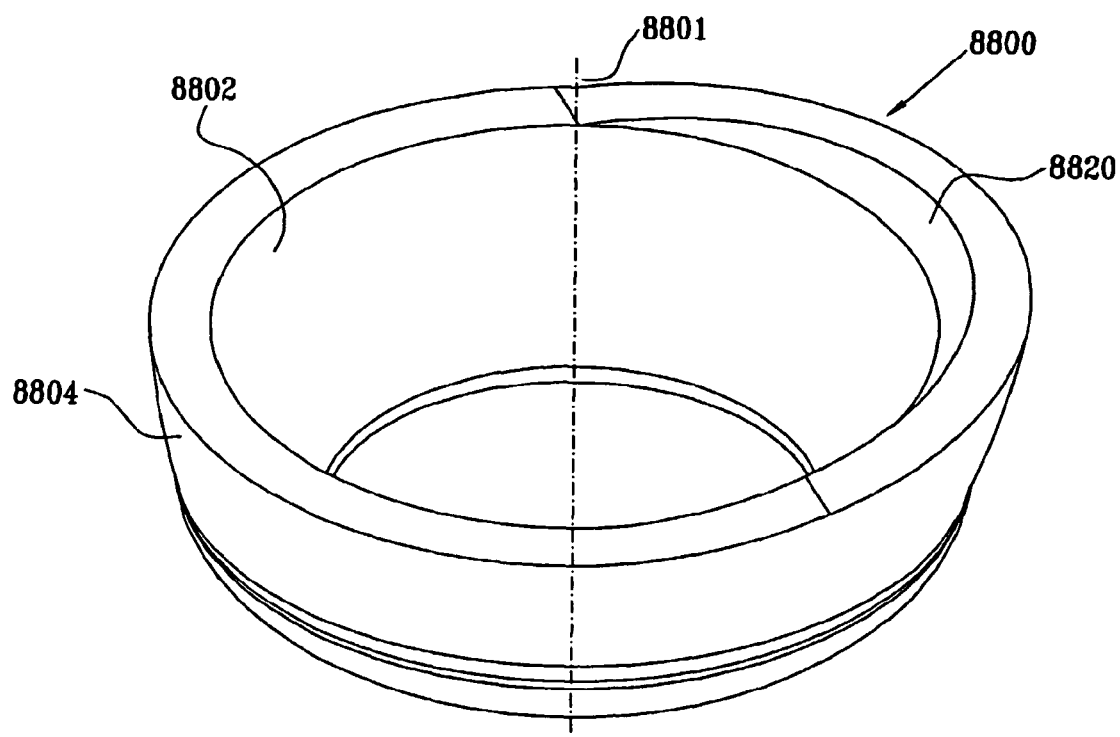
FIGS. 78A and 78B are respective pictorial and sectional illustrations of an implantable artificial acetabular socket constructed and operative in accordance with still another preferred embodiment of the present invention.
Figure 78B:
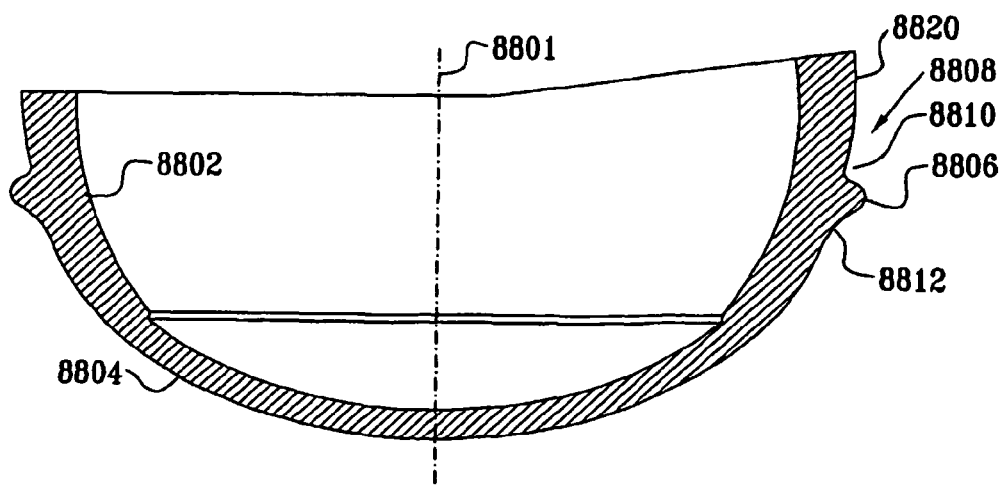

Reference is now made to FIGS. 78A and 78B, which are respective Pictorial and sectional illustrations of an implantable artificial acetabular socket constructed and operative in accordance with a preferred embodiment of the present invention and which is particularly suitable for use in a hip joint.

As seen in FIGS. 78A and 78B, an implantable artificial acetabular socket, designated by reference numeral 8800, is formed preferably by injection molding of polyurethane. Preferred polyurethane materials are described hereinbelow.

Preferably, implantable artificial acetabular socket 8800 is of generally uniform thickness, is symmetric about an axis 8801 and defines an hemispherical concave inner articulation surface 8802 and a generally hemispherical outer bone engagement surface 8804, which preferably has formed thereon, at any suitable location between its apex and its rim, a generally annular outwardly extending protrusion 8806, preferably defining a generally annular undercut 8808. Alternatively, the protrusion 8806 may be any other suitable non-annular, open or closed, generally peripheral, protrusion. The protrusion 8806 is preferably arranged for snap-fit engagement with a corresponding groove formed by reaming of a bone, examples of which are described hereinabove.

Preferably, the protrusion 8806 has a cross-sectional configuration, as can be readily seen in FIG. 78B, which is characterized in that an underlying surface portion 8810 of protrusion 8806, at the undercut 8808, defines a slope which is sharper than a corresponding slope of an overlying surface portion 8812 of protrusion 8806.

Implantable artificial acetabular socket 8800 also includes an extended portion 8820, preferably provided to prevent dislocation of the femoral head following insertion.

Figure 79A:
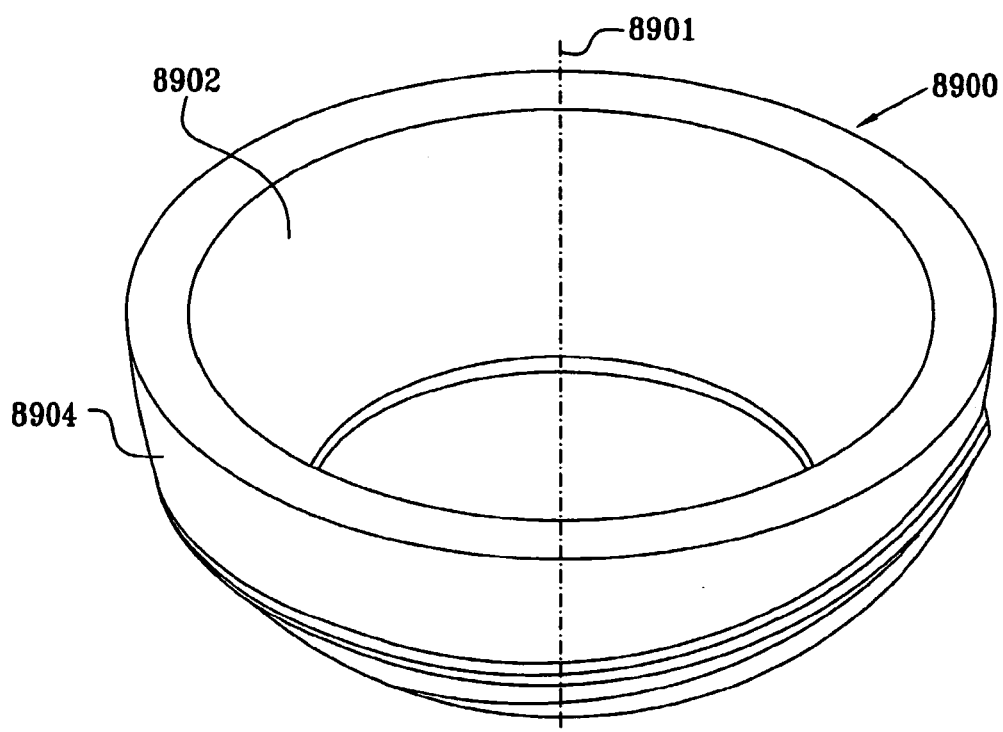
FIGS. 79A and 79B are respective pictorial and sectional illustrations of an implantable artificial acetabular socket constructed and operative in accordance with a further preferred embodiment of the present invention.
Figure 79B:
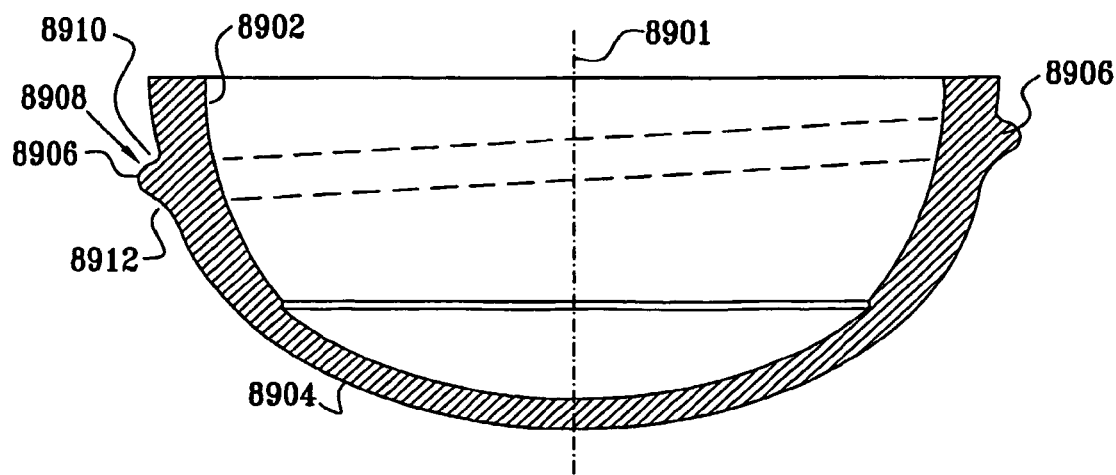

Reference is now made to FIGS. 79A and 79B, which are respective pictorial and sectional illustrations of an implantable artificial acetabular socket constructed and operative in accordance with a preferred embodiment of the present invention and which is particularly suitable for use in a hip joint.

As seen in FIGS. 79A and 79B, an implantable artificial acetabular socket, designated by reference numeral 8900, is formed preferably by injection molding of polyurethane. Preferred polyurethane materials are described hereinbelow.

Preferably, implantable artificial acetabular socket 8900 is of generally uniform thickness, is symmetric about an axis 8901 and defines an hemispherical concave inner articulation surface 8902 and a generally hemispherical outer bone engagement surface 8904, which preferably has formed thereon, at any suitable location between its apex and its rim, a generally annular outwardly extending protrusion 8906, preferably defining a generally annular undercut 8908. Alternatively, the protrusion 8906 may be any other suitable non-annular, open or closed, generally peripheral, protrusion. The protrusion 8906 is preferably arranged for snap-fit engagement with a corresponding groove formed by reaming of a bone, examples of which are described hereinabove.

Preferably, the protrusion 8906 has a cross-sectional configuration, as can be readily seen in FIG. 79B, which is characterized in that an underlying surface portion 8910 of protrusion 8906, at the undercut 8908, defines a slope which is sharper than a corresponding slope of an overlying surface portion 8912 of protrusion 8906.

It is a particular feature of the implantable artificial acetabular socket 8900 that protrusion 8906 is arranged such that it is not orthogonal to axis 8901 and thus allows proper orientation of the artificial acetabular socket in an improperly reamed natural acetabulum. Implantable artificial acetabular socket 8900 is provided with protrusion 8906 for engagement with a reamed acetabulum, where the reaming was performed in a less than desirable orientation.

Figure 80A:
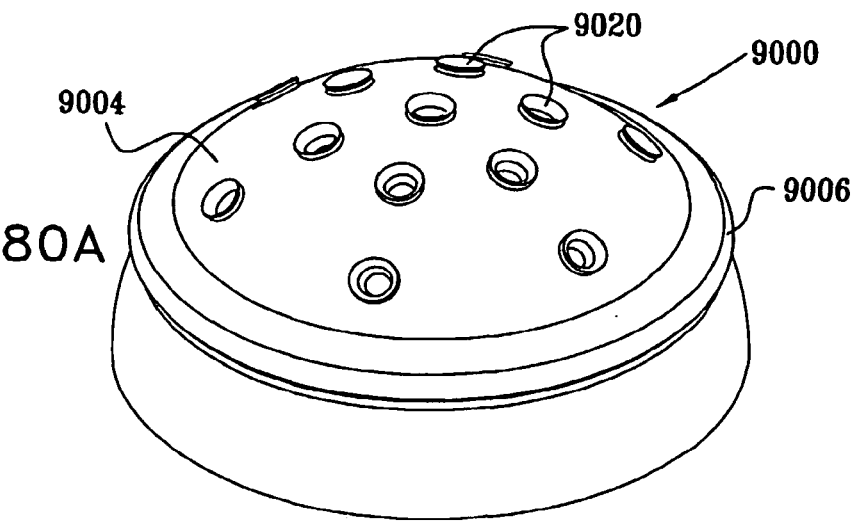
FIGS. 80A, 80B, and 80C are respective pictorial, sectional and partially cut away illustrations of an implantable artificial acetabular socket constructed and operative in accordance with another preferred embodiment of the present invention.
Figure 80B:
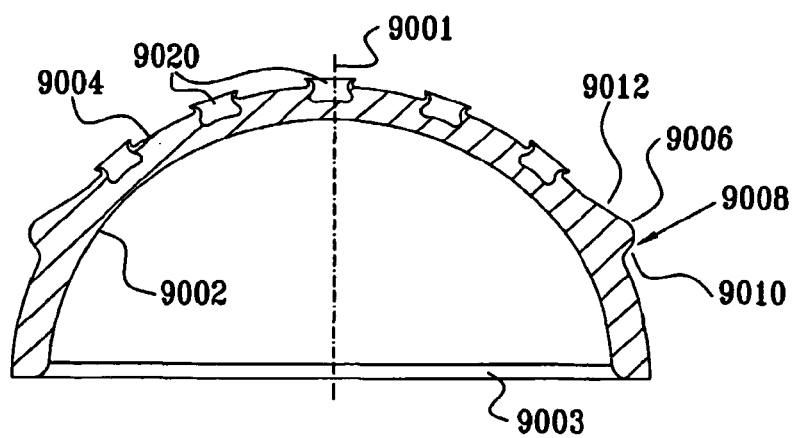
Figure 80C:
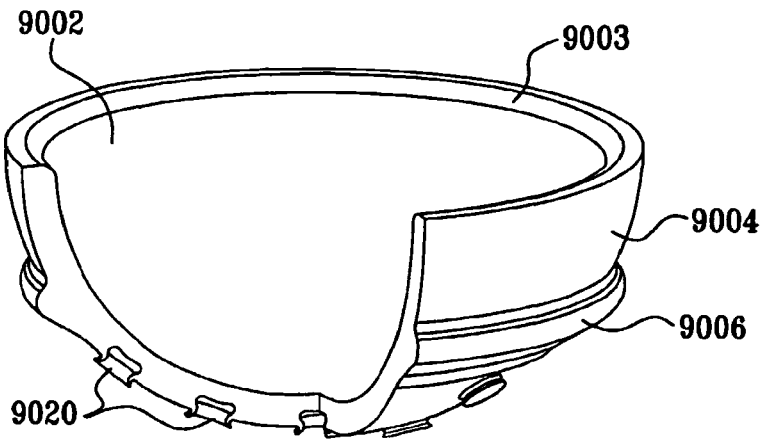

Reference is now made to FIGS. 80A, 80B, and 80C, which are respective pictorial, sectional and partially cut away illustrations of an implantable artificial acetabular socket constructed and operative in accordance with a preferred embodiment of the present invention and which is particularly suitable for use in a hip joint.

As seen in FIGS. 80A, 80B and 80C, an implantable artificial acetabular socket designated by reference numeral 9000, is formed preferably by injection molding of polyurethane. Preferred polyurethane materials are described hereinbelow.

Preferably, implantable artificial acetabular socket 9000 is of generally uniform thickness, is symmetric about an axis 9001 and defines an hemispherical concave inner articulation surface 9002, having a beveled edge 9003, and a generally hemispherical outer bone engagement surface 9004, which preferably has formed thereon, at any suitable location between its apex and its rim, a generally annular outwardly extending protrusion 9006, preferably defining a generally annular undercut 9008. Alternatively, the protrusion 9006 may be any other suitable non-annular, open or closed, generally peripheral, protrusion. The protrusion 9006 is preferably arranged for snap-lit engagement with a corresponding groove formed by reaming of a bone, examples of which are described hereinabove.

Preferably, the protrusion 9006 has a cross-sectional configuration, as can be readily seen in FIG. 80B, which is characterized in that an underlying surface portion 9010 of protrusion 9006, at the undercut 9008, defines a slope which is sharper than a corresponding slope of an overlying surface portion 9012 of protrusion 9006.

It is a particular feature of the implantable artificial acetabular socket 9000 that a portion of outer bone engagement surface 9004, preferably the portion located between protrusion 9006 and the apex thereof, includes a plurality of hollow annular protrusions 9020 integral with surface 9004 but protruding beyond surface 9004. Annular protrusions 9020 are shaped with an undercut and are in contact with prepared acetabulum leaving a gap between the prepared acetabular surface and implant surface 9004. Annular protrusions 9020 provide localized areas of low contact area and thus high localized stress. With time, the high localized stress allows controlled subsidence of the implant until surface 9004 comes into contact with the acetabular hone surface. The controlled subsidence of the implant also enables the bony surface to completely surround the undercut shape of annular protrusions 9020, thus further improving the fixation of the implant.

Figure 81A:
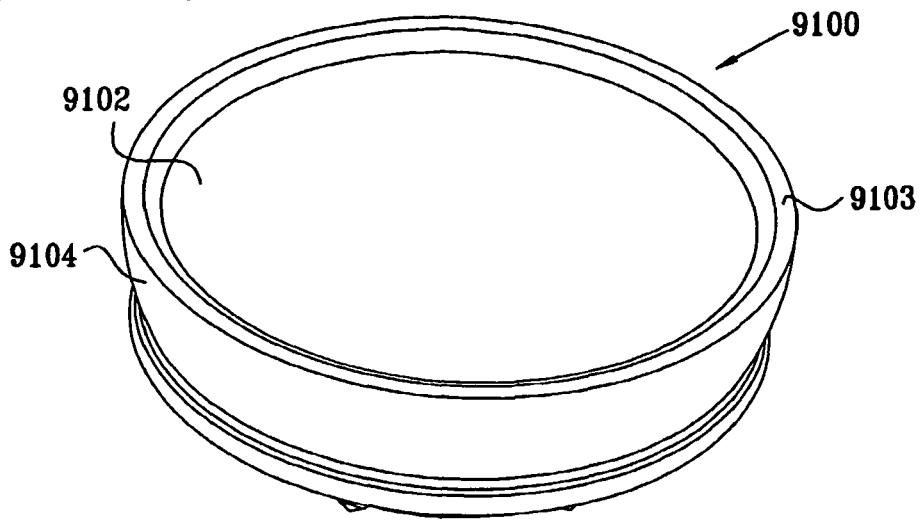
FIGS. 81A, 81B, and 81C are respective pictorial, sectional and partially cut away illustrations of an implantable artificial acetabular socket constructed and operative in accordance with still another preferred embodiment of the present invention.
Figure 81B:
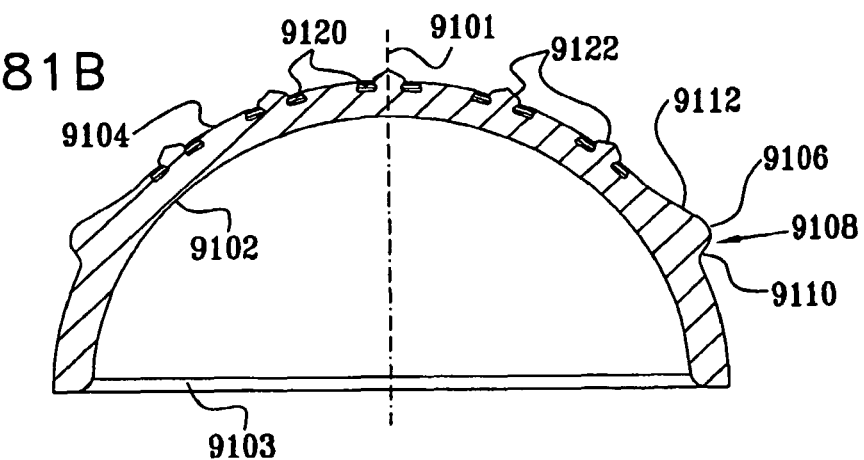
Figure 81C:
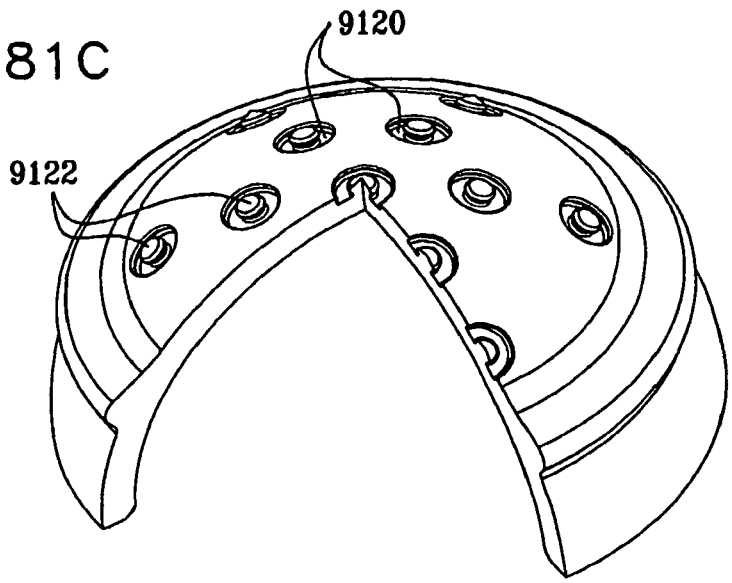

Reference is now made to FIGS. 81A, 81B, and 81C, which are respective pictorial, sectional and partially cut away illustrations of an implantable artificial acetabular socket constructed and operative in accordance with a preferred embodiment of the present invention and which is particularly suitable for use in a hip joint.

As seen in FIGS. 81A, 81B and 81C, an implantable artificial acetabular socket, designated by reference numeral 9100, is formed preferably by injection molding of polyurethane. Preferred polyurethane materials are described hereinbelow.

Preferably, implantable artificial acetabular socket 9100 is of generally uniform thickness, is symmetric about an axis 9101 and defines an hemispherical concave inner articulation surface 9102, having a beveled edge 9103, and a generally hemispherical outer bone engagement surface 9104, which preferably has formed thereon, at any suitable location between its apex and its rim, a generally annular outwardly extending protrusion 9106, preferably defining a generally annular undercut 9108. Alternatively, the protrusion 9106 may be any other suitable non-annular, open or closed, generally peripheral, protrusion. The protrusion 9106 is preferably arranged for snap-fit engagement with a corresponding groove formed by reaming of a bone, examples of which are described hereinabove.

Preferably, the protrusion 9106 has a cross-sectional configuration, as can be readily seen in FIG. 81B, which is characterized in that an underlying surface portion 9110 of protrusion 9106, at the undercut 9108, defines a slope which is sharper than a corresponding slope of an overlying surface portion 9112 of protrusion 9106.

It is a particular feature of the implantable artificial acetabular socket 9100 that a portion of outer bone engagement surface 9104, preferably the portion located between protrusion 9106 and the apex thereof, includes a plurality of annular recesses 9120 enclosing annular protrusions 9122. Annular protrusions 9122 are designed with an undercut and are in contact with prepared acetabulum leaving a gap between the prepared acetabular surface and implant surface 9104. Annular protrusions 9122 provide localized areas of low contact area and thus high localized stress. With time, the high localized stress allows controlled subsidence of the implant until implant surface 9104 comes into contact with the acetabular bone surface. The controlled subsidence of the implant also enables bone or fibrous tissue to completely fill in the annular recesses 9120 and undercut of annular protrusion 9122 to further stabilize the implant in place through biological fixation.

Figure 82A:
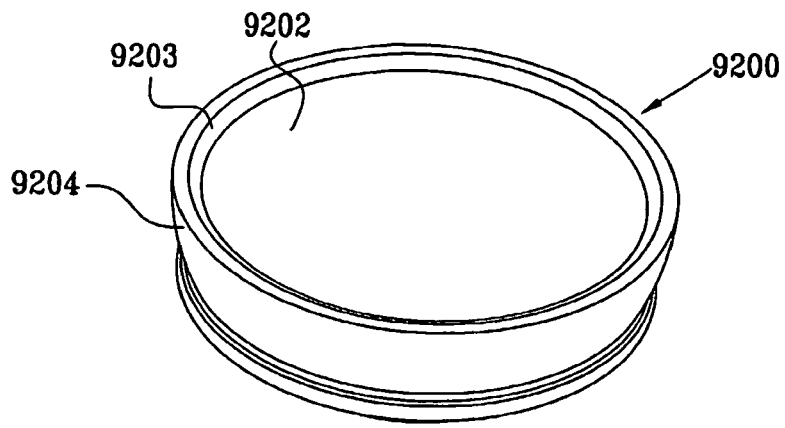
FIGS. 82A, 82B, and 82C are respective pictorial, sectional and partially cut away illustrations of an implantable artificial acetabular socket constructed and operative in accordance with a further preferred embodiment of the present invention.
Figure 82B:
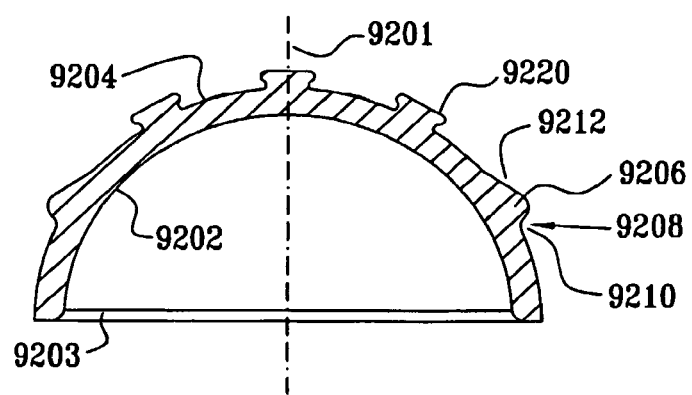
Figure 82C:
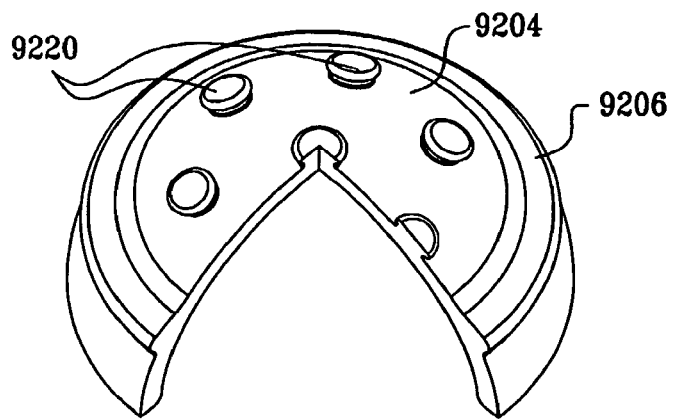

Reference is now made to FIGS. 82A, 82B, and 82C, which are respective pictorial, sectional and partially cut away illustrations of an implantable artificial acetabular socket constructed and operative in accordance with a preferred embodiment of the present invention and which is particularly suitable for use in a hip joint.

As seen in FIGS. 82A, 82B and 82C, an implantable artificial acetabular socket, designated by reference numeral 9200, is formed preferably by injection molding of polyurethane. Preferred polyurethane materials are described hereinbelow.

Preferably, implantable artificial acetabular socket 9200 is of generally uniform thickness, is symmetric about an axis 9201 and defines an hemispherical concave inner articulation surface 9202, having a beveled edge 9203, and a generally hemispherical outer bone engagement surface 9204, which preferably has formed thereon, at any suitable location between its apex and its rim, a generally annular outwardly extending protrusion 9206, preferably defining a generally annular undercut 9208. Alternatively, the protrusion 9206 may be any other suitable non-annular, open or closed, generally peripheral, protrusion. The protrusion 9206 is preferably arranged for snap-fit engagement with a corresponding groove formed by reaming of a bone, examples of which are described hereinabove.

Preferably, the protrusion 9206 has a cross-sectional configuration, as can be readily seen in FIG. 82B, which is characterized in that an underlying surface portion 9210 of protrusion 9206, at the undercut 9208, defines a slope which is sharper than a corresponding slope of an overlying surface portion 9212 of protrusion 9206.

It is a particular feature of the implantable artificial acetabular socket 9200 that a portion of outer bone engagement surface 9204, preferably the portion located between protrusion 9206 and the apex thereof, includes a plurality of annular protrusions 9220. Annular protrusions 9220 are preferably arranged for engagement with corresponding recesses formed by reaming of a bone, to provide enhanced biological fixation of acetabular socket 9200 following insertion thereof.

Figure 83:
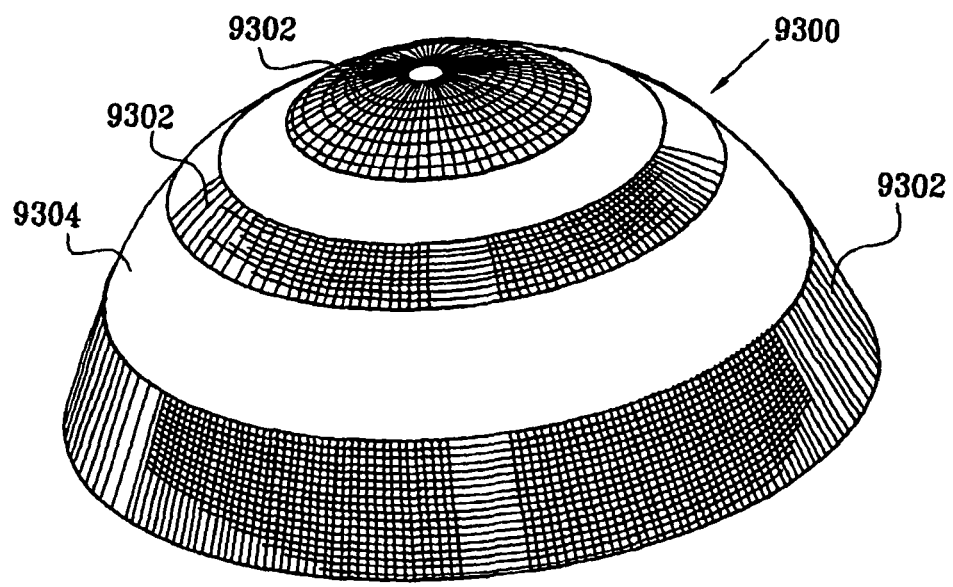
FIG. 83 is a pictorial illustration of an implantable artificial acetabular socket constructed and operative in accordance with another preferred embodiment of the present invention.

Reference is now made to FIG. 83, which is a pictorial illustration of an implantable artificial acetabular socket 9300, constructed and operative in accordance with another preferred embodiment of the present invention, which is particularly suitable tier use in a hip joint. Implantable artificial acetabular socket 9300 is constructed with a textured thin element 9302, preferably made of titanium, with an annular configuration, molded onto an outer surface 9304 of acetabular socket 9300. The provision of element 9302 provides enhanced biological fixation of acetabular socket 9300 following insertion thereof. It is appreciated that element 9302 may cover the entire surface 9304 or any suitable portion thereof.

Figure 84:
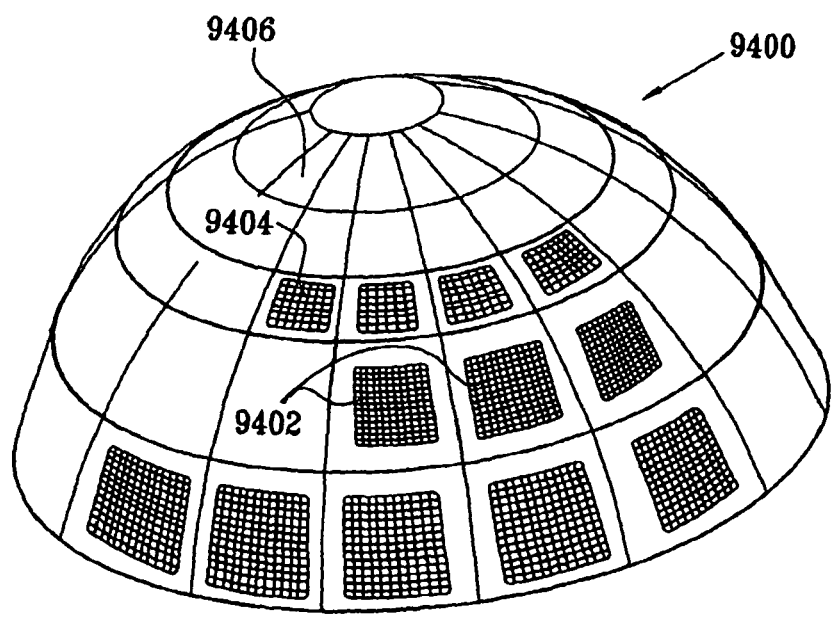
FIG. 84 is a pictorial illustration of an implantable artificial acetabular socket constructed and operative in accordance with still another preferred embodiment of the present invention.

Reference is now made to FIG. 84, which is a pictorial illustration of an implantable artificial acetabular socket 9400, constructed and operative in accordance with another preferred embodiment of the present invention, which is particularly suitable for use in a hip joint. Implantable artificial acetabular socket 9400 is constructed with an array 9402 of textured thin elements 9404, preferably made of titanium, with segmented configuration, molded onto outer surface 9406 of acetabular socket 9400. The provision of elements 9404 provides enhanced biological fixation of acetabular socket 9400 following insertion thereof. It is appreciated that, even though the illustrated embodiment shows elements 9404 having a square configuration arranged symmetrically, elements 9404 may have any suitable shape and arrangement.

Figure 85A:
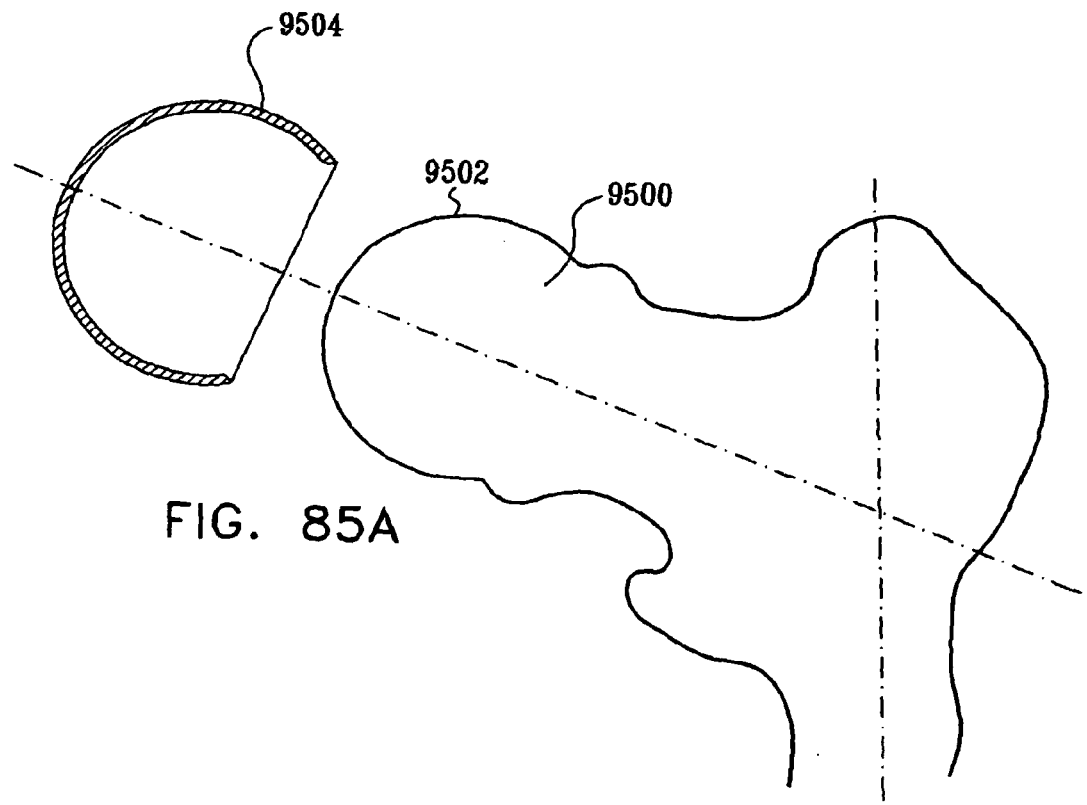
FIGS. 85A and 85B are sectional illustrations of the installation of an artificial femoral head on a reamed femoral head, in accordance with a preferred embodiment of the present invention.
Figure 85B:
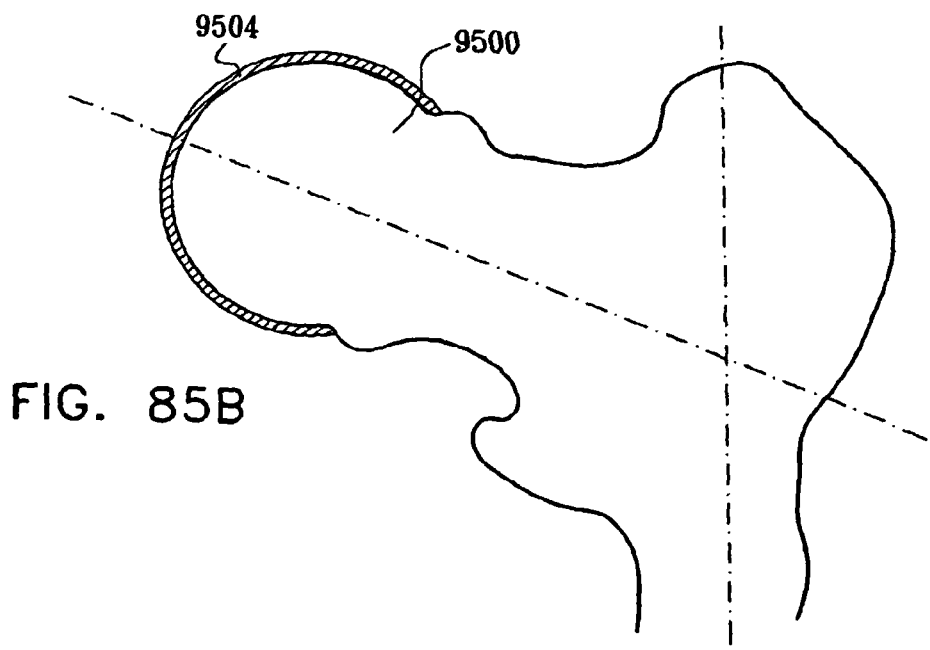

Reference is now made to FIGS. 85A and 85B, which are sectional illustrations of the installation of an artificial femoral resurfacing head on a reamed femoral head, in accordance with a preferred embodiment of the present invention. As seen in FIG. 85A, femoral head 9500 has been reamed to define a seating location 9502, preparatory to the placement of a press fit femoral head resurfacing element 9504. FIG. 85B shows element 9504 following placement thereof on reamed femoral head 9500.

Figure 86A:
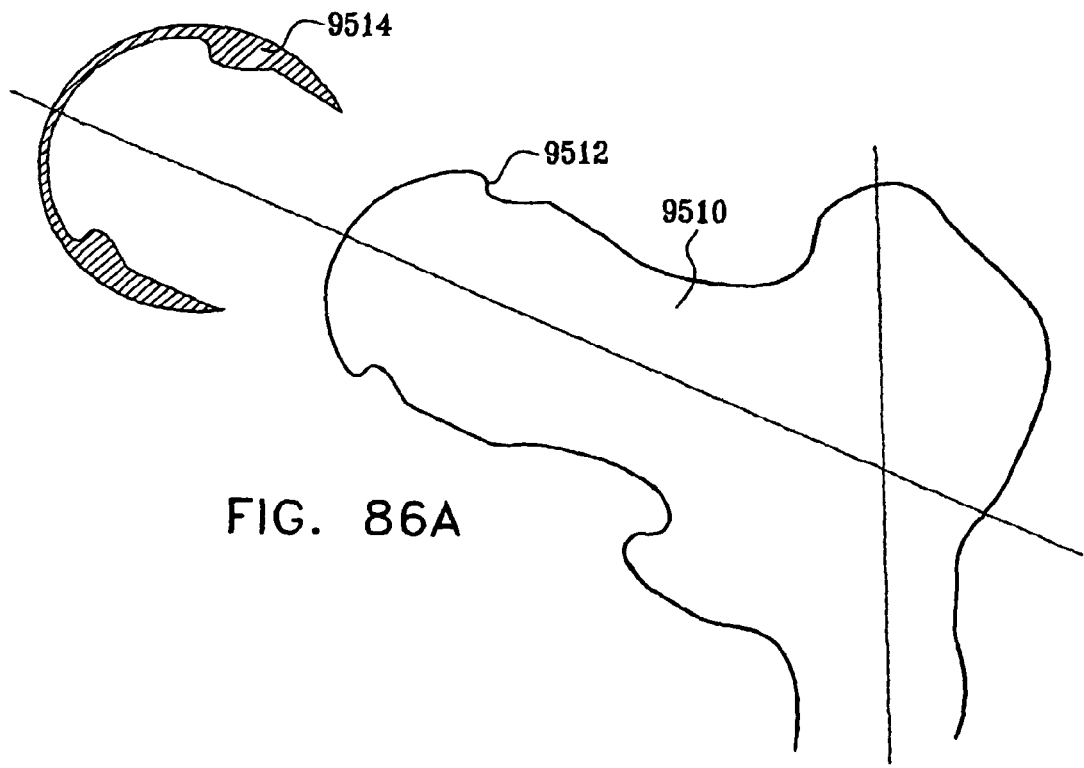
FIGS. 86A and 86B are sectional illustrations of the installation of an artificial femoral head on a reamed femoral head, in accordance with another preferred embodiment of the present invention.
Figure 86B:
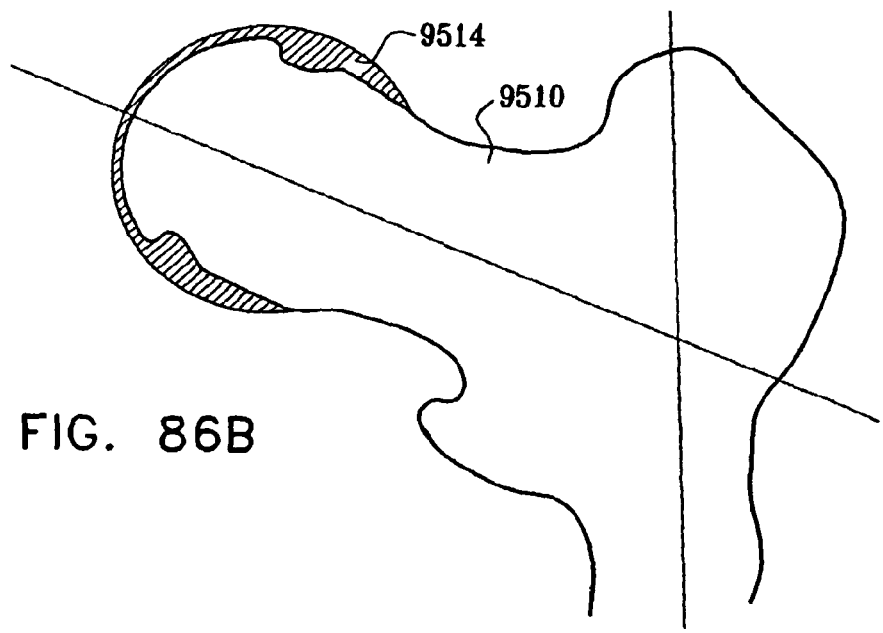

Reference is now made to FIGS. 86A and 86B, which are sectional illustrations of the installation of an artificial femoral resurfacing head on a reamed femoral head, in accordance with a preferred embodiment of the present invention. As seen in FIG. 86A, femoral head 9510 has been reamed to define a seating location 9512, preparatory to the placement of a snap fit femoral head resurfacing element 9514. FIG. 86B shows element 9514 following placement thereof on reamed femoral head 9510.

Figure 87A:
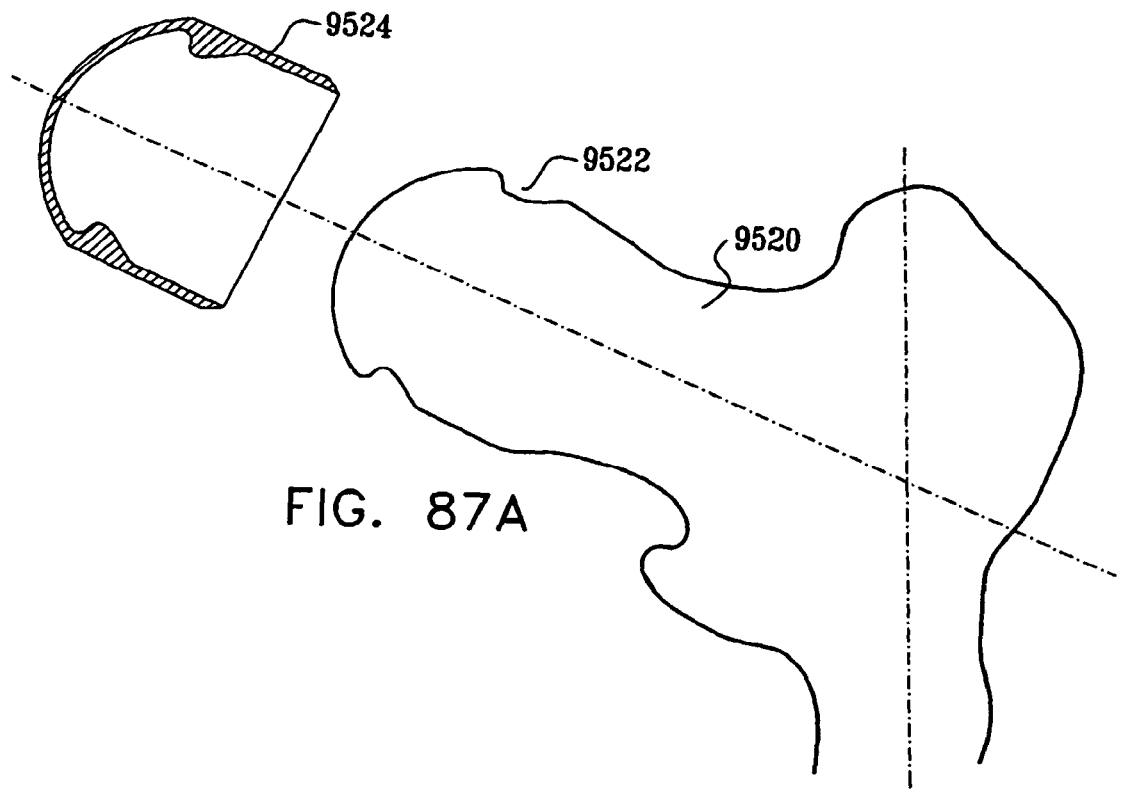
FIGS. 87A, 87B, 87C and 87D are sectional illustrations of various stages of installation of a multi-part artificial femoral head on a reamed femoral head in accordance with still another preferred embodiment of the present invention.
Figure 87B:
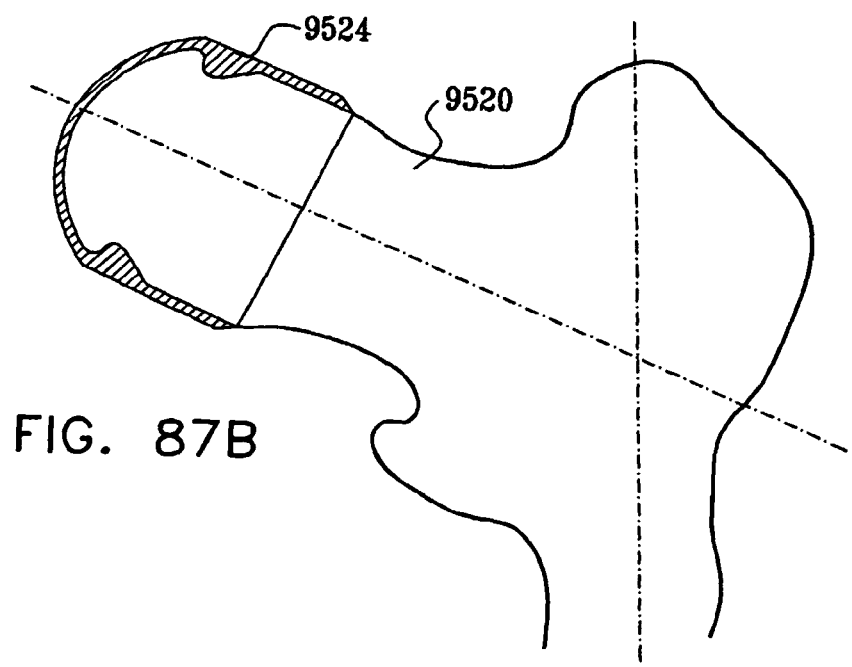
Figure 87C:
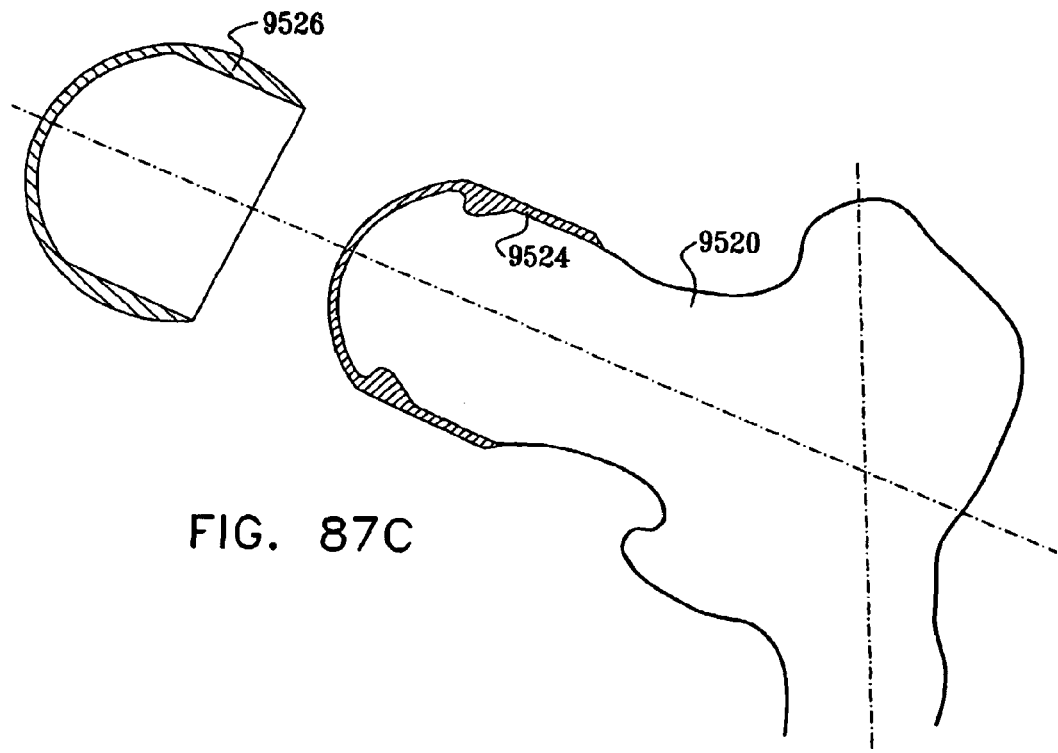
Figure 87D:
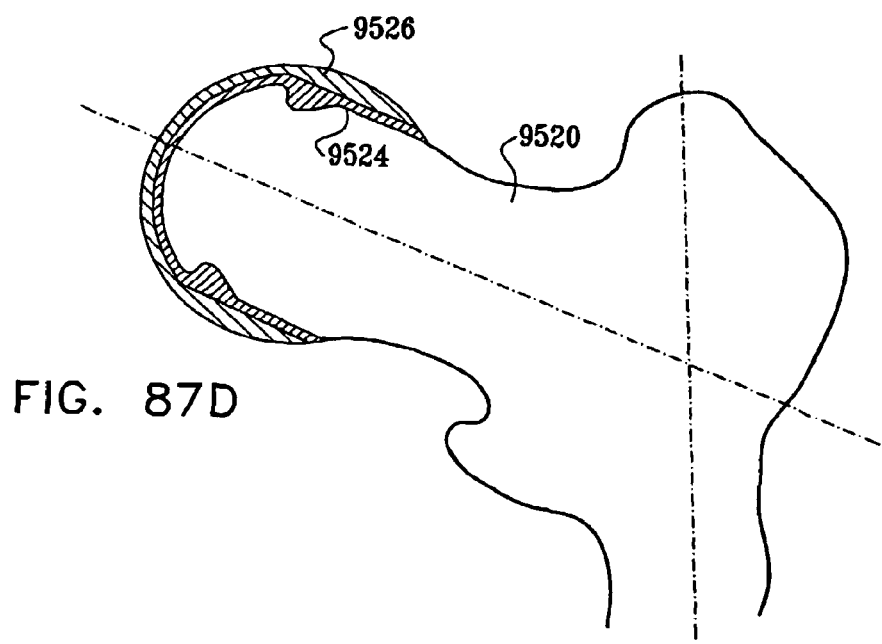

Reference is now made to FIGS. 87A, 87B, 87C and 87D, which are sectional illustrations of various stages of installation of a multi-part artificial femoral resurfacing head on a reamed femoral head in accordance with still another preferred embodiment of the present invention. As seen in FIG. 87A, femoral head 9520 has been reamed to define a seating location 9522, preparatory to the placement of a snap fit femoral head interface element 9524. FIG. 87B shows element 9524, preferably made of polyurethane, following placement thereof on reamed femoral head 9520. FIG. 87C shows the femoral head of FIG. 87B, preparatory to the placement of a press fit femoral head resurfacing element 9526. Press fit femoral head resurfacing element 9526 is made of any suitable bearing surface materials, such as polyurethane, metal or ceramic. FIG. 87D shows element 9526 following placement thereof on femoral head interface element 9524.

Figure 88A:
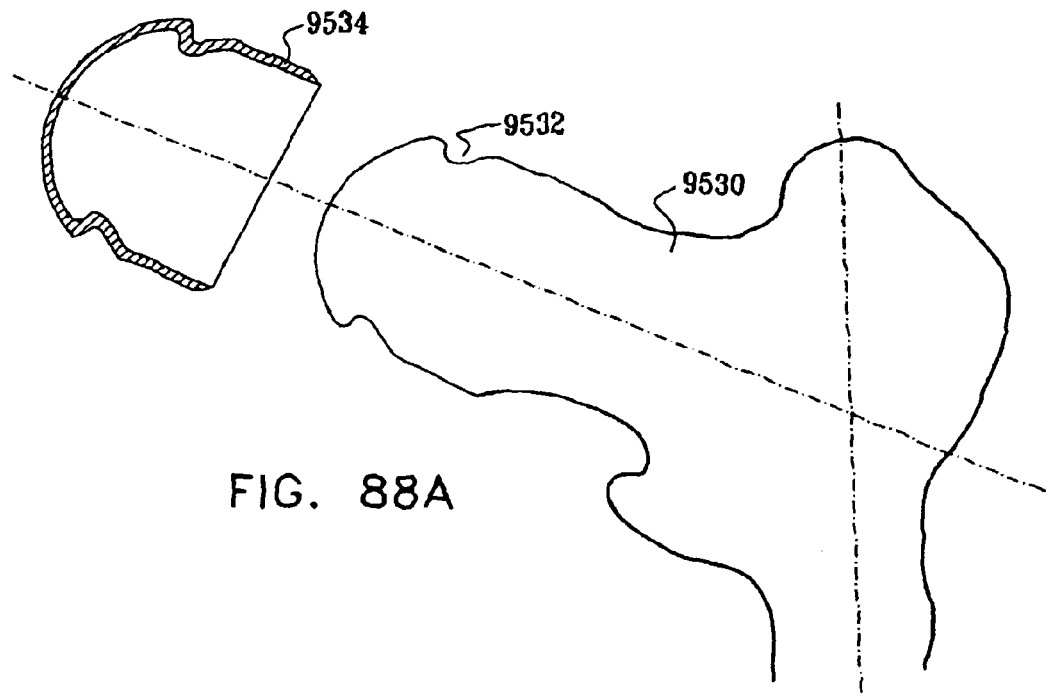
FIGS. 88A, 88B, 88C and 88D are sectional illustrations of various stages of installation of a multi-part artificial femoral head on a reamed femoral head in accordance with yet another preferred embodiment of the present invention.
Figure 88B:
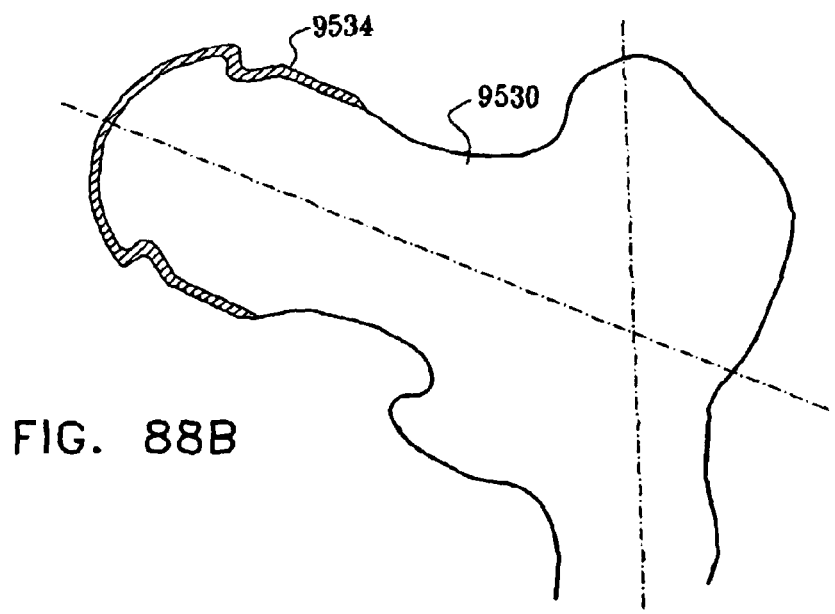
Figure 88C:
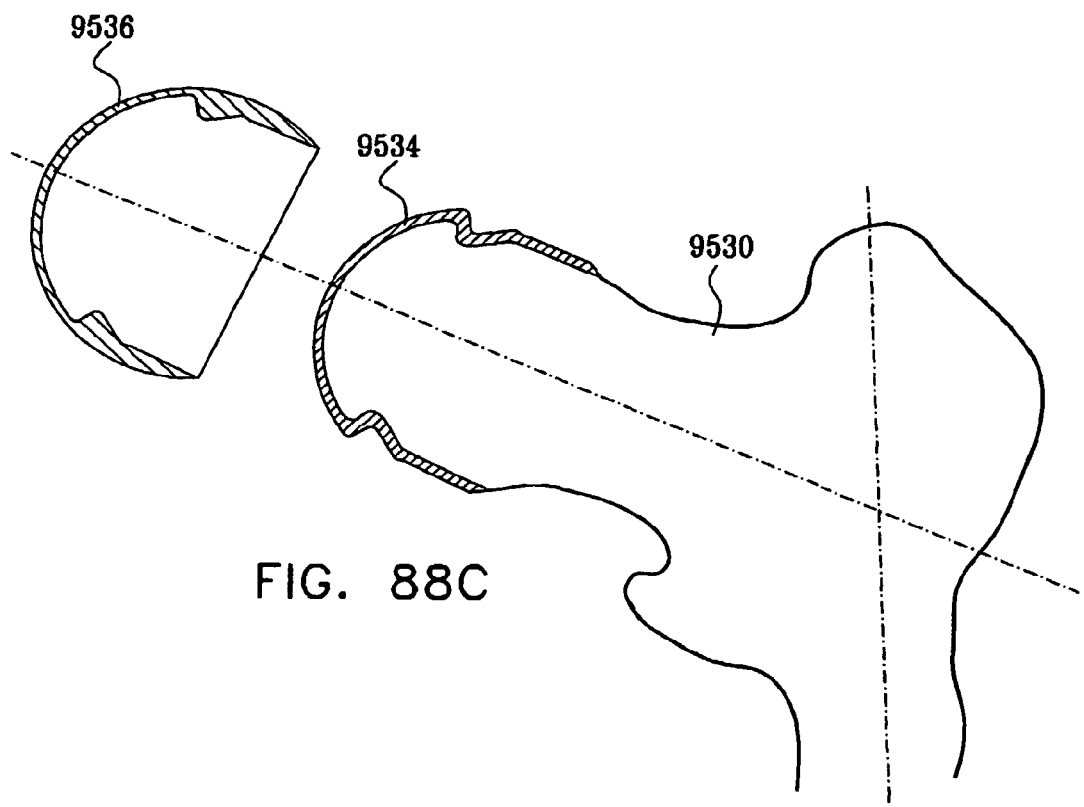
Figure 88D:
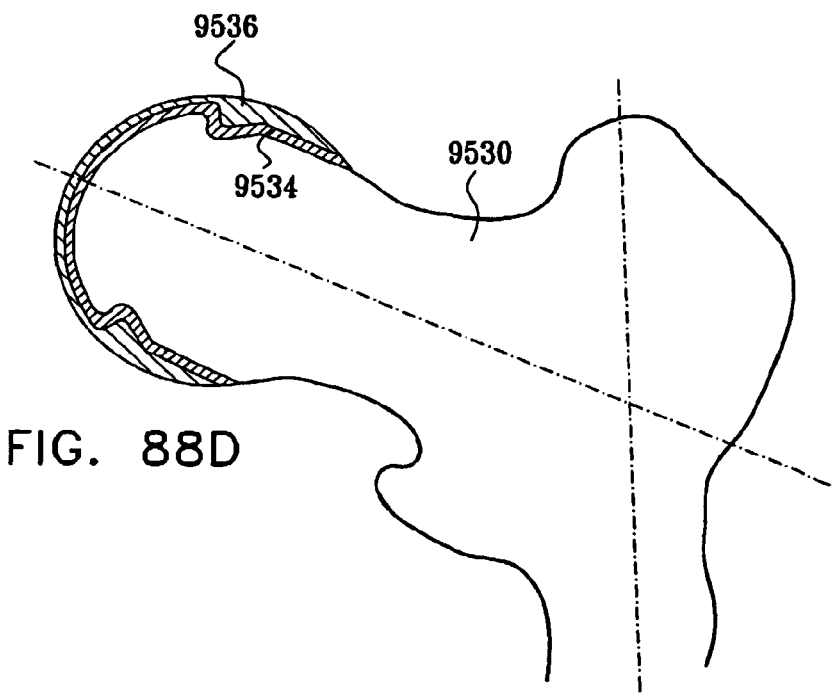

Reference is now made to FIGS. 88A, 88B, 88C and 88D, which are sectional illustrations of various stages of installation of a multi-part artificial femoral resurfacing head on a reamed Femoral head in accordance with still another preferred embodiment of the present invention. As seen in FIG. 88A, femoral head 9530 has been reamed to define a seating location 9532, preparatory to the placement of a snap fit femoral head interface element 9534. FIG. 88B shows element 9534, preferably made of polyurethane, following placement thereof on reamed femoral head 9530. FIG. 88C shows the femoral head of FIG. 88B, preparatory to the placement of a press fit femoral head resurfacing element 9536. Press fit femoral head resurfacing element 9536 is made of any suitable bearing surface materials, such as polyurethane, metal or ceramic. FIG. 88D shows element 9536 following placement thereof on femoral head interface element 9534.

Figure 89A:
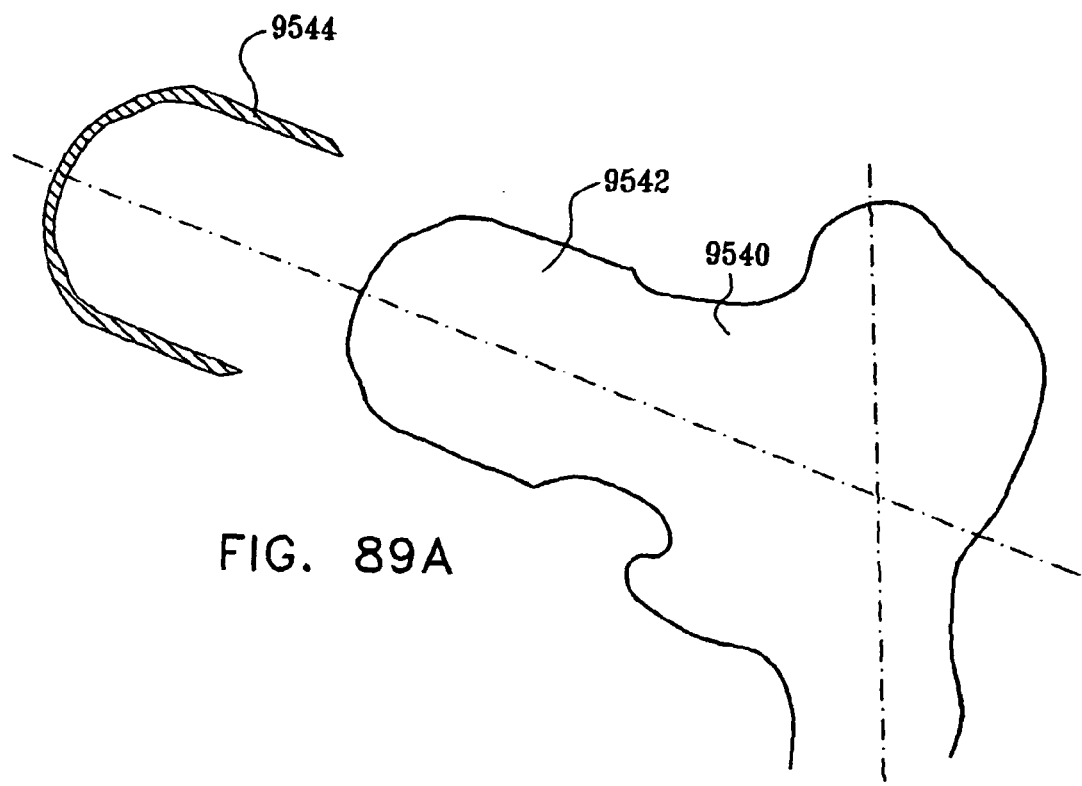
FIGS. 89A and 89B are sectional illustrations of various stages of installation of a multi-part artificial femoral head on a reamed femoral head, in accordance with a further preferred embodiment of the present invention.
Figure 89B:
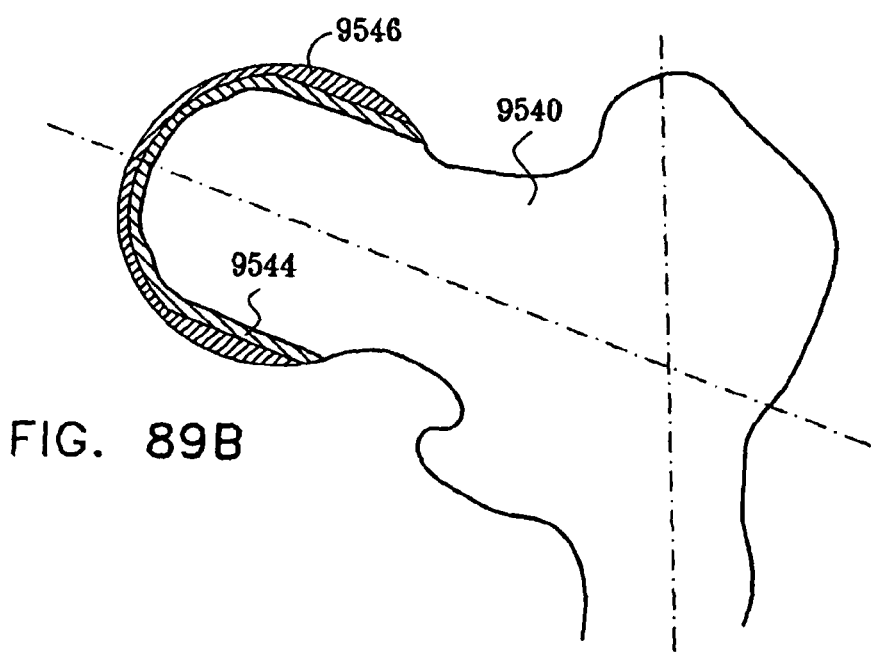

Reference is now made to FIGS. 89A and 89B, which are sectional illustrations of various stages of installation of a multi-part artificial femoral resurfacing head on a reamed femoral head in accordance with still another preferred embodiment of the present invention. As seen in FIG. 89A, femoral head 9540 has been reamed to define a seating location 9542, preparatory to the placement of a press fit femoral head interface element 9544. Press fit femoral head interface element 9544 may be made of polyurethane, metal or any other suitable material. FIG. 89B shows element 9544, following placement thereof on reamed femoral head 9540 and the placement of a press fit femoral head resurfacing element 9546 thereon. Press fit femoral head resurfacing element 9546 is preferably made of any suitable bearing surface materials such as polyurethane, metal or ceramic.

It is appreciated that the embodiments shown in FIGS. 85A-89B allow for a variety of combinations of snap fit and press fit femoral head interface elements and resurfacing elements. These elements may be comprised of different substances, to provide suitable rigidity and flexibility of the articulation surface, as well as suitable configurations for implantation. Generally, the snap fit devices provide for more flexibility, and are formed preferably by injection molding of polyurethane, while the press fit devices generally provide more rigidity, and may be formed by injection molding of polyurethane, or may be formed from any other suitable material, such as metal or ceramic, by any suitable method. Additionally, resurfacing elements 9526, 9536 and 9546, described in reference to FIGS. 87A-89B, may be molded or sprayed directly onto interface elements 9524, 9534 or 9544, respectively, or may be formed by dipping onto interface elements 9524, 9534 or 9544, prior to their implantation on machined femoral head 9520, 9530 or 9540, respectively.

Figure 90A:
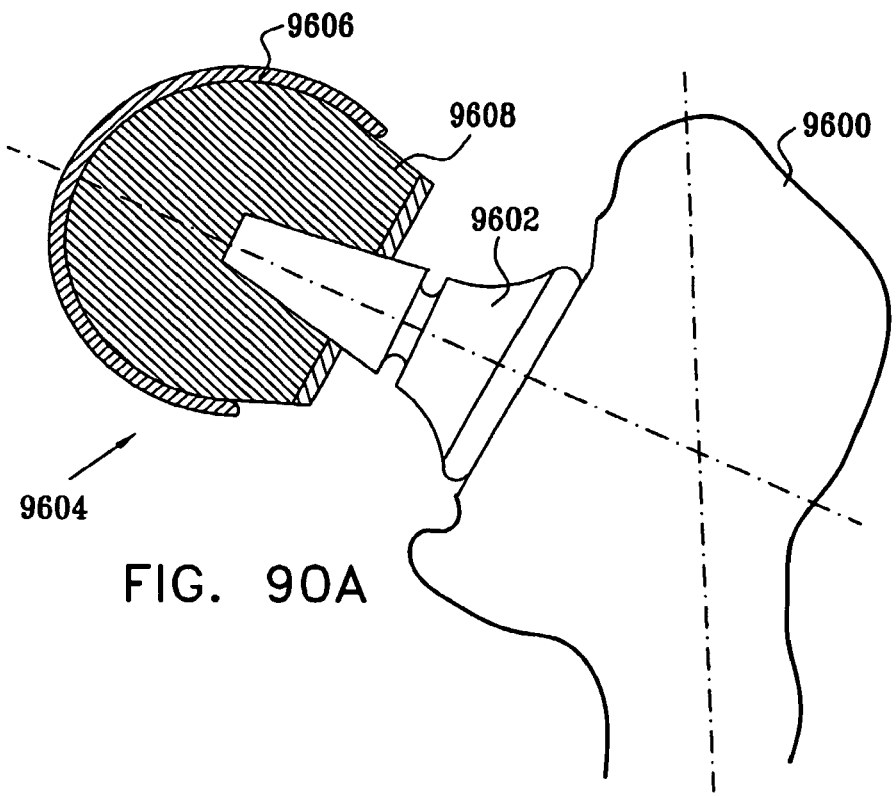
FIG. 90A is a sectional illustration of the installation of a multi-part artificial femoral head on a conventional stem in accordance with still another preferred embodiment of the present invention.

Reference is now made to FIG. 90A, which is a sectional illustration of a femoral head in accordance with another preferred embodiment of the present invention. As seen in FIG. 90A, femoral head 9600 has been fitted with a conventional femoral stem 9602. An artificial femoral head element 9604 is mounted onto stem 9602. Artificial femoral head element 9604 includes an articulation element 9606, preferably formed of polyurethane, overlying a rigid metal core element 9608, which also includes a tapered trunnion for mounting core element 9608 onto conventional stem 9602. Core element 960S may be constructed of metal, ceramic or any other rigid material, and is preferably less flexible than articulation element 9606. Articulation element 9606 may be mounted or formed onto core element 9608 by spraying, dipping, injection or blow molding or formed separately by any suitable means and assembled thereafter onto core element 9608.

Figure 90B:
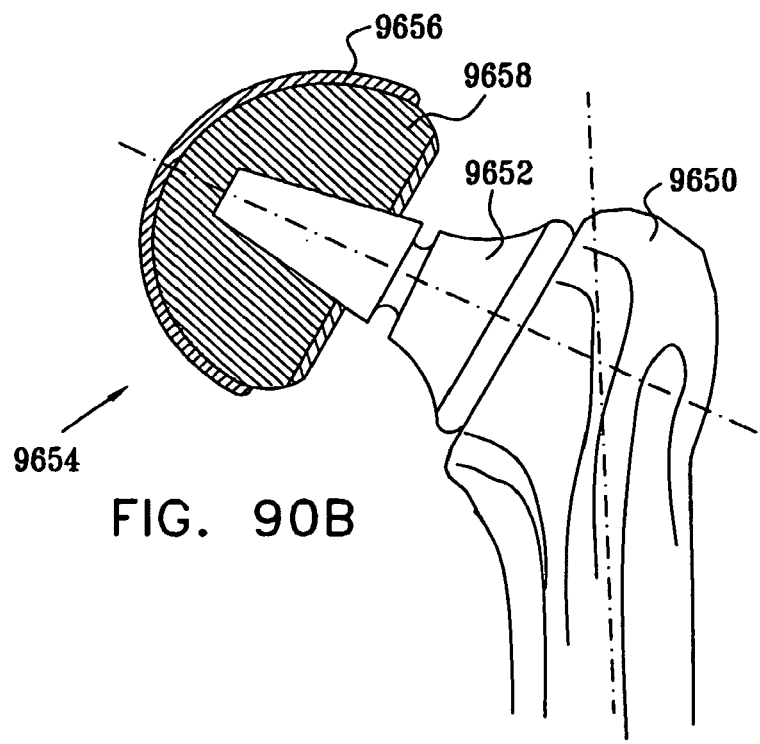
FIG. 90B is a sectional illustration of the installation of a multi-part artificial humeral head on a conventional stem in accordance with yet another preferred embodiment of the present invention.

Reference is now made to FIG. 90B, which is a sectional illustration of a humeral head in accordance with another preferred embodiment of the present invention. As seen in FIG. 90B, humeral head 9650 has been fitted with a conventional humeral stem 9652. An artificial humeral head element 9654 is mounted onto stem 9652. Artificial humeral head element 9654 includes an articulation element 9656, preferably formed of polyurethane, overlying a rigid metal core element 9658, which also includes a tapered trunnion for mounting core element 9658 onto conventional stem 9652. Core element 9658 may be constructed of metal, ceramic or any other rigid material, and is preferably less flexible than articulation element 9656. Articulation element 9556 may be mounted or formed onto core element 9658 by spraying, dipping, injection or blow molding or formed separately by any suitable means and assembled thereafter onto core element 9658.

It is further appreciated that femoral and humeral heads of FIGS. 90A-90B could be resurfacing implants positioned directly to a suitably prepared natural femoral or humeral head without a conventional stem.

Reference is now made to FIGS. 91A, 91B and 91C, which are sectional illustrations showing bone growth adjacent to an implanted acetabular socket in accordance with another preferred embodiment of the present invention. As seen in FIG. 91A, an acetabular socket 9700, similar to acetabular socket 9100 of FIGS. 81A-81C, is implanted in reamed acetabulum 9702. Acetabular socket 9700 includes recesses 9704. As seen in FIG. 91A, over time the acetabulum has remodeled itself to fill recesses 9704. As seen in FIGS. 91B and 91C, different shaped recesses may be provided along acetabular socket 9700. It is appreciated that the configuration pattern of recesses 9704 of the hone engagement surface 9706 provides enhanced adhesion of acetabulum 9702 to socket 9700 and thus improves the stability of socket 9700. This configuration pattern could apply to any of the implant devices disclosed herein.

Figure 92:
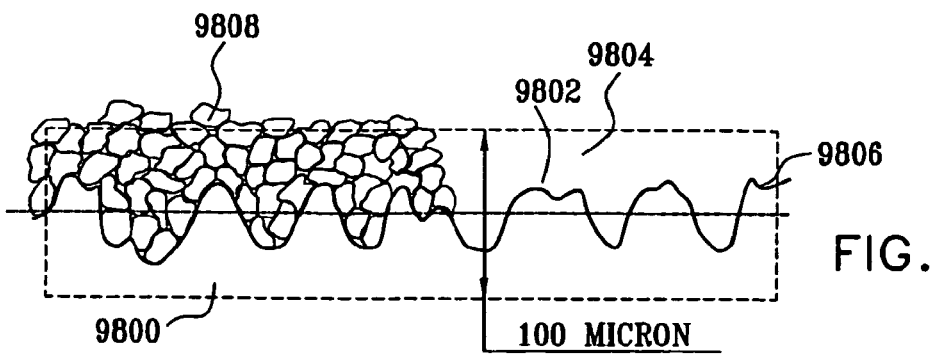
FIG. 92 is a simplified sectional illustration of a bone engagement surface, textured in accordance with another preferred embodiment of the present invention.

Reference is now made to FIG. 92, which is a simplified sectional illustration of a bone engagement surface, textured in accordance with another preferred embodiment of the present invention. The bone engagement surface of FIG. 92 provides enhanced bone adhesion and improved stability.

As seen in FIG. 92, a portion of an artificial implantation device 9800, such as acetabular sockets described hereinabove, but not limited to acetabular sockets, having a hone engagement surface 9802, engages bone 9804. Bone engagement surface 9802 includes a rough texture 9806 superimposed on to at least a portion thereof. It is appreciated that bone engagement surface 9802 may be uniform, such as surface 1104 in socket 1100 shown in FIGS. 1A-1C, or may include various protrusions or recesses, such as surface 9104 in socket 9100 of FIGS. 81A-81C. Over time, bone cells, fibroblasts and tissue matrix 9808 fill the crevices of rough texture 9806 along surface 9802, as shown in FIG. 92.

Figure 93A:
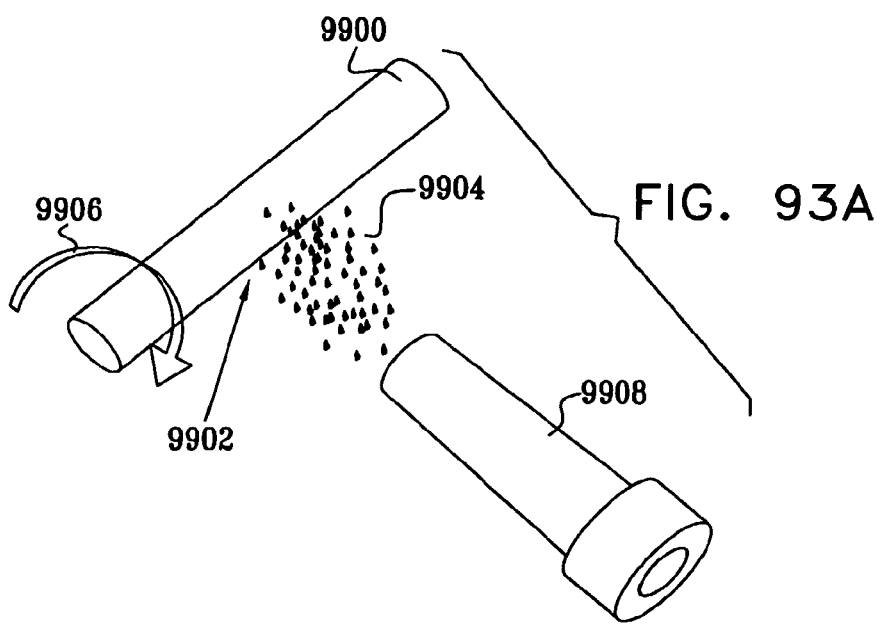
FIGS. 93A and 93B are simplified pictorial illustrations of a method of modifying the texture of a bone engagement surface of an artificial implantation device, in accordance with another preferred embodiment of the present invention.
Figure 93B:
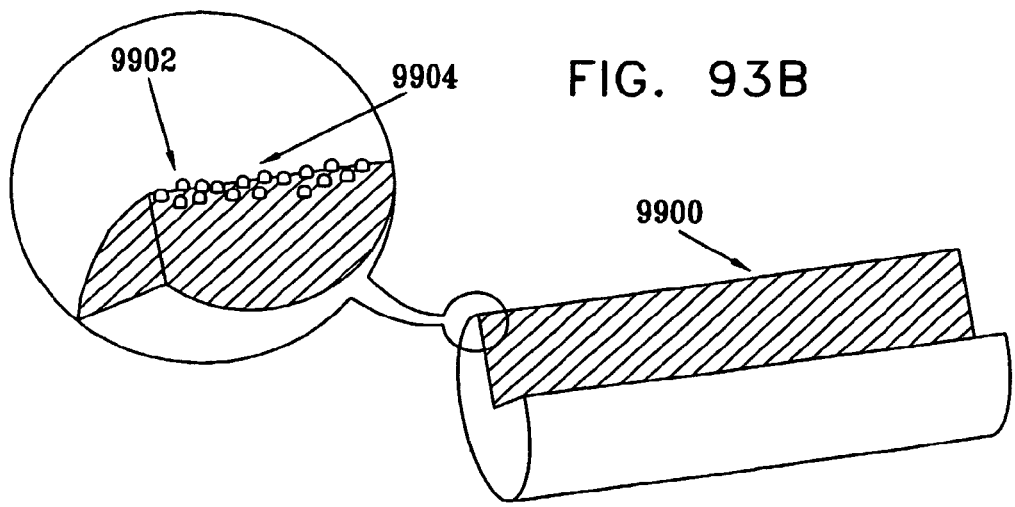

Reference is now made to FIGS. 93A and 93B, which are simplified pictorial illustrations of a method of modifying the texture of a bone engagement surface of an artificial implantation device, in accordance with another preferred embodiment of the present invention.

FIG. 93A illustrates a method for modifying the surface of the artificial implantation device 9900, by mechanically providing surface roughness, such as by grit blasting. Grit blasting may be conducted without any preparatory steps, other than cleaning the contact surface 9902 of implantation device 9900. Grit blasting can be accomplished with any suitable media capable of creating a texturized surface. If a non medical grade media is used then residual is preferably cleaned from the implant surface to prevent initiation of a foreign body reaction. Alternatively, grit blasting may utilize Hydroxylapatite or any other bioactive materials as the grit media 9904. Artificial implantation device 9900 is rotated around its axis, as indicated by arrow 9906, and the blast nozzle 9908 will be generally positioned at a right angle to the rotating part.

Grit blasting may be hot grit blasting, utilizing heated gas. A heating cycle, which is meant to soften the outer layers of the artificial implantation device 9900, will precede the blasting phase in order to help embed the bioactive particles of grit media 9904 into the surface 9902 of artificial implantation device 9900. Since the bioactive particles of grit media 9904 are harder than the heated surface 9902, particles will become embedded into surface 9902. This process will form a roughened texture that will act as the anchor for bone attachment. In addition, the resorption of the Hydroxylapatite with time will cause bone growth into the voids that are created by the resorption of the grit media. FIG. 93B shows the grit media 9902 implanted into contact surface 9902 of artificial implantation device 9900.

Figure 94:
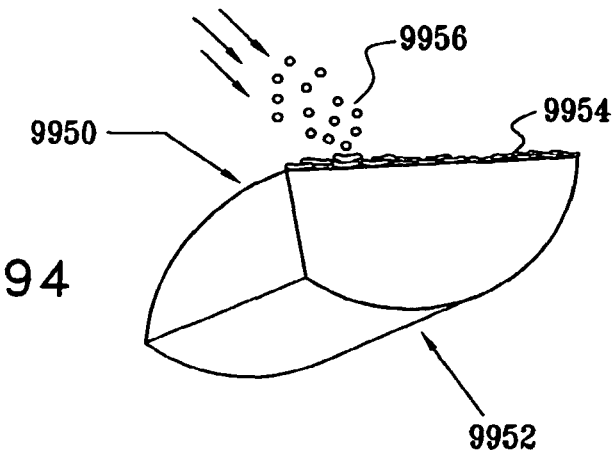
FIG. 94 is a simplified pictorial illustration of another method of modifying the texture of the bone engagement surface of an artificial implantation device, in accordance with yet another preferred embodiment of the present invention.

Reference is now made to FIG. 94, which is a simplified pictorial illustration of another method of modifying the texture of the bone engagement surface of an artificial implantation device, in accordance with yet another preferred embodiment of the present invention.

As seen in FIG. 94, contact surface 9950 of artificial implantation device 9952 is treated to provide surface roughness and surface porosity by forming at least one additional layer 9954 of sprayed material 9956. The spraying apparatus, described hereinbelow with reference to FIG. 95, may use feedstock configured as a rod or provided as powder. The feedstock rod or powder may be a neat elastomer, preferably of an equal or similar type of elastomer to the material from which artificial implantation device is formed therefrom, such as polyurethane. The feedstock rod may be extruded from a premix of an elastomer and Bioactive materials.

The surface roughness and surface porosity is provided preferably by co-spraying of an elastomer and bioactive materials composite coating. The premixed feedstock may be PU/HA (polyurethane/Hydroxylapatite), thus providing a co-spraying of PU/HA composite coating. The bioactive materials are preferably hydroxylapatite or any other suitable calcium phosphate-containing materials. These bioactive materials cause the contact surface 9950 of artificial implantation device 9952 to become bioactive, stimulating bone growth to provide an adhesion of the implant to the bone and accelerate osteointegration.

The feedstock for this coating can be in powder form, where a combination of PU and HA powders are preferably blended in suitable ratios and sprayed to form the desired coating. Alternatively, the feedstock can be a PU rod that is co-sprayed with HA powder particles that are fed separately into the molten particle flow. The PU rod can also be extruded with HA powder mixed within it so that a composite rod feedstock is obtained. Alternatively, any other suitable method of combining the PU and the bioactive materials may be used. The rod will then be fed directly though the spray device and the resulting coating will contain both HA and PU particles forming the desired matrix.

Figure 95:
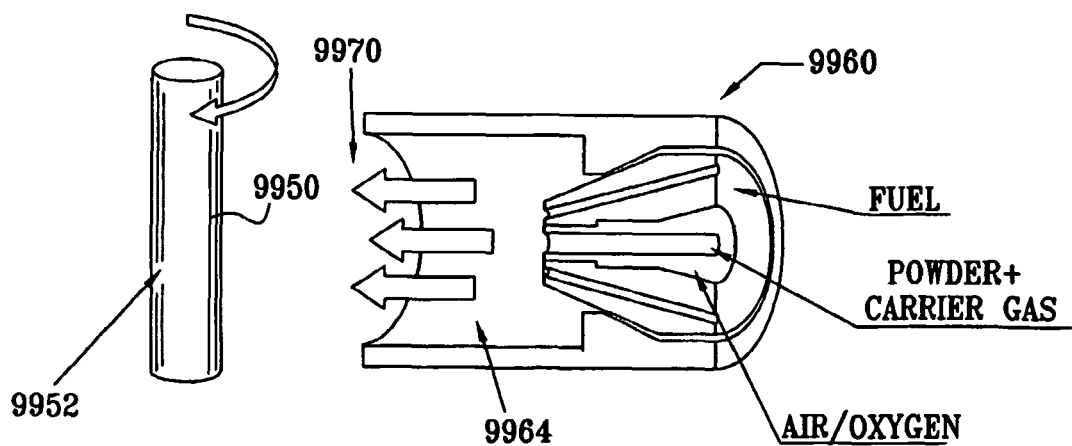
FIG. 95 is a simplified pictorial illustration of a spraying apparatus which may be used in the embodiment of FIG. 94.

Reference is now made to FIG. 95, which is a simplified pictorial illustration of a spraying apparatus which may be used in the embodiment of FIG. 94.

As seen in FIG. 95, spraying apparatus 9960 is used, as described hereinabove with reference to FIG. 94, to modify the contact surface 9950 of artificial implantation device 9952 by coating contact surface 9950. This coating is preferably provided using a combustion process, which utilizes an oxygen-fuel mixture and heats the particles as they are fed through a gravity hopper through the center of the spraying apparatus 9960. A nozzle 9964 directs the combustion gasses and the molten particles towards the contact surface 9950 of artificial implantation device 9952. The combustion of the gasses occurs within a chamber in the nozzle and a carrier gas is used to propel the molten particles forward, in the direction of arrows 9970, and prevent them from sticking to the nozzle walls. When using rod feedstock (in place of powder), atomizing gas is used to break the tip of the molten rod into discrete particles.

A coating of molten polyurethane particles can be applied to contact surface 9950 of artificial implantation device 9952 in order to create a rough porous surface into which the bone can grow. The process may start with a preheating step that is designed to melt the surface of the implant and provide for a chemical bond between the surface and the polyurethane particles, although the process can be applied to a cold surface as well. The thickness of the coating can be regulated.

The coating deposited using the above mentioned combustion spray process may be a Polymer-Hydroxylapatite composite coating. This coating system consists of a combination of polyurethane particles that will be co-sprayed with HA powder The resulting coating will form a polymer scaffold like structure that will entrap the HA particles within. This composite structure will help anchor the implant by enabling bone attachment to the exposed HA particles and eventually bone interdigitation in the pores created as the HA resorbs with time.

Alternatively, a coating can be deposited onto the contact surface 9950 of artificial implantation device 9952 by means of dipping, whereby a slurry is made of a polymer material, having a certain quantity of bioactive particles mixed within it. The artificial implantation device 9952 is dipped into the slurry, after which it is allowed to dry. As the slurry dries, a composite polymer/bioactive material coating is created, where the bioactive particles are trapped within the polymer matrix.

The coating may be an elastomer on elastomer coating, such as a polyurethane on polyurethane coating. The polyurethane coating can have a hardness of 55 D and upwards for enhancing bio-stability on the outer surface, while the artificial implantation device 9952 and contact surface 9950 is of hardness 80 A.

In addition to the enhanced bone adhesion methods described in reference to FIGS. 91A-95, the contact surface of an artificial implantation device may also be treated using one of the following Surface Modification processes: Atomic cleaning, adhesion promotion, molecular grafting, cell attachment enhancement, and Plasma Enhanced Chemical Vapor Deposition (PECVD) coatings, such as implemented by the MetroLine Surface, Inc. Surface modification processes improve the articulating properties of the contact surface by reducing friction and thereby enhance the resistance to wear.

It is known in the art that in the vicinity of rigid implants, such as metal implants, there are regions of stress shielding in some parts of the bone, meaning that such rigid implants take load formerly transferred to the bone, thereby shielding the bone from the load and causing bone resorption. This process has been observed in regions such as in the proximal medial calcar after hip replacement, and such as under the tibial component of knee replacements.

The implants of the present invention comprise flexible elements, and also preferably include deformation control elements, resulting in improved load distribution, which prevents or significantly reduces stress shielding.

As discussed hereinabove, it is appreciated that the stresses produced in the natural bone, such as in the natural acetabular socket, produce corresponding strains therein. Both the stresses and the strains have positive medical implications which are expressed in bone remodeling.

It is further appreciated that the implants of the present invention are constructed to control the stress distribution at the bone-implant interface, and within the surrounding bone, resulting in a positive bone remodeling, creating a mechanical environment with conditions that initiate net remodeling activity growing new bone cells of structural characteristics. This process prevents loosening of the devices according to this invention and enhances the anchoring.

The following is a brief description of a best mode manufacturing process of the implantable artificial socket 1100 shown in FIGS. 1A to 1C. The manufacturing process typically comprises the steps as described hereinbelow. It is appreciated that the steps of the manufacturing process are monitored and controlled in order to assure the quality of the products meets the required standards.

Step 1. Material Identification:

A preferable material used for manufacturing a cup used for preparing the implantable artificial socket 1100 is Polycarbonate Urethane Bionate 80A, which is supplied by Polymer Technology Group Inc., 2810 7$^{th}$ Street, Berkeley, Calif. 94710, U.S.A.

Step 2. Equipment Used for Cup Manufacturing:

Step 2.1. Equipment Use for Pre-Injection Drying:

A desiccant that has the ability to be connected directly to the screw of an injection molding machine and reach 50 deg dew point, is preferably used.

Step 2.2. Equipment Use for Cup Injection:

The injection molding machine includes computerized data acquisition ability and an 18-20 mm diameter cylinder, for example an ARBURG 4020 device.

Step 2.3. Equipment Use for Post-Injection Curing:

Industrial oven capable of maintaining 80° C.±2° C. for approximately 15 hours.

Step 3. Preprocess for the Raw Material:

The drying of the raw material is performed using a desiccant dehumidifier, outside of a clean room.

Step 3.1 The Drying Process Typically Includes the Steps:

I. 12 hours at 65° C. [−50 dew point]

II. 4 hours at 93° C. [−50 dew point]

The final product humidity should be preferably between 0.01%-0.02%.

Step 4. The Manufacturing Process:

1. Drying of the material for 16 hours by special drier (−50° C.) desiccant.
2. Direct transfer of the material in the drier to the injection machine, i.e. connecting a drier device directly to the machine.
3. Injection molding.
4. Curing in an oven for 16 hours.
5. Packaging.
6. Sterilization in Gamma.

Preferred polyurethane materials for use in the embodiments described hereinabove include the following materials.

The following materials are manufactured by POLYMER TECHNOLOGY GROUP PTG.

Bionate® polycarbonate-urethane is among the most extensively tested biomaterials ever developed. The Polymer Technology Group Incorporated acquired the license to manufacture this thermoplastic elastomer from Corvita Corporation (who marketed it under the name Corethane®) in 1996.

Carbonate linkages adjacent to hydrocarbon groups give this family of materials oxidative stability, making these polymers attractive in applications where oxidation is a potential mode of degradation, such as in pacemaker leads, ventricular assist devices, catheters, stents, and many other biomedical devices. Polycarbonate urethanes were the first biomedical polyurethanes promoted for their biostability.

Bionate® polycarbonate-urethane is a thermoplastic elastomer formed as the reaction product of a hydroxyl terminated polycarbonate, an aromatic diisocyanate, and a low molecular weight glycol used as a chain extender.

The scope of Bionate PCU's tests—encompassing Histology, Carcinogenicity, Biostability, and Tripartite Biocompatibility Guidance for Medical Device—reassures medical device and implant manufacturers of the material's biocompatibility. This allows biomaterials decision makers the ability to choose an a efficacious biomaterial that will add to the cost-effectiveness of the development of their device or implant. Below is a summary of the extensive biocompatibility testing conducted on Bionate PCUs, including its successful completion of a 2-year carcinogenicity study.

Copolymers of silicone with poplyurethanes:

PurSil™ Silicone Polyether Urethane

CarboSil™ Silicone Polycarbonate Urethane

Silicones have long been known to be biostable and biocompatible in most implants, and also frequently have the low hardness and low modulus useful for many device applications. Conventional silicone elastomers can have very high ultimate elongations, but only low to moderate tensile strengths. Consequently, the toughness of most biomedical silicone elastomers is not particularly high. Another disadvantage of conventional silicone elastomers in device manufacturing is the need for cross-linking to develop useful properties. Once cross-linked, the resulting thermoset silicone cannot be redissolved or remelted.

In contrast, conventional polyurethane elastomers are generally thermoplastic with excellent physical properties. Thermoplastic urethane elastomers (TPUs) combine high elongation and high tensile strength to form tough, albeit fairly high-modulus elastomers. Aromatic polyether TPUs can have excellent flex life, tensile strength exceeding 5000 psi, and ultimate elongations greater than 700 percent. They are often used for continuously flexing, chronic implants such as ventricular-assist devices, intraaortic balloons, and artificial heart components. TPUs can easily be processed by melting or dissolving the polymer to fabricate it into useful shapes.

The prospect of combining the biocompatibility and biostability of conventional silicone elastomers with the processability and toughness of TPUs is an attractive approach to what would appear to be a nearly ideal biomaterial. For instance, it has been reported that silicone acts synergistically with both polycarbonate- and polyether-based polyurethanes to improve in vivo and in vitro stability. In polycarbonate-based polyurethanes, silicone copolymerization has been shown to reduce hydrolytic degradation of the carbonate linkage, whereas in polyether urethanes, the covalently bonded silicone seems to protect the polyether soft segment from oxidative degradation in vivo.

PTG synthesized and patented silicone-polyurethane copolymers by combining two previously reported methods: copolymerization of silicone (PSX) together with organic (non-silicone) soft segments into the polymer backbone, and the use of surface-modifying end groups to terminate the copolymer chains. Proprietary synthesis methods make high-volume manufacturing possible.

PurSil™ silicone-polyether-urethane and CarboSil™ silicone-polycarbonate-urethane are true thermoplastic copolymers containing silicone in the soft segment. These high-strength thermoplastic elastomers are prepared through a multi-step bulk synthesis where polydimethylsiloxane (PSX) is incorporated into the polymer soft segment with polytetramethyleneoxide (PTMO) (PurSil) or an aliphatic, hydroxyl-terminated polycarbonate (CarboSil). The hard segment consists of an aromatic diisocyanate, MDI, with a low molecular weight glycol chain extender. The copolymer chains are then terminated with silicone (or other) Surface-Modifying End Groups™. We also offer aliphatic (AL) versions of these materials, with a hard segment synthesized from an aliphatic diisocyanate.

Many of these silicone urethanes demonstrate previously unavailable combinations of physical properties. For example, aromatic silicone polyetherurethanes have a higher modulus at a given shore hardness than conventional polyether urethanes—the higher the silicone content, the higher the modulus (see PurSil Properties). Conversely, the aliphatic silicone polyetherurethanes have a very low modulus and a high ultimate elongation typical of silicone homopolymers or even natural rubber (see PurSil AL Properties). This makes them very attractive as high-performance substitutes for conventional cross-linked silicone rubber. In both the PTMO and PC families, certain polymers have tensile strengths three to five times higher than conventional silicone biomaterials.

Surface Modifying End Groups™ (SMEs) are surface-active oligomers covalently bonded to the base polymer during synthesis. SMEs—which include silicone (S), (SO), fluorocarbon (F), polyethylene oxide (P), and hydrocarbon (H) groups—control surface chemistry without compromising the bulk properties of the polymer. The result is key surface properties, such as thromboresistance, biostability, and abrasion resistance, are permanently enhanced without additional post-fabrication treatments or topical coatings. This patented technology is applicable to a wide range of polymers.

SMEs provide a series of (biomedical) base polymers that can achieve a desired surface chemistry without the use of additives. Polyurethanes prepared according to PTG's development process couple endgroups to the backbone polymer during synthesis via a terminal isocyanate group, not a hard segment. The added mobility of endgroups relative to the backbone is thought to facilitate the formation of uniform overlayers by the surface-active (end) blocks. The use of the surface active endgroups leaves the original polymer backbone intact so the polymer retains strength and processability. The fact that essentially all polymer chains carry the surface-modifying moiety eliminates many of the potential problems associated with additives.

The SME approach also allows the incorporation of mixed endgroups into a single polymer. For example, the combination of hydrophobic and hydrophilic endgroups gives the polymer amphipathic characteristics in which the hydrophobic versus hydrophilic balance may be easily controlled.

The following Materials are manufactured by CARDIOTECH CTE:

CHRONOFLEX®: Biodurable Polyurethane Elastomers are polycarbonate aromatic polyurethanes.

The ChronoFlex® family of medical-grade segmented polyurethane elastomers have been specifically developed by CardioTech International to overcome the in vivo formation of stress-induced microfissures.

HYDROTHANE™: Hydrophilic Thermoplastic Polyurethanes

HydroThane™ is a family of super-adsorbent, thermoplastic, polyurethane hydrogels, ranging in water content from 5 to 25% by weight, HydroThane™ is offered as a clear resin in durometer hardness of 80 A and 93 Shore A.

The outstanding characteristic of this family of materials is the ability to rapidly absorb water, high tensile strength, and high elongation. The result is a polymer having some lubricious characteristics, as well as being inherently bacterial resistant due to their exceptionally high water content at the surface.

HydroThane™ hydrophilic polyurethane resins are thermoplastic hydrogels, and can be extruded or molded by conventional means. Traditional hydrogels on the other hand are thermosets and difficult to process.

The following materials are manufactured by THERMEDICS:

Tecothane® (aromatic polyether-based polyurethane), Carbothane® (aliphatic polycarbonate-based polyurethane), Tecophilic® (high moisture absorption aliphatic polyether-based polyurethane) and Tecoplast® (aromatic polyether-based polyurethane).

Polyurethanes are designated aromatic or aliphatic on the basis of the chemical nature of the diisocyanate component in their formulation. Tecoflex, Tecophilic and Carbothane resins are manufactured using the aliphatic compound, hydrogenated methylene diisocyanate (HMDI). Tecothane and Tecoplast resins use the aromatic compound methylene diisocyanate (MDI). All the formulations, with the exception of Carbothane, are formulated using polytetramethylene ether glycol (PTMEG) and 1,4 butanediol chain extender. Carbothane is specifically formulated with a polycarbonate diol (PCDO).

These represent the major chemical composition differences among the various families. Aromatic and aliphatic polyurethanes share similar properties that make them outstanding materials for use in medical devices. In general, there is not much difference between medical grade aliphatic and aromatic polyurethanes with reward to the following chemical, mechanical and biological properties:
High tensile strength (4,000 10,000 psi)
High ultimate elongation (250 700%)
Wide range of durometer (72 Shore A to 84 Shore D)
Good biocompatibility
High abrasion resistance
Good hydrolytic stability
Can be sterilized with ethylene oxide and gamma irradiation
Retention of elastomeric properties at low temperature
Good melt processing characteristics for extrusion, injection molding, etc.

With such an impressive array of desirable features, it is no wonder that both aliphatic and aromatic polyurethanes have become increasingly the material of choice in the design of medical grade components. There are, however, distinct differences between these two families of polyurethane that could dictate the selection or one over the other for a particular application:
Yellowing In their natural states, both aromatic and aliphatic polyurethanes are clear to very light yellow in color. Aromatics, however, can turn dark yellow to amber as a result of melt processing or sterilization, or even with age. Although the primary objection to the discoloration of aromatic clear tubing or injection molded parts is aesthetic, the yellowing, which is caused by the formation of a chromophore in the MDI portion of the polymer, does not appear to affect other physical properties of the material. Radiopaque grades of Tecothane also exhibit some discoloration during melt processing or sterilization. However, both standard and custom compounded radiopaque grades of Tecothane have been specifically formulated to minimize this discoloration.
Solvent Resistance Aromatic polyurethanes exhibit better resistance to organic solvents and oils than do aliphatics—especially as compared with low durometer (80 85 Shore A) aliphatics, where prolonged contact can lead to swelling of the polymer and short-term contact can lead to surface tackiness. While these effects become less noticeable at higher durometers, aromatics exhibit little or no sensitivity upon exposure to the common organic solvents used in the health care industry.
Softening at Body Temperature Both aliphatic and aromatic polyether-based polyurethanes soften considerably within minutes of insertion in the body. Many device manufacturers promote this feature or their urethane products because of patient comfort advantage as well as the reduced risk of vascular trauma. However, this softening effect is less pronounced with aromatic resins than with aliphatic resins.

Melt Processing Temperatures

Tecothane, Tecoplast and Carbothane melt at temperatures considerably higher than Tecoflex and Tecophilic. Therefore, processing by either extrusion or injection molding puts more heat history into products manufactured from Tecothane, Tecoplast and Carbothane. For example, Tecoflex EG-80A and EG-60D resins mold at nozzle temperatures of approximately 310° F. and 340° F. respectively.

Tecothane and Carbothane products of equivalent durometers mold at nozzle temperatures in the range of 380° F. to 435° F.

Tecoflex®

A family of aliphatic, polyether-based TPU's. These resins are easy to process and do not yellow upon aging. Solution grade versions are candidates to replace latex.

Tecothane®

A family of aromatic, polyether-based TPU's available over a wide range of durometers, colors, and radiopacifiers. One can expect Tecothane resins to exhibit improved solvent resistance and biostability when compared with Tecoflex resins of equal durometers.

Carbothane®

A family of aliphatic, polycarbonate-based TPU's available over a wide range of durometers, colors, and radiopacifiers. This type of TPU has been reported to exhibit excellent oxidative stability, a property which may equate to excellent long-term biostability. This family, like Tecoflex, is easy to process and does not yellow upon Tecophilic®

A family of aliphatic, polyether-based TPU's which have been specially formulated to absorb equilibrium water contents of up to 150% of the weight of dry resin.

Tecogel, a new member to the Tecophilic family, is a hydrogel that can be formulated to absorb equilibrium water contents between 500% and 2000% of the weight of dry resin. The materials were designed as a coating cast from an ethanol/water solvent system.

Tecoplast®

A family of aromatic, polyether-based TPU's formulated to produce rugged injection molded components exhibiting high durometers and heat deflection temperatures.

Four families of polyurethanes, named Elast-Eon™, are available from AorTech Biomaterials.

Elast-Eon™ 1, a Polyhexamethylene oxide (PHMO), aromatic polyurethane, is an improvement on conventional polyurethane in that it has a reduced number of the susceptible chemical groups. Elast-Eon™ 2, a Siloxane based macrodiol, aromatic polyurethane, incorporates siloxane into the soft segment. Elast-Eon™ 3, a Siloxane based macrodiol, modified hard segment, aromatic polyurethane, is a variation of Elast-Eon™ 2 with further enhanced flexibility due to incorporation of siloxane into the hard segment. Elast-Eon™ 4 is a modified aromatic hard segment polyurethane.

The following materials are manufactured by Bayer Corporation:

Texin 4210—Thermoplastic polyurethane/polycarbonate blend for inject ion molding and extrusion.

Texin 4215—Thermoplastic polyurethane/polycarbonate blend for injection molding and extrusion.

Texin 5250—Aromatic polyether-based medical grade with a Shore D hardness of approximately 50 for injection molding and extrusion. Complies with 21 CFR 177.1680 and 177.2600.

Texin 5286—Aromatic polyether-based medical grade with Shore A hardness of approximately 86 for injection molding or extrusion. Complies with 21 CFR 177.1680 and 177.2600.

Texin 5290—Aromatic polyether-based medical grade with a Shore A hardness of approximately 90. Complies with 21 CFR 177.1680 and 177.2600.

It is appreciated that the devices described hereinabove, while preferably formed by injection molding of polyurethane, may also be formed by any suitable manufacturing method and may be formed of any suitable medical grade elastomers. It is further appreciated that any of the following manufacturing methods may be utilized: injection molding including inserting inserts, compression molding including inserting inserts, injection—compression molding including inserting inserts, compression molding of prefabricated elements pre-formed by any of the above methods including inserting inserts spraying including inserting inserts, dipping including inserting inserts, machining from stock or rods, machining from prefabricated elements including inserting inserts.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

The invention claimed is:

1. An orthopedic implant for use in a joint, the implant comprising:
　a body portion comprising a polycarbonate polyurethane having a durometer hardness of approximately 80 Shore A, the body portion comprising:
　　a first engagement surface defining an articulating surface sized and shaped to interface with a femoral portion of the joint; and
　　a second engagement surface opposite the first surface; and
　a deformation control element having a generally annular configuration defined by a first thickened portion having a first thickness, a second thickened portion having a second thickness, and a third portion connecting the first and second portions, the third portion having a third thickness less than the first and second thicknesses and the third portion having a cross-sectional profile different than the first and second portions, the deformation control element positioned entirely within the body portion between the first and second engagement surfaces such that no portion of the deformation control element is exposed and such that there is no space between the body portion and the deformation control element, the deformation control element comprising a polymer having a durometer hardness harder than 80 Shore A, wherein the deformation control element extends circumferentially within the body portion such that the deformation control element is spaced from and does not extend through a central section of the body portion, wherein the deformation control element is positioned adjacent to an outer boundary of the body portion extending between the first and second engagement surfaces, wherein the deformation control element limits outward deformation of the body portion while allowing inward deformation of the body portion such that the body portion is deformable between a first configuration and a second configuration, the first configuration having a reduced outer profile relative to the second configuration.

2. The implant of claim 1, wherein the second thickened portion of the deformation control element is positioned closer to a bottom portion of the implant than the first thickened portion of the deformation control element.

3. The implant of claim 1, wherein the first thickened portion of the deformation control element has a generally circular cross section.

4. The implant of claim 3, wherein the second thickened portion of the deformation control element has a generally circular cross section.

5. The implant of claim 3, wherein the second thickened portion of the deformation control element has a generally rectangular cross section.

6. The implant of claim 1, wherein the first thickened portion of the deformation control element has a generally rectangular cross section.

7. The implant of claim 1, wherein the body portion further includes an outwardly extending protrusion configured to engage a corresponding recess formed in a bone structure.

8. An orthopedic prosthetic device for use in a joint, comprising:
a body portion comprising a polycarbonate polyurethane, the body portion comprising:
a first surface defining an articulating surface sized and shaped for articulating engagement with a femoral portion of the joint; and
a second surface opposite the first surface; and
a deformation control element having a generally annular configuration positioned entirely within the body portion between the first and second surfaces such that no portion of the deformation control element is exposed and such that there is no space between the body portion and the deformation control element, the deformation control element comprising a polymer having a durometer hardness harder than the polycarbonate polyurethane of the body portion, wherein the deformation control element includes a first portion extending circumferentially within the body portion, a second portion spaced from the first portion and extending circumferentially within the body portion, the second portion having an increased thickness relative to the first portion, and a third portion connecting the first portion to the second portion, the third portion having a cross-sectional profile different than the first and second portions, the deformation control element positioned adjacent an outer boundary of the body portion extending between the first and second surfaces such that the deformation control element is spaced from and does not extend through a central section of the body portion, the deformation control element limiting outward deformation of the body portion while allowing inward deformation of the body portion such that the body portion is deformable between a first unloaded configuration and a second loaded configuration, the first unloaded configuration having a reduced profile relative to the second loaded configuration.

9. The device of claim 8, wherein the second portion of the deformation control element is positioned closer to a bottom portion of the implant than the first portion of the deformation control element.

10. The device of claim 8, wherein the body portion further includes an outwardly extending protrusion configured to engage a recess defined in a bone structure.

11. The device of claim 8, wherein the deformation control element comprises at least one fiber.

12. The device of claim 11, wherein the at least one fiber is formed of a polyethylene.

13. An orthopedic prosthetic device for use in a joint, comprising:
a body portion comprising a polycarbonate polyurethane having a durometer hardness of approximately 80 Shore A, the body portion comprising:
a first surface defining an articulating surface sized and shaped for articulating engagement with a bony portion of the joint; and
a second surface opposite the first surface;
wherein the body portion includes a central portion and an outer portion surrounding the central portion, wherein the outer portion has an increased thickness relative to the central portion such that at least a section of the outer portion of the body portion is configured to engage a recess defined in a bone structure of the joint; and
a deformation control element having a generally annular configuration positioned entirely within the body portion such that no portion of the deformation control element is exposed, the deformation control element including a first thickened portion having a first thickness, a second thickened portion having a second thickness, and a third portion connecting the first and second portions, the third portion having a third thickness less than the first and second thicknesses and the third portion having a cross-sectional profile different than the first and second portions, the deformation control element comprising a polymer having a durometer hardness harder than the polycarbonate polyurethane of the body portion, wherein the deformation control element is positioned within the outer portion of the body portion and spaced from the central portion of the body portion to limit outward deformation of the body portion while allowing inward deformation of the body portion such that the body portion is deformable between a first configuration and a second configuration, the first configuration having a reduced profile relative to the second configuration.

14. The prosthetic device of claim 13, wherein the polycarbonate polyurethane of the body portion is configured to increasingly conform to the portion of the joint that the first surface of the body portion articulatingly engages with over time.

* * * * *